United States Patent
Downham et al.

(10) Patent No.: US 8,604,029 B2
(45) Date of Patent: *Dec. 10, 2013

(54) 2-[(2-SUBSTITUTED)-INDOLIZIN-3-YL]-2-OXO-ACETAMIDE DERIVATIVES AS ANTIFUNGAL AGENTS

(75) Inventors: Robert Downham, Newmarket (GB); Graham Edward Morris Sibley, Manchester (GB); Lloyd James Payne, Hale (GB); Philip Edwards, Stockport (GB); Gareth Morse Davies, Macclesfield (GB)

(73) Assignee: F2G Ltd British Body Corporate, Greater Manchester (GB)

( * ) Notice: Subject to any disclaimer, the term of this patent is extended or adjusted under 35 U.S.C. 154(b) by 413 days.

This patent is subject to a terminal disclaimer.

(21) Appl. No.: 12/515,354

(22) PCT Filed: Nov. 21, 2007

(86) PCT No.: PCT/GB2007/004449
§ 371 (c)(1), (2), (4) Date: Sep. 14, 2009

(87) PCT Pub. No.: WO2008/062182
PCT Pub. Date: May 29, 2008

(65) Prior Publication Data
US 2010/0056511 A1  Mar. 4, 2010

(30) Foreign Application Priority Data
Nov. 21, 2006  (GB) .................................. 0623209.4

(51) Int. Cl.
*A61K 31/437* (2006.01)
*A61K 31/5377* (2006.01)
*A61K 31/496* (2006.01)
*A61K 31/438* (2006.01)
*A01N 43/90* (2006.01)
*C07D 471/04* (2006.01)
*C07D 491/107* (2006.01)
*A61P 31/10* (2006.01)

(52) U.S. Cl.
USPC .................. 514/233.2; 514/299; 514/253.04; 514/278; 546/112; 546/94; 546/127; 546/16; 544/362

(58) Field of Classification Search
USPC .......... 514/233.2, 299, 253.04, 278; 546/112, 546/94, 127, 362, 16
See application file for complete search history.

(56) References Cited

U.S. PATENT DOCUMENTS
6,645,976 B1  11/2003  Dillard et al.

FOREIGN PATENT DOCUMENTS
| WO | WO-96/03383 A1 | 2/1996 |
| WO | WO-02/098876 A1 | 12/2002 |
| WO | WO-2004/082606 A2 | 9/2004 |
| WO | WO-2006/123145 A1 | 11/2006 |

OTHER PUBLICATIONS

Chemical Abstracts Registry Database (compounds corresponding to answer Nos. 1-258, as accessed May 7, 2012, p. 1-125).*
Ames et al., "The Preparation of Aminoalkylpyrrocolines"; Journal of the Chemistry Society; Abstracts; 1959; pp. 620-622.
Blondeau et al., "Synthesis of New Phenols. Part 1. Derivatives of 8-Hydroxy-indolizine"; Journal of Chemical Research; 1981; pp. 366-367; 12; France.
Dick et al., "Heterocyclic Compounds with Bridgehead Nitrogen Atoms. Part 9. Synthesis in the Pyrrolo[2,1,5-de]Quinolizine ([2.3.3] Cyclazine) Series Starting from Indolizines"; Journal of Chemical Society; Perkin Trans. 1; 1981; pp. 3150-3157.
Galbraith et al., "The Formation of Cycl[3.2.2]azine Derivatives Via the Reaction of Pyrrocoline with Dimethyl Acetylenedicarboxylate"; Journal American Chemistry Society; 1961; pp. 453-458; vol. 83(2).
Groll et al., "Trends in the Postmortem Epidemiology of Invasive Fungal Infections at a University Hospital"; The Journal of infection; 1996; pp. 23-32; vol. 33.
Guet et al., "Synthesis of New Phenols, Part 2. Derivatives of 6-Hydroxy-2-Phenylindolizine"; Journal of Chemical Research; 1982; p. 245; vol. 9; France.
Hagishita et al., "Potent Inhibitors of Secretory Phospholipase A2: Synthesis and Inhibitory Activities of Indolizine and Indene Derivatives"; J. Med. Chem.; 1996; pp. 3636-3658; vol. 39(19).
Holland et al., "The Chemistry of the Pyrrocolines. Part VII. Further Experiments with 2-Methylpyrrocoline"; Journal of the Chemical Society; 1955; pp. 1504-1511; London; W.C.I.
Ribaud et al., "Survival and Prognostic Factors of Invasive Aspergillosis After Allogeneic Bone Marrow Transplantation"; Clinical Infectious Diseases 1999; pp. 322-330; vol. 28.
Shipman, "Product Class 16: Indolizines, Science of Synthesis"; 2001; pp. 745-787; vol. 10.
Venturella et al., "Arylindolizines III. Methoxyl and Glyoxyl Derivatives of Several Substituted Phenylindolizines"; Journal of Pharmaceutical Sciences; 1964; pp. 1166-1169; vol. 53(10).
International Search Report issued Apr. 15, 2008 (published May 29, 2008) during the prosecution of International Application No. PCT/GB2007/004449.
Written Opinion issued Apr. 15, 2008 (published May 21, 2009) during the prosecution of International Application No. PCT/GB2007/004449.
International Preliminary Report on Patentability issued May 26, 2009 (published May 26, 2009) during the prosecution of International Application No. PCT/GB2007/004449.
Australian Examination Report, issued Jan. 13, 2013 (published Jan. 13, 2013) during the prosecution of Australian Patent Application No. 2007324385.
Series of compounds taken from the Chemical Abstract Registry Copyright 2012 ACS on STN cited in a Japanese Office Action, issued Dec. 18, 2012 (published Dec. 18, 2012) during the prosecution of Japanese Application No. 2009-537692.

* cited by examiner

Primary Examiner — Kortney L Klinkel

(57) ABSTRACT

The invention provides compounds of formula (I), and pharmaceutically acceptable salts thereof wherein: R1, R2, R3, R4, R5, R6, R7, X and $X^1$ are as defined herein. These compounds are useful in the manufacture of medicaments for use in the prevention or treatment of a fungal disease. Compounds of formula (I), and agriculturally acceptable salts thereof, may also be used as agricultural fungicides.

(I)

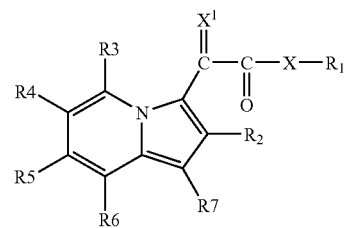

23 Claims, No Drawings

2-[(2-SUBSTITUTED)-INDOLIZIN-3-YL]-2-OXO-ACETAMIDE DERIVATIVES AS ANTIFUNGAL AGENTS

FIELD OF THE INVENTION

This invention relates to indolizine compounds and their therapeutic use in prevention or treatment of fungal diseases. It also relates to the use of the compounds as agricultural fungicides.

BACKGROUND OF THE INVENTION

Invasive fungal infections are well recognised as diseases of the immunocompromised host. Over the last twenty years there have been significant rises in the number of recorded instances of fungal infection (Groll et al., 1996. *J Infect* 33, 23-32). In part this is due to increased awareness and improved diagnosis of fungal infection. However, the primary cause of this increased incidence is the vast rise in the number of susceptible individuals. This is due to a number of factors including new and aggressive immunosuppressive therapies, increased survival in intensive care, increased numbers of transplant procedures and the greater use of antibiotics worldwide.

In certain patient groups, fungal infection occurs at high frequency; lung transplant recipients have a frequency of up to 20% colonisation and infection with a fungal organism and fungal infection in allogenic haemopoetic stem cell transplant recipients is as high as 15% (Ribaud et al., 1999, *Clin Infect Dis.* 28:322-30).

Currently only four classes of antifungal drug are available to treat systemic fungal infections. These are the polyenes (e.g., amphotericin B), the azoles (e.g., ketoconazole or itraconazole), the echinocandins (e.g., caspofungin) and flucytosine.

The polyenes are the oldest class of antifungal agent being first introduced in the 1950's. The exact mode of action remains unclear but polyenes are only effective against organisms that contain sterols in their outer membranes. It has been proposed that amphotericin B interacts with membrane sterols to produce pores allowing leakage of cytoplasmic components and subsequent cell death.

Azoles work by inhibition of the 14α-demethylase via a cytochrome P450-dependent mechanism. This leads to a depletion of the membrane sterol ergosterol and the accumulation of sterol precursors resulting in a plasma membrane with altered fluidity and structure.

Echinocandins work by the inhibition of the cell wall synthetic enzyme β-glucan synthase. This leads to abnormal cell wall formation, osmotic sensitivity and cell lysis.

Flucytosine is a pyrimidine analogue interfering with cellular pyrimidine metabolism as well DNA, RNA and protein synthesis. However widespread resistance to flucyotosine limits its therapeutic use.

It can be seen that to date the currently available antifungal agents act primarily against only two cellular targets; membrane sterols (polyenes and azoles) and β-glucan synthase (echinocandins).

Resistance to both azoles and polyenes has been widely reported leaving only the recently introduced echinocandins to combat invasive fungal infections. As the use of echinocandins increases, resistance by fungi will inevitably occur.

The identification of new classes of antifungal agent is required to give the promise of positive therapeutic outcomes to patients.

WO-A-2004/082606 discloses certain 2-indolizin-3-yl-2-oxo-acetamides as TNFα and/or PDE4 inhibitors, which may be used for the treatment of cancer, inflammatory disorders, and autoimmune diseases. These compounds differ from the present invention as the 2-position of the indolizine (i.e. R2 in this invention) is unsubstituted.

U.S. Pat. No. 6,645,976, WO-A-96/03383 and J. Med. Chem. 1996, 39, (19), 3636 disclose the preparation of (1-benzyl-6-(3-carboxypropyloxy)-2-ethyl-indolizin-3-yl) glyoxylamide and its use as a sPLA$_2$ inhibitor. This compound and its intermediates differ from the present invention as they contain a benzyl group in position 1 of the indolizine (i.e. R7 in this invention).

SUMMARY OF THE INVENTION

The present inventors have found that certain indolizine compounds are antifungal. In particular, the compounds inhibit the growth of human pathogenic fungi such as *Aspergillus* and therefore may be used to treat fungal infection and disease.

Accordingly, the present invention provides a compound which is an indolizinyl derivative of formula (I) or a pharmaceutically acceptable salt thereof:

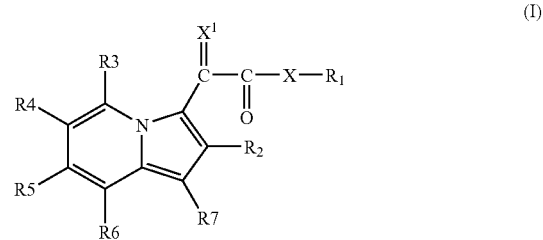

wherein:

X is a bond, —NR8-, —O—, —S—, —SO—, or —SO$_2$—;

X$^1$ is O or NOR9, wherein R9 is hydrogen or an unsubstituted or substituted C1-C4 alkyl group;

either (i) R1 and R8 independently represent hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z, (ii) R1 represents -A3-L3-A4, -A3-L1-(A4)$_p$-(A11)$_q$-L3-A5, -A6-L1-A7, -A3-L4-A8, -A3-W, -A9, -A3-L1-A9 or -A10, wherein p and q are the same or different and represent zero or 1, and R8 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z, or (iii) when X is NR8, R1 and R8 together with the nitrogen to which they are attached may form an unsubstituted or substituted, aromatic or non-aromatic 5- to 12-membered heterocyclyl group;

L1 is a bond, —NR'—, —O—, —CO—, —OCO—, —OCONR'R" or —CONR'R"—;

L2 is a substituted or unsubstituted C1-C4 alkylene or C2-C4 alkenylene group;

L3 is a bond or a group of formula -(Het)$_r$-Alk$^1$-(Het)$_s$-, -(Alk$^2$)$_m$-C(=O)-Het-(Alk$^3$)$_n$-, -Alk$^4$- or —SO$_2$—, wherein Alk$^1$, Alk$^2$, Alk$^3$ and Alk$^4$ are the same or different and represent unsubstituted C1-C4 alkylene groups, m, n, r and s are the same or different and represent zero or 1, and Het represents —O— or —NR9- where R9 is hydrogen or unsubstituted C1-C4 alkyl;

L4 is an imino group —N═ wherein the double bond is bonded to group A8;

A1 is an unsubstituted or substituted C6-C10 arylene group;

A2, A3, A4, A5, A7 and A11 are the same or different and are unsubstituted or substituted C6-C10 aryl or 5- to 12-membered heterocyclyl groups;

A6 is a C6-C10 aryl or 5- to 12-membered heterocyclyl group which is substituted with at least a C6-C10 aryl or a 5- to 12-membered heterocyclyl group which is itself unsubstituted or substituted;

A8 is an unsubstituted or substituted 5- to 12-membered heterocyclyl group;

A9 is an unsubstituted or substituted 5- to 12-membered heterocyclyl group wherein 1 or 2 ring carbon atoms are replaced with a group selected from >C(═O), >S(═O)$_2$, >C(═NOR11) where R11 is hydrogen or a C1-C4 alkyl group, >C═CH$_2$ or >C(—OCH$_2$CH$_2$O—);

A10 is an unsubstituted or substituted tricyclic 13- to 15-membered heterocyclyl group;

W is a group of formula —C(═O)—NR10-S(═O)$_2$—R'" where R10 and R'" are the same or different and represent hydrogen or C1-C4 alkyl;

R2 is an unsubstituted or substituted group selected from C6-C10 aryl, a 5- to 12-membered heterocyclyl group, C1-C8 alkyl and C3-C6 cycloalkyl, halogen or a group of formula -B1-B2 or -B3;

B1 is an unsubstituted or substituted C6-C10 aryl group;

B2 is an unsubstituted or substituted C6-C10 aryl or 5- to 12-membered heterocyclyl group;

B3 is an unsubstituted or substituted 5- to 12-membered heterocyclyl group where 1 or 2 ring carbon atoms are replaced with a group selected from >C(═O), >S(═O)$_2$, >C(═NOR11) where R11 is hydrogen or a C1-C4 alkyl group, >C═CH$_2$ or >C(—OCH$_2$CH$_2$O—);

either (i) R3 represents C6-C10 aryl, a 5- to 12-membered heterocyclyl group, —(C 1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z, and R4 represents C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, —Y—Z or a group of formula -Het-Alk$^5$-A11 where Het is —NR12 or —O— with R12 being hydrogen or C1-C4 alkyl, Alk$^5$ is C1-C6 alkylene and A11 is C6-C10 aryl or a 5- to 12-membered heterocyclyl group, or (ii) R3 and R4, together with the ring carbon atoms to which they are bonded, form an unsubstituted or substituted C6-C10 aryl or 5- to 12-membered heterocyclyl group, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, —Y—Z, C6-C10 aryl or a group of formula -Alk$^6$-L5-A12, where Alk$^6$ is a C1-C4 alkylene group, L5 is a group of formula —O—C(═O)—, —C(═O)— or —NR13-C(═O)— and R13 is hydrogen or C1-C4 alkyl, and A12 is an unsubstituted or substituted C6-C10 aryl or 5- to 12-membered heterocyclyl group;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'═NOR"; and R' and R" independently represent hydrogen, C1-C8 alkyl, C2-C8 alkenyl or C2-C8 alkynyl, provided the compound is not:

N-(2-Methoxy-phenyl)-2-oxo-2-(2-phenyl-indolizin-3-yl)-acetamide,

4-[2-Oxo-2-(2-phenyl-indolizin-3-yl)-acetylamino]-benzoic acid methyl ester,

2-Oxo-N-phenyl-2-(2-phenyl-indolizin-3-yl)-acetamide,

4-[2-Oxo-2-(-phenyl-indolizin-3-yl)-acetylamino]-benzoic acid propyl ester,

2-[2-Oxo-2-(2-phenyl-indolizin-3-yl)-acetylamino]-benzoic acid methyl ester,

3-[2-Oxo-2-(2-phenyl-indolizin-3-yl)-acetylamino]-benzoic acid methyl ester,

4-[2-Oxo-2-(2-phenyl-indolizin-3-yl)-acetylamino]-benzoic acid butyl ester,

N-(3-Methoxy-phenyl)-2-oxo-2-(2-phenyl-indolizin-3-yl)-acetamide,

N-(4-Methoxy-phenyl)-2-oxo-2-(2-phenyl-indolizin-3-yl)-acetamide,

N-(4-Hydroxy-phenyl)-2-oxo-2-(2-phenyl-indolizin-3-yl)-acetamide,

N-(4-Chloro-phenyl)-2-oxo-2-(2-phenyl-indolizin-3-yl)-acetamide,

N-(4-Cyano-phenyl)-2-oxo-2-(2-phenyl-indolizin-3-yl)-acetamide,

2-Oxo-2-(2-phenyl-indolizin-3-yl)-N-p-tolyl-acetamide,

2-Oxo-2-(2-phenyl-indolizin-3-yl)-N-pyridin-4-yl-acetamide,

2-Oxo-2-(2-phenyl-indolizin-3-yl)-N-pyridin-3-yl-acetamide,

2-Oxo-2-(2-phenyl-indolizin-3-yl)-N-pyridin-2-yl-acetamide,

4-[2-Oxo-2-(2-phenyl-indolizin-3-yl)-acetylamino]-benzoic acid,

N-(2,4-Dimethoxy-phenyl-phenyl)-2-oxo-2-(2-phenyl-indolizin-3-yl)-acetamide,

N-(6-Methoxy-pyridin-3-yl)-2-oxo-2-(2-phenyl-indolizin-3-yl)-acetamide,

4-[2-Oxo-2-(2-phenyl-indolizin-3-yl)-acetylamino]-benzamide,

N-Methyl-4-[2-oxo-2-(2-phenyl-indolizin-3-yl)-acetylamino]-benzamide,

N,N-Dimethyl-4-[2-oxo-2-(2-phenyl-indolizin-3-yl)-acetamino]-benzamide,

5-[2-Oxo-2-(2-phenyl-indolizin-3-yl)-acetylamino]-thiophene-3-carboxylic acid methyl ester, N-(4-Methoxy-phenyl)-2-oxo-2-(2-pyridin-4-yl-indolizin-3-yl)-acetamide, N-(4-Methoxy-phenyl)-2-oxo-2-(2-pyridin-3-yl-indolizin-3-yl)-acetamide, N-(4-Methoxy-phenyl)-2-oxo-2-(2-pyridin-2-yl-indolizin-3-yl)-acetamide, N-(4-Methoxy-phenyl)-2-oxo-2-(2-thiophen-2-yl-indolizin-3-yl)-acetamide, 2-(2-Furan-2-yl-indolizin-3-yl)-N-(4-methoxy-phenyl)-2-oxo-acetamide, 2-[2-(4-Fluoro-phenyl)-indolizin-3-yl]-N-(4-methoxy-phenyl)-2-oxo-acetamide, 2-[2-(4-Fluoro-phenyl)-indolizin-3-yl]-2-oxo-N-p-tolyl-acetamide, N-(2-,4-Dimethoxy-phenyl)-2-[2-(4-fluoro-phenyl)-indolizin-3-yl]-2-oxo-acetamide,
2-[2-(4-Fluoro-phenyl)-indolizin-3-yl]-N-(6-methoxy-pyridin-3-yl)-2-oxo-acetamide,
2-Oxo-2-(2-thiophen-2-yl-indolizin-3-yl)-N-p-tolyl-acetamide,
N-(2,4-Dimethoxy-phenyl)-2-oxo-2-(2-thiophen-2-yl-indolizin-3-yl)-acetamide,
N-(6-Methoxy-pyridin-3-yl)-2-oxo-2-(2-thiophen-2-yl-indolizin-3-yl)-acetamide,
2-(2-Furan-2-yl-indolizin-3-yl)-2-oxo-N-p-tolyl-acetamide,
N-(2,4-Dimethoxy-phenyl)-2-(2-furan-2-yl-indolizin-3-yl)-2-oxo-acetamide,
2-(2-Furan-2-yl-indolizin-3-yl)-N-(6-methoxy-pyridin-3-yl)-2-oxo-acetamide,
2-Oxo-2-(2-pyridin-4-yl-indolizin-3-yl)-N-p-tolyl-acetamide,
N-(2,4-Dimethoxy-phenyl)-2-oxo-2-(2-pyridin-4-yl-indolizin-3-yl)-acetamide,
N-(6-Methoxy-pyridin-3-yl)-2-oxo-2-(2-pyridin-4-yl-indolizin-3-yl)-acetamide,
2-Oxo-2-(2-pyridin-3-yl-indolizin-3-yl)-N-p-tolyl-acetamide,
N-(2,4-Dimethoxy-phenyl)-2-oxo-2-(2-pyridin-3-yl-indolizin-3-yl)-acetamide,
N-(6-Methoxy-pyridin-3-yl)-2-oxo-2-(2-pyridin-3-yl-indolizin-3-yl)-acetamide,
2-Oxo-2-(2-pyridin-2-yl-indolizin-3-yl)-N-p-tolyl-acetamide,
N-(2,4-Dimethoxy-phenyl)-2-oxo-2-(2-pyridin-2-yl-indolizin-3-yl)-acetamide,
N-(6-Methoxy-pyridin-3-yl)-2-oxo-2-(2-pyridin-2-yl-indolizin-3-yl)-acetamide,
Oxo-(2-phenyl-indolizin-3-yl)-thioacetic acid S-(2-methoxy-phenyl)ester,
4-[2-Oxo-2-(2-phenyl-indolizin-3-yl)-acetoxy]-benzoic acid methyl ester,
N-Cyclohexyl-2-oxo-2-(2-phenyl-indolizin-3-yl)-acetamide,
N-Methyl-2-oxo-2-(2-phenyl-indolizin-3-yl)-acetamide,
N-Isopropyl-2-oxo-2-(2-phenyl-indolizin-3-yl)-acetamide,
N-(2-Methoxy-ethyl)-2-oxo-2-(2-phenyl-indolizin-3-yl)-acetamide,
N-Benzyl-2-oxo-2-(2-phenyl-indolizin-3-yl)-acetamide,
N,N-Dimethyl-2-oxo-2-(2-phenyl-indolizin-3-yl)-acetamide,
1-(2-Phenyl-indolizin-3-yl)-2-piperidin-1-yl-ethane-1,2-dione,
N-(2-Methoxy-ethyl)-2-oxo-2-(2-pyridin-3-yl-indolizin-3-yl)-acetamide,
N-Methyl-2-oxo-N-phenyl-2-(2-phenyl-indolizin-3-yl)-acetamide,
N-Methyl-2-oxo-N-phenyl-2-(2-pyridin-3-yl-indolizin-3-yl)-acetamide,
2-(5-Methyl-2-phenyl-indolizin-3-yl)-2-oxo-N-p-tolyl-acetamide,
N-(6-Methoxy-pyridin-3-yl)-2-(5-methyl-2-phenyl-indolizin-3-yl)-2-oxo-acetamide,
2-(6-Methyl-2-phenyl-indolizin-3-yl)-2-oxo-N-p-tolyl-acetamide,
2-(7-Methyl-2-phenyl-indolizin-3-yl)-2-oxo-N-p-tolyl-acetamide,
N-(6-Methoxy-pyridin-3-yl)-2-(6-methyl-2-phenyl-indolizin-3-yl)-2-oxo-acetamide,
N-(6-Methoxy-pyridin-3-yl)-2-(7-methyl-2-phenyl-indolizin-3-yl)-2-oxo-acetamide,
N-(6-Methoxy-pyridin-3-yl)-2-(8-methyl-2-phenyl-indolizin-3-yl)-2-oxo-acetamide,
2-(6-Methoxy-2-phenyl-indolizin-3-yl)-N-(6-methoxy-pyridin-3-yl)-2-oxo-acetamide,
2-(6-Methoxy-2-phenyl-indolizin-3-yl)-2-oxo-N-p-tolyl-acetamide,
N-(4-Chloro-phenyl)-2-oxo-2-(2-pyridin-3-yl-indolizin-3-yl)-acetamide,
N-(4-Fluoro-phenyl)-2-oxo-2-(2-pyridin-3-yl-indolizin-3-yl)-acetamide,
2-(6-Methyl-2-pyridin-3-yl-indolizin-3-yl)-2-oxo-N-p-tolyl-acetamide,
N-(4-Fluoro-phenyl)-2-oxo-2-(2-phenyl-indolizin-3-yl)-acetamide,
N-(2-Fluoro-phenyl)-2-oxo-2-(2-phenyl-indolizin-3-yl)-acetamide,
2-Oxo-2-(2-phenyl-indolizin-3-yl)-N-(4-trifluoromethyl-phenyl)-acetamide,
2-Oxo-2-(2-phenyl-indolizin-3-yl)-N-o-tolyl-acetamide,
N-(4-Dimethylamino-phenyl)-2-oxo-2-(2-phenyl-indolizin-3-yl)-acetamide,
N-(4-Bromo-phenyl)-2-oxo-2-(2-phenyl-indolizin-3-yl)-acetamide,
N-(4-Acetyl-phenyl)-2-oxo-2-(2-phenyl-indolizin-3-yl)-acetamide,
2-Oxo-2-(2-phenyl-indolizin-3-yl)-N-m-tolyl-acetamide,
N-(2-Chloro-phenyl)-2-oxo-2-(2-phenyl-indolizin-3-yl)-acetamide,
2-[2-Oxo-2-(2-phenyl-indolizin-3-yl)-acetylamino]-benzoic acid ethyl ester,
N-(2,4-Dichloro-phenyl)-2-oxo-2-(2-phenyl-indolizin-3-yl)-acetamide,
N-(4-Fluoro-phenyl)-2-[2-(4-fluoro-phenyl)-indolizin-3-yl]-2-oxo-acetamide,
N-(4-Chloro-phenyl)-2-[2-(4-fluoro-phenyl)-indolizin-3-yl]-2-oxo-acetamide,
N-(2-Fluoro-phenyl)-2-oxo-2-(2-pyridin-3-yl-indolizin-3-yl)-acetamide,
2-Oxo-2-(2-pyridin-3-yl-indolizin-3-yl)-N-(4-trifluoromethyl-phenyl)-acetamide,
2-Oxo-2-(2-pyridin-3-yl-indolizin-3-yl)-N-o-tolyl-acetamide,
N-(4-Bromo-phenyl)-2-oxo-2-(2-pyridin-3-yl-indolizin-3-yl)-acetamide,
2-Oxo-2-(2-pyridin-3-yl-indolizin-3-yl)-N-m-tolyl-acetamide,
N-(2-Chloro-phenyl)-2-oxo-2-(2-pyridin-3-yl-indolizin-3-yl)-acetamide,
N-(4-Acetyl-phenyl)-2-oxo-2-(2-pyridin-3-yl-indolizin-3-yl)-acetamide,
2-Oxo-2-(2-phenyl-indolizin-3-yl)-N-(3-trifluoromethyl-phenyl)-acetamide,
1-(2,3-Dihydro-indol-1-yl)-2-(2-phenyl-indolizin-3-yl)-ethane-1,2-dione,
N-(4-Methanesulfonylamino-phenyl)-2-oxo-2-(2-phenyl-indolizin-3-yl)-acetamide,
N-(3,5-Dichloro-phenyl)-2-oxo-2-(2-phenyl-indolizin-3-yl)-acetamide,
N-[4-(Cyano-dimethyl-methyl)-phenyl]-2-oxo-2-(2-phenyl-indolizin-3-yl)-acetamide,
2-Oxo-2-(2-phenyl-indolizin-3-yl)-N-(3,4,5-trimethoxy-phenyl)-acetamide,
2-Oxo-2-(2-pyridin-3-yl-indolizin-3-yl)-N-(3-trifluoromethyl-phenyl)-acetamide,
N-(2,4-Dichloro-phenyl)-2-oxo-2-(2-pyridin-3-yl-indolizin-3-yl)-acetamide, N-[4-(Cyano-dimethyl-methyl)-phenyl]-2-oxo-2-(2-pyridin-3-yl-indolizin-3-yl)-acetamide,
2-Oxo-2-(2-pyridin-3-yl-indolizin-3-yl)-N-(3,4,5-trimethoxy-phenyl)-acetamide,
N-(3,5-Dichloro-phenyl)-2-oxo-2-(2-pyridin-3-yl-indolizin-3-yl)-acetamide,
N-[3-(Cyano-dimethyl-methyl)-phenyl]-2-oxo-2-(2-phenyl-indolizin-3-yl)-acetamide,
N-(6-Dimethylamino-pyridin-3-yl)-2-oxo-2-(2-phenyl-indolizin-3-yl)-acetamide,
N-(4-Dimethylamino-phenyl)-2-oxo-2-(2-pyridin-3-yl-indolizin-3-yl)-acetamide,
N-[3-(Cyano-dimethyl-methyl)-phenyl]-2-oxo-2-(2-pyridin-3-yl-indolizin-3-yl)-acetamide,
2-[(E/Z)-Methoxyimino]-N-(4-methoxy-phenyl)-2-(2-phenyl-indolizin-3-yl)-acetamide,
N-(4-Methoxy-phenyl)-2-oxo-2-(2-o-tolyl-indolizin-3-yl)-acetamide,
N-(4-Methoxy-phenyl)-2-oxo-2-(2-m-tolyl-indolizin-3-yl)-acetamide,
N-(4-Methoxy-phenyl)-2-(8-methyl-2-phenyl-indolizin-3-yl)-2-oxo-acetamide,
2-[2-(3-Chloro-phenyl)-indolizin-3-yl]-N-(4-methoxy-phenyl)-2-oxo-acetamide,
2-[2-(3-Cyano-phenyl)-indolizin-3-yl]-N-(4-methoxy-phenyl)-2-oxo-acetamide,
N-(4-Methoxy-phenyl)-2-(5-methyl-2-phenyl-indolizin-3-yl)-2-oxo-acetamide,
N-(4-Methoxy-phenyl)-2-oxo-2-(2-p-tolyl-indolizin-3-yl)-acetamide,
N-(4-Methoxy-phenyl)-2-(6-methoxy-2-phenyl-indolizin-3-yl)-2-oxo-acetamide,
N-[3-(2-Dimethylamino-ethoxy)-phenyl]-2-oxo-2-(2-phenyl-indolizin-3-yl)-acetamide,
N-(3-Methyl-3H-benzoimidazol-5-yl)-2-oxo-2-(2-phenyl-indolizin-3-yl)-acetamide,
N-(1-Methyl-1H-benzoimidazol-5-yl)-2-oxo-2-(2-phenyl-indolizin-3-yl)-acetamide,
N-(4-Dimethylamino-phenyl)-2-(6-methoxy-2-phenyl-indolizin-3-yl)-2-oxo-acetamide,
N-(4-{1-[(E/Z)-Methoxyimino]-ethyl}-phenyl)-2-oxo-2-(2-phenyl-indolizin-3-yl)-acetamide,
N-(2,4-Difluoro-phenyl)-2-[2-(3-fluoro-phenyl)-indolizin-3-yl]-2-oxo-acetamide,
2-[2-(3-Cyano-phenyl)-indolizin-3-yl]-N-(2,4-difluoro-phenyl)-2-oxo-acetamide,
N-(5-Chloro-2-methyl-phenyl)-2-oxo-2-(2-phenyl-indolizin-3-yl)-acetamide,
{3-[2-Oxo-2-(2-phenyl-indolizin-3-yl)-acetylamino]-phenoxy}-acetic acid,
N-(2-Allyloxy-4-fluoro-phenyl)-2-oxo-2-(2-phenyl-indolizin-3-yl)-acetamide,
2-Methyl-2-[2-oxo-2-(2-phenyl-indolizin-3-yl)-acetylamino]-propionic acid ethyl ester,
2-Methyl-2-[2-oxo-2-(2-phenyl-indolizin-3-yl)-acetylamino]-3-phenyl-propionic acid ethyl ester,
N-(4-{1-[(E/Z)-Hydroxyimino]-ethyl}-phenyl)-2-oxo-2-(2-phenyl-indolizin-3-yl)-acetamide,
2-Oxo-2-(2-phenyl-indolizin-3-yl)-N-(4-piperidin-1-yl-phenyl)-acetamide,
N-(4-Morpholin-4-yl-phenyl)-2-oxo-2-(2-phenyl-indolizin-3-yl)-acetamide,
N-(4-Isopropyl-phenyl)-2-oxo-2-(2-phenyl-indolizin-3-yl)-acetamide,
N-(6-Dimethylamino-pyridin-3-yl)-2-oxo-2-(2-pyridin-3-yl-indolizin-3-yl)-acetamide,
2-[(E/Z)-2-Dimethylamino-ethoxyimino]-N-(4-methoxy-phenyl)-2-(2-phenyl-indolizin-3-yl)-acetamide,
2-[(E/Z)-3-Dimethylamino-propoxyimino]-N-(4-methoxy-phenyl)-2-(2-phenyl-indolizin-3-yl)-acetamide,
N-(3-Allyl-4-fluoro-2-methoxy-phenyl)-2-oxo-2-(2-phenyl-indolizin-3-yl)-acetamide,
N-[4-(1-Hydroxy-ethyl)-phenyl]-2-oxo-2-(2-phenyl-indolizin-3-yl)-acetamide,
N-(1-Methyl-1H-indol-5-yl)-2-oxo-2-(2-phenyl-indolizin-3-yl)-acetamide,
N-(4-Methanesulfonyl-phenyl)-2-oxo-2-(2-phenyl-indolizin-3-yl)-acetamide,
4-[1-(4-Methoxy-phenylcarbamoyl)-1-(2-phenyl-indolizin-3-yl)-meth-(E/Z)-ylideneaminooxy]-butyric acid,
2-Oxo-2-(2-phenyl-indolizin-3-yl)-N-(4-thiomorpholin-4-yl-phenyl)-acetamide,
2-Oxo-2-(2-phenyl-indolizin-3-yl)-N-(2,3,4-trimethyl-phenyl)-acetamide,
2-Oxo-2-(2-phenyl-indolizin-3-yl)-N-(4-pyrrolidin-1-yl-phenyl)-acetamide,
N-(1-Methyl-2,3-dihydro-1H-indol-5-yl)-2-oxo-2-(2-phenyl-indolizin-3-yl)-acetamide,
N-[4-(4-Methyl-piperazin-1-yl)-phenyl]-2-oxo-2-(2-phenyl-indolizin-3-yl)-acetamide,
N-Benzyl-N-methyl-3-[2-oxo-2-(2-phenyl-indolizin-3-yl)-acetylamino]-benzamide,
N-[4-(2-Methyl-[1,3]dioxolan-2-yl)-phenyl]-2-oxo-2-(2-phenyl-indolizin-3-yl)-acetamide,
N-(2,4-Difluoro-phenyl)-2-[2-(2,4-difluoro-phenyl)-indolizin-3-yl]-2-oxo-acetamide,
Diethyl-carbamic acid 3-[2-oxo-2-(2-phenyl-indolizin-3-yl)-acetylamino]-phenyl ester,
N-(3-Acetyl-phenyl)-2-oxo-2-(2-phenyl-indolizin-3-yl)-acetamide,
1-Methyl-4-{4-[2-oxo-2-(2-phenyl-indolizin-3-yl)-acetylamino]-phenyl}-thiomorpholin-1-ium,
N-(4-Oxazol-2-yl-phenyl)-2-oxo-2-(2-phenyl-indolizin-3-yl)-acetamide,
N-(2,4-Difluoro-phenyl)-2-[2-(2-methoxy-phenyl)-indolizin-3-yl]-2-oxo-acetamide,
2-Oxo-2-(2-phenyl-indolizin-3-yl)-N-[4-(pyridin-2-ylamino)-phenyl]-acetamide,
2-Oxo-2-(2-phenyl-indolizin-3-yl)-N-[4-(1H-tetrazol-5-yl)-phenyl]-acetamide,
2-Oxo-N-[4-(4-oxo-piperidin-1-yl)-phenyl]-2-(2-phenyl-indolizin-3-yl)-acetamide,
N-(4-Dimethylamino-3-methyl-phenyl)-2-oxo-2-(2-phenyl-indolizin-3-yl)-acetamide,
2-Dimethylamino-5-[2-oxo-2-(2-phenyl-indolizin-3-yl)-acetylamino]-benzoic acid,
1-{4-[2-Oxo-2-(2-phenyl-indolizin-3-yl)-acetylamino]-phenyl}-pyrrolidine-2-carboxylic acid methyl ester,
2-Oxo-2-(2-phenyl-indolizin-3-yl)-N-[4-(pyrimidin-2-ylamino)-phenyl]-acetamide,
2-[2-(2-Chloro-phenyl)-indolizin-3-yl]-N-(2,4-difluoro-phenyl)-2-oxo-acetamide,
N-(4-Dimethylaminomethyl-phenyl)-2-oxo-2-(2-phenyl-indolizin-3-yl)-acetamide,
N-(3-Acetyl-4-methoxy-phenyl)-2-oxo-2-(2-phenyl-indolizin-3-yl)-acetamide,
2-[2-(2-Methyl-pyridin-3-yl)-indolizin-3-yl]-2-oxo-N-[4-(2,2,3,3-tetrafluoro-propoxy)-phenyl]-acetamide,
2-Oxo-N-[4-(2-oxo-propyl)-phenyl]-2-(2-phenyl-indolizin-3-yl)-acetamide,
2-Oxo-2-(2-phenyl-indolizin-3-yl)-N-[4-(thiazol-2-ylamino)-phenyl]-acetamide, 2-Oxo-N-[6-(2,2,3,3-tetrafluoro-propoxy)-pyridin-3-yl]-2-(2-o-tolyl-indolizin-3-yl)-acetamide,
N-[4-(3,5-Dimethyl-isoxazol-4-yl)-phenyl]-2-oxo-2-(2-phenyl-indolizin-3-yl)-acetamide,
N-(3-Oxazol-2-yl-phenyl)-2-oxo-2-(2-phenyl-indolizin-3-yl)-acetamide,
N-(6-Dipropylamino-pyridin-3-yl)-2-oxo-2-(2-phenyl-indolizin-3-yl)-acetamide,
N-(4-Diethylamino-3-methyl-phenyl)-2-oxo-2-(2-phenyl-indolizin-3-yl)-acetamide,
N-(4-Oxazol-5-yl-phenyl)-2-oxo-2-(2-phenyl-indolizin-3-yl)-acetamide,
N-(4-Dimethylamino-oxazol-2-yl-phenyl)-2-oxo-2-(2-phenyl-indolizin-3-yl)-acetamide,
2-Oxo-2-(2-phenyl-indolizin-3-yl)-N-(4-thiazol-2-yl-phenyl)-acetamide,
1-Morpholin-4-yl-2-(2-phenyl-indolizin-3-yl)-ethane-1,2-dione,
1-Azepan-1-yl-2-(2-phenyl-indolizin-3-yl)-ethane-1,2-dione,
N-Ethyl-2-oxo-N-phenyl-2-(2-phenyl-indolizin-3-yl)-acetamide,
N-(1,5-Dimethyl-3-oxo-2-phenyl-2,3-dihydro-1H-pyrazol-4-yl)-2-oxo-2-(2-phenyl-indolizin -3-yl)-acetamide,
6-Hydroxy-alpha-oxo-2-phenyl-3-indolizineacetic acid ethyl ester,
5-Methyl-alpha-oxo-2-phenyl-3-indolizineacetic acid ethyl ester,
Ethyl 2-(2,5-dimethylindolizin-3-yl)-2-oxoacetate,
2-(p-Bromophenyl)-1-phenyl-3-indolizineglyoxylic acid ethyl ester,
1-[[2-(p-Bromophenyl)-1-(p-chlorophenyl)-3-indolizinyl]glyoxyloyl]-piperidine,
1-(p-Chlorophenyl)-2-(p-nitrophenyl)-3-indolizineglyoxylic acid ethyl ester,
2-(p-Nitrophenyl)-1-phenyl-3-indolizineglyoxylic acid,
1-[[2-(p-Bromophenyl)-1-phenyl-3-indolizinyl]glyoxyloyl]-piperidine,
(p-Chlorophenyl)-2-(p-nitrophenyl)-3-indolizineglyoxylic acid,
2-(p-Bromophenyl)-1-(p-chlorophenyl)-3-indolizineglyoxylic acid ethyl ester
2-(p-Bromophenyl)-1-(p-chlorophenyl)-3-indolizineglyoxylic acid,
2-(p-Bromophenyl)-1-phenyl-3-indolizineglyoxylic acid,
1-[[1-(p-Chlorophenyl)-2-(p-nitrophenyl)-3-indolizinyl]glyoxyloyl]-piperidine,
1-[[2-(p-Nitrophenyl)-1-phenyl-3-indolizinyl]glyoxyloyl]-piperidine,
2-(p-Nitrophenyl)-1-phenyl-3-indolizineglyoxylic acid ethyl ester,
N,N-dimethyl-2-oxo-2-(2-phenyl-indolizin-3-yl)-acetamide,
2-(2-methylindolizin-3-yl)-2-oxoacetic acid,
alpha-Oxo-2-phenyl-N-(4,5,6,7-tetrahydro-2-benzothiazolyl)-3-indolizineacetamide,
N-Cyclohexyl-alpha-oxo-2-phenyl-3-indolizineacetamide,
N-(2,4-Dimethyl-5-nitrophenyl)-alpha-oxo-2-phenyl-3-indolizineacetamide,
N-[3-[(Diethylamino)sulfonyl]phenyl]-alpha-oxo-2-phenyl-3-indolizineacetamide,
N-[2-[4-(Aminosulfonyl)phenyl]ethyl]-alpha-oxo-2-phenyl-3-indolizineacetamide,
2-Chloro-4-fluoro-benzoic acid 3-[[oxo-(2-phenyl-3-indolizinyl)acetyl]amino]propyl ester,
N-[2-(1,1-Dimethylethyl)phenyl]-alpha-oxo-2-phenyl-3-indolizineacetamide,
N-(3-Bromophenyl)-alpha-oxo-2-phenyl-3-indolizineacetamide,
3,5-Dimethyl-1-[oxo(2-phenyl-3-indolizinyl)acetyl]-piperidine,
N-(2-Hydroxyethyl)-alpha-oxo-2-phenyl-3-indolizineacetamide,
N-[2-[(4-Nitrobenzoyl)oxy]ethyl]-alpha-oxo-2-phenyl-3-indolizineacetamide,
2-(4-Chlorophenyl)-alpha-oxo-3-Indolizineacetic acid (2-fluorophenyl)methyl ester,
4-Fluoro-benzoic acid 2-[[[2-(4-chlorophenyl)-3-indolizinyl]oxoacetyl]amino]ethyl ester,
1-[[2-(4-Chlorophenyl)-3-indolizinyl]oxoacetyl]hexahydro-1H-azepine,
2-(4-Chlorophenyl)-alpha-oxo-3-indolizineacetic acid cyclopentyl ester,
2-(4-Chlorophenyl)-N-(2-hydroxyethyl)-alpha-oxo-3-indolizineacetamide,
4-(1,1-Dimethylethyl)-benzoic acid 2-[[[2-(4-chlorophenyl)-3-indolizinyl]oxoacetyl]amino]ethyl ester,
1-[Oxo(2-phenyl-3-indolizinyl)acetyl]-4-phenyl-piperazine,
2,6-Dimethyl-4-[oxo(2-phenyl-3-indolizinyl)acetyl]-morpholine,
N-1,3-Benzodioxol-5-yl-2-(4-chlorophenyl)-alpha-oxo-3-indolizineacetamide,
N-(4-Ethoxyphenyl)-alpha-oxo-2-phenyl-3-indolizineacetamide,
N-(2,4-Dimethylphenyl)-alpha-oxo-2-phenyl-3-indolizineacetamide,
N-(3-Hydroxypropyl)-alpha-oxo-2-phenyl-3-indolizineacetamide,
N-Methyl-N-(1-methyl-4-piperidinyl)-alpha-oxo-2-phenyl-3-indolizineacetamide,
N-[3-[(Diethylamino)sulfonyl]-4-methylphenyl]-alpha-oxo-2-phenyl-3-indolizineacetamide,
N-(6-Methoxy-3-pyridinyl)-alpha-oxo-2-phenyl-3-indolizineacetamide,
N-(3-Methoxyphenyl)-alpha-oxo-2-phenyl-3-indolizineacetamide,
N-[4-Methyl-3-(4-morpholinylsulfonyl)phenyl]-alpha-oxo-2-phenyl-3-indolizineacetamide,
alpha-Oxo-2-phenyl-N-[3-(1-piperidinylsulfonyl)phenyl]-3-indolizineacetamide,
N-(4-Chloro-2-methoxy-5-methylphenyl)-alpha-oxo-2-phenyl-3-indolizineacetamide,
N-(2-Chloro-3-pyridinyl)-alpha-oxo-2-phenyl-3-indolizineacetamide,
N-[2-[[(4-Chlorophenyl)amino]carbonyl]phenyl]-alpha-oxo-2-phenyl-3-indolizineacetamide,
N-[5-[(Diethylamino)sulfonyl]-2-(4-morpholinyl)phenyl]-alpha-oxo-2-phenyl-3-indolizineacetamide,
alpha-Oxo-N-(3-phenoxyphenyl)-2-phenyl-3-indolizineacetamide,
alpha-Oxo-2-phenyl-N-[4-(trifluoromethyl)phenyl]-3-indolizineacetamide,
alpha-Oxo-2-phenyl-N-[4-(1-piperidinyl)phenyl]-3-indolizineacetamide,
4-Chloro-2-nitro-benzoic acid 3-[[oxo(2-phenyl-3-indolizinyl)acetyl]amino]propyl ester,
3-[(2,6-Dimethyl-4-morpholinyl)sulfonyl]-benzoic acid 3-[[oxo(2-phenyl-3-indolizinyl)acetyl]amino]propyl ester,
N-(2,3-Dihydro-1,5-dimethyl-3-oxo-2-phenyl-1H-pyrazol-4-yl)-alpha-oxo-2-phenyl-3-indolizineacetamide,
N-(3,5-Dimethoxyphenyl)-alpha-oxo-2-phenyl-3-indolizineacetamide, N-(3-Chloro-4-fluorophenyl)-alpha-oxo-2-phenyl-3-indolizineacetamide,
N-[4-[(Diethylamino)sulfonyl]phenyl]-alpha-oxo-2-phenyl-3-indolizineacetamide,
N-(3,4-Dimethylphenyl)-alpha-oxo-2-phenyl-3-indolizineacetamide,
alpha-Oxo-N-(2-phenoxyphenyl)-2-phenyl-3-indolizineacetamide,
N-[5-(1,1-Dimethylethyl)-2-methoxyphenyl]-alpha-oxo-2-phenyl-3-indolizineacetamide,
alpha-Oxo-2-phenyl-N-[4-(1-piperidinylsulfonyl)phenyl]-3-indolizineacetamide,
N-(2,3-Dimethylphenyl)-alpha-oxo-2-phenyl-3-indolizineacetamide,
N-(4-Bromo-2-fluorophenyl)-alpha-oxo-2-phenyl-3-indolizineacetamide,
N-2-Naphthalenyl-alpha-oxo-2-phenyl-3-indolizineacetamide,
N-[2-Chloro-5-(4-morpholinylsulfonyl)phenyl]-alpha-oxo-2-phenyl-3-indolizineacetamide,
2,3-Dichloro-benzoic acid 3-[[oxo(2-phenyl-3-indolizinyl)acetyl]amino]propyl ester,
3,4-Dichloro-benzoic acid 3-[[oxo(2-phenyl-3-indolizinyl)acetyl]amino]propyl ester,
N-(2,4-Dimethoxyphenyl)-alpha-oxo-2-phenyl-3-indolizineacetamide,
2-(4-Chlorophenyl)-alpha-oxo-N-phenyl-3-indolizineacetamide,
4-[[2-(4-Chlorophenyl)-3-indolizinyl]oxoacetyl]-morpholine,
N-Ethyl-alpha-oxo-2-phenyl-3-indolizineacetamide,
alpha-Oxo-2-phenyl-N-[3-(trifluoromethyl)phenyl]-3-indolizineacetamide,
4-[[Oxo(2-phenyl-3-indolizinyl)acetyl]amino]-benzoic acid methyl ester,
N,N-Diethyl-alpha-oxo-2-phenyl-3-indolizineacetamide,
N-[2-(Dimethylamino)ethyl]-alpha-oxo-2-phenyl-3-indolizineacetamide,
2-Methyl-alpha-oxo-3-indolizineacetic acid,
N-(2-Methoxyphenyl)-alpha-oxo-2-phenyl-3-indolizineacetamide,
N-1-Naphthalenyl-alpha-oxo-2-phenyl-3-indolizineacetamide,
1,2,3,4-Tetrahydro-6,7-dimethoxy-2-[oxo(2-phenyl-3-indolizinyl)acetyl]-isoquinoline,
N-(1-Cyano-1-methylethyl)-alpha-oxo-2-phenyl-3-indolizineacetamide,
alpha-Oxo-2-phenyl-N-(2-phenylethyl)-3-indolizineacetamide,
Hexahydro-1-[oxo(2-phenyl-3-indolizinyl)acetyl]-1H-azepine,
alpha-Oxo-2-phenyl-N-4H-1,2,4-triazol-4-yl-3-indolizineacetamide,
1,2,3,4-Tetrahydro-1-[oxo(2-phenyl-3-indolizinyl)acetyl]-quinoline,
N-(6-Methoxy-2-benzothiazolyl)-alpha-oxo-2-phenyl-3-indolizineacetamide,
alpha-Oxo-2-phenyl-N-2-thiazolyl-3-indolizineacetamide,
N-[(4-Methoxyphenyl)methyl]-alpha-oxo-2-phenyl-3-indolizineacetamide,
N-[(4-Bromophenyl)methyl]-alpha-oxo-2-phenyl-3-indolizineacetamide,
N-(1,1-Dimethylethyl)-alpha-oxo-2-phenyl-3-indolizineacetamide,
N-Butyl-alpha-oxo-2-phenyl-3-indolizineacetamide,
alpha-Oxo-N-[(3-phenoxyphenyl)methyl]-2-phenyl-3-indolizineacetamide,
N-Ethyl-alpha-oxo-N,2-diphenyl-3-indolizineacetamide,
alpha-Oxo-N,2-diphenyl-3-indolizineacetamide,
N-[2-(3,4-Dimethoxyphenyl)ethyl]-alpha-oxo-2-phenyl-3-indolizineacetamide,
alpha-Oxo-2-phenyl-N-(phenylmethyl)-3-indolizineacetamide,
4-[Oxo(2-phenyl-3-indolizinyl)acetyl]-morpholine,
N-(4-Methylphenyl)-alpha-oxo-2-phenyl-3-indolizineacetamide,
2-Methyl-alpha-oxo-3-indolizineacetic acid ethyl ester,
N,N-Dimethyl-2-phenyl-3-indolizineglyoxylamide,
2-Oxo-2-(2-phenyl-indolizin-3-yl)-N-(4-trifluoromethyl-phenyl)-acetamide,
N-(2,4-Dichloro-phenyl)-2-oxo-2-(2-phenyl-indolizin-3-yl)-acetamide,
2-Oxo-2-(2-phenyl-indolizin-3-yl)-N-(3-trifluoromethyl-phenyl)-acetamide,
2-Oxo-2-(2-phenyl-indolizin-3-yl)-N-(4-piperidin-1-yl-phenyl)-acetamide,
N-(3-hydroxy-phenyl)-2-oxo-2-(2-phenyl-indolizin-3-yl) acetamide,
{3-[2-oxo-2-(2-phenyl-indolizin-3-yl)-acetylamino]-phenoxy}-acetic acid ethyl ester,
ethyl 2-oxo-2-(6-phenoxy-2-phenylindolizin-3-yl)acetate,
1-(5-methyl-2-phenyl-indolizin-3-yl)-propane-1,2-dione,
1-(5-methyl-2-phenyl-indolizin-3-yl)-propane-1,2-dione 1-oxime,
1-(2,5-dimethyl-indolizin-3-yl)-2-phenyl-ethane-1,2-dione 1-oxime,
1-(5-methyl-2-phenyl-indolizin-3-yl)-2-phenyl-ethane-1,2-dione 1-oxime,
1-(2,5-dimethyl-indolizin-3-yl)-propane-1,2-dione 1-oxime,
2-oxo-2-(2-phenylindolizin 3-yl)acetamide,
or a pharmaceutically acceptable salt thereof.

The invention also provides a compound as defined above for use in a method of treatment of the human or animal body. Also provided is the use of a compound as defined above for the manufacture of a medicament for the prevention or treatment of a fungal disease. The invention further provides a pharmaceutical composition comprising a compound as defined above and a pharmaceutically acceptable carrier or diluent, as well as a composition comprising a compound as defined above and an agriculturally acceptable carrier or diluent.

The invention also provides an agent for the treatment of a fungal disease comprising a compound as defined above. There is further provided a method of treating a subject suffering from or susceptible to a fungal disease, which method comprises administering to said subject an effective amount of a compound as defined above, as well as a method of controlling a fungal disease in a plant, which method comprises applying to the locus of the plant a compound as defined above. The invention also provides the use of a compound as defined above as an agricultural fungicide.

DETAILED DESCRIPTION OF THE INVENTION

As used herein, a C1-C8 alkyl group or moiety can be linear, branched or cyclic but is preferably linear. It is preferably a C1-C6 alkyl group, more preferably a C1-C4 alkyl group, most preferably a C1-C3 alkyl group. Suitable such alkyl groups and moieties include methyl, ethyl, n-propyl, i-propyl, n-butyl, sec-butyl and tert-butyl, as well as pentyl, hexyl, heptyl and octyl and isomers thereof. As used herein, a C1-C8 alkylene group or moiety is a divalent alkyl group or moiety as defined above. Preferred alkylene groups or moieties include C1-C6 alkylene groups or moieties, more preferably C1-C4 alkylene groups or moieties.

As used herein, a C2-C8 alkenyl group or moiety can be linear, branched or cyclic but is preferably linear. It contains one or more carbon-carbon double bonds. It is preferably a C2-C6 alkenyl group, more preferably a C2-C4 alkenyl group, most preferably a C2-C3 alkyl group. Suitable such alkenyl groups and moieties include vinyl, allyl, propenyl, butenyl, pentenyl, hexenyl, heptenyl and octenyl and isomers thereof.

As used herein, a C2-C8 alkynyl group or moiety can be linear, branched or cyclic but is preferably linear. It contains one or more carbon-carbon triple bonds. It is preferably a C2-C6 alkynyl group, more preferably a C2-C4 alkynyl group, most preferably a C2-C3 alkynyl group. Suitable such alkynyl groups and moieties include ethynyl, propynyl, butynyl, pentynyl, hexynyl, heptynyl and octynyl and isomers thereof.

An alkyl, alkenyl, alkynyl or alkylene group or moiety can be substituted or unsubstituted. Typically, it carries up to three substituents, e.g. one or two substituents. Suitable substituents are preferably themselves unsubstituted or may be further substituted with a C1-C4 alkoxy group. Suitable substituents include halogen such as fluorine, hydroxy, amino, (C1-C4 alkyl)amino, di(C1-C4 alkyl)amino, C1-C4 alkoxy such as methoxy or ethoxy, —$CO_2H$ and —$CO_2$(C1-C4 alkyl). Examples of these substituents include unsubstituted substituents such as halogen (for example fluorine), hydroxy, amino, (C1-C4 alkyl)amino, di(C1-C4 alkyl)amino and C1-C4 alkoxy such as methoxy or ethoxy.

As used herein, a C3-C6 cycloalkyl group is typically cyclopropyl, cyclopentyl or cyclohexyl group, e.g. a C5 or C6 cycloalkyl group. Typically a cycloalkyl group is unsubstituted or substituted with up to three substituents, e.g. one or two substituents. Suitable substituents include C1-C8 alkyl, C2-C8 alkenyl, C2-C8 alkynyl, Z and —Y—Z wherein Y and Z are as hereinbefore defined. Where present, preferably the substituents are themselves unsubstituted. Typically, a cycloalkyl group is unsubstituted.

When any of $R_1$ to $R_6$ or $R_8$ is (C1-C4 alkylene)-aryl or (C1-C4 alkylene)-heterocyclyl, the C1-C4 alkylene moiety is preferably methylene, ethylene, n-propylene or i-propylene, each of which is unsubstituted or substituted with one or two, e.g. one substituent selected from halogen, hydroxyl, amino, (C1-C4 alkyl)amino, di(C1-C4 alkyl)amino, C1-C4 alkoxy, —$CO_2H$ and —$CO_2$(C1-C4 alkyl). In one embodiment, the C1-C4 alkylene moiety is methylene.

When $R_1$ or $R_8$ is —(C2-C4 alkenylene)-aryl or —(C2-C4 alkenylene)-heterocyclyl, the C2-C4 alkenylene moiety is preferably ethenylene.

When Y is C1-C8 alkylene, it is preferably C1-C4 alkylene, more preferably methylene or ethylene.

When Y is C2-C8 alkenylene, it is preferably C2-C4 alkenylene, more preferably ethenylene.

When Y is C2-C8 alkynylene, it is preferably C2-C4 alkynylene, more preferably ethynylene.

When R' or R" is C1-C8 alkyl, it is preferably C1-C4 alkyl, more preferably methyl or ethyl. R' and R" may be unsubstituted or substituted as described above for an alkyl group or moiety.

When R' or R" is C2-C8 alkenyl, it is preferably C2-C4 alkenyl, more preferably ethenyl.

When R' or R" is C2-C8 alkynyl, it is preferably C2-C4 alkynyl, more preferably ethynyl.

As used herein, an aryl group or moiety is typically phenyl or naphthyl, more preferably phenyl.

As used herein and unless otherwise stated, a heterocyclyl group or moiety is a saturated or unsaturated, 5- to 12-membered ring system in which the ring contains at least one heteroatom. Typically, the ring contains up to three or four heteroatoms, e.g. one or two heteroatoms, selected from O, S and N. Thus, a heterocyclyl group or moiety is typically a 5- to 12-membered ring containing one, two or three heteroatoms selected from O, S and N. Suitable such heterocyclyl groups and moieties include, for example, monocyclic saturated 5- to 8-membered rings, such as tetrahydrofuranyl, piperidinyl, oxazolidinyl, morpholinyl, thiomorpholinyl, pyrrolidinyl, dioxolanyl, piperidonyl, azepanyl, diazepanyl, piperazinyl and tetrahydropyranyl, e.g. the 5- to 6-membered rings tetrahydrofuranyl, piperidinyl, oxazolidinyl, morpholinyl, thiomorpholinyl, pyrrolidinyl, dioxolanyl, piperidonyl, azepanyl, piperazinyl and tetrahydropyranyl; more preferably a monocyclic saturated 5- to 8-membered ring includes piperidinyl, diazepanyl, morpholinyl, piperazinyl, tetrahydropyranyl and pyrrolidinyl, e.g. morpholinyl, piperazinyl, tetrahydropyranyl and pyrrolidinyl. Suitable heterocyclyl groups and moieties also include, for example, monocyclic at least partially unsaturated 5- to 8-membered rings, more preferably 5- to 6-membered rings, such as furanyl, pyrrolyl, thiophenyl, oxazolyl, dihydro-oxazolyl, isoxazolyl, thiazolyl, pyrazolyl, imidazolyl, triazolyl, tetrazolyl, pyridinyl, pyrimidinyl, pyrazinyl, pyridazinyl and di- and tetrahydropyridinyl, for example furanyl, pyrrolyl, thiophenyl, oxazolyl, isoxazolyl, thiazolyl, pyrazolyl, imidazolyl, triazolyl, tetrazolyl, pyridinyl, pyrimidinyl, pyrazinyl, pyridazinyl and di- and tetrahydropyridinyl, more particularly oxazolyl, dihydro-oxazolyl, isoxazolyl, imidazolyl, furanyl, thiophenyl, pyrimidinyl or pyridinyl, e.g. oxazolyl, imidazolyl, furanyl, thiophenyl or pyridinyl; more preferably oxazolyl, imidazolyl or pyridinyl. Suitable heterocyclyl groups and moieties also include, for example, bicyclic 8- to 10-membered ring systems such as indolyl, benzofuranyl, benzothiophenyl, benzimidazolyl, benzoxazolyl, benzopyrazolyl, benzothiazolyl, benzotriazolyl, quinolinyl, quinazolinyl, quinoxalinyl, cinnolinyl, purinyl and cyclopentapyridines which may optionally be partially unsaturated, for example dihydroindolyl; and tricyclic 11- or 12-membered ring systems such as acridinyl, pteridinyl and benzathiazinyl.

Particular examples of such heterocyclyl groups and moieties include monocyclic saturated 5- to 8-membered rings, (e.g. monocyclic saturated 5- to 6-membered rings) such as oxazolidinyl, pyrrolidinyl tetrahydrofuranyl, piperidinyl, morpholinyl, azepanyl, diazepanyl, piperazinyl and tetrahydropyranyl, e.g. more preferably piperidinyl, diazepanyl, morpholinyl, piperazinyl, tetrahydropyranyl, oxazolidinyl and pyrrolidinyl, particularly morpholinyl, piperazinyl, tetrahydropyranyl, oxazolidinyl and pyrrolidinyl; monocyclic at least partially unsaturated 5- to 8-membered rings, more preferably monocyclic at least partially unsaturated 5- to 6-membered rings such as furanyl, pyrrolyl, thiophenyl, oxazolyl, dihydro-oxazolyl, isoxazolyl, thiazolyl, pyrazolyl, imidazolyl, triazolyl, tetrazolyl, pyridinyl, pyrimidinyl, pyrazinyl, pyridazinyl and di- and tetrahydropyridinyl, e.g. furanyl, thiophenyl, pyridinyl, oxazolyl, dihydro-oxazolyl, isoxazolyl, pyrimidinyl and imidazolyl, for example furanyl, thiophenyl, pyridinyl, oxazolyl and imidazolyl, more preferably pyridinyl, oxazolyl and imidazolyl; and bicyclic 8- to 10-membered ring systems such as indolyl, dihydroindolyl, benzofuranyl, benzothiophenyl, benzimidazolyl, benzoxazolyl, benzopyrazolyl, benzothiazolyl, benzotriazolyl, quinolinyl, quinazolinyl, quinoxalinyl, cinnolinyl, purinyl and cyclopentapyridines which may optionally be partially unsaturated, preferably indolyl.

Where specified, the heterocyclyl group can be a 13- to 15-membered tricyclic heterocyclyl group comprising three rings fused together. Suitable examples include unsaturated variants comprising 1 or 2 phenyl rings fused to 2 or 1 5- to 6-membered heterocyclyl rings, or 3 5- to 6-membered heterocyclyl rings fused together, for example a carbazolyl group. Other examples include partially unsaturated or fully saturated derivatives of the above groups. A suitable 13- to 15-membered tricyclic heterocyclyl group is tetrahydropyridoindolyl.

Where specified, a heterocyclyl group can be a 5- to 12-membered group having 1 or 2 ring carbon atoms being replaced with a group, which may be the same or different if two are present, selected from >C(=O)—, >S(=O)$_2$—, >C(=NOR11), >C(NR11), >C(=CH$_2$) or >C(—OCH$_2$CH$_2$O—), where R11 is hydrogen or C1-C4 alkyl. In such cases, preferably one ring carbon atom is replaced by a group selected from >C(=O)—, >S(=O)$_2$—, >C(=NOR11), >C(NR11), >C(=CH$_2$) or >C(—OCH$_2$CH$_2$O—), where R11 is hydrogen or C1-C4 alkyl. Preferably R11 is hydrogen or C1-C2 alkfyl, more preferably hydrogen or methyl. Suitable heterocyclyl groups on which these groups can be based include the heterocyclyl groups described above. Where a carbon atom is replaced with >C(—OCH$_2$CH$_2$O—), the carbon atom which is now a ring atom in the heterocyclyl ring is di-substituted with the —OCH$_2$CH$_2$O— group, forming a spiro compound.

Preferred examples—where a heterocyclyl group contains a group >C(=O)—, >S(=O)$_2$—, >C(=NOR11), >C(NR11), >C(=CH$_2$) or >C(—OCH$_2$CH$_2$O—) include oxo-dihydropyridinyl, oxo-dihydroindolyl, oxo-piperidinyl, 1,1-dioxo-thiomorpholinyl, methoxyiminopiperidinyl, methoxyimino pyrrolidinyl, methylenepiperidinyl and 1,4-dioxa-8-azaspiro[4.5]decyl.

A heterocyclyl or aryl group or moiety may be substituted or unsubstituted. Each ring atom may be unsubstituted or may carry one or two substituents. If desired, a nitrogen atom may be disubstituted and a sulphur atom may be substituted, providing a charged heteroatom. Typically, a heterocyclyl or aryl group or moiety carries up to three substituents, e.g. one or two substituents. The heterocycle may be connected to the remainder of the molecule by a bond to any of its available ring positions.

Suitable substituents include C1-C8 alkyl, C2-C8 alkenyl, C2-C8 alkynyl, unsubstituted phenyl, Z and —Y—Z wherein Y and Z are as hereinbefore defined. Preferred substituents on an aryl or heterocyclyl group or moiety are unsubstituted substituents selected from halogen, —CO$_2$R', —CONR'R", OCOR', hydroxyl, cyano, —NR'R", —COR', —COCF$_3$, —NSO$_2$R', —O(C2-C4 alkenyl), C2-C4 alkenyl, —SO$_2$R', —OCONR'R" and —CR'=NOR", or C1-C6 alkyl or C1-C6 alkoxy groups which are unsubstituted or substituted with one, two, three or four, for example one, two, or three, for example one, unsubstituted group selected from halogen, hydroxyl, amino, (C1-C4 alkyl)amino, di(C1-C4 alkyl) amino, C1-C4 alkoxy, —O—(C1-C4 alkyl)-O—(C1-C4 alkyl), cyano, —COR' and —CO$_2$R', wherein R' and R" are independently selected from hydrogen and C1-C4 alkyl which is unsubstituted or substituted by a hydroxyl or C1-C4 alkoxy group; e.g. unsubstituted substituents selected from halogen, —CO$_2$R', —CONR'R", OCOR', hydroxyl, cyano, —NR'R", —COR', —NSO$_2$R', —O(C2-C4 alkenyl), C2-C4 alkenyl, —SO$_2$R', —OCONR'R" and —CR'=NOR", or C1-C6 alkyl or C1-C6 alkoxy groups which are unsubstituted or substituted with one, two, three or four, for example one, two, or three, for example one, unsubstituted group selected from halogen, hydroxyl, amino, (C1-C4 alkyl)amino, di(C1-C4 alkyl)amino, C1-C4 alkoxy, cyano, —COR' and —CO$_2$R', wherein R' and R" are independently selected from hydrogen and C1-C4 alkyl. The substituents on such an alkyl or alkoxy substituent are in one aspect of the invention selected from halogen, hydroxyl, amino, (C1-C4 alkyl) amino, di(C1-C4 alkyl)amino, C1-C4 alkoxy, cyano and —CO$_2$R', wherein R' and R" are independently selected from hydrogen and C1-C4 alkyl. Where three or four substituents are present on an aryl or heterocyclyl group, preferably they are all selected from halogen, C1-C4 alkyl or C1-C4 alkoxy, more preferably they are all selected from halogen, C1-C2 alkyl or C1-C2 alkoxy, most preferably they are C1-C2 alkyl groups such as methyl groups.

Examples of more preferred substituents on an aryl or heterocyclyl group or moiety are unsubstituted substituents selected from halogen, C1-C6 alkyl, C1-C4 alkoxy, —CO$_2$R', —CONR'R", —OCOR', hydroxyl and cyano, in particular halogen, C1-C6 alkyl, C1-C4 alkoxy, —CO$_2$R', —CONR'R", —OCOR', hydroxyl and cyano wherein R' and R" are independently selected from hydrogen and C1-C4 alkyl. In some embodiments, preferred substituents can include amino, (C1-C4 alkyl)amino and di(C1-C4 alkyl)amino groups, more preferably amino groups.

Typically none or one cyano substituent is present. Typically none, one or two, e.g. none or one, phenyl substituent is present.

Most preferable substituents include 1, 2, 3 or 4 halogen atoms, hydroxyl groups, —CO$_2$H, —COCF$_3$, —OCONR'R", C2-C4 alkenyl, —NR'R", C1-C6 alkyl (for example methyl, ethyl, propyl and pentyl groups and their isomers) or C1-C4 alkoxy, or C1-C4 alkyl or C1-C4 alkoxy substituted with 1 or 2 groups selected from hydroxyl, C1-C4 alkoxy and —O—(C1-C4 alkyl)-O—(C1-C4 alkyl) groups. Examples of preferable substituents include 1, 2, 3 or 4 halogen atoms, hydroxyl groups or C1-C6 alkyl (for example methyl, ethyl, propyl and pentyl groups and their isomers) or C1-C4 alkyl substituted with 1 or 2 C1-C4 alkoxy groups. Suitable C1-C4 alkyl or alkoxy groups substituted with C1-C4 alkoxy groups include C1-C2 alkyl or alkoxy groups (e.g. C1-C2 alkyl groups) substituted with 1 or 2 C1-C2 alkoxy groups, more preferably C1-C2 alkyl or alkoxy groups (e.g. C1-C2 alkyl groups) substituted with a single C1-C2 alkoxy group. Particularly preferred is —CH$_2$—O—CH$_3$.

As used herein, a halogen is typically chlorine, fluorine, bromine or iodine, and is preferably chlorine, fluorine or bromine, more preferably chlorine or fluorine.

Preferably, X is —NR8-, —O— or —S—, preferably —NR8- or —O—, most preferably —NR8-. Preferably R8 is hydrogen or C1-C4 alkyl, more preferably hydrogen or C1-C2 alkyl, most preferably R8 is hydrogen.

Preferably, $X^1$ is O or NOR9, wherein R9 is hydrogen or C1-C4 alkyl which is unsubstituted or substituted with one, two or three substituents selected from halogen, hydroxyl, amino, (C1-C4 alkyl)amino, di(C1-C4 alky)amino, C1-C4 alkoxy, —CO$_2$H and —CO$_2$(C1-C4 alkyl). Preferably, R9 is a linear C1-C4 alkyl group which is unsubstituted or substituted with a single substituent on the terminal carbon atom. Preferred substituents are di(C1-C4 alkyl)amino and —CO$_2$H. Preferably $X^1$ is O.

In one embodiment of the invention, R1 is other than hydrogen, thiazolyl or 4-hydroxy-phenyl. In another embodiment, R1 is other than pyridyl, in particular other than methoxy-pyridyl, e.g. 6-methoxy-pyridyl. In another embodiment, R1 is phenyl, a monocyclic, unsaturated 5- to 8-membered heterocyclyl ring containing one heteroatom, C5-C6 cycloalkyl, (unsubstituted C1-C2 alkylene)-phenyl, or C1-C4 alkyl.

In one embodiment, R1 is phenyl, a 5- to 12-membered heterocyclyl group, C5-C6 cycloalkyl, C1-C4 alkyl, -A1-L1-A2 or -L2-A2 wherein A1 is phenyl, L1 is a bond, —NR'— or —CONR'R"—, wherein R' and R" are independently selected from hydrogen and C1-C4 alkyl groups and moieties which are unsubstituted or substituted with a C1-C4 alkoxy group, L2 is C1-C4 alkylene which is unsubstituted or substituted with one or two substituents selected from halogen, C1-C4 alkoxy and —$CO_2$(C1-C4 alkyl) and A2 is phenyl or a 5- to 6-membered heterocyclyl group containing one, two, three or four heteroatoms selected from N, O and S.

When R1 is phenyl, 5- to 12-membered heterocyclyl, C5-C6 cycloalkyl, -A1-L1-A2 or -L2-A2, the phenyl and heterocyclyl groups or moieties R1, A1 and A2 are typically unsubstituted or substituted with one, two or three substituents selected from the unsubstituted groups halogen, —$CO_2$R', —CONR'R", OCOR', hydroxyl, cyano, —NR'R", —COR', —$NSO_2$R', —O(C2-C4 alkenyl), C2-C4 alkenyl, —$SO_2$R', —OCONR'R" and —CR'=NOR", and from C1-C4 alkyl and C1-C4 alkoxy groups which are unsubstituted or substituted with one, two, three or four, for example one, two or three, for example one, unsubstituted group selected from halogen, hydroxyl, amino, (C1-C4 alkyl)amino, di(C1-C4 alkyl)amino, C1-C4 alkoxy, cyano, —COR' and —$CO_2$R', wherein R' and R" are independently selected from hydrogen and C1-C4 alkyl. Preferably, the substituents on the phenyl and heterocyclyl groups or moieties R1, A1 and A2 are selected from the unsubstituted groups halogen, —$CO_2$R', —CONR'R", —OCOR', hydroxyl, cyano, —NR'R", —COR', —$NSO_2$R', —O(C2-C4 alkenyl), C2-C4 alkenyl, —$SO_2$R', —OCONR'R", —CR'=NOR" and —$CF_3$, and from C1-C4 alkyl and C1-C4 alkoxy groups which are unsubstituted or substituted with from one to four, for example one unsubstituted group selected from halogen, hydroxyl, di(C1-C4 alkyl)amino, cyano, —COR' and —$CO_2$R', wherein R' and R" are independently selected from hydrogen and C1-C4 alkyl. In one aspect of the invention the alkyl and alkoxy substituents on the phenyl and heterocyclyl groups or moieties R1, A1 and A2 optionally bear substituent(s) selected from halogen, hydroxyl, amino, (C1-C4 alkyl)amino, di(C1-C4 alkyl)amino, C1-C4 alkoxy, cyano and —$CO_2$R', for example from hydroxyl, di(C1-C4 alkyl) amino, cyano and —$CO_2$R', wherein R' and R" are independently selected from hydrogen and C1-C4 alkyl.

Preferably the group A1 is unsubstituted phenyl, or phenyl substituted with a group —NR'R", wherein R' and R" are independently hydrogen or C1-C4 alkyl. In one embodiment A1 is unsubstituted phenyl. Preferred substituents on the group A2 are C1-C4 alkyl, —$CO_2$(C1-C4 alkyl) and —OCONR'R", wherein R' and R" are independently selected from hydrogen and C1-C4 alkyl. Particular examples of substituents on the group A2 are C1-C4 alkyl and —$CO_2$(C1-C4 alkyl).

In another embodiment, when R1 is phenyl, 5- to 12-membered heterocyclyl, C5-C6 cycloalkyl, -A1-L1-A2 or -L2-A2, the phenyl and heterocyclyl groups or moieties R1 are typically unsubstituted or substituted with one, two or three unsubstituted groups selected from halogen, C1-C4 alkyl, C1-C4 alkoxy, —$CO_2$R', —CONR'R", —OCONR'R", —OCOR', hydroxyl, cyano and phenyl, e.g. one, two or three unsubstituted groups selected from halogen, C1-C4 alkyl, C1-C4 alkoxy, —$CO_2$R', —CONR'R", —OCOR', hydroxyl, cyano and phenyl, wherein R' and R" are independently selected from hydrogen and C1-C4 alkyl. In this embodiment, the substituents on the phenyl and heterocyclyl groups or moieties are preferably unsubstituted groups selected from halogen, C1-C4 alkyl, C1-C4 alkoxy, —$CO_2$R', —CONR'R", —OCONR'R", —OCOR' and cyano, e.g. unsubstituted groups selected from halogen, C1-C4 alkyl, C1-C4 alkoxy, —$CO_2$R', —CONR'R", —OCOR' and cyano, wherein R' and R" are independently selected from hydrogen and C1-C4 alkyl.

When R1 is phenyl, 5- to 12-membered heterocyclyl, C5-C6 cycloalkyl, -A1-L1-A2 or -L2-A2, the cycloalkyl and alkyl groups and moieties R1 are typically unsubstituted or substituted with one or two unsubstituted groups selected from C1-C4 alkoxy, halogen, hydroxyl, amino, (C1-C4 alkyl) amino, di(C1-C4 alkyl)amino or $CO_2$(C1-C4 alkyl), for example C1-C4 alkoxy, halogen, hydroxyl, amino, (C1-C4 alkyl)amino or di(C1-C4 alkyl)amino.

In a preferred embodiment of the invention, R1 is phenyl, pyridinyl, thiophenyl, furanyl, benzimidazolyl, indolyl, dihydroindolyl, unsubstituted C5-C6 cycloalkyl, C1-C4 alkyl which is unsubstituted or substituted with C1-C4 alkoxy or —$CO_2$(C1-C4 alkyl), -A1-L1-A2 or -L2-A2, wherein A1 is unsubstituted phenyl or phenyl substituted with a group —NR'R" (e.g. A1 is unsubstituted phenyl), L1 is a bond, —NH—, —N—(C1-C4 alkyl)-O—(C1-C4 alkyl)- or —CONR'R"— (e.g. L1 is a bond, —NH— or —CONR'R"), wherein R' and R" are individually selected from hydrogen and C1-C4 alkyl groups and moieties, L2 is C1-C4 alkylene which is unsubstituted or substituted with one or two substituents selected from halogen, C1-C4 alkoxy and —$CO_2$(C1-C4 alkyl), and A2 is phenyl or a 5- to 6-membered heterocyclyl group containing one, two, three or four heteroatoms selected from N, O and S. In this embodiment, the aryl and heterocyclyl groups R1 and A2 are unsubstituted or substituted with one, two or three substituents selected from the unsubstituted groups halogen, —$CO_2$R', —CONR'R", OCOR', hydroxyl, cyano, —NR'R", —COR', —$NSO_2$R', —O(C2-C4 alkenyl), C2-C4 alkenyl, —$SO_2$R', —OCONR'R", —CR'=NOR" and $CF_3$, and from C1-C4 alkyl and C1-C4 alkoxy groups which are unsubstituted or substituted with from one to four e.g. one unsubstituted group selected from halogen, hydroxyl, di(C1-C4 alkyl)amino, cyano, —COR' and —$CO_2$R' (for example selected from hydroxyl, di(C1-C4 alkyl)amino, cyano and —$CO_2$R'), wherein R' and R" are independently selected from hydrogen and C1-C4 alkyl. Typically only one cyano substituent is present.

In another embodiment of the invention, R1 is phenyl, pyridinyl, thiophenyl, furanyl, unsubstituted C5-C6 cycloalkyl, benzyl or C1-C4 alkyl which is unsubstituted or substituted with C1-C4 alkoxy. In this embodiment the phenyl, pyridinyl, thiophenyl, furanyl and benzyl groups are unsubstituted or substituted with one or two unsubstituted substituents selected from halogen, C1-C4 alkyl, C1-C4 alkoxy, —$CO_2$R', —CONR'R", —OCOR' and cyano, wherein R' and R" are independently selected from hydrogen and C1-C4 alkyl. Typically only one cyano substituent is present.

In another preferred embodiment of the invention, R1 is a group selected from -A3-L3-A4, -A3-L1-(A4)$_p$-(A11)$_q$-L3-A5, -A6-L1-A7, -A3-L4-A8, -A3-W, -A9, -A3-L1-A9 and -A10, wherein p and q are the same or different and represent zero or 1. When R1 represents -A3-L1-(A4)$_p$-(A11)$_q$-L3-A5, in one embodiment p is 1 and q is zero. In this case, R1 represents -A3-L1-A4-L3-A5 or in the case that L3 is a bond, R1 represents -A3-L1-A4-A5. In another embodiment, p is 1 and q is 1. In this case, L1 is typically a bond such that R1 represents -A3-A4-A11-L3-A5. In a further embodiment, p and q are both zero and L1 is a bond such that R1 represents -A3-L3-A5. In one particular embodiment, L3 is a bond, p is 1 and q is zero, such that R1 represents -A3-L1-A4-A5.

When R1 is -A3-L3-A4, -A3-L1-(A4)$_p$-(A11)$_q$-L3-A5, -A3-L4-A8, -A3-W or -A3-L1-A9, preferably A3 is an unsubstituted or substituted C6-C10 aryl group or 5- to 6-membered unsaturated heterocyclyl group, more preferably an unsubstituted or substituted phenyl or pyridyl ring, e.g. a phenyl ring. When A3 is substituted, it is preferably substituted by 1, 2 or 3 unsubstituted substituents selected from halogen, C1-C4 alkoxy, —CO$_2$R', —CONR'R", —OCOR', hydroxyl and cyano, and from C1-C6 alkyl groups which are unsubstituted or substituted with a C1-C4 alkoxy group, in particular the substituents on A3 are selected from the unsubstituted substituents halogen, C1-C6 alkyl, hydroxyl, C1-C4 alkoxy, —CO$_2$R', —CONR'R", —OCOR' and cyano, wherein R' and R" are independently selected from hydrogen and C1-C4 alkyl. Most preferable substituents include 1 or 2 (more preferably 1) unsubstituted substituents selected from C1-C4 alkyl, (C1-C4 alkyl)-O—(C1-C2 alkyl), —CO$_2$H and hydroxyl, e.g. C1-C4 alkyl and hydroxyl.

When R1 is -A3-L3-A4 or -A3-L1-(A4)$_p$-(A11)$_q$-L3-A5, L3 is a bond, -(Het)$_r$-Alk$^1$-(Het)$_s$-, -(Alk$^2$)$_m$-C(=O)-Het-(Alk$^3$)$_n$-, -Alk$^4$- or —SO$_2$—, for example -(Het)$_r$-Alk$^1$-(Het)$_s$-, -(Alk$^2$)$_m$-C(=O)-Het-(Alk$^3$)$_n$- or -Alk$^4$-, wherein Alk$^1$, Alk$^2$, Alk$^3$ and Alk$^4$ are the same or different and represent unsubstituted C1-C4 alkylene groups. When L3 is -(Het)$_r$-Alk$^1$-(Het)$_s$-, preferably Alk$^1$ is an unsubstituted C1-C3, e.g. C2-C3 alkylene group, and each Het is the same or different and is selected from —O— or —NR9-, wherein R9 is preferably hydrogen or unsubstituted C1-C2 alkyl, e.g. hydrogen or methyl. In one embodiment, -(Het)$_r$-Alk$^1$-(Het)$_s$- represents —O-Alk$^1$-. When L3 is -(Alk$^2$)$_m$-C(=O)-Het-(Alk$^3$)$_n$-, preferably Alk$^2$ is unsubstituted C2-C3 alkylene, in particular a group —C(Me)$_2$-. When L3 is -(Alk$^2$)$_m$-C(=O)-Het-(Alk$^3$)$_n$-, Het is preferably —O— or —NR9- where R9 is hydrogen or unsubstituted C1-C2 alkyl. More preferably Het is —O— or —NH—, more preferably Het is —O—. When L3 is -(Alk$^2$)$_m$-C(=O)-Het-(Alk$^3$)$_n$-, Alk$^3$ is preferably an unsubstituted C1-C2 alkylene group, for example a —CH$_2$— or —CH$_2$CH$_2$— group. When L3 is -(Alk$^2$)$_m$-C(=O)-Het-(Alk$^3$)$_n$-, m and n are the same or different and represent zero or 1. In one embodiment m and n are both zero and L3 can be —C(=O)-Het-. In another embodiment m is one and n is zero. In a further embodiment, m and n are both 1. When L3 is -Alk$^4$-, Alk$^4$ is preferably unsubstituted C1-C4, e.g. C2-C3 alkylene, more preferably a group —C(Me)$_2$- or —CH$_2$CH$_2$—, more preferably a group —C(Me)$_2$-.

When R1 is -A3-L3-A4 or -A3-L1-(A4)$_p$-(A11)$_q$-L3-A5, preferably A4 is an unsubstituted or substituted 5- to 12-membered heterocyclyl group, more preferably an unsubstituted or substituted 5- to 7-membered heterocyclyl group, e.g. an unsubstituted or substituted 5- to 6-membered heterocyclyl group. More preferably, A4 is an unsubstituted or substituted-imidazolyl, piperidinyl, piperazinyl, diazepanyl or oxazolyl group, e.g. an unsubstituted or substituted imidazolyl, piperidinyl or piperazinyl group. More preferably A4 is unsubstituted or substituted with 1 or 2 substituents selected from halogen atoms or hydroxyl, C2-C4 alkenyl, —COCF$_3$, C1-C6 alkyl or C1-C4 alkyl groups substituted with 1 or 2 C1-C4 alkoxy groups, for example the substituents may be selected from halogen atoms or hydroxyl, C1-C4 alkyl or C1-C4 alkyl groups substituted with 1 or 2 C1-C4 alkoxy groups. In one embodiment, A4 is unsubstituted or substituted by 1 or 2 C1-C4 alkyl groups, more preferably it is unsubstituted or substituted by 1 C1-C4 alkyl group such as propyl.

When R1 is -A3-L1-(A4)$_p$-(A11)$_q$-L3-A5, -A6-L1-A7 or -A3-L1-A9, L1 is preferably a bond or a group —NR'— or —CONR'R" where R' and R" are the same or different and represent hydrogen or unsubstituted C1-C4 alkyl. More preferably L1 is a bond or a group —NH— or —CONR'R" where R' and R" are the same or different and represent hydrogen or unsubstituted C1-C4 alkyl, more preferably where R' and R" are the same or different and represent hydrogen or methyl. More preferably still L1 is a bond.

When R1 is -A3-L1-(A4)$_p$-(A11)$_q$-L3-A5, A5 is preferably an unsubstituted or substituted 5- to 12-membered heterocyclyl group, more preferably an unsubstituted or substituted 5- to 6-membered heterocyclyl group, more preferably an unsubstituted or substituted furanyl, thiophenyl, pyridinyl, pyrimidinyl, morpholinyl, tetrahydropyranyl or piperazinyl group, e.g. an unsubstituted or substituted morpholinyl or pyridinyl group. More preferably A5 is unsubstituted or substituted by 1, 2 or 3 substituents selected from halogen, C1-C6 alkyl, C1-C4 alkoxy, —NR'R", —CO$_2$R', —CONR'R", —OCOR', hydroxyl and cyano, in particular halogen, C1-C6 alkyl, hydroxyl, C1-C4 alkoxy, —CO$_2$R', —CONR'R", —OCOR' and cyano wherein R' and R" are independently selected from hydrogen and C1-C4 alkyl. Each substituent may itself be unsubstituted or substituted by a further group selected from C1-C4 alkoxy, —O—(C1-C4 alkyl)-O—(C1-C4 alkyl) and hydroxyl. In one embodiment, substituents include 1 or 2 unsubstituted substituents selected from C1-C4 alkyl and hydroxyl, more preferably methyl substituents.

When R1 is -A3-L1-(A4)$_p$-(A11)$_q$-L3-A5, preferably A11 is an unsubstituted or substituted C6-C10 aryl group or 5- to 6-membered unsaturated heterocyclyl group, more preferably an unsubstituted or substituted phenyl or pyridyl ring. When A11 is substituted, it is preferably substituted by 1, 2 or 3 unsubstituted substituents selected from halogen, C1-C4 alkoxy, —CO$_2$R', —CONR'R", —OCOR', hydroxyl and cyano, and from C1-C6 alkyl groups which are unsubstituted or substituted with a C1-C4 alkoxy group, wherein R' and R" are independently selected from hydrogen and C1-C4 alkyl. Most preferable substituents include 1 or 2 (more preferably 1) unsubstituted substituents selected from C1-C4 alkyl, (C1-C4 alkyl)-O—(C1-C2 alkyl), —CO$_2$H and hydroxyl, e.g. C1-C4 alkyl and hydroxyl. More preferably, A11 is unsubstituted.

When R1 is -A6-L1-A7, preferably A6 is a C6-C10 aryl which is substituted with at least a C6-C10 aryl or a 5- to 12-membered heterocyclyl group which is itself unsubstituted or substituted. More preferably A6 is a phenyl group which is substituted with a phenyl or a 5- to 6-membered heterocyclyl group which is itself unsubstituted or substituted. More preferably A6 is a phenyl group which is substituted with only a single unsubstituted 5- to 6-membered heterocyclyl group, most preferably A6 is a phenyl group which is substituted with only a single unsubstituted oxazolyl group.

When R1 is -A6-L1-A7, preferably A7 is an unsubstituted or substituted 5- to 12-membered heterocyclyl group, more preferably an unsubstituted or substituted 5- to 6-membered heterocyclyl group, more preferably an unsubstituted or substituted piperazinyl group. More preferably A7 is unsubstituted or substituted by 1, 2 or 3 unsubstituted substituents selected from halogen, C1-C6 alkyl, C1-C4 alkoxy, —CO$_2$R', —CONR'R", —OCOR', hydroxyl and cyano, in particular halogen, C1-C6 alkyl, hydroxyl, C1-C4 alkoxy, —CO$_2$R', —CONR'R", —OCOR' and cyano wherein R' and R" are independently selected from hydrogen and C1-C4 alkyl. Most preferable substituents include 1 or 2 (more preferably 1) unsubstituted substituents selected from C1-C4 alkyl and hydroxyl, more preferably methyl.

When R1 is -A3-L4-A8, L4 is an imino group —N= wherein the double bond is bonded to group A8. When R1 is -A3-L4-A8, preferably A8 is unsubstituted or substituted 5- to 6-membered heterocyclyl group, more preferably an unsubstituted oxazolidinyl group. More preferably A8 is unsubstituted or substituted by 1, 2 or 3 unsubstituted substituents selected from halogen, C1-C6 alkyl, C1-C4 alkoxy, —$CO_2R'$, —CONR'R", —OCOR', hydroxyl and cyano, in particular halogen, C1-C6 alkyl, hydroxyl, C1-C4 alkoxy, —$CO_2R'$, —CONR'R", —OCOR' and cyano wherein R' and R" are independently selected from hydrogen and C1-C4 alkyl. Most preferable substituents include 1, 2 or 3 (more preferably 3) unsubstituted substituents selected from C1-C4 alkyl and hydroxyl, more preferably methyl groups.

When R1 is -A3-W, W is preferably a group of formula —C(=O)—NR10-S(=O)$_2$—R''' where R10 and R''' are the same or different and represent hydrogen or C1-C2 alkyl. More preferably R10 is hydrogen or methyl, most preferably hydrogen. More preferably R''' is hydrogen or methyl, most preferably methyl.

When R1 is -A9, preferably A9 is an unsubstituted or substituted 8- to 12-membered heterocyclyl group wherein 1 ring carbon atom has been replaced with a group selected from >C(=O), >S(=O)$_2$, >C(=NOR11) where R11 is hydrogen or a C1-C4 alkyl group, >C=$CH_2$ or >C(—$OCH_2CH_2O$—). More preferably A9 is an unsubstituted or substituted 8- to 12-membered heterocyclyl group wherein 1 ring carbon atom has been replaced with a C(=O) group. Preferred 8- to 12-membered heterocyclyl groups include phenyl rings fused to 5- to 6-membered heterocyclyl groups, for example indolyl.

When R1 is -A3-L1-A9, preferably A9 is an unsubstituted or substituted 5- to 6-membered heterocyclyl group wherein 1 ring carbon atom has been replaced with a group selected from >C(=O), >S(=O)$_2$, >C(=NOR11) where R11 is hydrogen or a C1-C4 alkyl group, >C=$CH_2$ or >C(—$OCH_2CH_2O$—). Preferred A9 groups include unsubstituted or substituted dioxothiomorpholinyl, methoxyiminopiperidinyl, methoxyiminopyrrolidinyl, methylenepiperidinyl, dioxoazaspirodecyl and oxadihydropyrazolyl groups. The A9 groups can be unsubstituted or substituted; more preferably they are unsubstituted.

When R1 is -A10, preferably A10 is an unsubstituted or substituted tricyclic 13- to 15-membered heterocyclyl group as described earlier, more preferably it is unsubstituted or substituted tetrahydropyridoindolyl. When A10 is substituted, it is preferably substituted by 1 or 2 unsubstituted C1-C4 alkyl groups, more preferably by 1 or 2 (most preferably 1) C1-C2 alkyl groups, in particular ethyl.

In another embodiment, when X is —NR8- and R8 is hydrogen or methyl, R1 is phenyl, phenol, benzoic acid methyl ester, pyridyl, dimethoxyphenyl, benzoic acid-butyl ester, dimethoxyphenyl, cyanophenyl, methoxypyridyl, thienyl-carboxylic acid-methylester, N,N-dimethylbenzamide, N-methylbenzamide, benzamide, cyclohexyl, isopropyl, methyl, methoxyethyl or tolyl.

Typically R8 is hydrogen, C1-C8 alkyl, C2-C8 alkenyl or C2-C8 alkynyl, preferably hydrogen or unsubstituted C1-C4 alkyl. Alternatively, when X is NR8, R1 and R8 together form a 5- to 12-membered heterocyclyl group, e.g. a monocyclic, saturated, 5- to 8-membered heterocyclyl ring, which is typically unsubstituted. The heterocyclyl group is typically piperidinyl, morpholinyl, azepanyl or dihydroindolyl e.g. piperidinyl, morpholinyl or azepanyl, preferably piperidinyl. Most preferably X is —NR8- and R8 is hydrogen or C1-C4 alkyl, more preferably X is —NR8- and R8 is hydrogen.

In one embodiment, R2 is phenyl, a monocyclic 5- to 8-membered heterocyclyl ring, a C3-C6 cycloalkyl group or unsubstituted C1-C8 alkyl, e.g. phenyl, a monocyclic, unsaturated 5- to 8-membered heterocyclyl ring or unsubstituted C1-C8 alkyl. The heterocyclyl ring is typically pyridinyl, thiophenyl, furanyl, tetrahydropyranyl or piperidinyl. The phenyl and heterocyclyl groups are unsubstituted or substituted with one, two or three unsubstituted substituents selected from halogen, C1-C4 alkyl, C1-C4 alkoxy, —$CO_2R'$, —CONR'R", —OCOR' or cyano, wherein R' and R" are independently selected from hydrogen and C1-C4 alkyl. Typically only one cyano substituent is present. Most preferably R2 is an unsubstituted phenyl.

In another embodiment, R2 is unsubstituted or substituted phenyl, unsubstituted C3-C6 cycloalkyl, unsubstituted or substituted pyridinyl or piperidinyl, or unsubstituted thiophenyl, furanyl or tetrahydropyranyl, (e.g. unsubstituted or substituted phenyl, unsubstituted or substituted pyridinyl or unsubstituted thiophenyl or furanyl), the substituents being selected from halogen, unsubstituted C1-C4 alkyl, unsubstituted C1-C4 alkoxy or cyano, e.g. halogen, unsubstituted C1-C4 alkyl or unsubstituted C1-C4 alkoxy. In this embodiment R2 is, for example, unsubstituted or substituted phenyl or unsubstituted pyridinyl, thiophenyl or furanyl.

In one embodiment, when R1 is 6-methoxy-pyridinyl, R2 is not pyridyl. In this embodiment, typically when R1 is methoxy-pyridyl, R2 is unsubstituted or substituted phenyl or unsubstituted thiophenyl or furanyl, the substituents being selected from halogen, unsubstituted C1-C4 alkyl or unsubstituted C1-C4 alkoxy. For example, when R1 is pyridyl, R2 may be unsubstituted or substituted phenyl or unsubstituted thiophenyl or furanyl, the substituents being selected from halogen, unsubstituted C1-C4 alkyl or unsubstituted C1-C4 alkoxy.

In another embodiment, R2 is a group -B1-B2 or -B3. When R2 is -B1-B2, B1 is typically an unsubstituted or substituted phenyl group. More preferably B1 is an unsubstituted phenyl group. When R2 is -B1-B2, B2 is typically an unsubstituted or substituted phenyl or 5- to 6-membered heterocyclyl group, more preferably an unsubstituted or substituted phenyl, piperazinyl or morpholinyl group, e.g. an unsubstituted or substituted phenyl or piperazinyl group. When substituted, preferred substituents are 1 or 2 groups selected from halogen atoms and C1-C4 alkyl and C1-C4 alkoxy groups, more preferably halogen atoms or C1-C2 alkyl or C1-C2 alkoxy groups, more preferably C1-C2 alkyl groups such as methyl.

When R2 is B3, typically B3 is a 5- to 6-membered heterocyclyl group where 1 or 2 ring carbon atoms are replaced with >C(=O)—, >S(=O)$_2$—, >C(=NOR11), >C(NR11), >C(=$CH_2$) or >C(—$OCH_2CH_2O$—), where R11 is hydrogen or C1-C4 alkyl. Preferably R11 is hydrogen or C1-C2 alkyl, more preferably hydrogen or methyl. When R2 is B3, more preferably B3 is a 5- to 6-membered heterocyclyl group where 1 ring carbon atom is replaced with >C(=O)—, >S(=O)$_2$—, >C(=NOR11), >C(NR11), >C(=$CH_2$) or >C(—$OCH_2CH_2O$—), where R11 is hydrogen or C1-C2 alkyl, more preferably 1 ring carbon atom is replaced with >C(=O). A preferred B3 group is oxo-dihydropyridinyl. When R2 is B3, B3 can be unsubstituted or substituted. Preferably it is unsubstituted.

Typically, when R3, R4, R5 or R6 is aryl, heterocyclyl, —(C1-C4 alkylene)-aryl or (C1-C4 alkylene)-heteroaryl, it is phenyl, benzyl or pyridyl. Typically, none, one or two, preferably none or one, of R3, R4, R5 and R6 is aryl, heterocyclyl, —(C1-C4 alkylene)-aryl or (C1-C4 alkylene)-heteroaryl. Preferably, no more than one of R3, R4, R5, R6 and R7 is $NO_2$, and no more than one of R3, R4, R5 and R6 is CN. R3, R4, R5 and R6 are typically unsubstituted.

In one embodiment, R3, R4, R5 and R6 independently represent phenyl, benzyl, pyridyl, hydrogen, halogen, C1-C8 alkyl, C2-C8 alkenyl, C2-C8 alkynyl, —OR', —CO₂R', CONR'R", —COR', —CN, —NO₂, —NR'R" or —CF₃ wherein R' and R" are independently hydrogen or C1-C4 alkyl and wherein only one or two of R3, R4, R5 and R6 is selected from phenyl, benzyl and pyridyl.

In another embodiment, R3, R4, R5 and R6 independently represent hydrogen, halogen, C1-C8 alkyl, C2-C8 alkenyl, C2-C8 alkynyl, —OR', —CO₂R', CONR'R", —COR', —CN, —NO₂, —NR'R" or —CF₃ wherein R' and R" are independently hydrogen or C1-C4 alkyl. In yet another embodiment, R3, R4, R5 and R6 independently represent hydrogen, halogen, C1-C4 alkyl, or C1-C4 alkoxy, e.g. hydrogen, halogen or C1-C4 alkyl, preferably hydrogen.

In another embodiment, R3, R5 and R6 are as defined above and R4 is -Het-Alk⁵-A11. Het preferably represents —NR12- or —O— where R12 is hydrogen or C1-C4 alkyl, more preferably hydrogen. More preferably Het is —O—. Alk⁵ is an unsubstituted or substituted C1-C4 alkylene group, more preferably a C3 alkylene group (preferably n-propylene). Preferably Alk⁵ is unsubstituted. A11 is preferably an unsubstituted or substituted 5- to 6-membered heterocyclyl group, more preferably morpholinyl. Preferably A11 is unsubstituted.

In another embodiment, R5 and R6 are as defined above, and R3 and R4, together with the ring carbon atoms to which they are bonded, form an unsubstituted or substituted phenyl or 5- to 6-membered heterocyclyl group, more preferably a phenyl ring. In this embodiment, preferably R5 and R6 are the same or different and represent hydrogen, halogen, C1-C4 alkyl or C1-C4 alkoxy, more preferably hydrogen, halogen or C1-C4 alkyl, most preferably both R5 and R6 are hydrogen.

Typically, R7 represents hydrogen, halogen, C1-C4 alkyl, C2-C4 alkenyl, C2-C4 alkynyl, —OR', —CO₂R', CONR'R", —COR', —CN, —NO₂, —NR'R" or —CF₃ wherein R' and R" are independently hydrogen or C1-C4 alkyl. In another embodiment R7 represents hydrogen, halogen or C1-C4 alkyl, preferably hydrogen or methyl, e.g. hydrogen. Where R7 is capable of being substituted, it is typically unsubstituted.

In a further embodiment, R7 represents an unsubstituted or substituted C6-C10 aryl, more preferably a phenyl ring. More preferably R7 represents an unsubstituted phenyl ring. In another embodiment, R7 represents -Alk⁶-L5-A12. Alk⁶ is preferably an unsubstituted or substituted C1-C4 alkylene group, more preferably an unsubstituted C1-C4 alkylene group, most preferably methylene. L5 preferably represents a group of formula —O—C(=O)—, —C(=O)— or —NR13-C(=O)— where R13 is hydrogen or C1-C2 alkyl, more preferably wherein R13 is hydrogen. More preferably L5 represents —O—C(=O)—. A12 is preferably an unsubstituted or substituted 5- to 6-membered heterocyclyl group, most preferably a piperazinyl group. When A12 is substituted, it is preferably substituted with 1 or 2 halogen atoms or C1-C4 alkyl or C1-C4 alkoxy groups, where the C1-C4 alkyl and alkoxy groups are themselves unsubstituted. More preferably, when A12 is substituted it is substituted with 1 or 2 halogen atoms or C1-C2 alkyl or C1-C2 alkoxy groups, more preferably with 1 or 2 C1-C2 alkyl groups for example methyl.

Typically, Z is halogen, OR', SR', —NR'R', —CO₂R', —CONR'R", —COR', —OCOR' or CN, wherein R' and R" are independently hydrogen or C1-C4 alkyl.

In yet another embodiment of the invention, the indolizinyl derivative is of formula (I), wherein:

X is —NR8- or —O—; preferably —NR8- where R8 is hydrogen or C1-C4 alkyl;

R1 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', —Y—Z, -A3-L3-A4, -A3-L1-(A4)ₚ-(A11)_q-L3-A5, -A6-L1-A7, -A3-L4-A8, -A3-W, -A9, -A3-L1-A9 or -A10;

R2 is an unsubstituted or substituted group selected from C6-C10 aryl, a 5- to 12-membered heterocyclyl group, C1-C8 alkyl and C3-C6 cycloalkyl, halogen or a group of formula -B1-B2 or -B3; and R3, R4, R5, R6 and R7 are independently selected from hydrogen, halogen, C1-C4 alkyl (e.g. methyl) and C1-C4 alkoxy (e.g. methoxy).

In yet another embodiment of the invention, the indolizinyl derivative is of formula (IA):

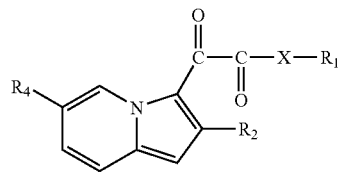

wherein:

X is —NR8- or —O—; preferably —NR8- where R8 is hydrogen or C1-C4 alkyl;

R1 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', —Y—Z, -A3-L3-A4, -A3-L1-(A4)ₚ-(A11)_q-L3-A5, -A6-L1-A7, -A3-L4-A8, -A3-W, -A9, -A3-L1-A9 or -A10;

R2 is an unsubstituted or substituted group selected from C6-C10 aryl, a 5- to 12-membered heterocyclyl group, C1-C8 alkyl and C3-C6 cycloalkyl, halogen or a group of formula -B1-B2 or -B3; and R4 is hydrogen or halogen.

In this embodiment, when R1 is 6-methoxy-pyridinyl, R2 is typically unsubstituted or substituted phenyl or unsubstituted thiophenyl or furanyl. In an alternative aspect of this embodiment, R2 is unsubstituted or substituted phenyl or unsubstituted thiophenyl or furanyl, the substituents being selected from halogen, unsubstituted C1-C4 alkyl or unsubstituted C1-C4 alkoxy.

In this and other embodiments, when R1 is -A3-L3-A4, -A3-L1-(A4)ₚ-(A11)_q-L3-A5, -A3-L4-A8, -A3-W or -A3-L1-A9, preferably A3 is an unsubstituted or substituted C6-C10 aryl group or 5- to 6-membered unsaturated heterocyclyl group, more preferably an unsubstituted or substituted phenyl or pyridyl ring, e.g. a phenyl ring. When A3 is substituted, it is preferably substituted by 1, 2 or 3 unsubstituted substituents selected from halogen, C1-C4 alkoxy, —CO₂R', —CONR'R", —OCOR', hydroxyl and cyano, and from C1-C6 alkyl groups which are unsubstituted or substituted with a C1-C4 alkoxy group, in particular the substituents on A3 are selected from the unsubstituted substituents halogen, C1-C6 alkyl, hydroxyl, C1-C4 alkoxy, —CO₂R', —CONR'R", —OCOR' and cyano, wherein R' and R" are independently selected from hydrogen and C1-C4 alkyl. Most preferable substituents include 1 or 2 (more preferably 1) unsubstituted substituents selected from C1-C4 alkyl, (C1-C4 alkyl)-O—(C1-C2 alkyl), —CO₂H and hydroxyl, e.g. C1-C4 alkyl and hydroxyl.

When R1 is -A3-L3-A4 or -A3-L1-(A4)$_p$-(A11)$_q$-L3-A5, L3 is a bond, -(Het)$_r$-Alk$^1$-(Het)$_s$-, -(Alk$^2$)$_m$-C(=O)-Het-(Alk$^3$)$_n$-, -Alk$^4$- or —SO$_2$—, for example -(Het)$_r$-Alk$^1$-(Het)$_s$-, -(Alk$^2$)$_m$-C(=O)-Het-(Alk$^3$)$_n$- or -Alk$^4$-, wherein Alk$^1$, Alk$^2$, Alk$^3$ and Alk$^4$ are the same or different and represent unsubstituted C1-C4 alkylene groups. When L3 is -(Het)$_r$-Alk$^1$-(Het)$_s$-, preferably Alk$^1$ is an unsubstituted C1-C3, e.g. C2-C3 alkylene group, and each Het is the same or different and is selected from —O— or —NR9-, wherein R9 is preferably hydrogen or unsubstituted C1-C2 alkyl, e.g. hydrogen or methyl. In one embodiment, -(Het)$_r$-Alk$^1$-(Het)$_s$- represents —O-Alk$^1$-. When L3 is -(Alk$^2$)$_m$-C(=O)-Het-(Alk$^3$)$_n$-, preferably Alk$^2$ is unsubstituted C2-C3 alkylene, in particular a group —C(Me)$_2$-. When L3 is -(Alk$^2$)$_m$-C(=O)-Het-(Alk$^3$)$_n$-, Het is preferably —O— or —NR9- where R9 is hydrogen or unsubstituted C1-C2 alkyl. More preferably Het is —O— or —NH—, more preferably Het is —O—. When L3 is -(Alk$^2$)$_m$-C(=O)-Het-(Alk$^3$)$_n$-, Alk$^3$ is preferably an unsubstituted C1-C2 alkylene group, for example a —CH$_2$— or —CH$_2$CH$_2$— group. When L3 is -(Alk$^2$)$_m$-C(=O)-Het-(Alk$^3$)$_n$-, m and n are the same or different and represent zero or 1. In one embodiment m and n are both zero and L3 can be —C(=O)-Het-. In another embodiment m is one and n is zero. In a further embodiment, m and n are both 1. When L3 is -Alk$^4$-, Alk$^4$ is preferably unsubstituted C1-C4, e.g. C2-C3 alkylene, more preferably a group —C(Me)$_2$- or —CH$_2$CH$_2$—, more preferably a group —C(Me)$_2$-.

When R1 is -A3-L3-A4 or -A3-L1-(A4)$_p$-(A11)$_q$-L3-A5, preferably A4 is an unsubstituted or substituted 5- to 12-membered heterocyclyl group, more preferably an unsubstituted or substituted 5- to 7-membered heterocyclyl group, e.g. an unsubstituted or substituted 5- to 6-membered heterocyclyl group. More preferably, A4 is an unsubstituted or substituted imidazolyl, piperidinyl, piperazinyl, diazepanyl or oxazolyl group, e.g. an unsubstituted or substituted imidazolyl, piperidinyl or piperazinyl group. More preferably A4 is unsubstituted or substituted with 1 or 2 substituents selected from halogen atoms or hydroxyl, C2-C4 alkenyl, —COCF$_3$, C1-C6 alkyl or C1-C4 alkyl groups substituted with 1 or 2 C1-C4 alkoxy groups, for example the substituents may be selected from halogen atoms or hydroxyl, C1-C4 alkyl or C1-C4 alkyl groups substituted with 1 or 2 C1-C4 alkoxy groups. In one embodiment, A4 is unsubstituted or substituted by 1 or 2 C1-C4 alkyl groups, more preferably it is unsubstituted or substituted by 1 C1-C4 alkyl group such as propyl.

When R1 is -A3-L1-(A4)$_p$-(A11)$_q$-L3-A5, -A6-L1-A7 or -A3-L1-A9, L1 is preferably a bond or a group —NR'— or —CONR'R" where R' and R" are the same or different and represent hydrogen or unsubstituted C1-C4 alkyl. More preferably L1 is a bond or a group —NH— or —CONR'R" where R' and R" are the same or different and represent hydrogen or unsubstituted C1-C4 alkyl, more preferably where R' and R" are the same or different and represent hydrogen or methyl. More preferably still L1 is a bond.

When R1- is -A3-L1-(A4)$_p$-(A11)$_q$-L3-A5, A5 is preferably an unsubstituted or substituted 5- to 12-membered heterocyclyl group, more preferably an unsubstituted or substituted 5- to 6-membered heterocyclyl group, more preferably an unsubstituted or substituted furanyl, thiophenyl, pyridinyl, pyrimidinyl, morpholinyl, tetrahydropyranyl or piperazinyl group, e.g. an unsubstituted or substituted morpholinyl or pyridinyl group. More preferably A5 is unsubstituted or substituted by 1, 2 or 3 substituents selected from halogen, C1-C6 alkyl, C1-C4 alkoxy, —NR'R", —CO$_2$R', —CONR'R", —OCOR', hydroxyl and cyano, in particular halogen, C1-C6 alkyl, hydroxyl, C1-C4 alkoxy, —CO$_2$R', —CONR'R", —OCOR' and cyano wherein R' and R" are independently selected from hydrogen and C1-C4 alkyl. Each substituent may itself be unsubstituted or substituted by a further group selected from C1-C4 alkoxy, —O—(C1-C4 alkyl)-O—(C1-C4 alkyl) and hydroxyl. In one embodiment, substituents include 1 or 2 unsubstituted substituents selected from C1-C4 alkyl and hydroxyl, more preferably methyl substituents.

When R1 is -A3-L1-(A4)$_p$-(A11)$_q$-L3-A5, preferably A11 is an unsubstituted or substituted C6-C10 aryl group or 5- to 6-membered unsaturated heterocyclyl group, more preferably an unsubstituted or substituted phenyl or pyridyl ring. When A11 is substituted, it is preferably substituted by 1, 2 or 3 unsubstituted substituents selected from halogen, C1-C4 alkoxy, —CO$_2$R', —CONR'R", —OCOR', hydroxyl and cyano, and from C1-C6 alkyl groups which are unsubstituted or substituted with a C1-C4 alkoxy group, wherein R' and R" are independently selected from hydrogen and C1-C4 alkyl. Most preferable substituents include 1 or 2 (more preferably 1) unsubstituted substituents selected from C1-C4 alkyl, (C1-C4 alkyl)-O—(C1-C2 alkyl), —CO$_2$H and hydroxyl, e.g. C1-C4 alkyl and hydroxyl. More preferably, A11 is unsubstituted.

When R1 is -A6-L1-A7, preferably A6 is a C6-C10 aryl which is substituted with at least a C6-C10 aryl or a 5- to 12-membered heterocyclyl group which is itself unsubstituted or substituted. More preferably A6 is a phenyl group which is substituted with a phenyl or a 5- to 6-membered heterocyclyl group which is itself unsubstituted or substituted. More preferably A6 is a phenyl group which is substituted with only a single unsubstituted 5- to 6-membered heterocyclyl group, most preferably A6 is a phenyl group which is substituted with only a single unsubstituted oxazolyl group.

When R1 is -A6-L1-A7, preferably A7 is an unsubstituted or substituted 5- to 12-membered heterocyclyl group, more preferably an unsubstituted or substituted 5- to 6-membered heterocyclyl group, more preferably an unsubstituted or substituted piperazinyl group. More preferably A7 is unsubstituted or substituted by 1, 2 or 3 unsubstituted substituents selected from halogen, C1-C6 alkyl, C1-C4 alkoxy, —CO$_2$R', —CONR'R", —OCOR', hydroxyl and cyano, in particular halogen, C1-C6 alkyl, hydroxyl, C1-C4 alkoxy, —CO$_2$R', —CONR'R", —OCOR' and cyano wherein R' and R" are independently selected from hydrogen and C1-C4 alkyl. Most preferable substituents include 1 or 2 (more preferably 1) unsubstituted substituents selected from C1-C4 alkyl and hydroxyl, more preferably methyl.

When R1 is -A3-L4-A8, L4 is an imino group —N= wherein the double bond is bonded to group A8. When R1 is -A3-L4-A8, preferably A8 is unsubstituted or substituted 5- to 6-membered heterocyclyl group, more preferably an unsubstituted oxazolidinyl group. More preferably A8 is unsubstituted or substituted by 1, 2 or 3 unsubstituted substituents selected from halogen, C1-C6 alkyl, C1-C4 alkoxy, —CO$_2$R', —CONR'R", —OCOR', hydroxyl and cyano, in particular halogen, C1-C6 alkyl, hydroxyl, C1-C4 alkoxy, —CO$_2$R', —CONR'R", —OCOR' and cyano wherein R' and R" are independently selected from hydrogen and C1-C4 alkyl. Most preferable substituents include 1, 2 or 3 (more preferably 3) unsubstituted substituents selected from C1-C4 alkyl and hydroxyl, more preferably methyl groups.

When R1 is -A3-W, W is preferably a group of formula —C(=O)—NR10-S(=O)$_2$—R''' where R10 and R''' are the same or different and represent hydrogen or C1-C2 alkyl. More preferably R10 is hydrogen or methyl, most preferably hydrogen. More preferably R''' is hydrogen or methyl, most preferably methyl.

When R1 is -A9, preferably A9 is an unsubstituted or substituted 8- to 12-membered heterocyclyl group wherein 1 ring carbon atom has been replaced with a group selected from >C(=O), >S(=O)$_2$, >C(=NOR11) where R11 is hydrogen or a C1-C4 alkyl group, >C=CH$_2$ or >C(—OCH$_2$CH$_2$O—). More preferably A9 is an unsubstituted or substituted 8- to 12-membered heterocyclyl group wherein 1 ring carbon atom has been replaced with a C(=O) group. Preferred 8- to 12-membered heterocyclyl groups include phenyl rings fused to 5- to 6-membered heterocyclyl groups, for example indolyl.

When R1 is -A3-L1-A9, preferably A9 is an unsubstituted or substituted 5- to 6-membered heterocyclyl group wherein 1 ring carbon atom has been replaced with a group selected from >C(=O), >S(=O)$_2$, >C(=NOR11) where R11 is hydrogen or a C1-C4 alkyl group, >C=CH$_2$ or >C(—OCH$_2$CH$_2$O—). Preferred A9 groups include unsubstituted or substituted dioxothiomorpholinyl, methoxyiminopiperidinyl, methoxyiminopyrrolidinyl, methylenepiperidinyl, dioxoazaspirodecyl and oxadihydropyrazolyl groups. The A9 groups car, be unsubstituted or substituted; more preferably they are unsubstituted.

When R1 is -A10, preferably A10 is an unsubstituted or substituted tricyclic 13- to 15-membered heterocyclyl group as described earlier, more preferably it is unsubstituted or substituted tetrahydropyridoindolyl. When A10 is substituted, it is preferably substituted by 1 or 2 unsubstituted C1-C4 alkyl groups, more preferably by 1 or 2 (most preferably 1) C1-C2 alkyl groups, in particular ethyl.

When R1 is -A3-L3-A4, -A3-L1-(A4)$_p$-(A11)$_q$-L3-A5, -A6-L1-A7, -A3-L4-A8, -A3-W, -A9, -A3-L1-A9 or -A10, preferred compounds are indolizinyl derivatives of formula (I) or pharmaceutically acceptable salts thereof wherein:

X is a bond, —NR8-, —O—, —S—, —SO—, or —SO$_2$—;

X$^1$ is O or NOR9, wherein R9 is hydrogen or an unsubstituted or substituted C1-C4 alkyl group;

R8 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z, L3 is a bond or a group of formula -(Het)$_r$-Alk$^1$-(Het)$_s$-, -(Alk$^2$)$_m$-C(=O)-Het-(Alk$^3$)$_n$-, -Alk$^4$- or —SO$_2$—, preferably a group of formula —O-Alk$^1$-, -(Alk$^2$)$_m$-C(=O)-Het-(Alk$^3$)$_n$- or -Alk$^4$-, wherein Alk$^1$, Alk$^2$, Alk$^3$ and Alk$^4$ are the same or different and represent unsubstituted C1-C4 alkylene groups, m, n, r and s are the same or different and represent zero or 1, and Het represents —O— or —NR9- where R9 is hydrogen or unsubstituted C1-C4 alkyl;

L4 is an imino group —N= wherein the double bond is bonded to group A8;

A3, A4, A5, A7 and A11 are the same or different and are unsubstituted or substituted C6-C10 aryl or 5- to 12-membered-heterocyclyl groups;

A6 is a C6-C10 aryl or 5- to 12-membered heterocyclyl group which is substituted with at least a C6-C10 aryl or a 5- to 12-membered heterocyclyl group which is itself unsubstituted or substituted;

A8 is an unsubstituted or substituted 5- to 12-membered heterocyclyl group;

A9 is an unsubstituted or substituted 5- to 12-membered heterocyclyl group wherein 1 or 2 ring carbon atoms are replaced with a group selected from >C(=O), >S(=O)$_2$, >C(=NOR11) where R11 is hydrogen or a C1-C4 alkyl group, >C=CH$_2$ or >C(—OCH$_2$CH$_2$O—);

A10 is an unsubstituted or substituted tricyclic 13- to 15-membered heterocyclyl group;

W is a group of formula —C(=O)—NR10-S(=O)$_2$—R'" where R10 and R'" are the same or different and represent hydrogen or C1-C4 alkyl;

R2 is an unsubstituted or substituted group selected from C6-C10 aryl, a 5- to 12-membered heterocyclyl group, C1-C8 alkyl and C3-C6 cycloalkyl, halogen or a group of formula -B1-B2 or -B3;

B1 is an unsubstituted or substituted C6-C10 aryl group;

B2 is an unsubstituted or substituted C6-C10 aryl or 5- to 12-membered heterocyclyl group;

B3 is an unsubstituted or substituted 5- to 12-membered heterocyclyl group where 1 or 2 ring carbon atoms are replaced with a group selected from >C(=O), >S(=O)$_2$, >C(=NOR11) where R11 is hydrogen or a C1-C4 alkyl group, >C=CH$_2$ or >C(—OCH$_2$CH$_2$O—);

either (i) R3 represents C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z, and R4 represents C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, —Y—Z or a group of formula -Het-Alk$^5$-A11 where Het is —NR12 or —O— with R12 being hydrogen or C1-C4 alkyl, Alk$^5$ is C1-C6 alkylene and A11 is C6-C10 aryl or a 5- to 12-membered heterocyclyl group, or (ii) R3 and R4, together with the ring carbon atoms to which they are bonded, form an unsubstituted or substituted C6-C10 aryl or 5- to 12-membered heterocyclyl group, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, —Y—Z, C6-C10 aryl or a group of formula -Alk$^6$-L5-A12, where Alk$^6$ is a C1-C4 alkylene group, L5 is a group of formula —O—C(=O)—, —C(=O)— or —NR13-C(=O)— and R13 is hydrogen or C1-C4 alkyl, and A12 is an unsubstituted or substituted C6-C10 aryl or 5- to 12-membered heterocyclyl group;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'=NOR"; and R' and R" independently represent hydrogen, C1-C8 alkyl, C2-C8 alkenyl or C2-C8 alkynyl.

When R1 is -A3-L3-A4, -A3-L1-(A4)$_p$-(A11)$_q$-L3-A5, -A6-L1-A7, -A3-L4-A8, -A3-W, -A9, -A3-L1-A9 or -A10, more preferred compounds are indolizinyl derivatives of formula (I) or pharmaceutically acceptable salts thereof wherein:

X is a bond, —NR8-, —O—, —S—, —SO—, or —SO$_2$—;

X$^1$ is O or NOR9, wherein R9 is hydrogen or an unsubstituted or substituted C1-C4 alkyl group;

R8 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', and —Y—Z;

R2 is an unsubstituted or substituted group selected from C6-C10 aryl, a 5- to 12-membered heterocyclyl group, C1-C8 alkyl and C3-C6 cycloalkyl, or halogen;

R3, R4, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'=NOR"; and R' and R" independently represent hydrogen, C1-C8 alkyl, C2-C8 alkenyl or C2-C8 alkynyl.

When R1 is -A3-L3-A4, -A3-L1-(A4)$_p$-(A11)$_q$-L3-A5, -A6-L1-A7, -A3-L4-A8, -A3-W, -A9, -A3-L1-A9 or -A10, preferably X is —NR8- or —O— and R8 is hydrogen, C1-C8 alkyl, C2-C8 alkenyl or C2-C8 alkynyl. More preferably X is —NR8- or —O— and R8 is hydrogen or C1-C4 alkyl, more preferably R8 is hydrogen or C1-C2 alkyl, most preferably R8 is hydrogen. Preferably X is —NH—.

When R1 is -A3-L3-A4, -A3-L1-(A4)$_p$-(A11)$_q$-L3-A5, -A6-L1-A7, -A3-L4-A8, -A3-W, -A9, -A3-L1-A9 or -A10, preferably X$^1$ is O or NOR9 wherein R9 is hydrogen or C1-C4 alkyl which is unsubstituted or substituted with 1, 2 or 3 substituents selected from halogen, hydroxyl, amino, (C1-C4 alkyl)amino, di(C1-C4 alkyl)amino, C1-C4 alkoxy, —CO$_2$H and —CO$_2$(C1-C4 alkyl). More preferably X$^1$ is O.

When R1 is -A3-L3-A4, -A3-L1-(A4)$_p$-(A11)$_q$-L3-A5, -A6-L1-A7, -A3-L4-A8, -A3-W, -A9, -A3-L1-A9 or -A10, preferably R2 is an unsubstituted or substituted C1-C4 alkyl, C6-C10 aryl, a 5- to 12-membered heterocyclyl group or a C3-C6 cycloalkyl group, e.g. an unsubstituted or substituted C1-C4 alkyl, C6-C10 aryl or a 5- to 12-membered heterocyclyl group. More preferably R2 is an unsubstituted or substituted C1-C4 alkyl, phenyl, 5- to 12-membered heterocyclyl group or a C3-C6 cycloalkyl group; e.g. an unsubstituted or substituted C1-C2 alkyl, phenyl or 5- to 12-membered heterocyclyl group. Preferred substituents on the cyclic groups include 1 or 2 (more preferably 1) halogen atom or C1-C4 alkyl groups, more preferably chlorine atoms or methyl groups. Preferably when R2 is C1-C4 alkyl (e.g. C1-C2 alkyl, most preferably methyl) it is unsubstituted. Preferred 5- to 12-membered heterocyclyl groups include pyridinyl, pyrimidinyl, dihydroindolyl, tetrahydropyranyl and piperidinyl, e.g. pyridinyl, pyrimidinyl and dihydroindolyl.

When R1 is -A3-L3-A4, -A3-L1-(A4)$_p$-(A11)$_q$-L3-A5, -A6-L1-A7, -A3-L4-A8, -A3-W, -A9, -A3-L1-A9 or -A10, preferably R3 and R4 are the same or different and represent phenyl, benzyl, pyridyl, hydrogen, halogen, C1-C8 alkyl, C2-C8 alkenyl, C2-C8 alkynyl, —OR', —CO$_2$R', CONR'R", —COR', —CN, —NO$_2$, —NR'R" or —CF$_3$ wherein R' and R" are independently hydrogen or C1-C4 alkyl, or R3 and R4 together form an unsubstituted or substituted C6-C10 aryl group. More preferably R3 and R4 are the same or different and represent hydrogen, unsubstituted C1-C4 alkyl or unsubstituted C1-C4 alkoxy, or R3 and R4 together form an unsubstituted or substituted phenyl group. When R3 R4 together form a phenyl group, preferably it is unsubstituted. More preferably R3 and R4 are the same or different and represent hydrogen, halogen, unsubstituted C1-C4 alkyl or unsubstituted C1-C4 alkoxy, for example hydrogen or unsubstituted C1-C4 alkyl. Most preferably R3 and R4 are hydrogen.

When R1 is -A3-L3-A4, -A3-L1-(A4)$_p$-(A11)$_q$-L3-A5, -A6-L1-A7, -A3-L4-A8, -A3-W, -A9, -A3-L1-A9 or -A10, preferably R5 and R6 are the same or different and represent phenyl, benzyl, pyridyl, hydrogen, halogen, C1-C8 alkyl, C2-C8 alkenyl, C2-C8 alkynyl, —OR', —CO$_2$R', CONR'R", —COR', —CN, —NO$_2$, —NR'R" or —CF$_3$ wherein R' and R" are independently hydrogen or C1-C4 alkyl. More preferably R5 and R6 are the same or different and represent hydrogen, unsubstituted C1-C4 alkyl or unsubstituted C1-C4 alkoxy. More preferably, R5 and R6 are the same or different and represent hydrogen, halogen, unsubstituted C1-C4 alkyl or unsubstituted C1-C4 alkoxy, for example hydrogen or unsubstituted C1-C4 alkyl. Most preferably R5 and R6 are hydrogen.

When R1 is -A3-L3-A4, -A3-L1-(A4)$_p$-(A11)$_q$-L3-A5, -A6-L1-A7, -A3-L4-A8, -A3-W, -A9, -A3-L1-A9 or -A10, preferably R7 is hydrogen, halogen, C1-C4 alkyl, C2-C4 alkenyl, C2-C4 alkynyl, C1-C4 alkoxy, —OR', —CO$_2$R', CONR'R", —COR', —CN, —NO$_2$, —NR'R" or —CF$_3$ wherein R' and R" are independently hydrogen or C1-C4 alkyl. More preferably R7 is hydrogen, halogen, unsubstituted C1-C4 alkyl or unsubstituted C1-C4 alkoxy, more preferably hydrogen or unsubstituted C1-C4 alkyl, most preferably hydrogen.

When R2 represents a group -B1-B2 or -B3, preferred compounds are indolizinyl derivatives of formula (I) or pharmaceutically acceptable salts thereof wherein:

X is a bond, —NR8-, —O—, —S—, —SO—, or —SO$_2$—;

X$^1$ is O or NOR9, wherein R9 is hydrogen or an unsubstituted or substituted C1-C4 alkyl group;

either (i) R1 and R8 independently represent hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z, (ii) R1 represents -A3-L3-A4, -A3-L1-A4-A5, -A6-L1-A7, -A3-L4-A8, -A3-W, -A9, -A3-L1-A9 or -A10, and R8 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z, or (iii) when X is NR8, R1 and R8 together with the nitrogen to which they are attached may form an unsubstituted or substituted, aromatic or non-aromatic 5- to 12-membered heterocyclyl group;

L1 is a bond, —NR'—, —O—, —CO—, —OCO—, —OCONR'R" or —CONR'R"—;

L2 is a substituted or unsubstituted C1-C4 alkylene or C2-C4 alkenylene group;

L3 is a group of formula —O-Alk$^1$-, -(Alk$^2$)$_m$-C(=O)-Het-(Alk$^3$)$_n$- or -Alk$^4$-, wherein Alk$^1$, Alk$^2$, Alk$^3$ and Alk$^4$ are the same or different and represent unsubstituted C1-C4 alkylene groups, m and n are the same or different and represent zero or 1, and Het represents —O— or —NR9- where R9 is hydrogen or unsubstituted C1-C4 alkyl;

L4 is an imino group —N= wherein the double bond is bonded to group A8;

A1 is an unsubstituted or substituted C6-C10 arylene group;

A2, A3, A4, A5 and A7 are the same or different and are unsubstituted or substituted C6-C10 aryl or 5- to 12-membered heterocyclyl groups;

A6 is a C6-C10 aryl or 5- to 12-membered heterocyclyl group which is substituted with at least a C6-C10 aryl or a 5- to 12-membered heterocyclyl group which is itself unsubstituted or substituted;

A8 is an unsubstituted or substituted 5- to 12-membered heterocyclyl group;

A9 is an unsubstituted or substituted 5- to 12-membered heterocyclyl group wherein 1 or 2 ring carbon atoms are replaced with a group selected from >C(=O), >S(=O)$_2$, >C(=NOR11) where R11 is hydrogen or a C1-C4 alkyl group, >C=CH$_2$ or >C(—OCH$_2$CH$_2$O—);

A10 is an unsubstituted or substituted tricyclic 13- to 15-membered heterocyclyl group;

W is a group of formula —C(=O)—NR10-S(=O)$_2$—R''' where R10 and R''' are the same or different and represent hydrogen or C1-C4 alkyl;

either (i) R3 represents C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R'', —COR', —CN, —NO$_2$, —NR'R'', CF$_3$, or —Y—Z, and R4 represents C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R'', —COR', —CN, —NO$_2$, —NR'R'', CF$_3$, —Y—Z or a group of formula -Het-Alk$^5$-A11 where Het is —NR12 or —O— with R12 being hydrogen or C1-C4 alkyl, Alk$^5$ is C1-C6 alkylene and A11 is C6-C10 aryl or a 5- to 12-membered heterocyclyl group, or (ii) R3 and R4, together with the ring carbon atoms to which they are bonded, form an unsubstituted or substituted C6-C10 aryl or 5- to 12-membered heterocyclyl group, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R'', —COR', —CN, —NO$_2$, —NR'R'', CF$_3$, or —Y—Z;

R7 represents hydrogen, halogen, C1-C8 alkyl, C2-C8 alkenyl, C2-C8 alkynyl, —OR', —CO$_2$R', —CONR'R'', —COR', —CN, —NO$_2$, —NR'R'', CF$_3$, —Y—Z, C6-C10 aryl or a group of formula -Alk$^6$-L5-A12, where Alk$^6$ is a C1-C4 alkylene group, L5 is a group of formula —O—C(=O)—, —C(=O)— or —NR13-C(=O)— and R13 is hydrogen or C1-C4 alkyl, and A12 is an unsubstituted or substituted C6-C10 aryl or 5- to 12-membered heterocyclyl group;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R'', —SO$_3$H, —NR'R'', —NR'COR', —NO$_2$, —CO$_2$R', —CONR'R'', —COR', —OCOR', —CN, —CF$_3$—NSO$_2$R', —OCONR'R'' or —CR'=NOR''; and R' and R'' independently represent hydrogen, C1-C8 alkyl, C2-C8 alkenyl or C2-C8 alkynyl.

When R2 is a group -B1-B2 or -B3-, more preferred compounds are indolizinyl derivatives of formula (I) or pharmaceutically acceptable salts thereof wherein:

X is a bond, —NR8-, —O—, —S—, —SO—, or —SO$_2$—;

X$^1$ is O or NOR9, wherein R9 is hydrogen or an unsubstituted or substituted C1-C4 alkyl group;

R1 and R8 independently represent hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', and —Y—Z;

or when X is NR8, R1 and R8 together with the nitrogen to which they are attached may form an unsubstituted or substituted, aromatic or non-aromatic 5- to 12-membered heterocyclyl group;

A1 is an unsubstituted or substituted C6-C10 arylene group;

L1 is a bond, —NR'—, —O—, —CO—, —OCO—, —OCONR'R'' or —CONR'R''—;

L2 is a substituted or unsubstituted C1-C4 alkylene or C2-C4 alkenylene group;

A2 is a substituted or unsubstituted C6-C10 aryl or 5- to 12-membered-heterocyclyl group;

R3, R4, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R'', —COR', —CN, —NO$_2$, —NR'R'', CF$_3$, or —Y—Z;

R7 represents hydrogen, halogen, C1-C8 alkyl, C2-C8 alkenyl, C2-C8 alkynyl, —OR', —CO$_2$R', —CONR'R'', —COR', —CN, —NO$_2$, —NR'R'', CF$_3$, or —Y—Z;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R'', —SO$_3$H, —NR'R'', —NR'COR', —NO$_2$, —CO$_2$R', —CONR'R'', —COR', —OCOR', —CN, —CF$_3$—NSO$_2$R', —OCONR'R'' or —CR'=NOR''; and R' and R'' independently represent hydrogen, C1-C8 alkyl, C2-C8 alkenyl or C2-C8 alkynyl.

When R2 is a group -B1-B2 or -B3-, preferably X is —NR8- or —O— and R8 is hydrogen, C1-C8 alkyl, C2-C8 alkenyl or C2-C8 alkynyl. More preferably X is —NR8- or —O— and R8 is hydrogen or C1-C4 alkyl, more preferably R8 is hydrogen or C1-C2 alkyl, most preferably R8 is hydrogen. Preferably X is —NH—.

When R2 is a group -B1-B2 or -B3-, preferably X$^1$ is O or NOR9 wherein R9 is hydrogen or C1-C4 alkyl which is unsubstituted or substituted with 1, 2 or 3 substituents selected from halogen, hydroxyl, amino, (C1-C4 alkyl)amino, di(C1-C4 alkyl)amino, C1-C4 alkoxy, —CO$_2$H and —CO$_2$(C1-C4 alkyl). More preferably X$^1$ is O.

When R2 is a group -B1-B2 or -B3-, preferably R1 is hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', —Y—Z, -A3-L3-A4, -A3-L1-A4-A5, -A6-L1-A7, -A3-L4-A8, -A3-W, -A9, -A3-L1-A9 or -A10. More preferably R1 is an unsubstituted or substituted C6-C10 aryl group or a group -A1-L1-A2 where A1 is unsubstituted or substituted C6-C10 arylene group, L1 is a bond, —NR'—, —O—, —CO—, —OCO—, —OCONR'R'' or —CONR'R''—, and A2 is an unsubstituted or substituted C6-C10 aryl or 5- to 12-membered heterocyclyl group. More preferably R1 is an unsubstituted or substituted phenyl ring or a group -A1-L1-A2 where A1 is unsubstituted or substituted C6-C10 arylene group, L1 is a bond, and A2 is an unsubstituted or substituted phenyl or 5- to 6-membered heterocyclyl group. More preferably R1 is an unsubstituted or substituted phenyl ring or a group A1-L1-A2 where A1 is unsubstituted or substituted C6-C10 arylene group, L1 is a bond, —NR'— or —CONR'R'' and R' and R'' are hydrogen or C1-C4 alkyl, and A2 is an unsubstituted or substituted phenyl or 5- to 6-membered heterocyclyl group. Most preferably R1 is an unsubstituted or substituted phenyl group or a group -A1-A2 wherein A1 is unsubstituted phenyl and A2 is unsubstituted or substituted 5- to 6-membered heterocyclyl (in particular morpholinyl, oxazolyl or piperazinyl, e.g. morpholinyl or oxazolyl). The substituents on A2 are preferably selected from unsubstituted C1-C4 alkyl or C2-C4 alkenyl.

When R2 is a group -B1-B2 or -B3-, preferably R3 and R4 are the same or different and represent phenyl, benzyl, pyridyl, hydrogen, halogen, C1-C8 alkyl, C2-C8 alkenyl, C2-C8 alkynyl, —OR', —CO$_2$R', CONR'R", —COR', —CN, —NO$_2$, —NR'R" or —CF$_3$ wherein R' and R" are independently hydrogen or C1-C4 alkyl, or R3 and R4 together form an unsubstituted or substituted C6-C10 aryl group. More preferably R3 and R4 are the same or different and represent hydrogen, unsubstituted C1-C4 alkyl or unsubstituted C1-C4 alkoxy, or R3 and R4 together form an unsubstituted or substituted phenyl group. When R3 and R4 together form a phenyl group, preferably it is unsubstituted. More preferably R3 and R4 are the same or different and represent hydrogen or unsubstituted C1-C4 alkyl. Most preferably R3 and R4 are hydrogen.

When R2 is a group -B1-B2 or -B3-, preferably R5 and R6 are the same or different and represent phenyl, benzyl, pyridyl, hydrogen, halogen, C1-C8 alkyl, C2-C8 alkenyl, C2-C8 alkynyl, —OR', —CO$_2$R', CONR'R", —COR', —CN, —NO$_2$, —NR'R" or —CF$_3$ wherein R' and R" are independently hydrogen or C1-C4 alkyl. More preferably R5 and R6 are the same or different and represent hydrogen, unsubstituted C1-C4 alkyl or unsubstituted C1-C4 alkoxy. More preferably, R5 and R6 are the same or different and represent hydrogen or unsubstituted C1-C4 alkyl. Most preferably R5 and R6 are hydrogen.

When R2 is a group -B1-B2 or -B3-, preferably R7 is hydrogen, halogen, C1-C4 alkyl, C2-C4 alkenyl, C2-C4 alkynyl, C1-C4 alkoxy, —OR', —CO$_2$R', CONR'R", —COR', —CN, —NO$_2$, —NR'R" or —CF$_3$ wherein R' and R" are independently hydrogen or C1-C4 alkyl. More preferably R7 is hydrogen, halogen, unsubstituted C1-C4 alkyl or unsubstituted C1-C4 alkoxy, more preferably hydrogen or unsubstituted C1-C4 alkyl, most preferably hydrogen.

When R2 is a group -B1-B2 or -B3-, preferably R8 is hydrogen.

When R3 and R4, together with the ring carbon atoms to which they are bonded, form an unsubstituted or substituted C6-C10 aryl or 5- to 12-membered heterocyclyl group, preferred compounds are indolizinyl derivatives of formula (I) or pharmaceutically acceptable salts thereof wherein:

X is a bond, —NR8-, —O—, —S—, —SO—, or —SO$_2$—;

X$^1$ is O or NOR9, wherein R9 is hydrogen or an unsubstituted or substituted C1-C4 alkyl group;

either (i) R1 and R8 independently represent hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z, (ii) R1 represents -A3-L3-A4, -A3-L1-A4-A5, -A6-L1-A7, -A3-L4-A8, -A3-W, -A9, -A3-L1-A9 or -A10, and R8 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z, or (iii) when X is NR8, R1 and R8 together with the nitrogen to which they are attached may form an unsubstituted or substituted, aromatic or non-aromatic 5- to 12-membered heterocyclyl group;

L1 is a bond, —NR'—, —O—, —CO—, —OCO—, —OCONR'R" or —CONR'R"—;

L2 is a substituted or unsubstituted C1-C4 alkylene or C2-C4 alkenylene group;

L3 is a group of formula —O-Alk$^1$-, -(Alk$^2$)$_m$-C(=O)-Het-(Alk$^3$)$_n$- or -Alk$^4$-, wherein Alk$^1$, Alk$^2$, Alk$^3$ and Alk$^4$ are the same or different and represent unsubstituted C1-C4 alkylene groups, m and n are the same or different and represent zero or 1, and Het represents —O— or —NR9- where R9 is hydrogen or unsubstituted C1-C4 alkyl;

L4 is an imino group —N= wherein the double bond is bonded to group A8;

A1 is an unsubstituted or substituted C6-C10 arylene group;

A2, A3, A4, A5 and A7 are the same or different and are unsubstituted or substituted C6-C10 aryl or 5- to 12-membered heterocyclyl groups;

A6 is a C6-C10 aryl or 5- to 12-membered heterocyclyl group which is substituted with at least a C6-C10 aryl or a 5- to 12-membered heterocyclyl group which is itself unsubstituted or substituted;

A8 is an unsubstituted or substituted 5- to 12-membered heterocyclyl group;

A9 is an unsubstituted or substituted 5- to 12-membered heterocyclyl group wherein 1 or 2 ring carbon atoms are replaced with a group selected from >C(=O), >S(=O)$_2$, >C(=NOR11) where R11 is hydrogen or a C1-C4 alkyl group, >C=CH$_2$ or >C(—OCH$_2$CH$_2$O—);

A10 is an unsubstituted or substituted tricyclic 13- to 15-membered heterocyclyl group;

W is a group of formula —C(=O)—NR10-S(=O)$_2$—R'" where R10 and R'" are the same or different and represent hydrogen or C1-C4 alkyl;

R2 is an unsubstituted or substituted group selected from C6-C10 aryl, a 5- to 12-membered heterocyclyl group, C1-C8 alkyl and C3-C6 cycloalkyl, halogen or a group of formula -B1-B2 or -B3;

B1 is an unsubstituted or substituted C6-C10 aryl group;

B2 is an unsubstituted or substituted C6-C10 aryl or 5- to 12-membered heterocyclyl group;

B3 is an unsubstituted or substituted 5- to 12-membered heterocyclyl group where 1 or 2 ring carbon atoms are replaced with a group selected from >C(=O), >S(=O)$_2$, >C(=NOR11) where R11 is hydrogen or a C1-C4 alkyl group, >C=CH$_2$ or >C(—OCH$_2$CH$_2$O—);

R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, —Y—Z, C6-C10 aryl or a group of formula -Alk$^6$-L5-A12, where Alk$^6$ is a C1-C4 alkylene group, L5 is a group of formula —O—C(=O)—, —C(=O)— or —NR13-C(=O)— and R13 is hydrogen or C1-C4 alkyl, and A12 is an unsubstituted or substituted C6-C10 aryl or 5- to 12-membered heterocyclyl group;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'=NOR"; and R' and R" independently represent hydrogen, C1-C8 alkyl, C2-C8 alkenyl or C2-C8 alkynyl.

When R3 and R4, together with the ring carbon atoms to which they are bonded, form an unsubstituted or substituted C6-C10 aryl or 5- to 12-membered heterocyclyl group, more preferred compounds are indolizinyl derivatives of formula (I) or pharmaceutically acceptable salts thereof wherein:

X is a bond, —NR8-, —O—, —S—, —SO—, or —SO$_2$—;

X$^1$ is O or NOR9, wherein R9 is hydrogen or an unsubstituted or substituted C1-C4 alkyl group;

R1 and R8 independently represent hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', and —Y—Z, or when X is NR8, R1 and R8 together with the nitrogen to which they are attached may form an unsubstituted or substituted, aromatic or non-aromatic 5- to 12-membered heterocyclyl group;

A1 is an unsubstituted or substituted C6-C10 arylene group;

L1 is a bond, —NR'—, —O—, —CO—, —OCO—, —OCONR'R" or —CONR'R"—;

L2 is a substituted or unsubstituted C1-C4 alkylene or C2-C4 alkenylene group;

A2 is a substituted or unsubstituted C6-C10 aryl or 5- to 12-membered-heterocyclyl group;

R2 is an unsubstituted or substituted group selected from C6-C10 aryl, a 5- to 12-membered heterocyclyl group, C1-C8 alkyl and C3-C6 cycloalkyl, or halogen;

R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'=NOR"; and R' and R" independently represent hydrogen, C1-C8 alkyl, C2-C8 alkenyl or C2-C8 alkynyl.

When R3 and R4, together with the ring carbon atoms to which they are bonded, form an unsubstituted or substituted C6-C10 aryl or 5- to 12-membered heterocyclyl group, preferably X is —NR8- or —O— and R8 is hydrogen, C1-C8 alkyl, C2-C8 alkenyl or C2-C8 alkynyl. More preferably X is —NR8- or —O— and R8 is hydrogen or C1-C4 alkyl, more preferably R8 is hydrogen or C1-C2 alkyl, most preferably R8 is hydrogen. Preferably X is —NH—.

When R3 and R4, together with the ring carbon atoms to which they are bonded, form an unsubstituted or substituted C6-C10 aryl or 5- to 12-membered heterocyclyl group, preferably X$^1$ is O or NOR9 wherein R9 is hydrogen or C1-C4 alkyl which is unsubstituted or substituted with 1, 2 or 3 substituents selected from halogen, hydroxyl, amino, (C1-C4 alkyl)amino, di(C1-C4 alkyl)amino, C1-C4 alkoxy, —CO$_2$H and —CO$_2$(C1-C4 alkyl). More preferably X$^1$ is O.

When R3 and R4, together with the ring carbon atoms to which they are bonded, form an unsubstituted or substituted C6-C10 aryl or 5- to 12-membered heterocyclyl group, preferably R1 is hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', —Y—Z, -A3-L3-A4, -A3-L1-A4-A5, -A6-L1-A7, -A3-L4-A8, -A3-W, -A9, -A3-L1-A9 or -A10. More preferably R1 is an unsubstituted or substituted C6-C10 aryl group or a group -A1-L1-A2 where A1 is unsubstituted or substituted C6-C10 arylene group, L1 is a bond, —NR'—, —O—, —CO—, —OCO—, —OCONR'R" or —CONR'R"—, and A2 is an unsubstituted or substituted C6-C10 aryl or 5- to 12-membered heterocyclyl group. More preferably R1 is an unsubstituted or substituted phenyl ring or a group -A1-L1-A2 where A1 is unsubstituted or substituted C6-C10 arylene group, L1 is a bond, and A2 is an unsubstituted or substituted phenyl or 5- to 6-membered heterocyclyl groups. More preferably R1 is an unsubstituted or substituted phenyl ring or a group A1-L1-A2 where A1 is unsubstituted or substituted C6-C10 arylene group, L1 is a bond, —NR'— or —CONR'R" and R' and R" are hydrogen or C1-C4 alkyl, and A2 is an unsubstituted or substituted phenyl or 5- to 6-membered heterocyclyl groups. Most preferably R1 is an unsubstituted or substituted phenyl group or a group -A1-A2 wherein A1 is unsubstituted phenyl and A2 is unsubstituted 5- to 6-membered heterocyclyl (in particular morpholinyl or oxazolyl).

When R3 and R4, together with the ring carbon atoms to which they are bonded, form an unsubstituted or substituted C6-C10 aryl or 5- to 12-membered heterocyclyl group, preferably R2 is an unsubstituted or substituted C1-C4 alkyl, C6-C10 aryl or a 5- to 12-membered heterocyclyl group. More preferably R2 is an unsubstituted or substituted C1-C2 alkyl, phenyl or 5- to 12-membered heterocyclyl group. Preferred substituents on the cyclic groups include 1 or 2 (more preferably 1) halogen atom or C1-C4 alkyl groups, more preferably chlorine atoms or methyl groups. Preferably when R2 is C1-C2 alkyl (most preferably methyl) it is unsubstituted. Preferred 5- to 12-membered heterocyclyl groups include pyridinyl, pyrimidinyl and dihydroindolyl.

When R3 and R4, together with the ring carbon atoms to which they are bonded, form an unsubstituted or substituted C6-C10 aryl or 5- to 12-membered heterocyclyl group, preferably R5 and R6 are the same or different and represent phenyl, benzyl, pyridyl, hydrogen, halogen, C1-C8 alkyl, C2-C8 alkenyl, C2-C8 alkynyl, —OR', —CO$_2$R', CONR'R", —COR', —CN, —NO$_2$, —NR'R" or —CF$_3$ wherein R' and R" are independently hydrogen or C1-C4 alkyl. More preferably R5 and R6 are the same or different and represent hydrogen, unsubstituted C1-C4 alkyl or unsubstituted C1-C4 alkoxy. More preferably, R5 and R6 are the same or different and represent hydrogen or unsubstituted C1-C4 alkyl. Most preferably R5 and R6 are hydrogen.

When R3 and R4, together with the ring carbon atoms to which they are bonded, form an unsubstituted or substituted C6-C10 aryl or 5- to 12-membered heterocyclyl group, preferably R7 is hydrogen, halogen, C1-C4 alkyl, C2-C4 alkenyl, C2-C4 alkynyl, C1-C4 alkoxy, —OR', —CO$_2$R', CONR'R", —COR', —CN, —NO$_2$, —NR'R" or —CF$_3$ wherein R' and R" are independently hydrogen or C1-C4 alkyl. More preferably R7 is hydrogen, halogen, unsubstituted C1-C4 alkyl or unsubstituted C1-C4 alkoxy, more preferably hydrogen or unsubstituted C1-C4 alkyl, most preferably hydrogen.

When R3 and R4, together with the ring carbon atoms to which they are bonded, form an unsubstituted or substituted C6-C10 aryl or 5- to 12-membered heterocyclyl group, preferably R8 is hydrogen.

When R4 represents a group of formula -Het-Alk$^5$-A11, preferred compounds are indolizinyl derivatives of formula (I) or pharmaceutically acceptable salts thereof wherein:

X is a bond, —NR8-, —O—, —S—, —SO—, or —SO$_2$—;

X$^1$ is O or NOR9, wherein R9 is hydrogen or an unsubstituted or substituted C1-C4 alkyl group;

either (i) R1 and R8 independently represent hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z, (ii) R1 represents -A3-

L3-A4, -A3-L1-A4-A5, -A6-L1-A7, -A3-L4-A8, -A3-W, -A9, -A3-L1-A9 or -A10, and R8 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z, or (iii) when X is NR8, R1 and R8 together with the nitrogen to which they are attached may form an unsubstituted or substituted, aromatic or non-aromatic 5- to 12-membered heterocyclyl group;

L1 is a bond, —NR'—, —O—, —CO—, —OCO—, —OCONR'R" or —CONR'R"—;

L2 is a substituted or unsubstituted C1-C4 alkylene or C2-C4 alkenylene group;

L3 is a group of formula —O-Alk$^1$-, -(Alk$^2$)$_m$-C(=O)-Het-(Alk$^3$)$_n$- or -Alk$^4$-, wherein Alk$^1$, Alk$^2$, Alk$^3$ and Alk$^4$ are the same or different and represent unsubstituted C1-C4 alkylene groups, m and n are the same or different and represent zero or 1, and Het represents —O— or —NR9- where R9 is hydrogen or unsubstituted C1-C4 alkyl;

L4 is an imino group —N= wherein the double bond is bonded to group A8;

A1 is an unsubstituted or substituted C6-C10 arylene group;

A2, A3, A4, A5 and A7 are the same or different and are unsubstituted or substituted C6-C10 aryl or 5- to 12-membered heterocyclyl groups;

A6 is a C6-C10 aryl or 5- to 12-membered heterocyclyl group which is substituted with at least a C6-C10 aryl or a 5- to 12-membered heterocyclyl group which is itself unsubstituted or substituted;

A8 is an unsubstituted or substituted 5- to 12-membered heterocyclyl group;

A9 is an unsubstituted or substituted 5- to 12-membered heterocyclyl group wherein 1 or 2 ring carbon atoms are replaced with a group selected from >C(=O), >S(=O)$_2$, >C(=NOR11) where R11 is hydrogen or a C1-C4 alkyl group, >C=CH$_2$ or >C(—OCH$_2$CH$_2$O—);

A10 is an unsubstituted or substituted tricyclic 13- to 15-membered heterocyclyl group;

W is a group of formula —C(=O)—NR10-S(=O)$_2$—R''' where R10 and R''' are the same or different and represent hydrogen or C1-C4 alkyl;

R2 is an unsubstituted or substituted group selected from C6-C10 aryl, a 5- to 12-membered heterocyclyl group, C1-C8 alkyl and C3-C6 cycloalkyl, halogen or a group of formula -B1-B2 or -B3;

B1 is an unsubstituted or substituted C6-C10 aryl group;

B2 is an unsubstituted or substituted C6-C10 aryl or 5- to 12-membered heterocyclyl group;

B3 is an unsubstituted or substituted 5- to 12-membered heterocyclyl group where 1 or 2 ring carbon atoms are replaced with a group selected from >C(=O), >S(=O)$_2$, >C(=NOR11) where R11 is hydrogen or a C1-C4 alkyl group, >C=CH$_2$ or >C(—OCH$_2$CH$_2$O—);

R3 represents C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, —Y—Z, C6-C10 aryl or a group of formula -Alk$^6$-L5-A12, where Alk$^6$ is a C1-C4 alkylene group, L5 is a group of formula —O—C(=O)—, —C(=O)— or —NR13-C(=O)— and R13 is hydrogen or C1-C4 alkyl, and A12 is an unsubstituted or substituted C6-C10 aryl or 5- to 12-membered heterocyclyl group;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'=NOR"; and R' and R" independently represent hydrogen, C1-C8 alkyl, C2-C8 alkenyl or C2-C8 alkynyl.

When R4 represents a group of formula -Het-Alk$^5$-A11, more preferred compounds are indolizinyl derivatives of formula (I) or pharmaceutically acceptable salts thereof wherein:

X is a bond, —NR8-, —O—, —S—, —SO—, or —SO$_2$—;

X$^1$ is O or NOR9, wherein R9 is hydrogen or an unsubstituted or substituted C1-C4 alkyl group;

R1 and R8 independently represent hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', and —Y—Z, or when X is NR8, R1 and R8 together with the nitrogen to which they are attached may form an unsubstituted or substituted, aromatic or non-aromatic 5- to 12-membered heterocyclyl group;

A1 is an unsubstituted or substituted C6-C10 arylene group;

L1 is a bond, —NR'—, —O—, —CO—, —OCO—, —OCONR'R" or —CONR'R"—;

L2 is a substituted or unsubstituted C1-C4 alkylene or C2-C4 alkenylene group;

A2 is a substituted or unsubstituted C6-C10 aryl or 5- to 12-membered-heterocyclyl group;

R2 is an unsubstituted or substituted group selected from C6-C10 aryl, a 5- to 12-membered heterocyclyl group, C1-C8 alkyl and C3-C6 cycloalkyl, or halogen;

R3 represents C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'=NOR"; and R' and R" independently represent hydrogen, C1-C8 alkyl, C2-C8 alkenyl or C2-C8 alkynyl.

When R4 represents a group of formula -Het-Alk$^5$-A11, preferably X is —NR8- or —O— and R8 is hydrogen, C1-C8 alkyl, C2-C8 alkenyl or C2-C8 alkynyl. More preferably X is —NR8- or —O— and R8 is hydrogen or C1-C4 alkyl, more preferably R8 is hydrogen or C1-C2 alkyl, most preferably R8 is hydrogen. Preferably X is —NH—.

When R4 represents a group of formula -Het-Alk$^5$-A11, preferably X$^1$ is O or NOR9 wherein R9 is hydrogen or C1-C4 alkyl which is unsubstituted or substituted with 1, 2 or 3 substituents selected from halogen, hydroxyl, amino, (C1-C4 alkyl)amino, di(C1-C4 alkyl)amino, C1-C4 alkoxy, —CO$_2$H and —CO$_2$(C1-C4 alkyl). More preferably X$^1$ is O.

When R4 represents a group of formula -Het-Alk$^5$-A11, preferably R1 is hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', —Y—Z, -A3-L3-A4, -A3-L1-A4-A5, -A6-L1-A7, -A3-L4-A8, -A3-W, -A9, -A3-L1-A9 or -A10. More preferably R1 is an unsubstituted or substituted C6-C10 aryl group or a group -A1-L1-A2 where A1 is unsubstituted or substituted C6-C10 arylene group, L1 is a bond, —NR'—, —O—, —CO—, —OCO—, —OCONR'R" or —CONR'R"—, and A2 is an unsubstituted or substituted C6-C10 aryl or 5- to 12-membered heterocyclyl group. More preferably R1 is an unsubstituted or substituted phenyl ring or a group -A1-L1-A2 where A1 is unsubstituted or substituted C6-C10 arylene group, L1 is a bond, and A2 is an unsubstituted or substituted phenyl or 5- to 6-membered heterocyclyl groups. More preferably R1 is an unsubstituted or substituted phenyl ring or a group A1-L1-A2 where A1 is unsubstituted or substituted C6-C10 arylene group, L1 is a bond, —NR'— or —CONR'R" and R' and R" are hydrogen or C1-C4 alkyl, and A2 is an unsubstituted or substituted phenyl or 5- to 6-membered heterocyclyl groups. Most preferably R1 is an unsubstituted or substituted phenyl group or a group -A1-A2 wherein A1 is unsubstituted phenyl and A2 is unsubstituted 5- to 6-membered heterocyclyl (in particular morpholinyl or oxazolyl).

When R4 represents a group of formula -Het-Alk$^5$-A11, preferably R2 is an unsubstituted or substituted C1-C4 alkyl, C6-C10 aryl or a 5- to 12-membered heterocyclyl group. More preferably R2 is an unsubstituted or substituted C1-C2 alkyl, phenyl or 5- to 12-membered heterocyclyl group. Preferred substituents on the cyclic groups include 1 or 2 (more preferably 1) halogen atom or C1-C4 alkyl groups, more preferably chlorine atoms or methyl groups. Preferably when R2 is C1-C2 alkyl (most preferably methyl) it is unsubstituted. Preferred 5- to 12-membered heterocyclyl groups include pyridinyl, pyrimidinyl and dihydroindolyl.

When R4 represents a group of formula -Het-Alk$^5$-A11, preferably R3 represents phenyl, benzyl, pyridyl, hydrogen, halogen, C1-C8 alkyl, C2-C8 alkenyl, C2-C8 alkynyl, —OR', —CO$_2$R', CONR'R", —COR', —CN, —NO$_2$, —NR'R" or —CF$_3$ wherein R' and R" are independently hydrogen or C1-C4 alkyl. More preferably R3 represents hydrogen, unsubstituted C1-C4 alkyl or unsubstituted C1-C4 alkoxy. Most preferably R3 is hydrogen.

When R4 represents a group of formula -Het-Alk$^5$-A11, preferably R5 and R6 are the same or different and represent phenyl, benzyl, pyridyl, hydrogen, halogen, C1-C8 alkyl, C2-C8 alkenyl, C2-C8 alkynyl, —OR', —CO$_2$R', CONR'R", —COR', —CN, —NO$_2$, —NR'R" or —CF$_3$ wherein R' and R" are independently hydrogen or C1-C4 alkyl. More preferably R5 and R6 are the same or different and represent hydrogen, unsubstituted C1-C4 alkyl or unsubstituted C1-C4 alkoxy. More preferably, R5 and R6 are the same or different and represent hydrogen or unsubstituted C1-C4 alkyl. Most preferably R5 and R6 are hydrogen.

When R4 represents a group of formula -Het-Alk$^5$-A11, preferably R7 is hydrogen, halogen, C1-C4 alkyl, C2-C4 alkenyl, C2-C4 alkynyl, C1-C4 alkoxy, —OR', —CO$_2$R', CONR'R", —COR', —CN, —NO$_2$, —NR'R" or —CF$_3$ wherein R' and R" are independently hydrogen or C1-C4 alkyl. More preferably R7 is hydrogen, halogen, unsubstituted C1-C4 alkyl or unsubstituted C1-C4 alkoxy, more preferably hydrogen or unsubstituted C1-C4 alkyl, most preferably hydrogen.

When R4 represents a group of formula -Het-Alk$^5$-A11, preferably R8 is hydrogen.

When R7 represents C6-C10 aryl or a group of formula -Alk$^6$-L5-A12, preferred compounds are indolizinyl derivatives of formula (I) or pharmaceutically acceptable salts thereof wherein:

X is a bond, —NR8-, —O—, —S—, —SO—, or —SO$_2$—;

X$^1$ is O or NOR9, wherein R9 is hydrogen or an unsubstituted or substituted C1-C4 alkyl group;

either (i) R1 and R8 independently represent hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z, (ii) R1 represents -A3-L3-A4, -A3-L1-A4-A5, -A6-L1-A7, -A3-L4-A8, -A3-W, -A9, -A3-L1-A9 or -A10, and R8 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z, or (iii) when X is NR8, R1 and R8 together with the nitrogen to which they are attached may form an unsubstituted or substituted, aromatic or non-aromatic 5- to 12-membered heterocyclyl group;

L1 is a bond, —NR'—, —O—, —CO—, —OCO—, —OCONR'R" or —CONR'R"—;

L2 is a substituted or unsubstituted C1-C4 alkylene or C2-C4 alkenylene group;

L3 is a group of formula —O-Alk$^1$-, -(Alk$^2$)$_m$-C(=O)-Het-(Alk$^3$)$_n$- or -Alk$^4$-, wherein Alk$^1$, Alk$^2$, Alk$^3$ and Alk$^4$ are the same or different and represent unsubstituted C1-C4 alkylene groups, m and n are the same or different and represent zero or 1, and Het represents —O— or —NR9- where R9 is hydrogen or unsubstituted C1-C4 alkyl;

L4 is an imino group —N= wherein the double bond is bonded to group A8;

A1 is an unsubstituted or substituted C6-C10 arylene group;

A2, A3, A4, A5 and A7 are the same or different and are unsubstituted or substituted C6-C10 aryl or 5- to 12-membered heterocyclyl groups;

A6 is a C6-C10 aryl or 5- to 12-membered heterocyclyl group which is substituted with at least a C6-C10 aryl or a 5- to 12-membered heterocyclyl group which is itself unsubstituted or substituted;

A8 is an unsubstituted or substituted 5- to 12-membered heterocyclyl group;

A9 is an unsubstituted or substituted 5- to 12-membered heterocyclyl group wherein 1 or 2 ring carbon atoms are replaced with a group selected from >C(=O), >S(=O)$_2$, >C(=NOR11) where R11 is hydrogen or a C1-C4 alkyl group, >C=CH$_2$ or >C(—OCH$_2$CH$_2$O—);

A10 is an unsubstituted or substituted tricyclic 13- to 15-membered heterocyclyl group;

W is a group of formula —C(=O)—NR10-S(=O)$_2$—R'" where R10 and R'" are the same or different and represent hydrogen or C1-C4 alkyl;

R2 is an unsubstituted or substituted group selected from C6-C10 aryl, a 5- to 12-membered heterocyclyl group, C1-C8 alkyl and C3-C6 cycloalkyl, halogen or a group of formula -B1-B2 or -B3;

B1 is an unsubstituted or substituted C6-C10 aryl group;

B2 is an unsubstituted or substituted C6-C10 aryl or 5- to 12-membered heterocyclyl group;

B3 is an unsubstituted or substituted 5- to 12-membered heterocyclyl group where 1 or 2 ring carbon atoms are replaced with a group selected from >C(=O), >S(=O)$_2$, >C(=NOR11) where R11 is hydrogen or a C1-C4 alkyl group, >C=CH$_2$ or >C(—OCH$_2$CH$_2$O—);

R3 and R4 are the same or different and represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'=NOR"; and R' and R" independently represent hydrogen, C1-C8 alkyl, C2-C8 alkenyl or C2-C8 alkynyl.

When R7 represents C6-C10 aryl or a group of formula -Alk$^6$-L5-A12, more preferred compounds are indolizinyl derivatives of formula (I) or pharmaceutically acceptable salts thereof wherein:

X is a bond, —NR8-, —O—, —S—, —SO—, or —SO$_2$—;

X$^1$ is O or NOR9, wherein R9 is hydrogen or an unsubstituted or substituted C1-C4 alkyl group;

R1 and R8 independently represent hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', and —Y—Z, or when X is NR8, R1 and R8 together with the nitrogen to which they are attached may form an unsubstituted or substituted, aromatic or non-aromatic 5- to 12-membered heterocyclyl group;

A1 is an unsubstituted or substituted C6-C10 arylene group;

L1 is a bond, —NR'—, —O—, —CO—, —OCO—, —OCONR'R" or —CONR'R"—;

L2 is a substituted or unsubstituted C1-C4 alkylene or C2-C4 alkenylene group;

A2 is a substituted or unsubstituted C6-C10 aryl or 5- to 12-membered-heterocyclyl group;

R2 is an unsubstituted or substituted group selected from C6-C10 aryl, a 5- to 12-membered heterocyclyl group, C1-C8 alkyl and C3-C6 cycloalkyl, or halogen;

R3 and R4 are the same or different and represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'=NOR"; and R' and R" independently represent hydrogen, C1-C8 alkyl, C2-C8 alkenyl or C2-C8 alkynyl.

When R7 represents C6-C10 aryl or a group of formula -Alk$^6$-L5-A12, preferably X is —NR8- or —O— and R8 is hydrogen, C1-C8 alkyl, C2-C8 alkenyl or C2-C8 alkynyl. More preferably X is —NR8- or —O— and R8 is hydrogen or C1-C4 alkyl, more preferably R8 is hydrogen or C1-C2 alkyl, most preferably R8 is hydrogen. Preferably X is —NH—.

When R7 represents C6-C10 aryl or a group of formula -Alk$^6$-L5-A12, preferably X$^1$ is O or NOR9 wherein R9 is hydrogen or C1-C4 alkyl which is unsubstituted or substituted with 1, 2 or 3 substituents selected from halogen, hydroxyl, amino, (C1-C4 alkyl)amino, di(C1-C4 alkyl) amino, C1-C4 alkoxy, —CO$_2$H and —CO$_2$(C1-C4 alkyl). More preferably X$^1$ is O.

When R7 represents C6-C10 aryl or a group of formula -Alk$^6$-L5-A12, preferably R1 is hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', —Y—Z, -A3-L3-A4, -A3-L1-A4-A5, -A6-L1-A7, -A3-L4-A8, -A3-W, -A9, -A3-L1-A9 or -A10. More preferably R1 is an unsubstituted or substituted C6-C10 aryl group or a group -A1-L1-A2 where A1 is unsubstituted or substituted C6-C10 arylene group, L1 is a bond, —NR'—, —O—, —CO—, —OCO—, —OCONR'R" or —CONR'R"—, and A2 is an unsubstituted or substituted C6-C10 aryl or 5- to 12-membered heterocyclyl group. More preferably R1 is an unsubstituted or substituted phenyl ring or a group -A1-L1-A2 where A1 is unsubstituted or substituted C6-C10 arylene group, L1 is a bond, and A2 is an unsubstituted or substituted phenyl or 5- to 6-membered heterocyclyl groups. More preferably R1 is an unsubstituted or substituted phenyl ring or a group A1-L1-A2 where A1 is unsubstituted or substituted C6-C10 arylene group, L1 is a bond, —NR'— or —CONR'R" and R' and R" are hydrogen or C1-C4 alkyl, and A2 is an unsubstituted or substituted phenyl or 5- to 6-membered heterocyclyl groups. Most preferably R1 is an unsubstituted or substituted phenyl group or a group -A1-A2 wherein A1 is unsubstituted phenyl and A2 is unsubstituted 5- to 6-membered heterocyclyl (in particular morpholinyl or oxazolyl).

When R7 represents C6-C10 aryl or a group of formula -Alk$^6$-L5-A12, preferably R2 is an unsubstituted or substituted C1-C4 alkyl, C6-C10 aryl or a 5- to 12-membered heterocyclyl group. More preferably R2 is an unsubstituted or substituted C1-C2 alkyl; phenyl or 5- to 12-membered heterocyclyl group. Preferred substituents on the cyclic groups include 1 or 2 (more preferably 1) halogen atom or C1-C4 alkyl groups, more preferably chlorine atoms or methyl groups. Preferably when R2 is C1-C2 alkyl (most preferably methyl) it is unsubstituted. Preferred 5- to 12-membered heterocyclyl groups include pyridinyl, pyrimidinyl and dihydroindolyl.

When R7 represents C6-C10 aryl or a group of formula -Alk$^6$-L5-A12, preferably R3 and R4 are the same or different and represent phenyl, benzyl, pyridyl, hydrogen, halogen, C1-C8 alkyl, C2-C8 alkenyl, C2-C8 alkynyl, —OR', —CO$_2$R', CONR'R", —COR', —CN, —NO$_2$, —NR'R" or —CF$_3$ wherein R' and R" are independently hydrogen or C1-C4 alkyl, or R3 and R4 together form an unsubstituted or substituted C6-C10 aryl group. More preferably R3 and R4 are the same or different and represent hydrogen, unsubstituted C1-C4 alkyl or unsubstituted C1-C4 alkoxy, or R3 and R4 together form an unsubstituted or substituted phenyl group. When R3 and R4 together form a phenyl group, preferably it is unsubstituted. More preferably R3 and R4 are the same or different and represent hydrogen or unsubstituted C1-C4 alkyl. Most preferably R3 and R4 are hydrogen.

When R7 represents C6-C10 aryl or a group of formula -Alk$^6$-L5-A12, preferably R5 and R6 are the same or different and represent phenyl, benzyl, pyridyl, hydrogen, halogen, C1-C8 alkyl, C2-C8 alkenyl, C2-C8 alkynyl, —OR', —CO$_2$R', CONR'R", —COR', —CN, —NO$_2$, —NR'R" or —CF$_3$ wherein R' and R" are independently hydrogen or C1-C4 alkyl. More preferably R5 and R6 are the same or different and represent hydrogen, unsubstituted C1-C4 alkyl or unsubstituted C1-C4 alkoxy. More preferably, R5 and R6 are the same or different and represent hydrogen or unsubstituted C1-C4 alkyl. Most preferably R5 and R6 are hydrogen.

When R7 represents C6-C10 aryl or a group of formula -Alk$^6$-L5-A12, preferably R8 is hydrogen.

The invention specifically provides the following indolizine derivatives of formula (I) as well as their pharmaceutically and agriculturally acceptable salts:

N-(2-Fluoro-phenyl)-2-oxo-2-(2-phenyl-pyrrolo[1,2-a]quinolin-1-yl)-acetamide,
2-[6-(3-Morpholin-4-yl-propoxy)-2-phenyl-indolizin-3-yl]-2-oxo-N-phenyl-acetamide,
N-(4-Methoxy-phenyl)-2-(2-methyl-1-phenyl-indolizin-3-yl)-2-oxo-acetamide,
2-(2-Methyl-1-phenyl-indolizin-3-yl)-N-(4-morpholin-4-yl-phenyl)-2-oxo-acetamide,
4-Methyl-piperazine-1-carboxylic acid 2-phenyl-3-phenylaminooxalyl-indolizin-1-ylmethyl ester,
2-(2-Biphenyl-4-yl-indolizin-3-yl)-N-(4-oxazol-4-yl-phenyl)-2-oxo-acetamide,
2-{2-[4-(4-Methyl-piperazin-1-yl)-phenyl]-indolizin-3-yl}-2-oxo-N-phenyl-acetamide,
2-Oxo-2-[2-(2-oxo-1,2-dihydro-pyridin-3-yl)-indolizin-3-yl]-N-phenyl-acetamide,
N-{4-[3-(2-Isopropyl-imidazol-1-yl)-propoxy]-3-methyl-phenyl}-2-oxo-2-(2-phenyl-indolizin-3-yl)-acetamide,
N-{3-Isopropyl-4-[3-(2-methyl-imidazol-1-yl)-propoxy]-phenyl}-2-oxo-2-(2-phenyl-indolizin-3-yl)-acetamide,
N-[4-(2-Morpholin-4-yl-ethoxy)-phenyl]-2-oxo-2-(2-phenyl-indolizin-3-yl)-acetamide,
2-Hydroxy-4-[2-oxo-2-(2-phenyl-indolizin-3-yl)-acetylamino]-benzoic acid tetrahydro-pyran-4-yl ester,
2-Isopropyl-4-[2-oxo-2-(2-phenyl-indolizin-3-yl)-acetylamino]-benzoic acid 2-(2-isopropyl-imidazol-1-yl)-ethyl ester,
2-Methyl-2-{3-[2-oxo-2-(2-phenyl-indolizin-3-yl)-acetylamino]-phenyl}-propionic acid 2-(2-isopropyl-imidazol-1-yl)-ethyl ester,
N-[4-(2-Morpholin-4-yl-ethyl)-phenyl]-2-oxo-2-(2-phenyl-indolizin-3-yl)-acetamide,
N-{3-[1-(2-Isopropyl-1-methyl-1H-imidazol-4-yl)-1-methyl-ethyl]-phenyl}-2-oxo-2-(2-phenyl-indolizin-3-yl)-acetamide,
N-{4-[1-(2-Isopropyl-1-methyl-1H-imidazol-4-yl)-1-methyl-ethyl]-phenyl}-2-oxo-2-(2-phenyl-indolizin-3-yl)-acetamide,
N-{3-[1-(2-Isopropyl-3-methyl-3H-imidazol-4-yl)-1-methyl-ethyl]-phenyl}-2-oxo-2-(2-phenyl-indolizin-3-yl)-acetamide,
N-{4-[1-(2-Isopropyl-3-methyl-3H-imidazol-4-yl)-1-methyl-ethyl]-phenyl}-2-oxo-2-(2-phenyl-indolizin-3-yl)-acetamide,
N-{3-[1-(4-Isopropyl-2-methyl-imidazol-1-yl)-1-methyl-ethyl]-phenyl}-2-oxo-2-(2-phenyl-indolizin-3-yl)-acetamide,
N-{4-[4-(2,6-Dimethyl-morpholin-4-yl)-piperidin-1-yl]-phenyl}-2-oxo-2-(2-phenyl-indolizin-3-yl)-acetamide,
2-[2-(2-Chloro-phenyl)-indolizin-3-yl]-N-[4-(4-morpholin-4-yl-piperidin-1-yl)-phenyl]-2-oxo-acetamide,
N-{4-[4-(4,6-Dimethyl-pyridin-2-yl)-piperazin-1-yl]-phenyl}-2-oxo-2-(2-phenyl-indolizin-3-yl)-acetamide,
N-[4-(4-Methyl-piperazin-1-yl)-3-oxazol-2-yl-phenyl]-2-oxo-2-(2-phenyl-indolizin-3-yl)-acetamide,
2-Oxo-2-(2-phenyl-indolizin-3-yl)-N-{4-[3,4,4-trimethyl-oxazolidin-(2Z)-ylideneamino]-phenyl}-acetamide,
N-(4-Methanesulfonylaminocarbonyl-phenyl)-2-oxo-2-(2-phenyl-indolizin-3-yl)-acetamide,
2-Oxo-N-(2-oxo-2,3-dihydro-1H-indol-5-yl)-2-(2-phenyl-indolizin-3-yl)-acetamide
N-[4-(1,1-Dioxo-1λ$^6$-thiomorpholin-4-yl)-phenyl]-2-oxo-2-(2-phenyl-indolizin-3-yl)-acetamide,
N-[4-(4-Methoxyimino-piperidin-1-yl)-phenyl]-2-oxo-2-(2-phenyl-indolizin-3-yl)-acetamide,
N-(4-{3-[(Z)-Methoxyimino]-pyrrolidin-1-yl}-phenyl)-2-oxo-2-(2-phenyl-indolizin-3-yl)-acetamide,
N-[4-(4-Methylene-piperidin-1-yl)-phenyl]-2-oxo-2-(2-phenyl-indolizin-3-yl)-acetamide,
N-[4-(1,4-Dioxa-8-aza-spiro[4.5]dec-8-yl)-phenyl]-2-oxo-2-(2-phenyl-indolizin-3-yl)-acetamide,
2-[2-(2-Chloro-phenyl)-indolizin-3-yl]-N-(2-ethyl-2,3,4,5-tetrahydro-1H-pyrido[4,3-b]indol-7-yl)-2-oxo-acetamide,
2-methyl-2-{4-[2-oxo-2-(2-phenyl-indolizin-3-yl)-acetylamino]-phenyl}-propionic acid 2-(2-isopropyl-imidazol-1-yl)-ethyl ester,
Diethyl-carbamic acid-5-{4-[2-oxo-2-(2-phenyl-indolizin-3-yl)-acetyl amino]-phenyl}-isoxazol-3-yl ester,
N-{4-[(4,4-Dimethyl-4,5-dihydro-oxazol-2-yl)-(2-ethoxy-ethyl)-amino]-phenyl}-2-oxo-2-phenyl-indolizin-3-yl)-acetamide,
N-{4-[5-(4-Methyl-piperazin-1-yl)-4-(2,2,2-trifluoro-acetyl)-oxazol-2-yl]-phenyl}-2-oxo-2-(2-phenyl-indolizin-3-yl)-acetamide,
N-[4-(3-Ethyl-1H-imidazol-2yl methyl)-phenyl]-2-oxo-2-(2-o-tolyl-indolizin-3yl)-acetamide,
4-[4-(2-Furan-2-yl-methyl-piperazin-yl)-phenyl]-2-oxo-2-(2-phenyl-indolizin-3-yl)-acetamide,
N-{4-[4-(4,6-Dimethyl-pyridin-2-yl)-piperazin-1-yl]-phenyl}-2-(6-fluoro-2-phenyl-indolizin-3-yl)-2-oxo-acetamide,
2-Oxo-2-(2-phenyl indolizin-3-yl)-N-[4-(4-thiophen-2-yl methyl piperazin-1-yl)phenyl]acetamide,
N-[5-(2-Furan-2-yl-methyl-piperazin-yl)-peridin-2-yl]-2-oxo-2-(2-phenylindolizin-3-yl)-acetamide,
N-[5-(2-Furan-2-yl-methyl-piperazin-yl)-peridin-2-yl]-2-oxo-2-(2-o-tolyl-indolizin-3-yl)-acetamide,
2-Oxo-2-(2-phenyl-indolizin-3-yl)-N-{4-[4-(2-pyridin-yl-ethyl)-perazin-1-yl]-phenyl}-acetamide,
2-Oxo-2-(2-phenyl-indolizin-3-yl)-N-[4-{4-thiophen-2-yl-methyl-piperazin-1-yl}-pyridine-3-yl]-acetamide,
N-{4-[4-(2-Furan-2-yl-ethyl)-piperazin-1-yl]-pyridin-3-yl}-2-oxo-2-(2-phenyl-indolizin-3-yl)-acetamide,
N-{4-[4-(2-Furan-2-yl-ethyl)-piperazin-1-yl]-phenyl}-2-oxo-2-(2-phenyl-indolizin-3-yl)-acetamide, N-{4-[4-(2-Methyl-allyl)-piperazin-1-yl]-phenyl}-2-[2-(4-morpholin-4-yl-phenyl)-indolizin-3-yl]-2-oxo-acetamide,
2-Oxo-2-(2-phenyl-indolizin-3yl)-N-[4-(4-pyridin-2-yl-piperizin-1-yl)-phenyl]-acetamide,
2-(6-Fluoro-2-phenyl-indolizin-3-yl)-2-oxo-N-[4-(4-pyridin-2-yl-piperazin-1-yl)phenyl]acetamide,
N-{4-[4-(6-Methyl-pyridin-2-yl)-piperazin-1-yl]-phenyl}-2-oxo-2-(2-phenyl-indolizin-3-yl)-acetamide,
N-{4-[4-(4,6-Dimethyl-pyrimidin-2-yl)-piperazin-1-yl]-phenyl}-2-oxo-2-(2-phenyl-indolizin-3-yl)-acetamide,
N-{4-[4-(2,6-Dimethyl-pyrimidin-4-yl)-piperazin-1-yl]-phenyl}-2-(2-phenyl-indolizin-3-yl)-acetamide,
N-[4-(4-Methylene-piperidin-1-yl)-phenyl]-2-[2-(2-methyl-pyridin-3-yl)-indolizin-3-yl]-2-oxo-acetamide,
2-(2-Cyclopentyl-indolizin-3-yl)-N-{4-[4-(4,6-dimethyl-pyridin-2-yl)-piperazin-1-yl]-phenyl}-2-oxo-acetamide,
N-{3-[4-(4,6-Dimethyl-pyridin-2-yl)-piperazin-1-yl]-phenyl}-2-oxo-2-(2-phenyl-indolizin-3-yl)-acetamide,
N-{4-[4-(4-Methyl-pyridin-2-yl)-piperazin-1-yl]-phenyl}-2-oxo-2-(2-phenyl-indolizin-3-yl)-acetamide,
N-{5-[4-(2,2-Dimethyl-propyl)-piperazin-1-yl]-pyridin-2-yl}-2-oxo-2-(2-phenyl-indolizin-3-yl)-acetamide,
2-Oxo-2-(2-phenyl-indolizin-3-yl)-N-{4-[4-(pyridine-3-sulfonyl)-piperazin-1-yl]-phenyl}-acetamide,
N-{4-[4-(2,6-Dimethyl-pyridin-4-yl)-piperazin-1-yl]-phenyl}-2-oxo-2-(2-phenyl-indolizin-3-yl)-acetamide,
2-(6-Fluoro-2-phenyl-indolizin-3-yl)-2-oxo-N-{4-[4-(tetrahydro-pyran-4-ylmethyl)-piperazin-1-yl]-phenyl}-acetamide,
N-{4-[4-(4,6-Dimethyl-pyridin-2-yl)-[1,4]diazepan-1-yl]-phenyl}-2-oxo-2-(2-phenyl-indolizin-3-yl)-acetamide,
N-[4-({2-[(4,6-Dimethyl-pyridin-2-yl)-methyl-amino]-ethyl}-methyl-amino)-phenyl]-2-oxo-2-(2-phenyl-indolizin-3-yl)-acetamide,
N-{4-[4-(4-Morpholin-4-ylmethyl-phenyl)-piperazin-1-yl]-phenyl}-2-oxo-2-(2-phenyl-indolizin-3-yl)-acetamide,
N-(4-{4-[4-(2-Methoxy-ethoxy)-6-methyl-pyridin-2-yl]-piperazin-1-yl}-phenyl)-2-oxo-2-(2-phenyl-indolizin-3-yl)-acetamide,
2-(2-Cyclopropyl-indolizin-3-yl)-N-{4-[4-(4,6-dimethyl-pyridin-2-yl)-piperazin-1-yl]-phenyl}-2-oxo-acetamide,
2-Oxo-2-(2-phenyl-indolizin-3-yl)-N-[4-(4-pyridin-3-yl-piperazin-1-yl)-phenyl]-acetamide,
2-(2-Cyclohexyl-indolizin-3-yl)-N-{4-[4-(4,6-dimethyl-pyridin-2-yl)-piperazin-1-yl]-phenyl}-2-oxo-acetamide,
N-{4-[4-(4,6-Dimethyl-pyridin-2-yl)-piperazin-1-yl]-phenyl}-2-(2-isopropyl-indolizin-3-yl)-2-oxo-acetamide,
2-(2-tert-Butyl-indolizin-3-yl)-N-{4-[4-(4,6-dimethyl-pyridin-2-yl)-piperazin-1-yl]-phenyl}-2-oxo-acetamide,
N-{4-[4-(4,6-Dimethyl-pyridin-2-yl)-piperazin-1-yl]-phenyl}-2-[2-(1-methyl-piperidin-4-yl)-indolizin-3-yl]-2-oxo-acetamide,
N-(4-{2-[(4,6-Dimethyl-pyridin-2-yl)-methyl-amino]-ethoxy}-phenyl)-2-oxo-2-(2-phenyl-indolizin-3-yl)-acetamide,
N-{4-[2-(4,6-Dimethyl-pyridin-2-yloxy)-ethoxy]-phenyl}-2-oxo-2-(2-phenyl-indolizin-3-yl)-acetamide,
N-{4-[4-(4,6-Dimethyl-pyridin-2-yl)-piperazin-1-yl]-phenyl}-2-oxo-2-[2-(tetrahydro-pyran-4-yl)-indolizin-3-yl]-acetamide,
N-[4-({3-[(4,6-dimethyl-pyridin-2-yl)-methyl-amino]-propyl}-methyl-amino)-phenyl]-2-oxo-2-(2-phenyl-indolizin-3-yl)-acetamide,
N-[4-(4-{6-[(2-Methoxy-ethyl)-methyl-amino]-pyridin-3-yl}-piperazin-1-yl)-phenyl]-2-oxo-2-(2-phenyl-indolizin-3-yl)-acetamide,
N-(4-{[2-(4,6-dimethyl-pyridin-2-ylamino)-ethyl]-methyl-amino}-phenyl)-2-oxo-2-(2-phenyl-indolizin-3-yl)-acetamide,
N-(4-{3-[(4,6-Dimethyl-pyridin-2-yl)-methyl-amino]-propyl}-phenyl)-2-oxo-2-(2-phenyl-indolizin-3-yl)-acetamide,
N-{4-[2-(2,6-Dimethyl-pyridin-4-yloxy)-ethoxy]-phenyl}-2-oxo-2-(2-phenyl-indolizin-3-yl)-acetamide,
N-{4-[4-(4,6-Dimethyl-pyridin-2-yl)-butyl]-phenyl}-2-oxo-2-(2-phenyl-indolizin-3-yl)-acetamide,
N-{4-[4-(6-ethyl-pyridin-2-yl)-piperazin-1-yl]-phenyl}-2-oxo-2-(2-phenyl-indolizin-3-yl)-acetamide,
N-{4-[4-(5-Methyl-pyridin-2-yl)-piperazin-1-yl]-phenyl}-2-oxo-2-(2-phenyl-indolizin-3-yl)-acetamide,
N-{4-[4-(4-ethyl-pyridin-2-yl)-piperazin-1-yl]-phenyl}-2-oxo-2-(2-phenyl-indolizin-3-yl)-acetamide,
N-[4-(4-{4-[2-(2-methoxy-ethoxy)-ethoxy]-6-methyl-pyridin-2-yl}-piperazin-1-yl)-phenyl]-2-oxo-2-(2-phenyl-indolizin-3-yl)-acetamide,
N-{4-[4-(5-morpholin-4-yl-methyl-pyridin-2-yl)-piperazin-1-yl]-phenyl}-2-oxo-2-(2-phenyl-indolizin-3-yl)-acetamide,
N-(4-{2-[(4,6-Dimethyl-pyridin-2-yl)-methyl-amino]-ethylamino}-phenyl)-2-oxo-2-(2-phenyl-indolizin-3-yl)-acetamide,
N-[4-(4-hydroxy-4',6'-dimethyl-3,4,5,6-tetrahydro-2H-[1,2']-bipyridinyl-4-yl)-phenyl]-2-oxo-2-(2-phenyl-indolizin-3-yl)-acetamide,
N-{4-[4-(4,6-Dimethyl-pyridin-2-yl)-piperazin-1-yl]-2-methyl-phenyl}-2-oxo-2-(2-phenyl-indolizin-3-yl)-acetamide,
N-{4-[4-(4,6-Dimethyl-pyridin-2-yl)-piperazin-1-yl]-3-methoxymethyl-phenyl}-2-oxo-2-(2-phenyl-indolizin-3-yl)-acetamide,
N-{4-[4-(4,6-Dimethyl-pyridin-2-yl)-piperazin-1-yl]-3-methyl-phenyl}-2-oxo-2-(2-phenyl-indolizin-3-yl)-acetamide,
N-{4-[4-(4,6-Dimethyl-pyridin-2-yl)-piperazin-1-yl]-2-methoxymethyl-phenyl}-2-oxo-2-(2-phenyl-indolizin-3-yl)-acetamide,
2-[4-(4,6-Dimethyl-pyridin-2-yl)-piperazin-1-yl]-5-[2-oxo-2-(2-phenyl-indolizin-3-yl)-acetylamino]-benzoic acid,
N-[4-(4-{6-[Bis-(2-hydroxy-ethyl)-amino]-pyridin-2-yl}-piperazin-1-yl)-phenyl]-2-oxo-2-(2-phenyl-indolizin-3-yl)-acetamide,
N-(4-{4-[6-(2-hydroxy-ethylamino)-pyridin-2-yl]-piperazin-1-yl}-phenyl)-2-oxo-2-(2-phenyl-indolizin-3-yl)-acetamide,
N-(4-{4-[6-(2-hydroxy-ethyl)-pyridin-2-yl]-piperazin-1-yl}-phenyl)-2-oxo-2-(2-phenyl-indolizin-3-yl)-acetamide,
N-(4-{4-[4-(2-Hydroxy-ethoxy)-pyridin-2-yl]-piperazin-1-yl}-phenyl)-2-oxo-2-(2-phenyl-indolizin-3-yl)-acetamide,
2-Oxo-2-(2-phenyl-indolizin-3-yl)-N-{4-[2-(pyridin-2-yloxy)-ethylamino]-phenyl}-acetamide,
N-{4-[(4,6-Dimethyl-pyridin-2-ylmethyl)-amino]-phenyl}-2-oxo-2-(2-phenyl-indolizin-3-yl)-acetamide, and
N-{4-[2-(4,6-dimethyl-pyridin-2-yl-amino)-ethyl amino]-phenyl}-2-oxo-2-(2-phenyl-indolizin-3-yl)-acetamide.

The following compounds are also likely to be useful in the invention, and can be made by analogous processes to those defined in the examples which follow:

2-[6-(3-Morpholin-4-yl-propoxy)-2-phenyl-indolizin-3-yl]-2-oxo-N-phenyl-acetamide,
4-Methyl-piperazine-1-carboxylic acid 2-phenyl-3-phenylaminooxalyl-indolizin-1-ylmethyl ester, 2-[2-(2-Chloro-phenyl)-indolizin-3-yl]-N-(2-ethyl-2,3,4,5-tetrahydro-1H-pyrido[4,3-b]indol-7-yl)-2-oxo-acetamide,
N-(4-{3-[(Z)-Methoxyimino]-pyrrolidin-1-yl}-phenyl)-2-oxo-2-(2-phenyl-indolizin-3-yl)-acetamide,
N-[4-(2-Morpholin-4-yl-ethyl)-phenyl]-2-oxo-2-(2-phenyl-indolizin-3-yl)-acetamide,
N-[4-(2-Morpholin-4-yl-ethoxy)-phenyl]-2-oxo-2-(2-phenyl-indolizin-3-yl)-acetamide,
2-Oxo-2-[2-(2-oxo-1,2-dihydro-pyridin-3-yl)-indolizin-3-yl]-N-phenyl-acetamide,
2-{2-[4-(4-Methyl-piperazin-1-yl)-phenyl]-indolizin-3-yl}-2-oxo-N-phenyl-acetamide,
2-(2-Cyclopentyl-indolizin-3-yl)-2-oxo-N-[4-(4-pyridin-2-yl-piperazin-1-yl)-phenyl]-acetamide,
2-(2-Cyclohexyl-indolizin-3-yl)-2-oxo-N-[4-(4-pyridin-2-yl-piperazin-1-yl)-phenyl]-acetamide,
2-(2-Isopropyl-indolizin-3-yl)-2-oxo-N-[4-(4-pyridin-2-yl-piperazin-1-yl)-phenyl]-acetamide,
2-Oxo-N-[4-(4-pyridin-2-yl-piperazin-1-yl)-phenyl]-2-[2-(tetrahydro-pyran-4-yl)-indolizin-3-yl]-acetamide,
2-(2-Cyclopentyl-indolizin-3-yl)-N-{4-[4-(4-methyl-pyridin-2-yl)-piperazin-1-yl]-phenyl}-2-oxo-acetamide,
2-(2-Cyclohexyl-indolizin-3-yl)-N-{4-[4-(4-methyl-pyridin-2-yl)-piperazin-1-yl]-phenyl}-2-oxo-acetamide,
2-(2-Isopropyl-indolizin-3-yl)-N-{4-[4-(4-methyl-pyridin-2-yl)-piperazin-1-yl]-phenyl}-2-oxo-acetamide,
N-{4-[4-(4-Methyl-pyridin-2-yl)-piperazin-1-yl]-phenyl}-2-oxo-2-[2-(tetrahydro-pyran-4-yl)-indolizin-3-yl]-acetamide,
2-(2-Cyclopentyl-indolizin-3-yl)-N-{4-[4-(6-methyl-pyridin-2-yl)-piperazin-1-yl]-phenyl}-2-oxo-acetamide,
2-(2-Cyclohexyl-indolizin-3-yl)-N-{4-[4-(6-methyl-pyridin-2-yl)-piperazin-1-yl]-phenyl}-2-oxo-acetamide,
2-(2-Isopropyl-indolizin-3-yl)-N-{4-[4-(6-methyl-pyridin-2-yl)-piperazin-1-yl]-phenyl}-2-oxo-acetamide,
N-{4-[4-(6-Methyl-pyridin-2-yl)-piperazin-1-yl]-phenyl}-2-oxo-2-[2-(tetrahydro-pyran-4-yl)-indolizin-3-yl]-acetamide,
2-(2-Cyclopentyl-indolizin-3-yl)-N-{4-[4-(4-ethyl-pyridin-2-yl)-piperazin-1-yl]-phenyl}-2-oxo-acetamide,
2-(2-Cyclohexyl-indolizin-3-yl)-N-{4-[4-(4-ethyl-pyridin-2-yl)-piperazin-1-yl]-phenyl}-2-oxo-acetamide,
N-{4-[4-(4-Ethyl-pyridin-2-yl)-piperazin-1-yl]-phenyl}-2-(2-isopropyl-indolizin-3-yl)-2-oxo-acetamide,
N-{4-[4-(4-Ethyl-pyridin-2-yl)-piperazin-1-yl]-phenyl}-2-oxo-2-[2-(tetrahydro-pyran-4-yl)-indolizin-3-yl]-acetamide,
2-(2-Cyclopentyl-indolizin-3-yl)-N-{4-[4-(6-ethyl-pyridin-2-yl)-piperazin-1-yl]-phenyl}-2-oxo-acetamide,
2-(2-Cyclohexyl-indolizin-3-yl)-N-{4-[4-(6-ethyl-pyridin-2-yl)-piperazin-1-yl]-phenyl}-2-oxo-acetamide,
N-{4-[4-(6-Ethyl-pyridin-2-yl)-piperazin-1-yl]-phenyl}-2-(2-isopropyl-indolizin-3-yl)-2-oxo-acetamide,
N-{4-[4-(6-Ethyl-pyridin-2-yl)-piperazin-1-yl]-phenyl}-2-oxo-2-[2-(tetrahydro-pyran-4-yl)-indolizin-3-yl]-acetamide,
2-(6-Fluoro-2-phenyl-indolizin-3-yl)-N-{4-[4-(4-methyl-pyridin-2-yl)-piperazin-1-yl]-phenyl}-2-oxo-acetamide,
N-{4-[4-(4-Ethyl-pyridin-2-yl)-piperazin-1-yl]-phenyl}-2-(6-fluoro-2-phenyl-indolizin-3-yl)-2-oxo-acetamide,
2-(6-Fluoro-2-phenyl-indolizin-3-yl)-N-{4-[4-(6-methyl-pyridin-2-yl)-piperazin-1-yl]-phenyl}-2-oxo-acetamide,
N-{4-[4-(6-Ethyl-pyridin-2-yl)-piperazin-1-yl]-phenyl}-2-(6-fluoro-2-phenyl-indolizin-3-yl)-2-oxo-acetamide,
N-{4-[4-(5,6-Dimethyl-pyridin-2-yl)-piperazin-1-yl]-phenyl}-2-oxo-2-(2-phenyl-indolizin-3-yl)-acetamide,
N-{4-[4-(4,5-Dimethyl-pyridin-2-yl)-piperazin-1-yl]-phenyl}-2-oxo-2-(2-phenyl-indolizin-3-yl)-acetamide,
2-Oxo-2-(2-phenyl-indolizin-3-yl)-N-[4-(4-pyridin-2-yl-[1,4]diazepan-1-yl)-phenyl]-acetamide,
N-{4-[4-(4-Methyl-pyridin-2-yl)-[1,4]diazepan-1-yl]-phenyl}-2-oxo-2-(2-phenyl-indolizin-3-yl)-acetamide,
N-{4-[4-(4-Ethyl-pyridin-2-yl)-[1,4]diazepan-1-yl]-phenyl}-2-oxo-2-(2-phenyl-indolizin-3-yl)-acetamide,
N-{4-[4-(6-Methyl-pyridin-2-yl)-[1,4]diazepan-1-yl]-phenyl}-2-oxo-2-(2-phenyl-indolizin-3-yl)-acetamide,
N-{4-[4-(6-Ethyl-pyridin-2-yl)-[1,4]diazepan-1-yl]-phenyl}-2-oxo-2-(2-phenyl-indolizin-3-yl)-acetamide,
N-(4-{4-[4-(2-Methoxy-ethoxy)-pyridin-2-yl]-[1,4]diazepan-1-yl}-phenyl)-2-oxo-2-(2-phenyl-indolizin-3-yl)-acetamide,
2-(2-Cyclopentyl-indolizin-3-yl)-N-{4-[4-(4,6-dimethyl-pyridin-2-yl)-[1,4]diazepan-1-yl]-phenyl}-2-oxo-acetamide,
2-(2-Cyclohexyl-indolizin-3-yl)-N-{4-[4-(4,6-dimethyl-pyridin-2-yl)-[1,4]diazepan-1-yl]-phenyl}-2-oxo-acetamide,
N-{4-[4-(4,6-Dimethyl-pyridin-2-yl)-[1,4]diazepan-1-yl]-phenyl}-2-(2-isopropyl-indolizin-3-yl)-2-oxo-acetamide,
N-{4-[4-(4,6-Dimethyl-pyridin-2-yl)-[1,4]diazepan-1-yl]-phenyl}-2-oxo-2-[2-(tetrahydro-pyran-4-yl)-indolizin-3-yl]-acetamide,
N-{4-[4-(4,6-Dimethyl-pyridin-2-yl)-[1,4]diazepan-1-yl]-2-methyl-phenyl}-2-oxo-2-(2-phenyl-indolizin-3-yl)-acetamide,
N-{4-[4-(4,6-Dimethyl-pyridin-2-yl)-[1,4]diazepan-1-yl]-3-methyl-phenyl}-2-oxo-2-(2-phenyl-indolizin-3-yl)-acetamide,
N-{4-[4-(4,6-Dimethyl-pyridin-2-yl)-[1,4]diazepan-1-yl]-3-methoxymethyl-phenyl}-2-oxo-2-(2-phenyl-indolizin-3-yl)-acetamide,
N-[2-Methyl-4-(4-pyridin-2-yl-piperazin-1-yl)-phenyl]-2-oxo-2-(2-phenyl-indolizin-3-yl)-acetamide,
N-{2-Methyl-4-[4-(4-methyl-pyridin-2-yl)-piperazin-1-yl]-phenyl}-2-oxo-2-(2-phenyl-indolizin-3-yl)-acetamide,
N-{2-Methyl-4-[4-(6-methyl-pyridin-2-yl)-piperazin-1-yl]-phenyl}-2-oxo-2-(2-phenyl-indolizin-3-yl)-acetamide,
N-[3-Methyl-4-(4-pyridin-2-yl-piperazin-1-yl)-phenyl]-2-oxo-2-(2-phenyl-indolizin-3-yl)-acetamide,
N-{3-Methyl-4-[4-(4-methyl-pyridin-2-yl)-piperazin-1-yl]-phenyl}-2-oxo-2-(2-phenyl-indolizin-3-yl)-acetamide,
N-{3-Methyl-4-[4-(6-methyl-pyridin-2-yl)-piperazin-1-yl]-phenyl}-2-oxo-2-(2-phenyl-indolizin-3-yl)-acetamide,
N-[3-Methoxymethyl-4-(4-pyridin-2-yl-piperazin-1-yl)-phenyl]-2-oxo-2-(2-phenyl-indolizin-3-yl)-acetamide,
N-{3-Methoxymethyl-4-[4-(4-methyl-pyridin-2-yl)-piperazin-1-yl]-phenyl}-2-oxo-2-(2-phenyl-indolizin-3-yl)-acetamide,
N-{3-Methoxymethyl-4-[4-(6-methyl-pyridin-2-yl)-piperazin-1-yl]-phenyl}-2-oxo-2-(2-phenyl-indolizin-3-yl)-acetamide,
N-{4-[4-(4,6-Dimethyl-pyridin-2-yl)-piperazin-1-yl]-3-methyl-phenyl}-2-(6-fluoro-2-phenyl-indolizin-3-yl)-2-oxo-acetamide,
2-(2-Cyclopentyl-indolizin-3-yl)-N-{4-[4-(4,6-dimethyl-pyridin-2-yl)-piperazin-1-yl]-3-methyl-phenyl}-2-oxo-acetamide,
2-(2-Cyclohexyl-indolizin-3-yl)-N-{4-[4-(4,6-dimethyl-pyridin-2-yl)-piperazin-1-yl]-3-methyl-phenyl}-2-oxo-acetamide,
N-{4-[4-(4,6-Dimethyl-pyridin-2-yl)-piperazin-1-yl]-3-methyl-phenyl}-2-(2-isopropyl-indolizin-3-yl)-2-oxo-acetamide, N-{4-[4-(4,6-Dimethyl-pyridin-2-yl)-piperazin-1-yl]-3-methyl-phenyl}-2-oxo-2-[2-(tetrahydro-pyran-4-yl)-indolizin-3-yl]-acetamide, N-{4-[4-(4,6-Dimethyl-pyridin-2-yl)-piperazin-1-yl]-phenyl}-2-(6-fluoro-2-phenyl-indolizin-3-yl)-2-oxo-acetamide, 2-(2-Cyclopentyl-indolizin-3-yl)-N-{4-[4-(4,6-dimethyl-pyridin-2-yl)-piperazin-1-yl]-2-methyl-phenyl}-2-oxo-acetamide, 2-(2-Cyclohexyl-indolizin-3-yl)-N-{4-[4-(4,6-dimethyl-pyridin-2-yl)-piperazin-1-yl]-2-methyl-phenyl}-2-oxo-acetamide, N-{4-[4-(4,6-Dimethyl-pyridin-2-yl)-piperazin-1-yl]-2-methyl-phenyl}-2-(2-isopropyl-indolizin-3-yl)-2-oxo-acetamide, N-{4-[4-(4,6-Dimethyl-pyridin-2-yl)-piperazin-1-yl]-2-methyl-phenyl}-2-oxo-2-[2-(tetrahydro-pyran-4-yl)-indolizin-3-yl]-acetamide, N-{4-[4-(4,6-Dimethyl-pyridin-2-yl)-piperazin-1-yl]-3-methoxymethyl-phenyl}-2-(6-fluoro-2-phenyl-indolizin-3-yl)-2-oxo-acetamide, 2-(2-Cyclopentyl-indolizin-3-yl)-N-{4-[4-(4,6-dimethyl-pyridin-2-yl)-piperazin-1-yl]-3-methoxymethyl-phenyl}-2-oxo-acetamide, 2-(2-Cyclohexyl-indolizin-3-yl)-N-{4-[4-(4,6-dimethyl-pyridin-2-yl)-piperazin-1-yl]-3-methoxymethyl-phenyl}-2-oxo-acetamide, N-{4-[4-(4,6-Dimethyl-pyridin-2-yl)-piperazin-1-yl]-3-methoxymethyl-phenyl}-2-(2-isopropyl-indolizin-3-yl)-2-oxo-acetamide, N-{4-[4-(4,6-Dimethyl-pyridin-2-yl)-piperazin-1-yl]-3-methoxymethyl-phenyl}-2-oxo-2-[2-(tetrahydro-pyran-4-yl)-indolizin-3-yl]-acetamide, N-{4-[4-(4,6-Dimethyl-pyridin-2-yl)-piperazin-1-yl]-phenyl}-2-(5-methyl-2-phenyl-indolizin-3-yl)-2-oxo-acetamide, N-{4-[4-(4,6-Dimethyl-pyridin-2-yl)-piperazin-1-yl]-phenyl}-2-(6-methyl-2-phenyl-indolizin-3-yl)-2-oxo-acetamide, N-{4-[4-(4,6-Dimethyl-pyridin-2-yl)-piperazin-1-yl]-phenyl}-2-(6-methoxy-2-phenyl-indolizin-3-yl)-2-oxo-acetamide, 2-(6-Chloro-2-phenyl-indolizin-3-yl)-N-{4-[4-(4,6-dimethyl-pyridin-2-yl)-piperazin-1-yl]-phenyl}-2-oxo-acetamide, N-{4-[4-(4,6-Dimethyl-pyridin-2-yl)-piperazin-1-yl]-phenyl}-2-(7-methyl-2-phenyl-indolizin-3-yl)-2-oxo-acetamide, N-{4-[4-(4,6-Dimethyl-pyridin-2-yl)-piperazin-1-yl]-phenyl}-2-(1-methyl-2-phenyl-indolizin-3-yl)-2-oxo-acetamide, 2-(5-Methyl-2-phenyl-indolizin-3-yl)-2-oxo-N-[4-(4-pyridin-2-yl-piperazin-1-yl)-phenyl]-acetamide, 2-(6-Methyl-2-phenyl-indolizin-3-yl)-2-oxo-N-[4-(4-pyridin-2-yl-piperazin-1-yl)-phenyl]-acetamide, 2-(6-Methoxy-2-phenyl-indolizin-3-yl)-2-oxo-N-[4-(4-pyridin-2-yl-piperazin-1-yl)-phenyl]-acetamide, 2-(6-Chloro-2-phenyl-indolizin-3-yl)-2-oxo-N-[4-(4-pyridin-2-yl-piperazin-1-yl)-phenyl]-acetamide, 2-(7-Methyl-2-phenyl-indolizin-3-yl)-2-oxo-N-[4-(4-pyridin-2-yl-piperazin-1-yl)-phenyl]-acetamide, 2-(1-Methyl-2-phenyl-indolizin-3-yl)-2-oxo-N-[4-(4-pyridin-2-yl-piperazin-1-yl)-phenyl]-acetamide, 2-(5-Methyl-2-phenyl-indolizin-3-yl)-N-{4-[4-(4-methyl-pyridin-2-yl)-piperazin-1-yl]-phenyl}-2-oxo-acetamide, 2-(6-Methyl-2-phenyl-indolizin-3-yl)-1-{4-[4-(4-methyl-pyridin-2-yl)-piperazin-1-yl]-phenyl}-2-oxo-acetamide, 2-(6-Methoxy-2-phenyl-indolizin-3-yl)-N-{4-[4-(4-methyl-pyridin-2-yl)-piperazin-1-yl]-phenyl}-2-oxo-acetamide, 2-(6-Chloro-2-phenyl-indolizin-3-yl)-N-{4-[4-(4-methyl-pyridin-2-yl)-piperazin-1-yl]-phenyl}-2-oxo-acetamide, 2-(7-Methyl-2-phenyl-indolizin-3-yl)-N-{4-[4-(4-methyl-pyridin-2-yl)-piperazin-1-yl]-phenyl}-2-oxo-acetamide, 2-(1-Methyl-2-phenyl-indolizin-3-yl)-N-{4-[4-(4-methyl-pyridin-2-yl)-piperazin-1-yl]-phenyl}-2-oxo-acetamide, 2-(5-Methyl-2-phenyl-indolizin-3-yl)-N-{4-[4-(6-methyl-pyridin-2-yl)-piperazin-1-yl]-phenyl}-2-oxo-acetamide, 2-(6-Methyl-2-phenyl-indolizin-3-yl)-N-{4-[4-(6-methyl-pyridin-2-yl)-piperazin-1-yl]-phenyl}-2-oxo-acetamide, 2-(6-Methoxy-2-phenyl-indolizin-3-yl)-N-{4-[4-(6-methyl-pyridin-2-yl)-piperazin-1-yl]-phenyl}-2-oxo-acetamide, 2-(6-Chloro-2-phenyl-indolizin-3-yl)-N-{4-[4-(6-methyl-pyridin-2-yl)-piperazin-1-yl]-phenyl}-2-oxo-acetamide, 2-(7-Methyl-2-phenyl-indolizin-3-yl)-N-{4-[4-(6-methyl-pyridin-2-yl)-piperazin-1-yl]-phenyl}-2-oxo-acetamide, 2-(1-Methyl-2-phenyl-indolizin-3-yl)-N-{4-[4-(6-methyl-pyridin-2-yl)-piperazin-1-yl]-phenyl}-2-oxo-acetamide, N-[4-({2-[(4,6-Dimethyl-pyridin-2-yl)-methyl-amino]-ethyl}-methyl-amino)-phenyl]-2-(5-methyl-2-phenyl-indolizin-3-yl)-2-oxo-acetamide, N-[4-({2-[(4,6-Dimethyl-pyridin-2-yl)-methyl-amino]-ethyl}-methyl-amino)-phenyl]-2-(6-methyl-2-phenyl-indolizin-3-yl)-2-oxo-acetamide, N-[4-({2-[(4,6-Dimethyl-pyridin-2-yl)-methyl-amino]-ethyl}-methyl-amino)-phenyl]-2-(6-methoxy-2-phenyl-indolizin-3-yl)-2-oxo-acetamide, 2-(6-Chloro-2-phenyl-indolizin-3-yl)-N-[4-({2-[(4,6-dimethyl-pyridin-2-yl)-methyl-amino]-ethyl}-methyl-amino)-phenyl]-2-oxo-acetamide, N-[4-({2-[(4,6-Dimethyl-pyridin-2-yl)-methyl-amino]-ethyl}-methyl-amino)-phenyl]-2-(7-methyl-2-phenyl-indolizin-3-yl)-2-oxo-acetamide, N-[4-({2-[(4,6-Dimethyl-pyridin-2-yl)-methyl-amino]-ethyl}-methyl-amino)-phenyl]-2-(1-methyl-2-phenyl-indolizin-3-yl)-2-oxo-acetamide, N-{4-[2-(4,6-Dimethyl-pyridin-2-yloxy)-ethylamino]-phenyl}-2-(5-methyl-2-phenyl-indolizin-3-yl)-2-oxo-acetamide, N-{4-[2-(4,6-Dimethyl-pyridin-2-yloxy)-ethylamino]-phenyl}-2-(6-methyl-2-phenyl-indolizin-3-yl)-2-oxo-acetamide, N-{4-[2-(4,6-Dimethyl-pyridin-2-yloxy)-ethylamino]-phenyl}-2-(6-methoxy-2-phenyl-indolizin-3-yl)-2-oxo-acetamide, 2-(6-Chloro-2-phenyl-indolizin-3-yl)-N-{4-[2-(4,6-dimethyl-pyridin-2-yloxy)-ethylamino]-phenyl}-2-oxo-acetamide, N-{4-[2-(4,6-Dimethyl-pyridin-2-yloxy)-ethylamino]-phenyl}-2-(7-methyl-2-phenyl-indolizin-3-yl)-2-oxo-acetamide, N-{4-[2-(4,6-Dimethyl-pyridin-2-yloxy)-ethylamino]-phenyl}-2-(1-methyl-2-phenyl-indolizin-3-yl)-2-oxo-acetamide, N-(4-{2-[(4,6-Dimethyl-pyridin-2-yl)-methyl-amino]-ethoxy}-phenyl)-2-(5-methyl-2-phenyl-indolizin-3-yl)-2-oxo-acetamide, N-(4-{2-[(4,6-Dimethyl-pyridin-2-yl)-methyl-amino]-ethoxy}-phenyl)-2-(6-methyl-2-phenyl-indolizin-3-yl)-2-oxo-acetamide, N-(4-{2-[(4,6-Dimethyl-pyridin-2-yl)-methyl-amino]-ethoxy}-phenyl)-2-(6-methoxy-2-phenyl-indolizin-3-yl)-2-oxo-acetamide, 2-(6-Chloro-2-phenyl-indolizin-3-yl)-N-(4-{2-[(4,6-dimethyl-pyridin-2-yl)-methyl-amino]-ethoxy}-phenyl)-2-oxo-acetamide,
N-(4-{2-[(4,6-Dimethyl-pyridin-2-yl)-methyl-amino]-ethoxy}-phenyl)-2-(7-methyl-2-phenyl-indolizin-3-yl)-2-oxo-acetamide,
N-(4-{2-[(4,6-Dimethyl-pyridin-2-yl)-methyl-amino]-ethoxy}-phenyl)-2-(1-methyl-2-phenyl-indolizin-3-yl)-2-oxo-acetamide,
N-{4-[2-(4,6-Dimethyl-pyridin-2-yloxy)-ethoxy]-phenyl}-2-(5-methyl-2-phenyl-indolizin-3-yl)-2-oxo-acetamide,
N-{4-[2-(4,6-Dimethyl-pyridin-2-yloxy)-ethoxy]-phenyl}-2-(6-methyl-2-phenyl-indolizin-3-yl)-2-oxo-acetamide,
N-{4-[2-(4,6-Dimethyl-pyridin-2-yloxy)-ethoxy]-phenyl}-2-(6-methoxy-2-phenyl-indolizin-3-yl)-2-oxo-acetamide,
2-(6-Chloro-2-phenyl-indolizin-3-yl)-N-{4-[2-(4,6-dimethyl-pyridin-2-yloxy)-ethoxy]-phenyl}-2-oxo-acetamide,
N-{4-[2-(4,6-Dimethyl-pyridin-2-yloxy)-ethoxy]-phenyl}-2-(7-methyl-2-phenyl-indolizin-3-yl)-2-oxo-acetamide,
N-{4-[2-(4,6-Dimethyl-pyridin-2-yloxy)-ethoxy]-phenyl}-2-(1-methyl-2-phenyl-indolizin-3-yl)-2-oxo-acetamide,
N-(4-{[2-(4,6-Dimethyl-pyridin-2-ylamino)-ethyl]-methyl-amino}-phenyl)-2-(5-methyl-2-phenyl-indolizin-3-yl)-2-oxo-acetamide,
N-(4-{[2-(4,6-Dimethyl-pyridin-2-ylamino)-ethyl]-methyl-amino}-phenyl)-2-(6-methyl-2-phenyl-indolizin-3-yl)-2-oxo-acetamide,
N-(4-{[2-(4,6-Dimethyl-pyridin-2-ylamino)-ethyl]-methyl-amino}-phenyl)-2-(6-methoxy-2-phenyl-indolizin-3-yl)-2-oxo-acetamide,
2-(6-Chloro-2-phenyl-indolizin-3-yl)-N-(4-{[2-(4,6-dimethyl-pyridin-2-ylamino)-ethyl]-methyl-amino}-phenyl)-2-oxo-acetamide,
N-(4-{[2-(4,6-Dimethyl-pyridin-2-ylamino)-ethyl]-methyl-amino}-phenyl)-2-(7-methyl-2-phenyl-indolizin-3-yl)-2-oxo-acetamide,
N-(4-{[2-(4,6-Dimethyl-pyridin-2-ylamino)-ethyl]-methyl-amino}-phenyl)-2-(1-methyl-2-phenyl-indolizin-3-yl)-2-oxo-acetamide,
N-{4-[2-(4,6-Dimethyl-pyridin-2-ylamino)-ethylamino]-phenyl}-2-(5-methyl-2-phenyl-indolizin-3-yl)-2-oxo-acetamide,
N-{4-[2-(4,6-Dimethyl-pyridin-2-ylamino)-ethylamino]-phenyl}-2-(6-methyl-2-phenyl-indolizin-3-yl)-2-oxo-acetamide,
N-{4-[2-(4,6-Dimethyl-pyridin-2-ylamino)-ethylamino]-phenyl}-2-(6-methoxy-2-phenyl-indolizin-3-yl)-2-oxo-acetamide,
2-(6-Chloro-2-phenyl-indolizin-3-yl)-N-{4-[2-(4,6-dimethyl-pyridin-2-ylamino)-ethylamino]-phenyl}-2-oxo-acetamide,
N-{4-[2-(4,6-Dimethyl-pyridin-2-ylamino)-ethylamino]-phenyl}-2-(7-methyl-2-phenyl-indolizin-3-yl)-2-oxo-acetamide,
N-{4-[2-(4,6-Dimethyl-pyridin-2-ylamino)-ethylamino]-phenyl}-2-(1-methyl-2-phenyl-indolizin-3-yl)-2-oxo-acetamide,
N-(4-{2-[(4,6-Dimethyl-pyridin-2-yl)-methyl-amino]-ethylamino}-phenyl)-2-(5-methyl-2-phenyl-indolizin-3-yl)-2-oxo-acetamide,
N-(4-{2-[(4,6-Dimethyl-pyridin-2-yl)-methyl-amino]-ethylamino}-phenyl)-2-(6-methyl-2-phenyl-indolizin-3-yl)-2-oxo-acetamide,
N-(4-{2-[(4,6-Dimethyl-pyridin-2-yl)-methyl-amino]-ethylamino}-phenyl)-2-(6-methoxy-2-phenyl-indolizin-3-yl)-2-oxo-acetamide,
2-(6-Chloro-2-phenyl-indolizin-3-yl)-N-(4-{2-[(4,6-dimethyl-pyridin-2-yl)-methyl-amino]-ethylamino}-phenyl)-2-oxo-acetamide,
N-(4-{2-[(4,6-Dimethyl-pyridin-2-yl)-methyl-amino]-ethylamino}-phenyl)-2-(7-methyl-2-phenyl-indolizin-3-yl)-2-oxo-acetamide,
N-(4-{2-[(4,6-Dimethyl-pyridin-2-yl)-methyl-amino]-ethylamino}-phenyl)-2-(1-methyl-2-phenyl-indolizin-3-yl)-2-oxo-acetamide,
N-(4-{3-[(4,6-Dimethyl-pyridin-2-yl)-methyl-amino]-propyl}-phenyl)-2-(5-methyl-2-phenyl-indolizin-3-yl)-2-oxo-acetamide,
N-(4-{3-[(4,6-Dimethyl-pyridin-2-yl)-methyl-amino]-propyl}-phenyl)-2-(6-methyl-2-phenyl-indolizin-3-yl)-2-oxo-acetamide,
N-(4-{3-[(4,6-Dimethyl-pyridin-2-yl)-methyl-amino]-propyl}-phenyl)-2-(6-methoxy-2-phenyl-indolizin-3-yl)-2-oxo-acetamide,
2-(6-Chloro-2-phenyl-indolizin-3-yl)-N-(4-{3-[(4,6-dimethyl-pyridin-2-yl)-methyl-amino]-propyl}-phenyl)-2-oxo-acetamide,
N-(4-{3-[(4,6-Dimethyl-pyridin-2-yl)-methyl-amino]-propyl}-phenyl)-2-(7-methyl-2-phenyl-indolizin-3-yl)-2-oxo-acetamide,
N-(4-{3-[(4,6-Dimethyl-pyridin-2-yl)-methyl-amino]-propyl}-phenyl)-2-(1-methyl-2-phenyl-indolizin-3-yl)-2-oxo-acetamide,
N-{4-[4-(4,6-Dimethyl-pyridin-2-yl)-[1,4]diazepan-1-yl]-phenyl}-2-(5-methyl-2-phenyl-indolizin-3-yl)-2-oxo-acetamide,
N-{4-[4-(4,6-Dimethyl-pyridin-2-yl)-[1,4]diazepan-1-yl]-phenyl}-2-(6-methyl-2-phenyl-indolizin-3-yl)-2-oxo-acetamide,
N-{4-[4-(4,6-Dimethyl-pyridin-2-yl)-[1,4]diazepan-1-yl]-phenyl}-2-(6-methoxy-2-phenyl-indolizin-3-yl)-2-oxo-acetamide,
2-(6-Chloro-2-phenyl-indolizin-3-yl)-N-{4-[4-(4,6-dimethyl-pyridin-2-yl)-[1,4]diazepan-1-yl]-phenyl}-2-oxo-acetamide,
N-{4-[4-(4,6-Dimethyl-pyridin-2-yl)-[1,4]diazepan-1-yl]-phenyl}-2-(7-methyl-2-phenyl-indolizin-3-yl)-2-oxo-acetamide,
N-{4-[4-(4,6-Dimethyl-pyridin-2-yl)-[1,4]diazepan-1-yl]-phenyl}-2-(1-methyl-2-phenyl-indolizin-3-yl)-2-oxo-acetamide,
N-[4-({3-[(4,6-Dimethyl-pyridin-2-yl)-methyl-amino]-propyl}-methyl-amino)-phenyl]-2-(5-methyl-2-phenyl-indolizin-3-yl)-2-oxo-acetamide,
N-[4-({3-[(4,6-Dimethyl-pyridin-2-yl)-methyl-amino]-propyl}-methyl-amino)-phenyl]-2-(6-methyl-2-phenyl-indolizin-3-yl)-2-oxo-acetamide,
N-[4-({3-[(4,6-Dimethyl-pyridin-2-yl)-methyl-amino]-propyl}-methyl-amino)-phenyl]-2-(6-methoxy-2-phenyl-indolizin-3-yl)-2-oxo-acetamide,
2-(6-Chloro-2-phenyl-indolizin-3-yl)-N-[4-({3-[(4,6-dimethyl-pyridin-2-yl)-methyl-amino]-propyl}-methyl-amino)-phenyl]-2-oxo-acetamide,
N-[4-({3-[(4,6-Dimethyl-pyridin-2-yl)-methyl-amino]-propyl}-methyl-amino)-phenyl]-2-(7-methyl-2-phenyl-indolizin-3-yl)-2-oxo-acetamide, and
N-[4-({3-[(4,6-Dimethyl-pyridin-2-yl)-methyl-amino]-propyl}-methyl-amino)-phenyl]-2-(1-methyl-2-phenyl-indolizin-3-yl)-2-oxo-acetamide
and their pharmaceutically and agriculturally acceptable salts.

The structural similarity of these compounds to the other particularly preferred compounds also means that they are likely to have the same pharmacological effect.

Thus, suitable schemes and processes for their production, with reference to the examples section which follows, are:

(a) 2-[6-(3-Morpholin-4-yl-propoxy)-2-phenyl-indolizin-3-yl]-2-oxo-N-phenyl-acetamide

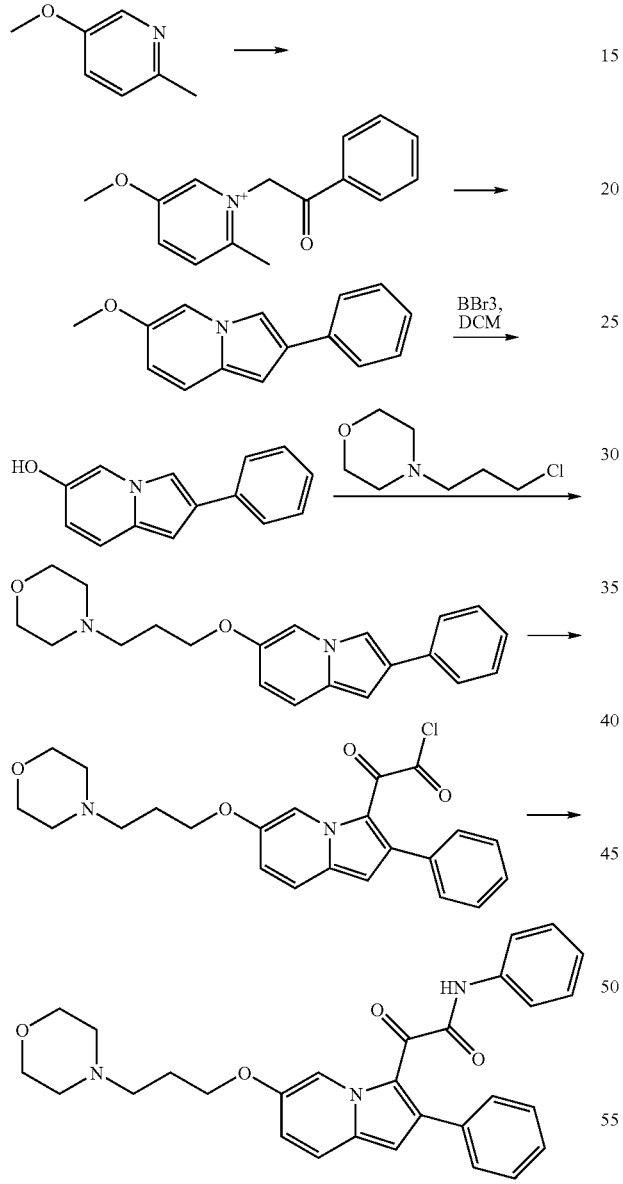

Reference Example 294 (reaction with oxalyl chloride). Step 6 is analogous to Example 1 (aniline coupling with acid chloride).

(b) 4-Methyl-piperazine-1-carboxylic acid 2-phenyl-3-phenylaminooxalyl-indolizin-1-ylmethyl ester

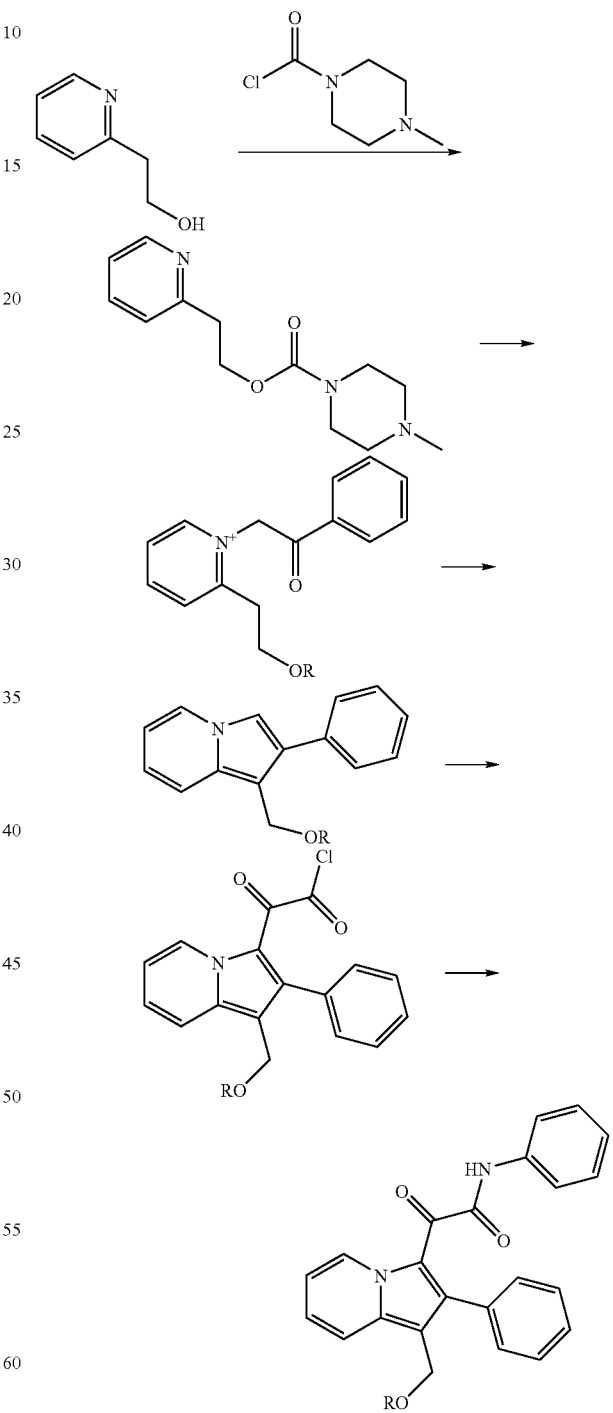

The starting material, 5-methoxy-2-methylpyridine, is commercially available. Step 1 is analogous to Reference Example 264 (alkylation of pyridine). Step 2 is analogous to Reference Example 279 (cyclisation in aqueous bicarbonate). Step 3 requires the reagent boron tribromide in dichloromethane. Step 4 is analogous to Reference Example 101 with 4-(3-Chloro-propyl)-morpholine. Step 5 is analogous to The starting materials, 2-pyridin-2-yl-ethanol and 4-methyl-piperazine-1-carbonyl chloride, are commercially available. Step 1 describes a carbamate preparation with triethylamine/DCM. Step 2 is analogous to Reference Example 264

(alkylation of pyridine). Step 3 is analogous to Reference Example 279 (cyclisation in aqueous bicarbonate). Step 4 is analogous to Reference Example 294 (reaction with oxalyl chloride). Step 5 is analogous to Example 1 (aniline coupling with acid chloride).

(c) 2-[2-(2-Chloro-phenyl)-indolizin-3-yl]-N-(2-ethyl-2,3,4,5-tetrahydro-1H-pyrido[4,3-b]indol-7-yl)-2-oxo-acetamide

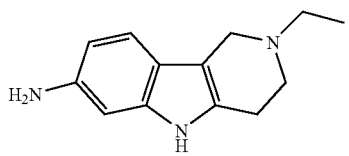 [SMILES: CCN1CCc2[nH]c3cc(N)ccc3c2C1]

This starting material for preparing this compound is prepared according to Synthetic Communications (2003), 33 (21), 3707-3716. It is then coupled with an acid chloride prepared in Reference Example 308, according to Example 1.

(d) N-(4-{3-[(Z)-Methoxyimino]-pyrrolidin-1-yl}-phenyl)-2-oxo-2-(2-phenyl-indolizin-3-yl)-acetamide

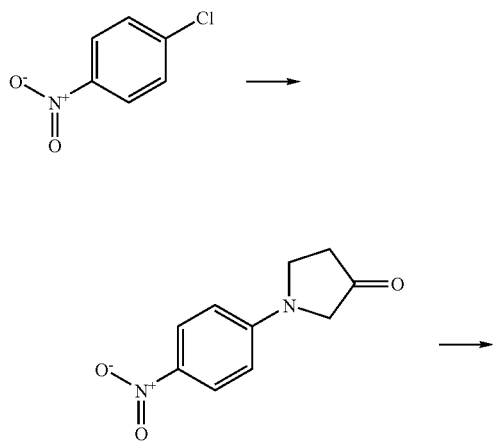

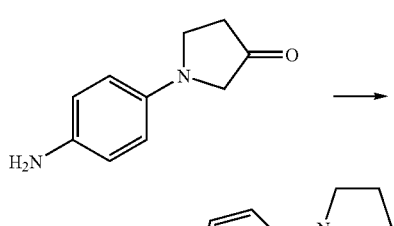

Step 1 is analogous to Reference Example 61. Step 2 is analogous to Reference Example 166, describing a Raney nickel reduction of the nitro group. Step 3 is analogous to Reference Example 247 (oxime preparation). Preparation of the final compound is analogous to Example 1.

(e) N-[4-(2-Morpholin-4-yl-ethyl)-phenyl]-2-oxo-2-(2-phenyl-indolizin-3-yl)-acetamide

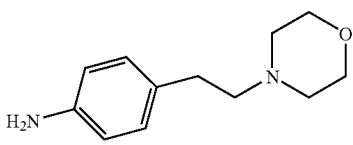 [SMILES: Nc1ccc(CCN2CCOCC2)cc1]

The starting material, 4-(2-morpholin-4-yl-ethyl)-phenylamine, is commercially-available. The final compound is then prepared in one step by a process analogous to Example 1.

(f) N-[4-(2-Morpholin-4-yl-ethoxy)-phenyl]-2-oxo-2-(2-phenyl-indolizin-3-yl)-acetamide

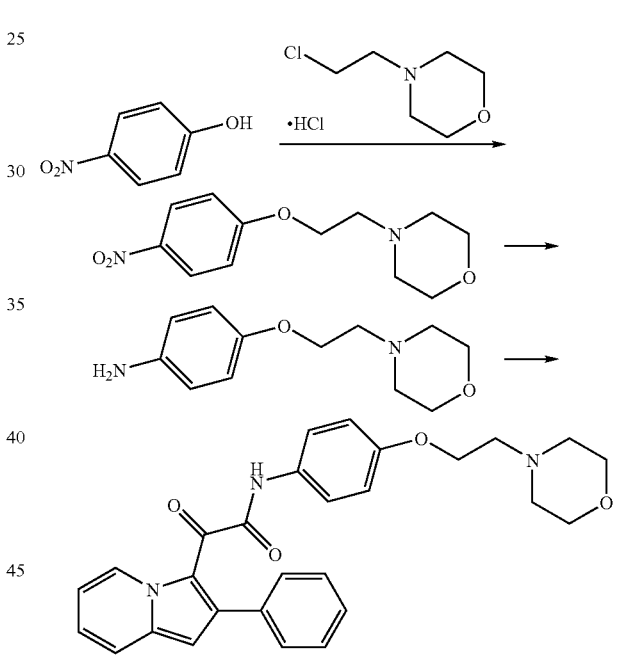

The starting material, 4-(2-chloro-ethyl)-morpholine hydrochloride, is commercially-available. Step 1 is analogous to Reference Example 101 (alkylation of phenol). Step 2 is analogous to Reference Example 166, describing a Raney nickel reduction of the nitro group. Step 3 is analogous to Example 1.

(g) 2-Oxo-2-[2-(2-oxo-1,2-dihydro-pyridin-3-yl)-indolizin-3-yl]-N-phenyl-acetamide

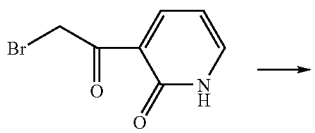

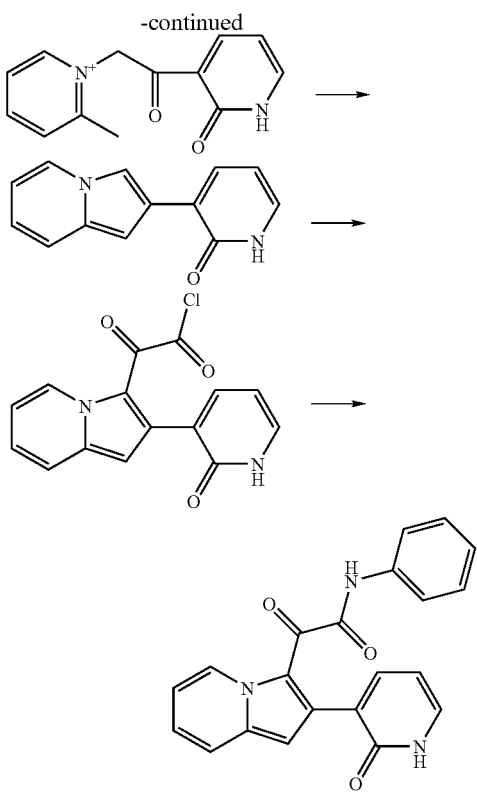

The starting material, 3-(2-bromo-acetyl)-1H-pyridin-2-one, is commercially available. Step 1 is analogous to Reference Example 264 (alkylation of pyridine). Step 2 is analogous to Reference Example 279 (cyclisation in aqueous bicarbonate). Step 3 is analogous to Reference Example 294 (reaction with oxalyl chloride). Step 4 is analogous to Example 1.

(h) 2-{2-[4-(4-Methyl-piperazin-1-yl)-phenyl]-indolizin-3-yl}-2-oxo-N-phenyl-acetamide

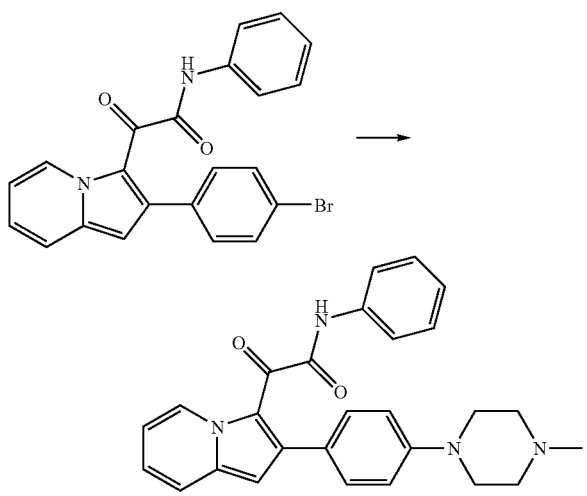

The starting material can be prepared from the compound of Reference Example 297, [2-(4-bromo-phenyl)-indolizin-3-yl]-oxo-acetyl chloride, and aniline. Step 1 describes a Buchwald reaction, e.g. with N-methylpiperazine, bis(triphenylphosphine) palladium(II) dichloride, cesium carbonate and DMF/toluene at 100° C.

In a final embodiment of the invention, there is provided a compound which is an indolizinyl derivative of formula (I) or a pharmaceutically acceptable salt thereof wherein:

X is a bond, —NR8-, —O—, —S—, —SO—, or —SO$_2$—;

$X^1$ is O or NOR9, wherein R9 is hydrogen or an unsubstituted or substituted C1-C4 alkyl group;

R1 and R8 independently represent hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR', and —Y—Z;

or when X is NR8, R1 and R8 together with the nitrogen to which they are attached may form an unsubstituted or substituted, aromatic or non-aromatic 5- to 12-membered heterocyclyl group;

A1 is an unsubstituted or substituted C6-C10 arylene group;

L1 is a bond, —NR'—, —O—, —CO—, —OCO—, —OCONR'R" or —CONR'R"—;

L2 is a substituted or unsubstituted C1-C4 alkylene or C2-C4 alkenylene group;

A2 is an unsubstituted or substituted C6-C10 aryl or 5- to 12-membered-heterocyclyl group wherein either (i) A2 is substituted by 3 or 4, more preferably by 4, substituents selected from unsubstituted substituents halogen atoms, hydroxyl groups or C1-C6 alkyl (for example methyl, ethyl, propyl and pentyl groups and their isomers) or C1-C4 alkyl substituted with 1 or 2 C1-C4 alkoxy groups; or (ii) A2 is substituted by 1 or 2, more preferably by 1, substituents which are C4-C8 alkyl groups, more preferably unsubstituted C4-C8 alkyl groups, more preferably unsubstituted C5 alkyl groups;

R2 is an unsubstituted or substituted group selected from C6-C10 aryl, a 5- to 12-membered heterocyclyl group, C1-C8 alkyl and C3-C6 cycloalkyl, or halogen;

R3, R4, R5 and R6 independently represent C6-C10 aryl, a 5- to 12-membered heterocyclyl group, —(C1-C4 alkylene)-(C6-C10 aryl), —(C1-C4 alkylene)-(5- to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R", —SO$_3$H, —NR'R", —NR'COR', —NO$_2$, —CO$_2$R', —CONR'R", —COR', —OCOR', —CN, —CF$_3$—NSO$_2$R', —OCONR'R" or —CR'=NOR"; and R' and R" independently represent hydrogen, C1-C8 alkyl, C2-C8 alkenyl or C2-C8 alkynyl, with the proviso that the compound is not N-(2-Methoxy-phenyl)-2-oxo-2-(2-phenyl-indolizin-3-yl)-acetamide, 4-[2-Oxo-2-(2-phenyl-indolizin-3-yl)-acetylamino]-benzoic acid methyl ester, 2-Oxo-N-phenyl-2-(2-phenyl-indolizin-3-yl)-acetamide, 4-[2-Oxo-2-(-phenyl-indolizin-3-yl)-acetylamino]-benzoic acid propyl ester, 2-[2-Oxo-2-(2-phenyl-indolizin-3-yl)-acetylamino]-benzoic acid methyl ester, 3-[2-Oxo-2-(2-phenyl-indolizin-3-yl)-acetylamino]-benzoic acid methyl ester, 4-[2-Oxo-2-(2-phenyl-indolizin-3-yl)-acetylamino]-benzoic acid butyl ester,
N-(3-Methoxy-phenyl)-2-oxo-2-(2-phenyl-indolizin-3-yl)-acetamide,
N-(4-Methoxy-phenyl)-2-oxo-2-(2-phenyl-indolizin-3-yl)-acetamide,
N-(4-Hydroxy-phenyl)-2-oxo-2-(2-phenyl-indolizin-3-yl)-acetamide,
N-(4-Chloro-phenyl)-2-oxo-2-(2-phenyl-indolizin-3-yl)-acetamide,
N-(4-Cyano-phenyl)-2-oxo-2-(2-phenyl-indolizin-3-yl)-acetamide,
2-Oxo-2-(2-phenyl-indolizin-3-yl)-N-p-tolyl-acetamide,
2-Oxo-2-(2-phenyl-indolizin-3-yl)-N-pyridin-4-yl-acetamide,
2-Oxo-2-(2-phenyl-indolizin-3-yl)-N-pyridin-3-yl-acetamide,
2-Oxo-2-(2-phenyl-indolizin-3-yl)-N-pyridin-2-yl-acetamide,
4-[2-Oxo-2-(2-phenyl-indolizin-3-yl)-acetylamino]-benzoic acid,
N-(2,4-Dimethoxy-phenyl-phenyl)-2-oxo-2-(2-phenyl-indolizin-3-yl)-acetamide,
N-(6-Methoxy-pyridin-3-yl)-2-oxo-2-(2-phenyl-indolizin-3-yl)-acetamide,
4-[2-Oxo-2-(2-phenyl-indolizin-3-yl)-acetylamino]-benzamide,
N-Methyl-4-[2-oxo-2-(2-phenyl-indolizin-3-yl)-acetylamino]-benzamide,
N,N-Dimethyl-4-[2-oxo-2-(2-phenyl-indolizin-3-yl)-acetamino]-benzamide,
5-[2-Oxo-2-(2-phenyl-indolizin-3-yl)-acetylamino]-thiophene-3-carboxylic acid methyl ester,
N-(4-Methoxy-phenyl)-2-oxo-2-(2-pyridin-4-yl-indolizin-3-yl)-acetamide,
N-(4-Methoxy-phenyl)-2-oxo-2-(2-pyridin-3-yl-indolizin-3-yl)-acetamide,
N-(4-Methoxy-phenyl)-2-oxo-2-(2-pyridin-2-yl-indolizin-3-yl)-acetamide,
N-(4-Methoxy-phenyl)-2-oxo-2-(2-thiophen-2-yl-indolizin-3-yl)-acetamide,
2-(2-Furan-2-yl-indolizin-3-yl)-N-(4-methoxy-phenyl)-2-oxo-acetamide,
2-[2-(4-Fluoro-phenyl)-indolizin-3-yl]-N-(4-methoxy-phenyl)-2-oxo-acetamide,
2-[2-(4-Fluoro-phenyl)-indolizin-3-yl]-2-oxo-N-p-tolyl-acetamide,
N-(2-,4-Dimethoxy-phenyl)-2-[2-(4-fluoro-phenyl)-indolizin-3-yl]-2-oxo-acetamide,
2-[2-(4-Fluoro-phenyl)-indolizin-3-yl]-N-(6-methoxy-pyridin-3-yl)-2-oxo-acetamide,
2-Oxo-2-(2-thiophen-2-yl-indolizin-3-yl)-N-p-tolyl-acetamide,
N-(2,4-Dimethoxy-phenyl)-2-oxo-2-(2-thiophen-2-yl-indolizin-3-yl)-acetamide,
N-(6-Methoxy-pyridin-3-yl)-2-oxo-2-(2-thiophen-2-yl-indolizin-3-yl)-acetamide,
2-(2-Furan-2-yl-indolizin-3-yl)-2-oxo-N-p-tolyl-acetamide,
N-(2,4-Dimethoxy-phenyl)-2-(2-furan-2-yl-indolizin-3-yl)-2-oxo-acetamide,
2-(2-Furan-2-yl-indolizin-3-yl)-N-(6-methoxy-pyridin-3-yl)-2-oxo-acetamide,
2-Oxo-2-(2-pyridin-4-yl-indolizin-3-yl)-N-p-tolyl-acetamide,
N-(2,4-Dimethoxy-phenyl)-2-oxo-2-(2-pyridin-4-yl-indolizin-3-yl)-acetamide,
N-(6-Methoxy-pyridin-3-yl)-2-oxo-2-(2-pyridin-4-yl-indolizin-3-yl)-acetamide,
2-Oxo-2-(2-pyridin-3-yl-indolizin-3-yl)-N-p-tolyl-acetamide,
N-(2,4-Dimethoxy-phenyl)-2-oxo-2-(2-pyridin-3-yl-indolizin-3-yl)-acetamide,
N-(6-Methoxy-pyridin-3-yl)-2-oxo-2-(2-pyridin-3-yl-indolizin-3-yl)-acetamide,
2-Oxo-2-(2-pyridin-2-yl-indolizin-3-yl)-N-p-tolyl-acetamide,
N-(2,4-Dimethoxy-phenyl)-2-oxo-2-(2-pyridin-2-yl-indolizin-3-yl)-acetamide,
N-(6-Methoxy-pyridin-3-yl)-2-oxo-2-(2-pyridin-2-yl-indolizin-3-yl)-acetamide,
Oxo-(2-phenyl-indolizin-3-yl)-thioacetic acid S-(2-methoxy-phenyl)ester,
4-[2-Oxo-2-(2-phenyl-indolizin-3-yl)-acetoxy]-benzoic acid methyl ester,
N-Cyclohexyl-2-oxo-2-(2-phenyl-indolizin-3-yl)-acetamide,
N-Methyl-2-oxo-2-(2-phenyl-indolizin-3-yl)-acetamide,
N-Isopropyl-2-oxo-2-(2-phenyl-indolizin-3-yl)-acetamide,
N-(2-Methoxy-ethyl)-2-oxo-2-(2-phenyl-indolizin-3-yl)-acetamide,
N-Benzyl-2-oxo-2-(2-phenyl-indolizin-3-yl)-acetamide,
N,N-Dimethyl-2-oxo-2-(2-phenyl-indolizin-3-yl)-acetamide,
1-(2-Phenyl-indolizin-3-yl)-2-piperidin-1-yl-ethane-1,2-dione,
N-(2-Methoxy-ethyl)-2-oxo-2-(2-pyridin-3-yl-indolizin-3-yl)-acetamide,
N-Methyl-2-oxo-N-phenyl-2-(2-phenyl-indolizin-3-yl)-acetamide,
N-Methyl-2-oxo-N-phenyl-2-(2-pyridin-3-yl-indolizin-3-yl)-acetamide,
2-(5-Methyl-2-phenyl-indolizin-3-yl)-2-oxo-N-p-tolyl-acetamide,
N-(6-Methoxy-pyridin-3-yl)-2-(5-methyl-2-phenyl-indolizin-3-yl)-2-oxo-acetamide,
2-(6-Methyl-2-phenyl-indolizin-3-yl)-2-oxo-N-p-tolyl-acetamide,
2-(7-Methyl-2-phenyl-indolizin-3-yl)-2-oxo-N-p-tolyl-acetamide,
N-(6-Methoxy-pyridin-3-yl)-2-(6-methyl-2-phenyl-indolizin-3-yl)-2-oxo-acetamide,
N-(6-Methoxy-pyridin-3-yl)-2-(7-methyl-2-phenyl-indolizin-3-yl)-2-oxo-acetamide,
N-(6-Methoxy-pyridin-3-yl)-2-(8-methyl-2-phenyl-indolizin-3-yl)-2-oxo-acetamide,
2-(6-Methoxy-2-phenyl-indolizin-3-yl)-N-(6-methoxy-pyridin-3-yl)-2-oxo-acetamide,
2-(6-Methoxy-2-phenyl-indolizin-3-yl)-2-oxo-N-p-tolyl-acetamide,
N-(4-Chloro-phenyl)-2-oxo-2-(2-pyridin-3-yl-indolizin-3-yl)-acetamide,
N-(4-Fluoro-phenyl)-2-oxo-2-(2-pyridin-3-yl-indolizin-3-yl)-acetamide,
2-(6-Methyl-2-pyridin-3-yl-indolizin-3-yl)-2-oxo-N-p-tolyl-acetamide,
N-(4-Fluoro-phenyl)-2-oxo-2-(2-phenyl-indolizin-3-yl)-acetamide,
N-(2-Fluoro-phenyl)-2-oxo-2-(2-phenyl-indolizin-3-yl)-acetamide,
2-Oxo-2-(2-phenyl-indolizin-3-yl)-N-(4-trifluoromethyl-phenyl)-acetamide,
2-Oxo-2-(2-phenyl-indolizin-3-yl)-N-o-tolyl-acetamide, N-(4-Dimethylamino-phenyl)-2-oxo-2-(2-phenyl-indolizin-3-yl)-acetamide,
N-(4-Bromo-phenyl)-2-oxo-2-(2-phenyl-indolizin-3-yl)-acetamide,
N-(4-Acetyl-phenyl)-2-oxo-2-(2-phenyl-indolizin-3-yl)-acetamide,
2-Oxo-2-(2-phenyl-indolizin-3-yl)-N-m-tolyl-acetamide,
N-(2-Chloro-phenyl)-2-oxo-2-(2-phenyl-indolizin-3-yl)-acetamide,
2-[2-Oxo-2-(2-phenyl-indolizin-3-yl)-acetylamino]-benzoic acid ethyl ester,
N-(2,4-Dichloro-phenyl)-2-oxo-2-(2-phenyl-indolizin-3-yl)-acetamide,
N-(4-Fluoro-phenyl)-2-[2-(4-fluoro-phenyl)-indolizin-3-yl]-2-oxo-acetamide,
N-(4-Chloro-phenyl)-2-[2-(4-fluoro-phenyl)-indolizin-3-yl]-2-oxo-acetamide,
N-(2-Fluoro-phenyl)-2-oxo-2-(2-pyridin-3-yl-indolizin-3-yl)-acetamide,
2-Oxo-2-(2-pyridin-3-yl-indolizin-3-yl)-N-(4-trifluoromethyl-phenyl)-acetamide,
2-Oxo-2-(2-pyridin-3-yl-indolizin-3-yl)-N-o-tolyl-acetamide,
N-(4-Bromo-phenyl)-2-oxo-2-(2-pyridin-3-yl-indolizin-3-yl)-acetamide,
2-Oxo-2-(2-pyridin-3-yl-indolizin-3-yl)-N-m-tolyl-acetamide,
N-(2-Chloro-phenyl)-2-oxo-2-(2-pyridin-3-yl-indolizin-3-yl)-acetamide,
N-(4-Acetyl-phenyl)-2-oxo-2-(2-pyridin-3-yl-indolizin-3-yl)-acetamide,
2-Oxo-2-(2-phenyl-indolizin-3-yl)-N-(3-trifluoromethyl-phenyl)-acetamide,
1-(2,3-Dihydro-indol-1-yl)-2-(2-phenyl-indolizin-3-yl)-ethane-1,2-dione,
N-(4-Methanesulfonylamino-phenyl)-2-oxo-2-(2-phenyl-indolizin-3-yl)-acetamide,
N-(3,5-Dichloro-phenyl)-2-oxo-2-(2-phenyl-indolizin-3-yl)-acetamide,
N-[4-(Cyano-dimethyl-methyl)-phenyl]-2-oxo-2-(2-phenyl-indolizin-3-yl)-acetamide,
2-Oxo-2-(2-phenyl-indolizin-3-yl)-N-(3,4,5-trimethoxy-phenyl)-acetamide,
2-Oxo-2-(2-pyridin-3-yl-indolizin-3-yl)-N-(3-trifluoromethyl-phenyl)-acetamide,
N-(2,4-Dichloro-phenyl)-2-oxo-2-(2-pyridin-3-yl-indolizin-3-yl)-acetamide,
N-[4-(Cyano-dimethyl-methyl)-phenyl]-2-oxo-2-(2-pyridin-3-yl-indolizin-3-yl)-acetamide,
2-Oxo-2-(2-pyridin-3-yl-indolizin-3-yl)-N-(3,4,5-trimethoxy-phenyl)-acetamide,
N-(3,5-Dichloro-phenyl)-2-oxo-2-(2-pyridin-3-yl-indolizin-3-yl)-acetamide,
N-[3-(Cyano-dimethyl-methyl)-phenyl]-2-oxo-2-(2-phenyl-indolizin-3-yl)-acetamide,
N-(6-Dimethylamino-pyridin-3-yl)-2-oxo-2-(2-phenyl-indolizin-3-yl)-acetamide,
N-(4-Dimethylamino-phenyl)-2-oxo-2-(2-pyridin-3-yl-indolizin-3-yl)-acetamide,
N-[3-(Cyano-dimethyl-methyl)-phenyl]-2-oxo-2-(2-pyridin-3-yl-indolizin-3-yl)-acetamide,
2-[(E/Z)-Methoxyimino]-N-(4-methoxy-phenyl)-2-(2-phenyl-indolizin-3-yl)-acetamide,
N-(4-Methoxy-phenyl)-2-oxo-2-(2-o-tolyl-indolizin-3-yl)-acetamide,
N-(4-Methoxy-phenyl)-2-oxo-2-(2-m-tolyl-indolizin-3-yl)-acetamide,
N-(4-Methoxy-phenyl)-2-(8-methyl-2-phenyl-indolizin-3-yl)-2-oxo-acetamide,
2-[2-(3-Chloro-phenyl)-indolizin-3-yl]-N-(4-methoxy-phenyl)-2-oxo-acetamide,
2-[2-(3-Cyano-phenyl)-indolizin-3-yl]-N-(4-methoxy-phenyl)-2-oxo-acetamide,
N-(4-Methoxy-phenyl)-2-(5-methyl-2-phenyl-indolizin-3-yl)-2-oxo-acetamide,
N-(4-Methoxy-phenyl)-2-oxo-2-(2-p-tolyl-indolizin-3-yl)-acetamide,
N-(4-Methoxy-phenyl)-2-(6-methoxy-2-phenyl-indolizin-3-yl)-2-oxo-acetamide,
N-[3-(2-Dimethylamino-ethoxy)-phenyl]-2-oxo-2-(2-phenyl-indolizin-3-yl)-acetamide,
N-(3-Methyl-3H-benzoimidazol-5-yl)-2-oxo-2-(2-phenyl-indolizin-3-yl)-acetamide,
N-(1-Methyl-1H-benzoimidazol-5-yl)-2-oxo-2-(2-phenyl-indolizin-3-yl)-acetamide,
N-(4-Dimethylamino-phenyl)-2-(6-methoxy-2-phenyl-indolizin-3-yl)-2-oxo-acetamide,
N-(4-{1-[(E/Z)-Methoxyimino]-ethyl}-phenyl)-2-oxo-2-(2-phenyl-indolizin-3-yl)-acetamide,
N-(2,4-Difluoro-phenyl)-2-[2-(3-fluoro-phenyl)-indolizin-3-yl]-2-oxo-acetamide,
2-[2-(3-Cyano-phenyl)-indolizin-3-yl]-N-(2,4-difluoro-phenyl)-2-oxo-acetamide,
N-(5-Chloro-2-methyl-phenyl)-2-oxo-2-(2-phenyl-indolizin-3-yl)-acetamide,
{3-[2-Oxo-2-(2-phenyl-indolizin-3-yl)-acetylamino]-phenoxy}-acetic acid,
N-(2-Allyloxy-4-fluoro-phenyl)-2-oxo-2-(2-phenyl-indolizin-3-yl)-acetamide,
2-Methyl-2-[2-oxo-2-(2-phenyl-indolizin-3-yl)-acetylamino]-propionic acid ethyl ester,
2-Methyl-2-[2-oxo-2-(2-phenyl-indolizin-3-yl)-acetylamino]-3-phenyl-propionic acid ethyl ester,
N-(4-{1-[(E/Z)-Hydroxyimino]-ethyl}-phenyl)-2-oxo-2-(2-phenyl-indolizin-3-yl)-acetamide,
2-Oxo-2-(2-phenyl-indolizin-3-yl)-N-(4-piperidin-1-yl-phenyl)-acetamide,
N-(4-Morpholin-4-yl-phenyl)-2-oxo-2-(2-phenyl-indolizin-3-yl)-acetamide,
N-(4-Isopropyl-phenyl)-2-oxo-2-(2-phenyl-indolizin-3-yl)-acetamide,
N-(6-Dimethylamino-pyridin-3-yl)-2-oxo-2-(2-pyridin-3-yl-indolizin-3-yl)-acetamide,
2-[(E/Z)-2-Dimethylamino-ethoxyimino]-N-(4-methoxy-phenyl)-2-(2-phenyl-indolizin-3-yl)-acetamide,
2-[(E/Z)-3-Dimethylamino-propoxyimino]-N-(4-methoxy-phenyl)-2-(2-phenyl-indolizin-3-yl)-acetamide,
N-(3-Allyl-4-fluoro-2-methoxy-phenyl)-2-oxo-2-(2-phenyl-indolizin-3-yl)-acetamide,
N-[4-(1-Hydroxy-ethyl)-phenyl]-2-oxo-2-(2-phenyl-indolizin-3-yl)-acetamide,
N-(1-Methyl-1H-indol-5-yl)-2-oxo-2-(2-phenyl-indolizin-3-yl)-acetamide,
N-(4-Methanesulfonyl-phenyl)-2-oxo-2-(2-phenyl-indolizin-3-yl)-acetamide,
4-[1-(4-Methoxy-phenylcarbamoyl)-1-(2-phenyl-indolizin-3-yl)-meth-(E/Z)-ylideneaminooxy]-butyric acid,
2-Oxo-2-(2-phenyl-indolizin-3-yl)-N-(4-thiomorpholin-4-yl-phenyl)-acetamide,
2-Oxo-2-(2-phenyl-indolizin-3-yl)-N-(2,3,4-trimethyl-phenyl)-acetamide,
2-Oxo-2-(2-phenyl-indolizin-3-yl)-N-(4-pyrrolidin-1-yl-phenyl)-acetamide, N-(1-Methyl-2,3-dihydro-1H-indol-5-yl)-2-oxo-2-(2-phenyl-indolizin-3-yl)-acetamide,
N-[4-(4-Methyl-piperazin-1-yl)-phenyl]-2-oxo-2-(2-phenyl-indolizin-3-yl)-acetamide,
N-Benzyl-N-methyl-3-[2-oxo-2-(2-phenyl-indolizin-3-yl)-acetylamino]-benzamide,
N-[4-(2-Methyl-[1,3]dioxolan-2-yl)-phenyl]-2-oxo-2-(2-phenyl-indolizin-3-yl)-acetamide,
N-(2,4-Difluoro-phenyl)-2-[2-(2,4-difluoro-phenyl)-indolizin-3-yl]-2-oxo-acetamide,
Diethyl-carbamic acid 3-[2-oxo-2-(2-phenyl-indolizin-3-yl)-acetylamino]-phenyl ester,
N-(3-Acetyl-phenyl)-2-oxo-2-(2-phenyl-indolizin-3-yl)-acetamide,
1-Methyl-4-{4-[2-oxo-2-(2-phenyl-indolizin-3-yl)-acetylamino]-phenyl}-thiomorpholin-1-ium,
N-(4-Oxazol-2-yl-phenyl)-2-oxo-2-(2-phenyl-indolizin-3-yl)-acetamide,
N-(2,4-Difluoro-phenyl)-2-[2-(2-methoxy-phenyl)-indolizin-3-yl]-2-oxo-acetamide,
2-Oxo-2-(2-phenyl-indolizin-3-yl)-N-[4-(pyridin-2-ylamino)-phenyl]-acetamide,
2-Oxo-2-(2-phenyl-indolizin-3-yl)-N-[4-(1H-tetrazol-5-yl)-phenyl]-acetamide,
2-Oxo-N-[4-(4-oxo-piperidin-1-yl)-phenyl]-2-(2-phenyl-indolizin-3-yl)-acetamide,
N-(4-Dimethylamino-3-methyl-phenyl)-2-oxo-2-(2-phenyl-indolizin-3-yl)-acetamide,
2-Dimethylamino-5-[2-oxo-2-(2-phenyl-indolizin-3-yl)-acetylamino]-benzoic acid,
1-{4-[2-Oxo-2-(2-phenyl-indolizin-3-yl)-acetylamino]-phenyl}-pyrrolidine-2-carboxylic acid methyl ester,
2-Oxo-2-(2-phenyl-indolizin-3-yl)-N-[4-(pyrimidin-2-ylamino)-phenyl]-acetamide,
2-[2-(2-Chloro-phenyl)-indolizin-3-yl]-N-(2,4-difluoro-phenyl)-2-oxo-acetamide,
N-(4-Dimethylaminomethyl-phenyl)-2-oxo-2-(2-phenyl-indolizin-3-yl)-acetamide,
N-(3-Acetyl-4-methoxy-phenyl)-2-oxo-2-(2-phenyl-indolizin-3-yl)-acetamide,
2-[2-(2-Methyl-pyridin-3-yl)-indolizin-3-yl]-2-oxo-N-[4-(2,2,3,3-tetrafluoro-propoxy)-phenyl]-acetamide,
2-Oxo-N-[4-(2-oxo-propyl)-phenyl]-2-(2-phenyl-indolizin-3-yl)-acetamide,
2-Oxo-2-(2-phenyl-indolizin-3-yl)-N-[4-(thiazol-2-ylamino)-phenyl]-acetamide,
2-Oxo-N-[6-(2,2,3,3-tetrafluoro-propoxy)-pyridin-3-yl]-2-(2-o-tolyl-indolizin-3-yl)-acetamide,
N-[4-(3,5-Dimethyl-isoxazol-4-yl)-phenyl]-2-oxo-2-(2-phenyl-indolizin-3-yl)-acetamide,
N-(3-Oxazol-2-yl-phenyl)-2-oxo-2-(2-phenyl-indolizin-3-yl)-acetamide,
N-(6-Dipropylamino-pyridin-3-yl)-2-oxo-2-(2-phenyl-indolizin-3-yl)-acetamide,
N-(4-Diethylamino-3-methyl-phenyl)-2-oxo-2-(2-phenyl-indolizin-3-yl)-acetamide,
N-(4-Oxazol-5-yl-phenyl)-2-oxo-2-(2-phenyl-indolizin-3-yl)-acetamide,
N-(4-Dimethylamino-3-oxazol-2-yl-phenyl)-2-oxo-2-(2-phenyl-indolizin-3-yl)-acetamide,
2-Oxo-2-(2-phenyl-indolizin-3-yl)-N-(4-thiazol-2-yl-phenyl)-acetamide,
1-Morpholin-4-yl-2-(2-phenyl-indolizin-3-yl)-ethane-1,2-dione,
1-Azepan-1-yl-2-(2-phenyl-indolizin-3-yl)-ethane-1,2-dione,
N-Ethyl-2-oxo-N-phenyl-2-(2-phenyl-indolizin-3-yl)-acetamide,
N-(1,5-Dimethyl-3-oxo-2-phenyl-2,3-dihydro-1H-pyrazol-4-yl)-2-oxo-2-(2-phenyl-indolizin-3-yl)-acetamide,
6-Hydroxy-alpha-oxo-2-phenyl-3-indolizineacetic acid ethyl ester,
5-Methyl-alpha-oxo-2-phenyl-3-indolizineacetic acid ethyl ester,
Ethyl 2-(2,5-dimethylindolizin-3-yl)-2-oxoacetate,
2-(p-Bromophenyl)-1-phenyl-3-indolizineglyoxylic acid ethyl ester,
1-[[2-(p-Bromophenyl)-1-(p-chlorophenyl)-3-indolizinyl]glyoxyloyl]-piperidine,
1-(p-Chlorophenyl)-2-(p-nitrophenyl)-3-indolizineglyoxylic acid ethyl ester,
2-(p-Nitrophenyl)-1-phenyl-3-indolizineglyoxylic acid,
1-[[2-(p-Bromophenyl)-1-phenyl-3-indolizinyl]glyoxyloyl]-piperidine,
1-(p-Chlorophenyl)-2-(p-nitrophenyl)-3-indolizineglyoxylic acid,
2-(p-Bromophenyl)-1-(p-chlorophenyl)-3-indolizineglyoxylic acid ethyl ester
2-(p-Bromophenyl)-1-(p-chlorophenyl)-3-indolizineglyoxylic acid,
2-(p-Bromophenyl)-1-phenyl-3-indolizineglyoxylic acid,
1-[[1-(p-Chlorophenyl)-2-(p-nitrophenyl)-3-indolizinyl]glyoxyloyl]-piperidine,
1-[[2-(p-Nitrophenyl)-1-phenyl-3-indolizinyl]glyoxyloyl]-piperidine,
2-(p-Nitrophenyl)-1-phenyl-3-indolizineglyoxylic acid ethyl ester,
N,N-dimethyl-2-oxo-2-(2-phenyl-indolizin-3-yl)-acetamide,
2-(2-methylindolizin-3-yl)-2-oxo acetic acid,
alpha-Oxo-2-phenyl-N-(4,5,6,7-tetrahydro-2-benzothiazolyl)-3-indolizineacetamide,
N-Cyclohexyl-alpha-oxo-2-phenyl-3-indolizineacetamide,
N-(2,4-Dimethyl-5-nitrophenyl)-alpha-oxo-2-phenyl-3-indolizineacetamide,
N-[3-[(Diethylamino)sulfonyl]phenyl]-alpha-oxo-2-phenyl-3-indolizineacetamide,
N-[2-[4-(Aminosulfonyl)phenyl]ethyl]-alpha-oxo-2-phenyl-3-indolizineacetamide,
2-Chloro-4-fluoro-benzoic acid 3-[[oxo-(2-phenyl-3-indolizinyl)acetyl]amino]propyl ester,
N-[2-(1,1-Dimethylethyl)phenyl]-alpha-oxo-2-phenyl-3-indolizineacetamide,
N-(3-Bromophenyl)-alpha-oxo-2-phenyl-3-indolizineacetamide,
3,5-Dimethyl-1-[oxo(2-phenyl-3-indolizinyl)acetyl]-piperidine,
N-(2-Hydroxyethyl)-alpha-oxo-2-phenyl-3-indolizineacetamide,
N-[2-[(4-Nitrobenzoyl)oxy]ethyl]-alpha-oxo-2-phenyl-3-indolizineacetamide,
2-(4-Chlorophenyl)-alpha-oxo-3-Indolizineacetic acid (2-fluorophenyl)methyl ester,
4-Fluoro-benzoic acid 2-[[[2-(4-chlorophenyl)-3-indolizinyl]oxoacetyl]amino]ethyl ester,
1-[[2-(4-Chlorophenyl)-3-indolizinyl]oxoacetyl]hexahydro-1H-azepine,
2-(4-Chlorophenyl)-alpha-oxo-3-indolizineacetic acid cyclopentyl ester,
2-(4-Chlorophenyl)-N-(2-hydroxyethyl)-alpha-oxo-3-indolizineacetamide,
4-(1,1-Dimethylethyl)-benzoic acid 2-[[[2-(4-chlorophenyl)-3-indolizinyl]oxoacetyl]amino]ethyl ester, 1-[Oxo(2-phenyl-3-indolizinyl)acetyl]-4-phenyl-piperazine,
2,6-Dimethyl-4-[oxo(2-phenyl-3-indolizinyl)acetyl]-morpholine,
N-1,3-Benzodioxol-5-yl-2-(4-chlorophenyl)-alpha-oxo-3-indolizineacetamide,
N-(4-Ethoxyphenyl)-alpha-oxo-2-phenyl-3-indolizineacetamide,
N-(2,4-Dimethylphenyl)-alpha-oxo-2-phenyl-3-indolizineacetamide,
N-(3-Hydroxypropyl)-alpha-oxo-2-phenyl-3-indolizineacetamide,
N-Methyl-N-(1-methyl-4-piperidinyl)-alpha-oxo-2-phenyl-3-indolizineacetamide,
N-[3-[(Diethylamino)sulfonyl]-4-methylphenyl]-alpha-oxo-2-phenyl-3-indolizineacetamide,
N-(6-Methoxy-3-pyridinyl)-alpha-oxo-2-phenyl-3-indolizineacetamide,
N-(3-Methoxyphenyl)-alpha-oxo-2-phenyl-3-indolizineacetamide,
N-[4-Methyl-3-(4-morpholinylsulfonyl)phenyl]-alpha-oxo-2-phenyl-3-indolizineacetamide,
alpha-Oxo-2-phenyl-N-[3-(1-piperidinylsulfonyl)phenyl]-3-indolizineacetamide,
N-(4-Chloro-2-methoxy-5-methylphenyl)-alpha-oxo-2-phenyl-3-indolizineacetamide,
N-(2-Chloro-3-pyridinyl)-alpha-oxo-2-phenyl-3-indolizineacetamide,
N-[2-[[(4-Chlorophenyl)amino]carbonyl]phenyl]-alpha-oxo-2-phenyl-3-indolizineacetamide,
N-[5-[(Diethylamino)sulfonyl]-2-(4-morpholinyl)phenyl]-alpha-oxo-2-phenyl-3-indolizineacetamide,
alpha-Oxo-N-(3-phenoxyphenyl)-2-phenyl-3-indolizineacetamide,
alpha-Oxo-2-phenyl-N-[4-(trifluoromethyl)phenyl]-3-indolizineacetamide,
alpha-Oxo-2-phenyl-N-[4-(1-piperidinyl)phenyl]-3-indolizineacetamide,
4-Chloro-2-nitro-benzoic acid 3-[[oxo(2-phenyl-3-indolizinyl)acetyl]amino]propyl ester,
3-[(2,6-Dimethyl-4-morpholinyl)sulfonyl]-benzoic acid 3-[[oxo(2-phenyl-3-indolizinyl)acetyl]amino]propyl ester,
N-(2,3-Dihydro-1,5-dimethyl-3-oxo-2-phenyl-1H-pyrazol-4-yl)-alpha-oxo-2-phenyl-3-indolizineacetamide,
N-(3,5-Dimethoxyphenyl)-alpha-oxo-2-phenyl-3-indolizineacetamide,
N-(3-Chloro-4-fluorophenyl)-alpha-oxo-2-phenyl-3-indolizineacetamide,
N-[4-[(Diethylamino)sulfonyl]phenyl]-alpha-oxo-2-phenyl-3-indolizineacetamide,
N-(3,4-Dimethylphenyl)-alpha-oxo-2-phenyl-3-indolizineacetamide,
alpha-Oxo-N-(2-phenoxyphenyl)-2-phenyl-3-indolizineacetamide,
N-[5-(1,1-Dimethylethyl)-2-methoxyphenyl]-alpha-oxo-2-phenyl-3-indolizineacetamide,
alpha-Oxo-2-phenyl-N-[4-(1-piperidinylsulfonyl)phenyl]-3-indolizineacetamide,
N-(2,3-Dimethylphenyl)-alpha-oxo-2-phenyl-3-indolizineacetamide,
N-(4-Bromo-2-fluorophenyl)-alpha-oxo-2-phenyl-3-indolizineacetamide,
N-2-Naphthalenyl-alpha-oxo-2-phenyl-3-indolizineacetamide,
N-[2-Chloro-5-(4-morpholinylsulfonyl)phenyl]-alpha-oxo-2-phenyl-3-indolizineacetamide,
2,3-Dichloro-benzoic acid 3-[[oxo(2-phenyl-3-indolizinyl)acetyl]amino]propyl ester,
3,4-Dichloro-benzoic acid 3-[[oxo(2-phenyl-3-indolizinyl)acetyl]amino]propyl ester,
N-(2,4-Dimethoxyphenyl)-alpha-oxo-2-phenyl-3-indolizineacetamide,
2-(4-Chlorophenyl)-alpha-oxo-N-phenyl-3-indolizineacetamide,
4-[[2-(4-Chlorophenyl)-3-indolizinyl]oxoacetyl]-morpholine,
N-Ethyl-alpha-oxo-2-phenyl-3-indolizineacetamide,
alpha-Oxo-2-phenyl-N-[3-(trifluoromethyl)phenyl]-3-indolizineacetamide,
4-[[Oxo(2-phenyl-3-indolizinyl)acetyl]amino]-benzoic acid methyl ester,
N,N-Diethyl-alpha-oxo-2-phenyl-3-indolizineacetamide,
N-[2-(Dimethylamino)ethyl]-alpha-oxo-2-phenyl-3-indolizineacetamide,
2-Methyl-alpha-oxo-3-indolizineacetic acid,
N-(2-Methoxyphenyl)-alpha-oxo-2-phenyl-3-indolizineacetamide,
N-1-Naphthalenyl-alpha-oxo-2-phenyl-3-indolizineacetamide,
1,2,3,4-Tetrahydro-6,7-dimethoxy-2-[oxo(2-phenyl-3-indolizinyl)acetyl]-isoquinoline,
N-(1-Cyano-1-methylethyl)-alpha-oxo-2-phenyl-3-indolizineacetamide,
alpha-Oxo-2-phenyl-N-(2-phenylethyl)-3-indolizineacetamide,
Hexahydro-1-[oxo(2-phenyl-3-indolizinyl)acetyl]-1H-azepine,
alpha-Oxo-2-phenyl-N-4H-1,2,4-triazol-4-yl-3-indolizineacetamide,
1,2,3,4-Tetrahydro-1-[oxo(2-phenyl-3-indolizinyl)acetyl]-quinoline,
N-(6-Methoxy-2-benzothiazolyl)-alpha-oxo-2-phenyl-3-indolizineacetamide,
alpha-Oxo-2-phenyl-N-2-thiazolyl-3-indolizineacetamide,
N-[(4-Methoxyphenyl)methyl]-alpha-oxo-2-phenyl-3-indolizineacetamide,
N-[(4-Bromophenyl)methyl]-alpha-oxo-2-phenyl-3-indolizineacetamide,
N-(1,1-Dimethylethyl)-alpha-oxo-2-phenyl-3-indolizineacetamide,
N-Butyl-alpha-oxo-2-phenyl-3-indolizineacetamide,
alpha-Oxo-N-[(3-phenoxyphenyl)methyl]-2-phenyl-3-indolizineacetamide,
N-Ethyl-alpha-oxo-N,2-diphenyl-3-indolizineacetamide,
alpha-Oxo-N,2-diphenyl-3-indolizineacetamide,
N-[2-(3,4-Dimethoxyphenyl)ethyl]-alpha-oxo-2-phenyl-3-indolizineacetamide,
alpha-Oxo-2-phenyl-N-(phenylmethyl)-3-indolizineacetamide,
4-[Oxo(2-phenyl-3-indolizinyl)acetyl]-morpholine,
N-(4-Methylphenyl)-alpha-oxo-2-phenyl-3-indolizineacetamide,
2-Methyl-alpha-oxo-3-indolizineacetic acid ethyl ester,
N,N-Dimethyl-2-phenyl-3-indolizineglyoxylamide,
2-Oxo-2-(2-phenyl-indolizin-3-yl)-N-(4-trifluoromethyl-phenyl)-acetamide,
N-(2,4-Dichloro-phenyl)-2-oxo-2-(2-phenyl-indolizin-3-yl)-acetamide,
2-Oxo-2-(2-phenyl-indolizin-3-yl)-N-(3-trifluoromethyl-phenyl)-acetamide,
2-Oxo-2-(2-phenyl-indolizin-3-yl)-N-(4-piperidin-1-yl-phenyl)-acetamide, N-(3-hydroxy-phenyl)-2-oxo-2-(2-phenyl-indolizin-3-yl) acetamide,
{3-[2-oxo-2-(2-phenyl-indolizin-3-yl)-acetylamino]-phenoxy}-acetic acid ethyl ester,
ethyl 2-oxo-2-(6-phenoxy-2-phenylindolizin-3-yl)acetate,
1-(5-methyl-2-phenyl-indolizin-3-yl)-propane-1,2-dione,
1-(5-methyl-2-phenyl-indolizin-3-yl)-propane-1,2-dione 1-oxime,
1-(2,5-dimethyl-indolizin-3-yl)-2-phenyl-ethane-1,2-dione 1-oxime,
1-(5-methyl-2-phenyl-indolizin-3-yl)-2-phenyl-ethane-1,2-dione 1-oxime,
1-(2,5-dimethyl-indolizin-3-yl)-propane-1,2-dione 1-oxime,
2-oxo-2-(2-phenylindolizin-3-yl) acetamide,
or a pharmaceutically acceptable salt thereof.

In this final embodiment, preferred X groups are as defined earlier. In particular, preferably X is a group —NR8-, preferably where R8 is hydrogen or C1-C4 alkyl. More preferably X is a group —NH—.

In this final embodiment, preferably $X^1$ is O.

In this final embodiment, preferably R1 is a C6-C10 aryl or a group -A1-L1-A2. When R1 is -A1-L1-A2, preferably A1 is an unsubstituted or substituted phenyl or 5- to 6-membered heterocyclyl group, more preferably an unsubstituted or substituted phenyl or pyridyl group. When R1 is -A1-L1-A2, preferably A1 is unsubstituted. When R1 is -A1-L1-A2, preferably L1 is as defined earlier, more preferably L1 is a bond. When R1 is -A1-L1-A2, preferably A2 is an unsubstituted or substituted phenyl or 5- to 6-membered heterocyclyl, more preferably an unsubstituted or substituted 5- to 6-membered heterocyclyl. When R1 is -A1-L1-A2, preferably A2 is an unsubstituted or substituted piperazinyl, pyrrolidinyl, oxazolyl, isoxazolyl or dihydro-oxazolyl, e.g. an unsubstituted or substituted piperazinyl, pyrrolidinyl or oxazolyl group. When A2 is piperazinyl or pyrrolidinyl, preferably it is substituted by a C4-C8 alkyl group, more preferably by a C5 alkyl group (including all isomers of C5 alkyl, but particularly groups —CH(CH$_2$CH$_3$)$_2$ or —CH$_2$—C(CH$_3$)$_3$. When A2 is oxazolyl, preferably it is unsubstituted. When A2 is isoxazolyl or dihydro-oxazolyl, preferably it is unsubstituted or substituted with one or two substituents selected from C1-C4 alkyl (e.g. methyl) and —OCONR'R", wherein R' and R" are the same or different and are hydrogen or C1-C4 alkyl.

In this final embodiment, when R1 is a C6-C10 aryl, preferably it is an unsubstituted or substituted phenyl ring, more preferably an unsubstituted phenyl ring.

In this final embodiment, when R7 is other than hydrogen, preferably it is a C1-C4 alkyl group substituted by 1 or 2 unsubstituted C1-C4 alkoxy groups, more preferably a C1-C2 alkyl group substituted by 1 C1-C2 alkoxy groups, more preferably a group —CH$_2$—O—CH$_3$. When R7 is a C1-C4 alkyl group substituted by 1 or 2 unsubstituted C1-C4 alkoxy groups, preferably R2 is an unsubstituted C6-C10 aryl group and R1 is an unsubstituted or substituted C6-C10 aryl group.

In this final embodiment, when R1 is -A1-L1-A2, preferably R7 is hydrogen.

In this final embodiment, preferred R2 groups include unsubstituted or substituted group selected from C6-C10 aryl or a 5- to 12-membered heterocyclyl groups. When R2 is an unsubstituted or substituted C6-C10 aryl group, preferably it is a phenyl ring which is unsubstituted or substituted. Preferred substituents include halogen atoms, C1-C4 alkyl and C1-C4 alkoxy groups, more preferably halogen atoms such as chlorine. When R2 is an unsubstituted 5- to 12-membered heterocyclyl group, preferably it is an unsubstituted or substituted nitrogen-containing ring, more preferably a pyridinyl, pyrimidinyl or indolyl group. When R2 is an unsubstituted 5- to 12-membered heterocyclyl group, preferred substituents include halogen atoms, hydroxyl groups or amino, C1-C4 alkyl or C1-C4 alkoxy groups, more preferably amino or C1-C2 alkyl groups. Preferably, when R2 is substituted, only a single substituent is present.

In this final embodiment, preferably each of R3, R4, R5 and R6 is as described above, more preferably each is the same or different and represents hydrogen or C1-C4 alkyl. More preferably still, R3, R4, R5 and R6 are all hydrogen.

Most preferred compounds of this final embodiment are:
2-[2-(2-Chloro-phenyl)-indolizin-3-yl]-N-{6-[4-(1-ethyl-propyl)-piperazin-1-yl]-pyridin-3-yl}-2-oxo-acetamide,
N-(6-Methoxy-pyridin-3-yl)-2-(6-methyl-2-pyridin-3-yl-indolizin-3-yl)-2-oxo-acetamide, and
N-(6-Methoxy-pyridin-3-yl)-2-(7-methyl-2-pyridin-3-yl-indolizin-3-yl)-2-oxo-acetamide,
and pharmaceutically and agriculturally acceptable salts thereof.

The following compounds are also likely to be useful in the final embodiment of the invention, and can be made by analogous processes to those defined in the examples which follow:
2-(1-Methoxymethyl-2-phenyl-indolizin-3-yl)-2-oxo-N-phenyl-acetamide,
N-{4-[4-(2,2-Dimethyl-propyl)-piperazin-1-yl]-phenyl}-2-oxo-2-(2-phenyl-indolizin-3-yl)-acetamide,
2-Oxo-2-(2-pyridin-3-yl-indolizin-3-yl)-N-[4-(3,3,4,4-tetramethyl-pyrrolidin-1-yl)-phenyl]-acetamide,
2-[2-(2-Amino-pyrimidin-5-yl)-indolizin-3-yl]-N-(4-oxazol-2-yl-phenyl)-2-oxo-acetamide, and
2-[2-(2-Methyl-2,3-dihydro-1H-isoindol-5-yl)-indolizin-3-yl]-N-(4-oxazol-2-yl-phenyl)-2-oxo-acetamide,
and pharmaceutically and agriculturally acceptable salts thereof.

The structural similarity of these compounds to the other particularly preferred compounds also means that they are likely to have the same pharmacological effect.

Thus, suitable schemes and processes for their production, with reference to the examples section which follows, are:

(a) 2-(1-Methoxymethyl-2-phenyl-indolizin-3-yl)-2-oxo-N-phenyl-acetamide

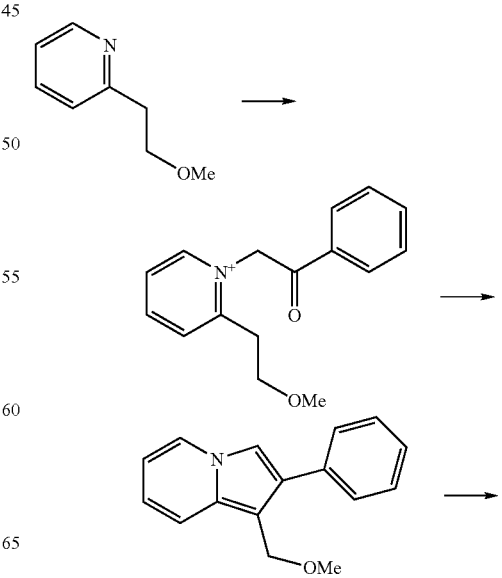

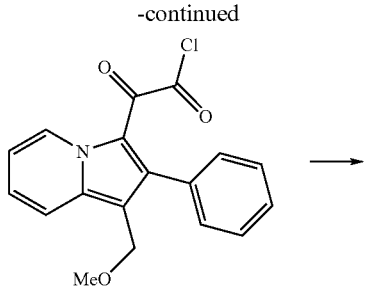

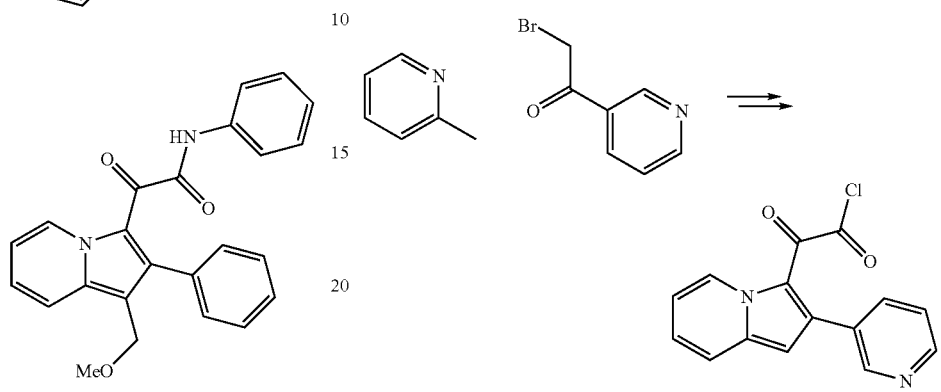

The starting material, 2-(2-methoxy-ethyl)-pyridine, is commercially available. Step 1 is analogous to Reference Example 264 (alkylation of pyridine). Step 2 is analogous to Reference Example 279 (cyclisation in aqueous bicarbonate). Step 3 is analogous to Reference Example 294 (reaction with oxalyl chloride). Step 4 is analogous to Example 1 (aniline coupling with acid chloride).

(b) N-{4-[4-(2,2-Dimethyl-propyl)-piperazin-1-yl]-phenyl}-2-oxo-2-(2-phenyl-indolizin-3-yl)-acetamide

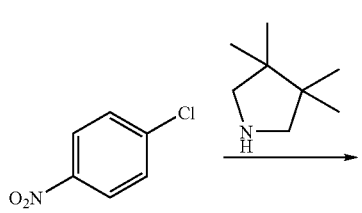

The starting material, 1-(4-nitro-phenyl)-piperazine is prepared according to Reference Example 14, requiring amine displacement on 1-chloro-4-nitrobenzene. Step 1 requires the reagents pivaloyl chloride, triethylamine and DCM. Step 2 requires the reagents sodium borohydride, boron trifluoride etherate and THF. Completion of the synthesis (not shown in the scheme) requires Raney nickel reduction of the nitro group corresponding to Reference Example 166, followed by aniline coupling with acid chloride as described in Example 1.

(c) 2-Oxo-2-(2-pyridin-3-yl-indolizin-3-yl)-N-[4-(3,3,4,4-tetramethyl-pyrrolidin-1-yl)-phenyl]-acetamide Step 1 is analogous to Reference Example 264 (alkylation of pyridine). Step 2 is analogous to Reference Example 279 (cyclisation in aqueous bicarbonate). Step 3 is analogous to Reference Example 294 (reaction with oxalyl chloride).

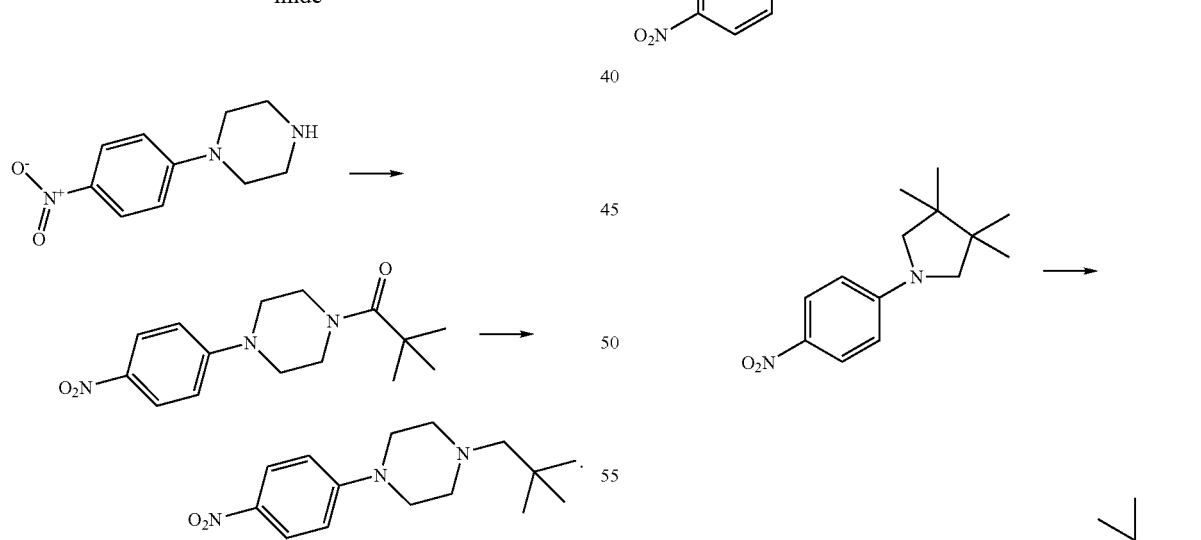

Step 5 is analogous to Reference Example 61 (3,3-4,4-tetramethylpyrrolidine is a known compound). Step 6 is analogous to Reference Example 166, describing a Raney nickel reduction of the nitro group. The final coupling step is analogous to Example 1.

(d) 2-[2-(2-Amino-pyrimidin-5-yl)-indolizin-3-yl]-N-(4-oxazol-2-yl-phenyl-2-oxo-acetamide

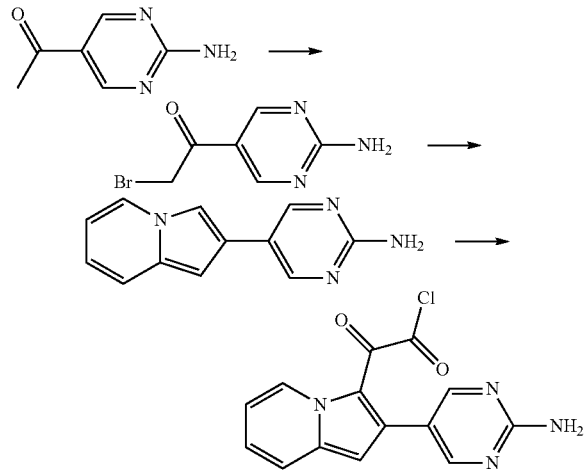

The starting material, 1-(2-amino-pyrimidin-5-yl)-ethanone, is commercially available. Step 1 is a bromination step analogous to Reference Example 104. Step 2 is a pyridine alkylation according to Reference Example 264, followed by cyclisation according to Reference Example 279. Step 3 is analogous to Reference Example 294 (reaction with oxalyl chloride). Step 4 (not shown in the above scheme) is analogous to Example 1, describing aniline coupling with an acid chloride.

(e) 2-[2-(2-Methyl-2,3-dihydro-1H-isoindol-5-yl)-indolizin-3-yl]-N-(4-oxazol-2-yl-phenyl)-2-oxo-acetamide

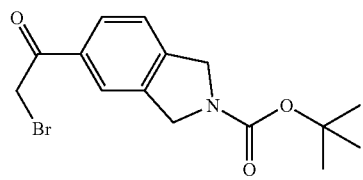 [SMILES: CC(C)(C)OC(=O)N1Cc2ccc(C(=O)CBr)cc2C1]

5-(2-Bromo-acetyl)-1,3-dihydro-isoindole-2-carboxylic acid tert-butyl ester is a known compound, as shown in WO-A-2005/095403.

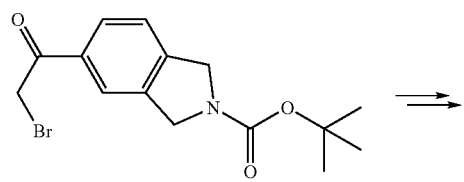

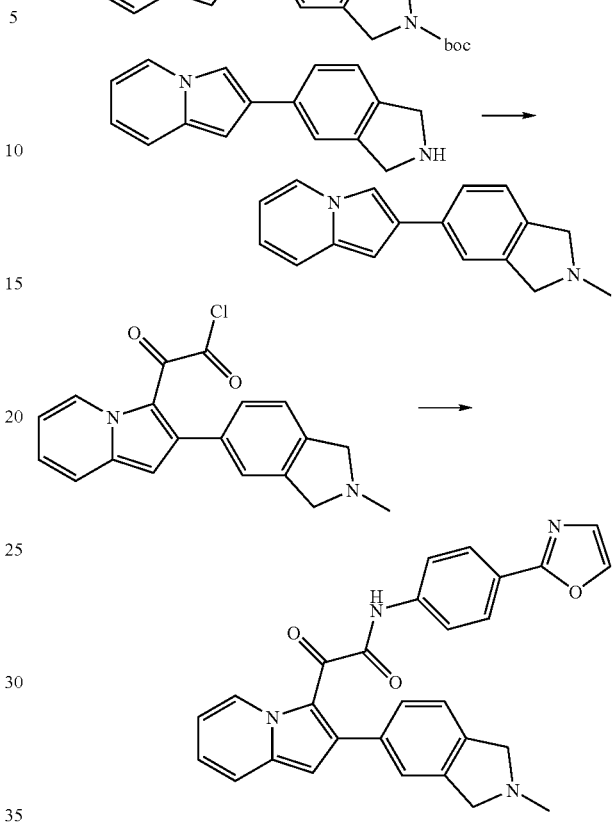

Steps 1 and 2 (the intermediate salt is not shown in the scheme) are analogous to Reference Example 264 (alkylation of pyridine) and Reference Example 279 (cyclisation in aqueous bicarbonate). Step 3 requires the reagents Trifluoroacetic acid/DCM. Step 4 requires the reagents Formaldehyde/formic acid (Eschweiler-Clarke procedure). Step 5 is analogous to Reference Example 294 (reaction with oxalyl chloride). Step 6 is analogous to Example 1. Note: the required aniline is a known compound, as shown in Rosenbaum et al, J. Am. Chem. Soc. (1942), 64, 2444-5.

Preferred compounds listed above in the final embodiment are those wherein R1 is other than pyridyl, in particular other than methoxy-pyridyl, for example 6-methoxypyridyl. Thus, preferred compounds include:
2-[2-(2-Chloro-phenyl)-indolizin-3-yl]-N-{6-[4-(1-ethyl-propyl)-piperazin-1-yl]-pyridin-3-yl}-2-oxo-acetamide,
2-(1-Methoxymethyl-2-phenyl-indolizin-3-yl)-2-oxo-N-phenyl-acetamide,
N-{4-[4-(2,2-Dimethyl-propyl)-piperazin-1-yl]-phenyl}-2-oxo-2-(2-phenyl-indolizin-3-yl)-acetamide,
2-Oxo-2-(2-pyridin-3-yl-indolizin-3-yl)-N-[4-(3,3,4,4-tetramethyl-pyrrolidin-1-yl)-phenyl]-acetamide,
2-[2-(2-Amino-pyrimidin-5-yl)-indolizin-3-yl]-N-(4-oxazol-2-yl-phenyl)-2-oxo-acetamide, and
2-[2-(2-Methyl-2,3-dihydro-1H-isoindol-5-yl)-indolizin-3-yl]-N-(4-oxazol-2-yl-phenyl)-2-oxo-acetamide,
and pharmaceutically and agriculturally acceptable salts thereof.

Compounds of the invention containing one or more chiral centre may be used in enantiomerically or diastereoisomerically pure form, or in the form of a mixture of isomers. For the avoidance of doubt, the compounds of the invention can, if desired, be used in the form of solvates. Further, for the avoidance of doubt, the compounds of the invention may be used in any tautomeric form.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

The present invention also provides prodrugs of the compounds of the invention. A prodrug is an analogue of a compound of the invention which will be converted in vivo to the desired active compound. Examples of suitable prodrugs include compounds of formula (I) which have been modified at a carboxylic acid group to form an ester, or at hydroxyl group to form an ester or carbamate. Other suitable methods will be known to those skilled in the art. Further suitable prodrugs include those in which a nitrogen atom of a compound of formula (I) is quaternised by addition of an ester or alkyl ester group. For example, the nitrogen atom of an amine group or heterocyclyl ring on a substituent $R_1$ or $R_2$ may be quaternised by addition of a —$CH_2$—O—COR group, wherein R is typically methyl or tert-butyl.

Suitable salts of the compounds of the invention include those mentioned herein as examples of pharmaceutically and agriculturally acceptable salts.

A derivative of formula (I), where $X^1$=NOR9, may be prepared by a process comprising reacting a compound of formula (I), where $X^1$=O, and a compound of formula (A), wherein R9 is hereinbefore defined. Typically, the reaction takes place in the presence of an organic solvent and a base. Preferably the solvent is ethanol and the base is potassium hydroxide. Typically, the reaction is heated to reflux.

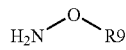

(A)

A compound of formula (A) may be prepared by reacting a compound of formula (B) with conc. hydrochloric acid, wherein R9 is hereinbefore defined. Typically, the reaction is heated to reflux overnight.

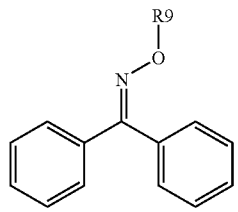

(B)

A compound of formula (B) may be prepared by reacting a compound of formula (C) with diphenyl-methanone oxime. In the compound of formula (C), Hal is defined as a halogen atom, typically chlorine or bromine, and R9 is hereinbefore defined. Typically, the reaction takes place in the presence of an organic solvent and a base. Preferably the solvent is DMSO or acetonitrile and the base is potassium hydroxide or potassium carbonate. The temperature required for the reaction to occur is dependent upon the reagents used.

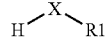

(C)

A derivative of formula (I), where X1=O, may be prepared by a process comprising reacting a compound of formula (II), wherein R2, R3, R4, R5, R6 and R7 are as hereinbefore defined, with a compound of formula (III), wherein R1 and X are as hereinbefore defined. Typically, the reaction takes place in the presence of an organic solvent and a base. Preferably the solvent is dichloromethane or tetrahydrofuran and the base is triethylamine or pyridine. Typically, the reaction is carried out at 0° C. initially while the reagents are added and then stirred at room temperature until the reaction is complete. Compounds of formula (III) are typically available from commercial sources or can be prepared by known methods. Details of the synthesis of certain compounds of formula (III) are provided hereinafter.

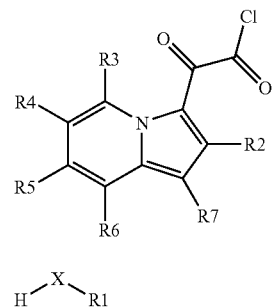

(II)

(III)

A compound of formula (II) may be prepared by reacting a compound of formula (IV), wherein R2, R3, R4, R5, R6 and R7 are as hereinbefore defined, with preferably oxalyl chloride. Typically the reaction takes place in an organic solvent. Preferably, the solvent is a tetrahydrofuran, a mixture of tetrahydrofuran/toluene, or diethyl ether. Typically, the reaction is carried out at 0° C. initially while the reagents are added and then stirred at room temperature until the reaction is complete.

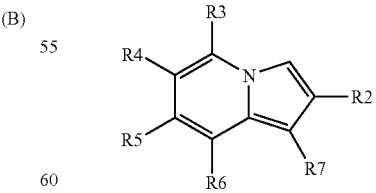

(IV)

A compound of formula (IV) may be prepared by reacting a compound of formula (V), wherein R2, R3, R4, R5, R6, and R7 are as hereinbefore defined, with a base. Preferably the solvent is water and the base is $NaHCO_3$. Typically, the reaction is heated to reflux.

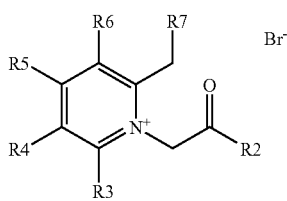

A compound of formula (V) may be prepared by reacting a compound of formula (VI), wherein R2 is hereinbefore defined, with a compound of formula (VII), wherein R3, R4, R5, R6, R7 are as hereinbefore defined. Typically, the reaction takes place in the presence of an organic solvent. Preferably the solvent is methanol. Typically, the reaction is heated to reflux.

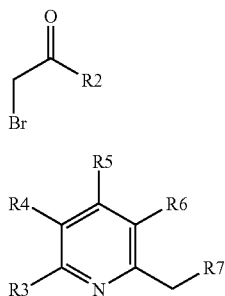

Compounds of formula (VI) are available from standard commercial sources or may be prepared by reacting a compound of formula (VIII), which are available from standard commercial sources, wherein R2 is hereinbefore defined, with a suitable brominating agent. Typically, the brominating conditions are hydrobromic acid in acetic acid, followed by pyridinium tribromide or bromine in dioxane/ether. Typically, the reaction is kept at room temperature.

Many of the starting materials referred to in the reactions described above are available from commercial sources or can be prepared by analogy with known methods.

The compounds of the invention have antifungal activity. Accordingly, they may be used in a method of treating a subject suffering from or susceptible to a fungal disease, which method comprises administering to said subject an effective amount of an indolizinyl derivative of formula (I) or (IA) or a pharmaceutically acceptable salt thereof. The indolizinyl derivatives of formula (I) or (IA) or the pharmaceutically acceptable salts thereof may also be used in the manufacture of a medicament for use in the prevention or treatment of a fungal disease.

Preferably, the fungal disease comprises an infection by a fungus, for example an Ascomycete. More preferably the fungal disease comprises an infection by an organism selected from the genera *Absidia; Acremonium; Alternaria; Aspergillus; Bipolaris; Blastomyces; Blumeria; Candida; Cladosporium; Coccidioides; Colletotrichium; Cryptococcus; Curvularia; Encephalitozoon; Epicoccum; Epidermophyton; Exophiala; Exserohilum; Fusarium; Histoplasma; Leptosphaeria; Microsporum; Mycosphaerella; Neurospora, Paecilomyces; Penicillium; Phytophthora; Plasmopara; Pneumocystis; Pyricularia; Pythium; Puccinia; Rhizoctonia; Rhizomucor; Scedosporium; Scopulariopsis; Trichophyton; Trichosporon*; and *Ustilago*.

Preferably, the fungal disease comprises an infection by an organism of the genus *Aspergillus* or *Candida*.

Preferably, the fungal disease comprises an infection by an organism selected from the species *Absidia corymbifera; Acremonium* spp; *Alternaria alternata; Aspergillus flavus; Aspergillus fumigatus; Aspergillus nidulans; Aspergillus niger; Aspergillus parasiticus; Aspergillus terreus; Bipolaris* spp; *Blastomyces dermatitidis; Blumeria-graminis; Candida albicans; Candida glabrata; Candida krusei; Candida parapsilosis; Candida tropicalis; Cladosporium cladosporoides; Cladosporium herbarium; Coccidioides immitis; Coccidioides posadasii; Curvularia lunata; Colletotrichium trifolii; Cryptococcus neoforinans; Encephalitozoon cuniculi; Epicoccum nigrum; Epidermophyton floccosum; Exophiala* spp; *Exserohilum rostratum; Fusarium graminarium; Fusarium solani; Fusarium sporotrichoides; Histoplasma capsulatum; Leptosphaeria nodorum; Microsporum canis; Mycosphaerella graminicola; Paecilomyces lilanicus; Paecilomyces varioti; Penicillium chrysogenum; Phytophthora capsici; Phytophthora infestans; Plasmopara viticola; Pneumocystis jiroveci; Puccinia coronata; Puccinia graminis; Pyricularia oryzae; Pythium ultimum; Rhizoctonia solani; Rhizomucor* spp; *Rhizopus* spp; *Scedosporium apiospermum; Scedosporium prolificans; Scopulariopsis brevicaulis; Trichophyton mentagrophytes; Trichophyton interdigitale; Trichophyton rubrum; Trichosporon asahii; Trichosporon beigelii*; and *Ustilago maydis*.

Preferably, the fungal disease comprises an infection by *Aspergillus fumigatus*.

Examples of fungal diseases, which can be prevented or treated using the compounds of the invention, include both systemic and superficial infections. The fungal diseases include invasive fungal diseases caused by *Aspergillus* and *Candida* species such as aspergillosis or candidiasis, but also local forms of these infections. The compounds of the invention are particularly useful against diseases caused by *Aspergillus* species, for which a fungicidal drug is required which has lower toxicity than amphotericin. The invention also provides for the treatment of dermatological infections.

The diseases caused by *Aspergillus* species include diseases caused by *A. fumigatus, A. flavus, A. terreus* and *A. niger*.

The diseases cause by *Candida* species include diseases caused by *C. albicans, C. glabrata, C. krusei, C. tropicalis* and *C. parapsillosis*.

Examples of systemic infections which might be prevented or treated using the compounds of the invention include: systemic candidiasis; pulmonary aspergillosis, e.g. in immunosuppressed patients such as bone marrow recipients or AIDS patients; systemic aspergillosis; cryptococcal meningitis; rhinocerebral mucomycosis; blastomycosis; histoplasmosis; coccidiomycosis; paracoccidiomycosis; lobomycosis; sporotrichosis; chromoblastomycosis; phaeohyphomycosis; zygomycosis; cryptococcosis and disseminated sporotrichosis.

Examples of superficial infections, which can be prevented or treated using the compounds of the invention, include: ring worm; athlete's foot; tinea unguium (nail infection); candidiasis of skin, mouth or vagina; and chronic mucocutaneous candidiasis.

Examples of diseases or conditions which are caused by fungi or where fungi exacerbate an allergic response, and which can be prevented or treated using the compounds of the invention, include allergic bronchopulmonary asthma (ABPA); asthma, rhinosinusitis and sinusitis.

The present invention includes a pharmaceutical composition comprising a compound according to the invention and a pharmaceutically acceptable carrier or diluent. Said pharmaceutical composition typically contains up to 85 wt % of a compound of the invention. More typically, it contains up to 50 wt % of a compound of the invention. Preferred pharmaceutical compositions are sterile and pyrogen free. Where a compound of the invention can exist as optical isomers, the pharmaceutical compositions provided by the invention typically contain a substantially pure optical isomer.

The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, either subcutaneously, intravenously, intramuscularly, intrasternally, transdermally or by infusion techniques. The compounds may also be administered as suppositories. The compounds may be administered by inhalation in the form of an aerosol via an inhaler or nebuliser.

A compound of the invention is typically formulated for administration with a pharmaceutically acceptable carrier or diluent. For example, solid oral forms may contain, together with the active compound, solubilising agents, e.g. cyclodextrins or modified cyclodextrins; diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be solutions, syrups, emulsions and suspensions. The solutions may contain solubilising agents e.g. cyclodextrins or modified cyclodextrins. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol; solubilising agents, e.g. cyclodextrins or modified cyclodextrins, and if desired, a suitable amount of lidocaine hydrochloride.

Solutions for intravenous or infusions may contain as carrier, for example, sterile water and solubilising agents, e.g. cyclodextrins or modified cyclodextrins or preferably they may be in the form of sterile, aqueous, isotonic saline solutions.

A therapeutically effective amount of a compound of the invention is administered to a patient. A typical daily dose is up to 50 mg per kg of body weight, for example from 0.001 to 50 mg per kg of body weight, according to the activity of the specific compound, the age, weight and conditions of the subject to be treated, the type and severity of the disease and the frequency and route of administration. Preferably, daily dosage levels are from 0.05 mg to 2 g, preferably from 0.1 mg to 10 mg. The compound of the invention is typically administered to the patient in a non-toxic amount.

The present invention also provides a method of controlling a fungal disease of a plant, which comprises applying to the locus of the plant a derivative of formula (I) or formula (IA) or an agriculturally acceptable salt thereof.

The compounds of the invention may, for example, be applied to the seeds of the plants, to the medium (e.g. soil or water) in which the plants are grown, or to the foliage of the plants.

Examples of fungal diseases of plants which can be controlled using the compounds of the invention include fungal diseases caused by the following plant pathogens: *Blumeria graminis; Colletotrichium trifolii; Fusarium graminearium; Fusarium solani; Fusarium sporotrichoides; Leptosphaeria nodorum; Magnaporthe grisea; Mycosphaerella graminicola; Neurospora crassa; Phytophthora capsici; Phytophthora infestans; Plasmopara viticola; Puccinia coronata; Puccinia graminis; Pyricularia oryzae; Pythium ultimum; Rhizoctonia solani; Trichophyton rubrum*; and *Ustilago maydis*.

The present invention includes a composition comprising a compound of the invention, or an agriculturally acceptable salt thereof, and an agriculturally acceptable carrier or diluent. Said agricultural composition typically contains up to 85 wt % of a compound of the invention. More typically, it contains up to 50 wt % of a compound of the invention.

Suitable agriculturally acceptable salts include salts with agriculturally acceptable acids, both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Salts may also be formed with agriculturally acceptable bases such as alkali metal (e.g. sodium or potassium) and alkaline earth metal (e.g. calcium or magnesium) hydroxides and organic bases such as alkyl amines, aralkyl amines or heterocyclic amines. A preferred agriculturally acceptable salt is the hydrochloride salt.

The compounds of the invention may be applied in combination with inert carriers or diluents, as in aqueous sprays, granules and dust formulations in accordance with established practice in the art. An aqueous spray is usually prepared by mixing a wettable powder or emulsifiable concentrate formulation of a compound of the invention with a relatively large amount of water to form a dispersion.

Wettable powders may comprise an intimate, finely divided mixture of a compound of the invention, an inert solid carrier and a surface-active agent. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates may comprise a solution of a compound of the invention in a liquid carrier which is a mixture of a water-immiscible solvent and a surfactant, including an emulsifier. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

The fungicide formulations desirably contain from 0.1 percent to 95 percent by weight of the compound of the invention and from 0.1 to 75 percent of an inert carrier or surfactant. The direct application to plant seeds prior to planting may be accomplished in some instances by mixing either a powdered solid compound of the invention or a dust formulation with seed to obtain a substantially uniform coating which is very thin and represents only one or two percent by weight or less, based on the weight of the seed. In some instances, however, a non-phytotoxic solvent such as methanol is conveniently employed as a carrier to facilitate the uniform distribution of the compound of the invention on the surface of the seed.

When a compound of the invention is to be applied to the soil, as for pre-emergence protection, granular formulations or dusts are sometimes more convenient than sprays. A typical granular formulation comprises a compound of the invention dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation. Dust formulations customarily employ essentially the same inert diluents as wettable powders and granules, but are well-mixed in powder form and do not usually contain emulsifiers. Dusts may contain some surface active agents to facilitate uniform distribution of the active ingredient in the formulation and to improve the uniformity and adhesion of the dust coating on seeds and plants. The colloidal dispersion of dust formulations in the air is usually prevented by incorporation of a minor amount of an oily or waxy material in the formulation to cause agglomeration of colloidal size particles. In this way the dust may be applied to seeds or plants without generation of an air-polluting aerosol.

The following examples illustrate the invention but are not intended to limit the scope of the invention. In this regard, it is important to understand that the particular assay used in the Examples section is designed only to provide an indication of anti-fungal activity. There are many assays available to determine such activity, and a negative result in any one particular assay is therefore not determinative.

EXAMPLES

Reference Example 1

Tetrahydro-pyran-4-carbonitrile

To a solution of tetrahydro-pyran-4-one (2.0 g, 20.0 mmol) and tosyl methyl isocyanide (5.06 g, 25.9 mmol) in dimethoxyethane (15 mL) was added ethanol (1.5 mL). The reaction mixture was cooled to 0° C. and potassium tert-butoxide (5.57 g, 49.7 mmol) was added. The resulting reaction mixture was warmed to r.t. and stirred for 1 h, then heated to 40° C. for 30 minutes. The mixture was cooled to r.t. and filtered. The resulting solid was washed with dimethoxyethane (3×15 mL), and the combined filtrates were evaporated to give a crude compound which was purified by column chromotography over 60-120 silica gel using 10-12% ethyl acetate in hexane to afford tetrahydro-pyran-4-carbonitrile (1.05 g, 47%) as a light yellow liquid.

Reference Example 2

Tetrahydropyran-4-carbaldehyde

To a solution of tetrahydro pyran-4-carbonitrile (1.0 g, 9.0 mmol) in toluene (10 mL) was added diisobutylaluminum hydride solution (DIBAL-H, 10.8 mL, 10.8 mmol, 1M in toluene) at −78° C. The reaction was stirred at −78° C. for 1 hour then allowed to warm to r.t. The reaction was quenched with saturated ammonium chloride solution and extracted with ethyl acetate. The combined organics were washed with brine, dried over sodium sulfate, filtered and concentrated under reduced pressure to afford tetrahydropyran-4-carbaldehyde (530 mg, 52%).

Reference Example 3

Tetrahydro-pyran-4,4-dicarboxylic acid diethyl ester

A solution of diethyl malonate (15.2 mL, 99.8 mmol) in ethanol (10 mL) was added dropwise to a solution of sodium ethoxide in ethanol [freshly prepared from sodium (2.3 g, 100 mmol) and ethanol (30 mL)] at ambient temperature and stirred for 10 min. Bis(2-chloroethyl)ether (12 mL, 102 mmol) was added dropwise and the whole mixture heated at reflux overnight. It was then cooled to 10° C. before another portion of freshly-prepared sodium ethoxide in ethanol [prepared from sodium (2.3 g, 100 mmol) and ethanol (30 mL)] was added. The mixture was heated at reflux for 48 h then cooled, filtered to remove the precipitated sodium chloride then the filtrate was concentrated to dryness. Water was added to the residue which was then extracted with ether (3×25 mL). The combined ether layers were washed with water, brine and dried over anhydrous sodium sulfate. Concentration under reduced pressure yielded tetrahydropyran-4,4-dicarboxylic acid diethyl ester (10.1 g, 44%) as a mobile oil.

Reference Example 4

Tetrahydro-pyran-4,4-dicarboxylic acid 6M potassium hydroxide solution (10 mL, 60 mmol) was added to an ice-cooled solution of tetrahydropyran-4,4-dicarboxylic acid diethyl ester (5 g, 21.7 mmol) in ethanol (40 mL) and heated at reflux for overnight. The volatiles were evaporated, the residue diluted with water and acidified with conc. hydrochloric acid. The mixture was allowed to stand overnight then extracted with ether (3×25 mL). The combined ether layers were washed with brine, dried over sodium sulfate, and concentrated in vacuo to afford tetrahydro-pyran-4,4-dicarboxylic acid (2.3 g, 61%) as a white solid.

Reference Example 5

Tetrahydro-pyran-4-carboxylic acid

Tetrahydro-pyran-4,4-dicarboxylic acid-(2.3 g, 13.2 mmol) was heated at 178-180° C. for 30 minutes. The reaction mixture was cooled to ambient temperature and washed with pentane to afford tetrahydro-pyran-4-carboxylic acid (1.1 g, 64%) as a solid.

Reference Example 6

(6-chloro-pyridin-2-yl)-acetic acid ethyl ester n-Butyl lithium (23% in hexane, 13.2 mL, 47.3 mmol) was added dropwise to a cold solution (−70° C.) of 2-chloro-6-methyl-pyridine (5.0 g, 39.4 mmol) in tetrahydrofuran (30 mL) and stirred for 30 min at −70° C. Diethyl carbonate (5.75 mL, 47.3 mmol) was added slowly and the reaction mixture stirred for 30 min at −70° C. before warming to room temperature and stirring for a further 1 h. The reaction mixture was quenched into saturated ammonium chloride solution and extracted with ethyl acetate. The organic layer was washed with water and brine, then dried over sodium sulfate, filtered and concentrated to yield the crude compound which was purified by column chromatography over silica gel (100-200 mesh), using 9% ethyl acetate in petroleum ether as eluent, to afford (6-chloro-pyridin-2-yl)-acetic acid ethyl ester (2.21 g, 28%) as an oil.

Reference Example 7

(6-chloro-pyridin-2-yl)-ethanol

A solution of (6-chloro-pyridin-2-yl)-acetic acid ethyl ester (1.8 g, 9.05 mmol) in dry tetrahydrofuran (25 mL) was cooled to 0° C. Borane-dimethylsulfide complex (4.35 mL, 45.25 mmol) was added dropwise and the reaction mixture warmed to room temperature before heating at reflux overnight. The mixture was cooled to room temperature and quenched into saturated ammonium chloride solution and extracted with ethyl acetate. The separated organic layer was washed with water, brine, dried over anhydrous sodium sulfate, filtered and concentrated to give the crude product which was purified by column chromatography over silica gel (60-120 mesh) using 30% ethyl acetate in chloroform as eluent to afford (6-chloro-pyridin-2-yl)-ethanol (0.76 g, 54%) as a liquid.

Reference Example 8

2-Chloro-pyridine-1-oxide

2-Chloropyridine (5.0 g, 44.3 mmol) was added dropwise to a stirred solution of 75% meta-chloroperbenzoic acid (15.2 g, 66.2 mmol) in chloroform (35 mL) and heated at reflux overnight. The reaction mixture was concentrated and poured onto ice-water, neutralised with saturated aq. sodium bicarbonate solution and extracted with chloroform. The organic layer was washed with water and brine, dried over sodium sulfate, filtered and concentrated under vacuum. The residue was triturated with petroleum ether and dried under high vacuum to afford 2-chloro-pyridine-1-oxide (2.13 g, 37%) as a solid.

Reference Example 9

The compound set out below was prepared a manner analogous to Reference Example 8:

| Example | Compound |
|---|---|
| 9 | 2,4,6-Trimethyl-pyridine-1-oxide |

Reference Example 10

2-Chloro-6-methyl-pyridine-1-oxide

30% Hydrogen peroxide solution (20 mL, 0.176 mol) was added slowly into a solution of 2-chloro-6-methylpyridine (5.0 g, 39.4 mmol) in glacial acetic acid (30 mL) whilst the mixture was kept below 20° C. The reaction mixture was then heated to 85-90° C. overnight. The reaction was cooled and neutralised with cold sodium bicarbonate solution. The aqueous layer was extracted with dichloromethane (4×50 mL) and the combined organic layers washed with water (50 mL) and brine (50 mL), dried over anhydrous sodium sulfate, filtered and concentrated in vacuo to afford 2-chloro-6-methyl-pyridine-1-oxide (5.43 g, 96.5%) as an oil.

Reference Example 11

5-Bromo-2-nitro-pyridine

A solution of 2-amino-5-bromo-pyridine (5 g, 28.9 mmol) in conc. sulfuric acid (10 mL) was added dropwise to a cold (0° C.) mixture of hydrogen peroxide (10 mL, 38%) and conc. sulfuric acid (10 mL). The mixture was warmed to r.t. and stirred overnight, then poured into ice cold water and filtered. The filtrate was basified with potassium hydroxide and extracted with ethyl acetate. The organic phase was dried over anhydrous sodium sulfate and concentrated to afford 5-bromo-2-nitro-pyridine (4.2 g, 72%).

Reference Example 12

4-Phenyloxazole

A solution of phenacyl bromide (4 g, 20.1 mmol) and ammonium formate (4.4 g, 70.35 mmol) in formic acid (20 mL) was refluxed for 5 h. The deep red mixture was cooled to r.t., diluted with water and basified with dilute sodium hydroxide solution. This was extracted with ethyl acetate (×3), then the combined organic layers were washed with water and brine, dried over sodium sulfate and concentrated under reduced pressure. The residue was purified by column chromatography on silica gel (60-120 mesh), eluting with 20% ethyl acetate-petroleum ether, to afford 4-phenyloxazole (1 g, 34%) as a pale yellow oil which solidifies at −20° C.

Reference Example 13

4-(4-Nitrophenyl) oxazole

4-Phenyloxazole (1 g, 6.89 mmol) was dissolved in concentrated sulfuric acid (5 mL) at 0° C. A cold solution of nitrating mixture (prepared by adding 3 mL conc. nitric acid to 5 mL of ice-cold conc. sulfuric acid) was added over 10 minutes. The mixture was allowed to warm to r.t. and stirred for 1 h. The resulting solution was poured into ice-cold water giving a white precipitate, which was filtered and washed thoroughly with water. The solid was dissolved in DCM and washed with water then brine. The organic phase was dried over sodium sulfate and concentrated to yield 4-(4-nitrophenyl)-oxazole (550 mg, 42%) as a white solid.

Reference Examples 14 to 16

The compounds set out below were prepared a manner analogous to Reference Example 13:

| Example | Compound |
|---|---|
| 14 | 5-Nitro-1,3-dihydro-indol-2-one |
| 15 | 2-Chloro-4-nitro-pyridine-1-oxide |
| 16 | 2-Chloro-6-methyl-4-nitro-pyridine-1-oxide |

Reference Example 17

2-Chloro-4-nitro-pyridine

Phosphorus trichloride (4.2 mL, 48.7 mmol) was added to a solution of 2-chloro-4-nitro-pyridine-1-oxide (1.70 g, 9.74 mmol) in dry chloroform (25 mL) at r.t. The reaction mixture was then heated to reflux and maintained at this temperature overnight. The reaction was cooled to r.t. then poured onto ice, basified to between pH 7-8 with saturated aq. sodium bicarbonate solution and extracted with chloroform (×2). The combined organic phase was washed with water and brine, dried over sodium sulfate and concentrated. Drying under high vacuum afforded 2-chloro-4-nitro-pyridine (1.2 g, 78%) as a solid.

Reference Example 18

Pyridine-3-sulfonyl chloride

A mixture of pyridine-3-sulfonic acid (3 g, 18.8 mmol), phosphorus pentachloride (6.04 g, 29.0 mmol) and phosphorus oxychloride (15 mL) was heated at 120° C. overnight. Excess phosphorus oxychloride was evaporated under reduced pressure, the residue quenched with ice and partitioned between water and diethyl ether. The pH of the aqueous phase was adjusted by addition of solid sodium bicarbonate to pH 7-8, then the organic layer was separated and washed successively with sat. sodium bicarbonate solution, water and brine. The organic phase was dried over anhydrous sodium sulfate and concentrated under reduced pressure to give a residue which was dried under high vacuum to afford pyridine-3-sulfonyl chloride (2.83 g, 85%) as a solid.

Reference Example 19

Trifluoro-methanesulfonic acid 2,6-dimethyl-pyridin-4-yl ester

Triethylamine (1.69 mL, 12.2 mmol) was added dropwise to a solution of 4-hydroxy-2,6-dimethylpyridine (0.50 g, 4.07 mmol) in dichloromethane (50 mL) at 0° C. After 10 min, trifluoromethanesulfonic anhydride (1.0 mL, 6.10 mmol) was slowly added followed by a catalytic amount of 4-dimethylaminopyridine (DMAP) and stirred at room temperature for 6 hrs under nitrogen. The reaction mixture was diluted with dichloromethane and washed with water (4×50 mL). The organic layer was separated, washed with sodium bicarbonate solution (4×50 mL), brine (4×50 mL), dried over sodium sulfate and filtered. The solvent was evaporate and the residue purified by column chromatography over silica gel (60-120 mesh) using 10% ethyl acetate:hexane as eluent to afford trifluoro-methanesulfonic acid 2,6-dimethyl-pyridin-4-yl ester (0.82 g, 79%) as a light brown liquid.

Reference Example 20

4-(2-Benzyloxy-ethoxy)-2-chloro-pyridine

Sodium hydride (50% in mineral oil; 0.54 g, 11.35 mmol) was added portionwise to a solution of 2-benzyloxyethanol (1.72 g, 11.4 mmol) in THF (15 mL) at r.t. under nitrogen. After 15 min. 2-chloro-4-nitro-pyridine (1.20 g, 7.57 mmol) was added and the reaction mixture stirred at r.t. overnight. The reaction mixture was quenched by slowly pouring onto ice and concentrated to remove the organic solvent. The residue was diluted with water and extracted with ethyl acetate. The organic phase was washed with water and brine then dried over sodium sulfate, filtered and concentrated. The crude material was subjected to column chromatography over silica gel (60-120 mesh) using 5%-25% ethyl acetate in petroleum ether as eluent to afford 4-(2-benzyloxy-ethoxy)-2-chloro-pyridine (1.91 g, 96%) as an oily liquid.

Reference Examples 21 to 24

The compounds set out below were prepared a manner analogous to Reference Example 20:

| Example | Reactant | Compound |
|---|---|---|
| 21 | 2-Chloro-6-methyl-4-nitro-pyridine 1-oxide | 2-Chloro-4-(2-methoxy-ethoxy)-6-methyl-pyridine-1-oxide |
| 22 | 2-Chloropyridine | 2-(Pyridine-2-yloxy)-ethylamine |
| 23 | 2-Chloro-5-nitro-pyridine/diethyl malonate | 4-Methoxy-2-(5-nitro-pyridin-2-yl)-2-oxo-butyric acid ethyl ester |
| 24 | 2-Chloro-6-methyl-4-nitro-pyridine 1-oxide | 2-Chloro-4-[2-(2-methoxy-ethoxy)-ethoxy]-6-methyl-pyridine 1-oxide |

Reference Example 25

(4-Nitro-phenoxy)-acetic acid 4-nitro-phenol (5.0 g, 36 mmol) was added to a stirred suspension of sodium hydride (3.13 g; 55% in mineral oil; 71.9 mmol) in dry tetrahydrofuran (100 mL) and stirred for 30 min at ambient temperature. Bromoacetic acid (6.0 g, 43.2 mmol) was added and the mixture then heated at reflux overnight. The reaction mixture was cooled to ambient temperature, neutralised with dilute hydrochloric acid and extracted with ethyl acetate. The separated organic layer was extracted with sodium bicarbonate solution and the aqueous solution was acidified with concentrated HCl to pH ~3 to afford a white precipitate, which was filtered and dried under vacuum to give (4-nitro-phenoxy)-acetic acid (3.5 g, 45%).

Reference Example 26

4-chloro-2-methoxymethyl-1-nitro-benzene

Sodium hydroxide (1.88 g, 44.0 mmol) in water (15 mL) was added to a solution of (5-chloro-2-nitro-phenyl)-methanol (1.1 g, 5.88 mmol) in dichloromethane (15 mL) and stirred for 10 min. Dimethyl sulfate (1.12 mL, 11.8 nmol) and tetrabutylammonium hydrogen sulfate (100 mg) were added and the mixture stirred vigorously for 8 h at room temperature. The reaction mixture was diluted with dichloromethane and the organic layer separated, washed with water, brine, dried over anhydrous sodium sulfate, filtered and concentrated under vacuum to give the crude compound. Purification by column chromatography over silica gel (100-200 mesh) using 2% ethyl acetate in petroleum ether as eluent afforded 4-chloro-2-methoxymethyl-1-nitro-benzene (850 mg, 72%) as a pale yellow liquid.

Reference Example 27

The compound set out below was prepared a manner analogous to Reference Example 26:

| Example | Compound |
| --- | --- |
| 27 | 1-Chloro-2-methoxymethyl-4-nitro-benzene |

Reference Example 28

5-Nitro-2-methylpyridine

To 2-(5-nitro-pyridin-2-yl)-malonic acid diethyl ester (12.0 g, 42.5 mmol) was added cold aq. 20% sulfuric acid (120 mL) and the mixture was heated to 100° C. for 2 h. The cooled reaction was added to cold dilute sodium hydroxide solution and the pH adjusted to pH ~10. The organics were extracted with dichloromethane (×4), then the combined organic phases were dried over sodium sulfate. The filtrate was concentrated to afford 2-methyl-5-nitro pyridine (5.0 g, 83%) as a brown solid.

Reference Example 29

(4,6-Dimethyl-pyridin-2-ylmethyl)-(4-nitro-phenyl)-amine a) Preparation of (4,6-dimethyl-pyridin-2-yl)-methanol
Trifluoroacetic anhydride (20 mL) was added to 2,4,6-trimethyl-pyridine-1-oxide (2.0 g, 14.6 mmol) at 0° C., then the mixture was stirred at room temperature for 5 h. The mixture was concentrated in vacuo, diluted with water and extracted with ethyl acetate. The organic phase was washed with water, dried over anhydrous sodium sulfate and concentrated to afford a residue which was purified by column chromatography on silica gel (60-120 mesh), eluting with 25% ethyl acetate/hexane, to afford (4,6-dimethyl-pyridin-2-yl)-methanol (1.0 g, 50%)-s a dark brown liquid b) Preparation of 4,6-dimethyl-pyridine-2-carbaldehyde
Manganese dioxide (3.17 g, 36.5 mmol) was added to a solution of (4,6-dimethyl-pyridin-2-yl)-methanol (1.0 g, 7.30 mmol) in chloroform (30 mL) and heated at reflux overnight. The reaction mixture was cooled to 0° C. and filtered over celite, washing with further chloroform. The filtrate was evaporated to give a residue which was purified by column chromatography over silica gel (60-120 mesh) using 10% ethyl acetate in hexane as eluent to afford 4,6-dimethyl-pyridine-2-carbaldehyde (0.5 g, 51%) as a light brown liquid.

c) Preparation of (4,6-dimethyl-pyridin-2-ylmethyl)-(4-nitro-phenyl)-amine
p-Nitroaniline (0.51 g, 3.7 mmol) was added to a solution of 4,6-dimethyl-pyridine-2-carbaldehyde (0.5 g, 3.7 mmol) in tetrahydrofuran (20 mL) at 0° C., followed by sulfuric acid and water (1 mL:1 mL). After stirring at 0° C. for 30 min. sodium cyanoborohydride (0.47 g, 7.4 mmol) was added portionwise at 0° C. The mixture stirred at room temperature for 1 h then concentrated in vacuo, diluted with water and extracted with ethyl acetate. The organic phase was washed with sodium carbonate solution, dried over anhydrous sodium sulfate and concentrated to give a residue which was purified by column chromatography on silica gel (60-120 mesh) using 18% ethyl acetate/hexane as eluent to afford (4,6-dimethyl-pyridin-2-ylmethyl)-(4-nitro-phenyl)-amine (0.35 g, 37%).

Reference Example 30

N-(2-Isopropyl-4-nitro-phenyl)-acetamide

2-Isopropyl aniline (10 g, 74 mmol) was added to ice-cold acetic anhydride (75 mL) and stirred for 1 hr at 0° C. Concentrated nitric acid (10 mL, 159 mmol) was added dropwise and the reaction mass stirred at this temp for a further 30 min. It was then poured into ice-cold water and the precipitated solid was filtered off. The resulting solid was added to a solution of potassium hydroxide (12 g) in a mixture of water (115 mL) and absolute ethanol (25 mL) and stirred for 15 min. The solid was filtered off and washed thoroughly with water to afford N-(2-isopropyl-4-nitro-phenyl)-acetamide (4.3 g, 26%) as a solid.

Reference Example 31

2-Isopropyl-4-nitro-phenylamine

N-(2-Isopropyl-4-nitro-phenyl)-acetamide (3 g, 13.5 mmol) was dissolved in absolute ethanol (20 mL) and 5N hydrochloric acid (20 mL) was added. The mixture was heated to reflux overnight, cooled to r.t. then concentrated in vacuo to remove the ethanol. The mixture was basified with dilute sodium hydroxide solution and extracted with ethyl acetate. The combined organic layers were washed with water and brine solution, dried over sodium sulfate and concentrated. The crude product was purified by column chromatography on silica gel (60-120 mesh), eluting with 17% ethyl acetate/petroleum ether to afford 2-isopropyl-4-nitro-phenylamine (2.1 g, 85%).

Reference Example 32

2-Isopropyl-4-nitro-benzonitrile

2-Isopropyl-4-nitro-phenylamine (1.0 g, 5.55 mmol) was dissolved in 5N hydrochloric acid (10 mL) and cooled to 0° C. A solution of sodium nitrite (0.96 g, 13.9 mmol) in water (5 mL) was added and the mixture stirred at this temperature for 1 hr. The mixture was filtered and the solids washed with ice-water, the filtrate then being added to a previously-prepared and cooled (0° C.) solution of CuCN (0.82 g, 9.16 mmol) and NaCN (0.68 g, 13.9 mmol) in water. This mixture was warmed to r.t. and stirred for 1 hr, then ethyl acetate was added and the mixture basified with ammonia solution. Precipitated copper salts were filtered off, and the filtrate was extracted with ethyl acetate. The organic phase was washed with water and brine, dried over sodium sulfate and concentrated. The crude product was purified by column chromatography on silica gel (60-120 mesh), eluting with 4% ethyl acetate/petroleum ether to yield 2-isopropyl-4-nitro-benzonitrile (440 mg, 42%).

Reference Example 33

2-Isopropyl-4-nitrophenol

2-Isopropyl-4-nitro-phenylamine (2.5 g, 13.9 mmol) was dissolved in 10% sulfuric acid (25 mL) and to this was added sodium nitrite (1.64 g, 23.8 mmol) in portions over 15 min at 0° C. The diazotized solution was added to boiling water and stirred for 15 min. the mixture was cooled to r.t. and extracted with ethyl acetate. The combined organic layers were washed with brine, dried over sodium sulfate and concentrated in vacuo to afford 2-isopropyl-4-nitro phenol (2 g, 80%) as a solid.

Reference Example 34

5-Bromo-2-chloro-pyridine a) Preparation of 6-chloro-pyridin-3-ylamine

2-Chloro-5-nitro-pyridine (15 g, 94.9 mmol) was hydrogenated over Raney nickel (2 g) in methanol (200 mL) at 70 psi and r.t. for 26 h. The mixture was filtered through Celite and concentrated to afford 6-chloro-pyridin-3-ylamine (10.4 g, 83%).

b) Preparation of 5-bromo-2-chloro-pyridine

6-Chloro-pyridin-3-ylamine (15 g, 117 mmol) was dissolved slowly with constant stirring in 48% HBr solution (50 mL) at r.t. and then the solution was chilled to −10° C. A solution of sodium nitrite (8.9 g, 129 mmol) in cold water (25 mL) was added dropwise at −10° C. with constant stirring over 2 h, followed by a solution of copper (I) bromide (25 g, 176 mmol) in 48% HBr (40 mL) dropwise. The mixture was then stirred at r.t. until complete. The mixture was neutralised with sodium carbonate and extracted with ethyl acetate. The organic phase was washed with brine, dried over sodium sulfate and concentrated. The residue was purified by column chromatography on silica gel (60-120 mesh) eluting with 1% ethyl acetate/petroleum ether to afford 5-bromo-2-chloro-pyridine (11.1 g, 49%).

Reference Example 35

2-Isopropyl-4-nitro-benzoic acid

2-Isopropyl-4-nitro-benzonitrile (0.4 g, 2.10 mmol) was dissolved in dioxane (10 mL) and 80% sulfuric acid (10 mL) was added. The mixture was heated at reflux for 2 days then dioxane was evaporated under reduced pressure. The residue was basified with dilute sodium hydroxide solution and washed with ethyl acetate. The aqueous layer was then acidified with dilute hydrochloric acid and extracted with ethyl acetate. The organic phase was separated, washed with water and brine, dried over sodium sulfate and concentrated to yield 2-isopropyl-4-nitro-benzoic acid (0.23 g, 52%) as a white solid.

Reference Example 36

2-Methyl-2-(4-nitrophenyl)-propionic acid a) Preparation of 2-methyl-2-(4-nitrophenyl)-propionitrile Sodium hydroxide (12.3 g, 0.30 mol) was added to (4-nitrophenyl)-acetonitrile (10 g, 61.7 mmol) and tetrabutylammonium hydroxide (6.4 g, 24.7 mmol) in a mixture of DCM (50 mL) and water (12 mL). When a clear solution had formed, it was cooled to 0° C. and iodomethane (70 g, 0.49 mol) was added, then the mixture was warmed to r.t. and stirred for 12 h. The mixture was partitioned between water and DCM then the separated organic phase was dried over sodium sulfate and concentrated to obtain the crude product. This was subjected to column chromatography on silica gel (60-120 mesh), eluting with 6% ethyl acetate/hexane which afforded 2-methyl-2-(4-nitrophenyl)-propionitrile (8 g, 68%).

b) Preparation of 2-methyl-2-(4-nitrophenyl)-propionic acid

2-Methyl-2-(4-nitrophenyl)-propionitrile (1 g, 5.26 mmol) was heated at reflux in 50% sulfuric acid (10 mL) overnight. The mixture was cooled and diluted with ice-cold water then extracted with ethyl acetate. The organic phase was extracted with dilute sodium hydroxide solution, then the aqueous layer was acidified with conc. hydrochloric acid to pH 2 and re-extracted with ethyl acetate. The organic phase was dried and concentrated to afford 2-methyl-2-(4-nitrophenyl)-propionic acid (1 g, 91%).

Reference Example 37

2-Methyl-2-(3-nitrophenyl)-propionic acid

This compound was prepared in a manner analogous to Reference Example 36.

Reference Example 38

2-methyl-2-(4-nitrophenyl)-propionic acid 2-bromo-ethyl ester

Thionyl chloride (3 mL, 41 mmol) was added to 2-methyl-2-(4-nitrophenyl)-propionic acid (1 g, 4.78 mmol) and heated at 90° C. overnight. Excess thionyl chloride was evaporated to give a crude acid chloride which was dissolved in acetonitrile (8 mL). To this was added 2-bromoethanol (0.41 mL, 5.78 mmol) then the mixture was heated at reflux overnight. After concentration in vacuo, the residue was diluted with ethyl acetate and washed with sodium bicarbonate solution, then the organic layer was dried and evaporated to afford 2-methyl-2-(4-nitrophenyl)-propionic acid, 2-bromo-ethyl ester (0.99 g, 65.5%).

Reference Example 39

2-Methyl-2-(3-nitro-phenyl)-propionic acid 2-bromo-ethyl ester

This compound was prepared in a manner analogous to Reference Example 38.

Reference Example 40

2-Isopropyl-4-nitro-benzoic acid 2-bromo-ethyl ester

A mixture of 2-isopropyl-4-nitro-benzoic acid (0.23 g, 1.10 mmol), 2-bromoethanol (1.0 mL, 14.1 mmol) and conc. sulfuric acid (0.2 mL) was heated at 80° C. overnight. The mixture was cooled to r.t., diluted with water and extracted twice with ethyl acetate. The organic phase was washed with sat. sodium bicarbonate solution, water and brine then dried over sodium sulfate and concentrated. The crude product was purified by column chromatography on silica (60-120 mesh), eluting with 7% ethyl acetate/petroleum ether, to afford 2-isopropyl-4-nitro-benzoic acid 2-bromo-ethyl ester (0.24 g, 69%) as a colourless oil.

Reference Example 41

Diethyl-carbamic acid-5-(4-nitro-phenyl)-isoxazol-3-yl ester a) Preparation of (4-nitrophenyl)-propynoic acid methyl ester 1-Iodo-4-nitrobenzene (2.5 g, 10 mmol) was added to a solution of triethylamine (2.0 g, 20 mmol) in THF (40 mL). $PdCl_2(PPh_3)_2$ (0.14 g, 0.20 mmol), cuprous iodide (0.076 g, 0.40 mmol) and methyl propiolate (3.4 g, 40 mmol) were added and the resulting mixture was heated to reflux overnight. The reaction mixture was cooled to r.t., the solvent evaporated, and the crude compound dissolved in dichloromethane. The organics were filtered to remove insoluble material and the filtrate was washed with water, brine solution and dried over sodium sulfate. The filtrate was concentrated and the residue purified over silica gel using 15% ethyl acetate in petroleum ether as eluent to afford (4-nitrophenyl)-propynoic acid methyl ester (1.20 g, 59%) as a white solid.

b) Preparation of 5-(4-nitrophenyl)-isoxasol-3-ol

A solution of (4-nitrophenyl)-propionic acid methyl ester (1.2 g, 5.8 mmol) in ethanol (15 mL) was added to a stirred solution of hydroxylamine hydrochloride (1.2 g, 17.5 mmol) in 10% NaOH (17 mL) and the resulting mixture stirred overnight at r.t. The reaction was cooled and acidified with conc. hydrochloric acid to pH 2 and the precipitated solid was filtered, washed with water and dried to give 5-(4-nitrophenyl)-isoxasol-3-ol (0.6 g, 50%) as a pale yellow solid.

c) Preparation of diethyl-carbamic acid-5-(4-nitro-phenyl)-isoxazol-3-yl ester

Diethyl carbamoyl chloride (0.5 g, 3.6 mmol) was added to a stirred solution of 5-(4-nitro-phenyl)-isoxasol-3-ol (0.5 g, 2.4 mmol) in pyridine (6 mL) at r.t. and the mixture stirred for 4 h. The solvent was evaporated and the residue dissolved in ethyl acetate which was then washed with water and brine solution, dried over sodium sulfate and concentrated in vacuo. Trituration with toluene afforded diethyl-carbamic acid-5-(4-nitro-phenyl)-isoxazol-3-yl ester (0.44 g, 59%) as an off white solid.

Reference Example 42

N*1*-(4-nitro-phenyl)-ethane-1,2-diamine

A mixture of 1-chloro-4-nitro-benzene (10 g, 64 mmol) and ethane-1,2-diamine (38 mL) was heated at reflux for 4 h. Excess ethane-1,2-diamine was evaporated under reduced pressure and water was added to the residue. The precipitated solid was filtered off and dried under vacuum to afford N*1*-(4-nitro-phenyl)-ethane-1,2-diamine (10.8 g, quantitative).

Reference Example 43

N-(4,6-Dimethyl-pyridin-2-yl)-N'-(4-nitrophenyl)-ethane-1,2-diamine

To a solution of trifluoro-methanesulfonic acid 4,6-dimethyl-pyridin-2-yl ester (0.6 g, 2.35 mmol) in diglyme (2 mL) was added N*1*-(4-nitro-phenyl)-ethane-1,2-diamine (0.51 g, 2.82 mmol). The reaction mixture was heated to 165° C. for 24 h. The resulting reaction mixture was concentrated under reduced pressure and the residue diluted with chloroform. The organic layer was washed with brine and water and dried over sodium sulfate. The solvent was evaporated and the crude residue was purified by column chromatography (60-120 mesh) using 20% ethyl acetate/petroleum ether as eluent to afford N-(4,6-dimethyl-pyridin-2-yl)-N'-(4-nitro-phenyl)-ethane-1,2-diamine (0.38 g, 55%) as a cream solid.

Reference Example 44

Methyl-(4-nitro-phenyl)-amine

1-Chloro-4-nitro-benzene (5.0 g, 31.7 mmol) was added to excess aqueous methylamine solution-(40%, 30 mL) and heated in a pressure bomb for 16 h. The reaction mass was cooled to room temperature and a solid filtered off. The filtrate was evaporated to dryness and the combined solids were purified by trituration with pentane to afford methyl-(4-nitrophenyl)-amine (4.5 g, 93%) as a solid.

Reference Example 45

3-[Methyl-(4-nitro-phenyl)-amino]-propionic acid

Methyl-(4-nitro-phenyl)-amine (3.0 g, 19.7 mmol) and acrylic acid (4.06 mL, 59.2 mmol) were added at 0° C. to a solution of concentrated sulfuric acid (2.15 mL, 39.5 mmol) in water-(28 mL). The reaction mixture was heated at 80° C. for 30 min, cooled to room temperature and diluted with water. The precipitated solid was filtered and dried to give a crude product which was purified by washing with diethyl ether and pentane, affording 3-[methyl-(4-nitro-phenyl)-amino]-propionic acid (4.0 g, 91%) as a yellow solid.

Reference Example 46

Preparation of (4-nitro-phenylamino)-acetic acid

Glycine (5.31 g, 70.8 mmol) was added to a mixture of 1-fluoro-4-nitro-benzene (5.0 g, 35.4 mmol) and sodium bicarbonate (5.94 g, 70.8 mmol) in dioxane (10 mL) and water (60 mL) and heated at reflux for 6 h. The reaction mixture was cooled to room temperature and washed with ethyl acetate. The aqueous layer was acidified with 1N hydrochloric acid to pH ~3 and extracted with ethyl acetate. The extract was washed with water, brine, dried over anhydrous sodium sulfate and concentrated to dryness to afford (4-nitrophenylamino)-acetic acid (5.0 g, 72%) as a yellow solid.

Reference Example 47

The compound set out below was prepared a manner analogous to Reference Example 46:

| Example | Compound |
| --- | --- |
| 46 | (4-Nitrophenyl)-[2-pyridin-2-yloxy)-ethyl]-amine |

Reference Example 48

[Methyl-(4-nitro-phenyl)-amino]-acetic acid

A solution of (4-nitro-phenylamino)-acetic acid (1.3 g, 6.6 mmol) in formic acid (5 mL) and formaldehyde (5 mL) was heated at reflux overnight. The mixture was concentrated in vacuo and 1N hydrochloric acid added to the residue giving a pH ~3. The mixture was extracted with ethyl acetate then the organic phase was washed with water and brine. Concentration in vacuo afforded [methyl-(4-nitro-phenyl)-amino]-acetic acid (1.2 g, 86%) as a yellow solid.

Reference Example 49

[(4-Nitro-phenyl)-(2,2,2-trifluoro-acetyl)-amino]-acetic acid

Sodium hydride (1.48 g, 55% in mineral oil; 34.1 mmol) was added to a solution of (4-nitro-phenylamino)-acetic acid (2.0 g, 11.4 mmol) in tetrahydrofuran at 0° C. and stirred for 1 h. Trifluoroacetic anhydride (6.9 g, 34.1 mmol) was added at 0° C. and the reaction mixture stirred overnight. Water was added and the mixture acidified with dilute acetic acid to pH ~6. This was extracted with ethyl acetate, the organic layer then being washed with saturated sodium bicarbonate solution, brine, dried over anhydrous sodium sulfate and concentrated in vacuo to obtain the crude compound. Purification by column chromatography over silica gel (60-120 mesh) using 2% methanol in chloroform as eluent gave [(4-nitro-phenyl)-(2,2,2-trifluoro-acetyl)-amino]-acetic acid (2.1 g, 64%) as a yellow solid.

Reference Examples 50 to 52

The compounds set out below were prepared a manner analogous to Reference Example 49:

| Example | Compound |
|---------|----------|
| 50 | 2,2,2-Trifluoro-N-(4-nitrophenyl)-N-[2-(pyridine-2-yloxy)-ethyl]-acetamide |
| 51 | N-[2-(4,6-Dimethyl-pyridin-2-ylamino)-ethyl]-2,2,2-trifluoro-N-(4-nitrophenyl)-acetamide |
| 52 | N-(4,6-Dimethyl-pyridin-2-ylmethyl)-2,2,2-trifluoro-N-(4-nitro-phenyl)-acetamide |

Reference Example 53

1-methyl-4-(4-nitro-2-oxazol-2-yl-phenyl)-piperazine a) Preparation of 2-chloro-N-(2,2-dimethoxy-ethyl)-5-nitro-benzamide Thionyl chloride (14 mL, 192 mmol) was added-dropwise to a solution of 2-chloro-5-nitrobenzoic acid (10 g, 49.6 mmol) in chloroform (150 mL) at 0° C. The mixture was heated to reflux for 4 h then cooled to r.t., concentrated in vacuo and dried under high vacuum to yield 2-chloro-5-nitrobenzoyl chloride (10 g, 91.7%) as a solid. Under nitrogen, triethylamine (19 mL, 136 mmol) was added slowly to a solution of aminoacetaldehyde dimethyl acetal (5.43 mL, 50.0 mmol) in dry DCM (20 mL) at 0° C. 2-Chloro-5-nitrobenzoyl chloride (10 g, 45.5 mmol) was slurried in dry DCM (30 mL) and added over a period of 30 minutes. The mixture was allowed to warm to r.t. and stirred overnight then partitioned between water and DCM. The organic phase was washed with saturated sodium bicarbonate solution, water and brine then dried over sodium sulfate and concentrated. The crude product was triturated with petroleum ether then diethyl ether and finally purified by column chromatography on silica gel (60-120 mesh) eluting with ethyl acetate/petroleum ether (2% to 40% gradient) to afford 2-chloro-N-(2,2-dimethoxy-ethyl)-5-nitro benzamide (8.3 g, 63%) as a yellow solid.

b) Preparation of 2-(2-chloro-5-nitrophenyl)-oxazole

Under nitrogen, phosphorus pentoxide (0.98 g, 6.90 mmol) was added portionwise to a slurry of 2-chloro-N-(2,2-dimethoxy-ethyl)-5-nitro-benzamide (0.5 g, 1.73 mmol) in methanesulfonic acid (5 mL) at r.t. The mixture was heated to 140-145° C. for 6 h. After cooling to r.t., the mixture was poured onto ice-water and extracted with ethyl acetate. The combined organic phases were washed with water then brine, dried over sodium sulfate, filtered and concentrated in vacuo. Further drying under high vacuum gave 2-(2-chloro-5-nitrophenyl)-oxazole (0.366 g, 94%) as a solid.

c) Preparation of 1-methyl-4-(4-nitro-2-oxazol-2-yl-phenyl)-piperazine 2-(2-Chloro-5-nitrophenyl)-oxazole (0.366 g, 1.63 mmol) was heated in N-methylpiperazine (15 mL) at reflux for 5 hrs. The mixture was allowed to cool and excess N-methylpiperazine was distilled under high vacuum. The residue was diluted with water and extracted with ethyl acetate. The organic phase was washed with water then brine, dried over sodium sulfate, filtered and concentrated. Drying under high vacuum gave 1-methyl-4-(4-nitro-2-oxazol-2-yl-phenyl)-piperazine (0.328 g, 70%) as a solid.

Reference Examples 54 to 58

The compound set out below was prepared in a manner analogous to step A of Reference Example 53 (above):

| Example | Compound |
|---------|----------|
| 54 | N-(4,6-Dimethyl-pyridin-2-yl)-2-(4-nitrophenoxy)-acetamide |
| 55 | N-(4,6-Dimethyl-pyridin-2-yl)-3-(4-nitrophenyl)-propionamide |
| 56 | N-(4,6-dimethyl-pyridin-2-yl)-2-[methyl-(4-nitro-phenyl)-amino]-acetamide |
| 57 | N-{[(4,6-Dimethyl-pyridin-2-yl)-methyl-carbamoyl]-methyl}-2,2,2-trifluoro-N-(4-nitro-phenyl)-acetamide |
| 58 | N-(4,6-Dimethyl-pyridin-2-yl)-N-methyl-3-[methyl-(4-nitro-phenyl)-amino]-propionamide |

Reference Example 59

N-(4,6-Dimethyl-pyridin-2-yl)-N-methyl-2-(4-nitro-phenylamino)-acetamide

Lithium hydroxide monohydrate (56 mg, 1.34 mmol) was added to a solution of N-{[(4,6-Dimethyl-pyridin-2-yl)-methyl-carbamoyl]-methyl}-2,2,2-trifluoro-N-(4-nitro-phenyl)-acetamide (550 mg, 1.34 mmol) in methanol (20 mL) at 0° C. and stirred for 1 h. The pH was adjusted to approximately pH 6 by the addition of acetic acid. Methanol was evaporated in vacuo to yield a solid residue, which was stirred in water and filtered to afford N-(4,6-dimethyl-pyridin-2-yl)-N-methyl-2-(4-nitro-phenylamino)-acetamide (350 mg, 53%) as a yellow solid.

Reference Example 60

2,4-dimethyl-6-[4-(4-nitro-phenyl)-buta-1,3-dienyl]-pyridine 2,4,6-Trimethylpyridine (2.24 mL, 16.9 mmol) and sodium acetate (0.92 g, 11.3 mmol) were added to a solution of trans-4-nitrocinnamaldehyde (1.0 g, 5.64 mmol) in acetic anhydride (20 mL). The reaction mixture was refluxed for 8 h, then brought to room temperature and quenched with 5% sodium bicarbonate solution (40 mL). The compound was extracted with ethyl acetate and the organic layer was washed with water, brine solution, dried over anhydrous sodium sulfate, filtered and concentrated. The crude compound was purified by column chromatography over silica gel (60-120 mesh) using 30% ethyl acetate in hexane as eluent to afford 2,4-dimethyl-6-[4-(4-nitro-phenyl)-buta-1,3-dienyl]-pyridine (800 mg, 51%) as a yellow solid.

Reference Example 61

4-(4-Nitro-phenyl)-thiomorpholine

A solution of 1-chloro-4-nitrobenzene (1.5 g, 9.5 mmol) and thiomorpholine (1.0 g, 9.7 mmol) in n-butanol was heated at reflux for 24 h. The solvent was evaporated under reduced pressure to give a residue, which on trituration with water gave a solid. This was filtered off and washed thoroughly with water then with a small amount of petroleum ether. This gave a solid which was recrystallised from ethanol to yield 4-(4-nitro-phenyl)-thiomorpholine (1.6 g, 76%).

Reference Examples 62 to 65

The compounds set out below were prepared a manner analogous to Reference Example 61:

| Reference Example | Compound |
|---|---|
| 62 | 1-(4-Nitro-phenyl)-piperidin-4-one |
| 63 | 1-(5-Nitro-pyridin-2-yl)-piperazine |
| 64 | 1-(6-Nitro-pyridin-3-yl)-piperazine |
| 65 | 1-(4-Nitro-phenyl)-[1,4]-diazepane |

Reference Example 66

2-(5-Bromo-pyridin-2-ylamino)-ethanol

A mixture of 2-chloro-4-bromo-pyridine (6.0 g, 31.3 mmol) and 2-amino-ethanol (15.3 g, 250 mmol) in diglyme (30 mL) was heated at 120° C. for 30 h. After allowing to cool, water (200 mL) was added and the mixture was extracted with chloroform. The organic phase was washed repeatedly with brine, dried over sodium sulfate and concentrated to afford 2-(5-bromo-pyridin-2-ylamino)-ethanol (6.0 g, 89%).

Reference Example 67

2-(6-chloro-pyridin-2-ylamino)-ethanol

2-Amino-ethanol (0.82 g, 13.5 mmol) was added to a solution of 2,6-dichloropyridine (2.0 g, 13.5 mmol) in pyridine (10 mL) at room temperature and then heated at 100° C. overnight. The reaction mixture was concentrated in vacuo to obtain a residue which was dissolved in ethyl acetate. The solution was washed with water, brine, dried over anhydrous sodium sulfate and evaporated in vacuo to afford 2-(6-chloro-pyridin-2-ylamino)-ethanol (2.3 g, 99%) as a white solid.

| Reference Example | Compound |
|---|---|
| 68 | 2-[(6-Chloro-pyridin-2-yl)-(2-hydroxy-ethyl)-amino]-ethanol |

Reference Example 69

4-(4-Nitro-phenyl)-thiomorpholine 1,1-dioxide

Hydrogen peroxide (0.2 g, 5.5 mmol) was added to a solution of 4-(4-nitro-phenyl)-thiomorpholine (0.5 g, 2.2 mmol) in acetic acid (3 mL) and the mixture was stirred at r.t. for 3 h. The mixture was diluted with ethyl acetate and washed with water then the organic phase was concentrated to dryness. The crude product was purified by column chromatography on silica gel, eluting with 20% methanol/chloroform, to afford 4-(4-nitro-phenyl)-thiomorpholine 1,1-dioxide (0.155 g, 27%).

Reference Example 70

4-Methylene-1-(4-nitrophenyl)-piperidine

To a solution of methyltriphenylphosphonium bromide (1.07 g, 3 mmol) in THF (10 mL) was added 2.5 M n-BuLi solution (1.6 mL, 4 mmol) at −70° C. The mixture was warmed to r.t. and stirred for 15 min then cooled once more to −70° C. A solution of 1-(4-nitro-phenyl)-piperidin-4-one (396 mg, 1.8 mmol) in THF (10 mL) was added then the mixture was allowed to warm to r.t. and stirred overnight. The reaction was quenched by addition of ice and extracted with ethyl acetate. The combined organic layers were then washed with water, brine and dried over sodium sulfate. Concentration to dryness afforded 4-methylene-1-(4-nitrophenyl)-piperidine (240 mg, 61%) as a solid.

Reference Example 71

8-(4-Nitrophenyl)-1,4-dioxa-8-aza-spiro[4,5]decane

A mixture of 1-(4-nitrophenyl)-4-piperidone (0.6 g, 2.7 mmol), ethylene glycol (0.3 mL, 5.4 mmol) and p-toluene-sulfonic acid (0.1 g in toluene (20 mL) was heated at reflux in a Dean-Stark apparatus until no more water accumulation occurred. The reaction was evaporated to dryness and the residue partitioned between ethyl acetate and water. The organic layer was separated and washed with water then brine and dried over sodium sulfate. Concentration under reduced pressure afforded 8-(4-nitrophenyl)-1,4-dioxa-8-aza-spiro[4,5]decane (0.48 g, 66%).

Reference Example 72

Bis-[2-(tert-butyl-dimethyl-silanyloxy)-ethyl]-(6-chloro-pyridin-2-yl)-amine To a solution of 2-[(6-chloro-pyridin-2-yl)-(2-hydroxy-ethyl)-amino]-ethanol (1.5 g, 6.92 mmol) and imidazole (2.3 g, 33.8 mmol) in THF (10 mL), was added tert-butyldimethylsilyl chloride (TBDMS-Cl, 3.1 g, 20.5 mmol) in THF (10 mL) slowly at 0° C. and stirred for 4 h at r.t. The reaction mixture was quenched into water and extracted with ethyl acetate. The organic layer was washed with brine, dried over sodium sulfate, filtered and evaporated under vacuum to afford bis-[2-(tert-butyl-dimethyl-silanyloxy)-ethyl]-(6-chloro-pyridin-2-yl)-amine (2.1 g, 68%) as a brown oil.

Reference Examples 73 to 74

The compounds set out below were prepared a manner analogous to Reference Example 72:

| Reference Example | Compound |
|---|---|
| 73 | [2-(tert-butyl-dimethyl-silanyloxy)-ethyl]-(6-chloro-pyridin-2-yl)-amine |
| 74 | 2-[2-tert-butyl-dimethyl-silanyloxy)-ethyl]-6-chloro-pyridine |

Reference Example 75

2-(2-Bromo-ethyl)-pyridine

To an ice-cold solution of 2-pyridin-2-yl-ethanol (1 g, 8.1 mmol) in diethyl ether (20 mL) was added freshly distilled phosphorous tribromide (0.75 g, 2.7 mmol) over 15 min. The reaction mixture was warmed to r.t. and stirred for a further 5 hours. The reaction mixture was poured into an excess of cooled bicarbonate solution and extracted with dichloromethane (×2). The combined organic layers were washed with brine, dried over sodium sulfate, filtered and concentrated to afford 2-(2-bromo-ethyl)-pyridine (0.87 g, 58%) as a liquid.

Reference Example 76

Toluene-4-sulfonic acid 2-furan-2-yl-ethyl ester a) Preparation of furan-2-yl-acetic acid ethyl ester
Ethyl iodo acetate (12.0 g, 56.0 mmol), furan (76.3 g, 112 mmol) and $Fe_2SO_4.7H_2O$ (7.8 g, 28.0 mmol) were added to DMSO (100 mL). 30% hydrogen peroxide (19.1 g, 56.0 mmol) was added dropwise at 0° C. and the resulting mixture stirred for 2 h while warming to r.t. The reaction mixture was diluted with brine and extracted with ether. The combined extracts were washed with brine, dried over anhydrous sodium sulfate, filtered and concentrated in vacuo to give the crude compound. Purification by column chromatography over silica gel (60-120 mesh) using 8% ether/petroleum ether as eluent afforded furan-2-yl-acetic acid ethyl ester (3.3 g, 38%) as an oil.

b) Preparation of 2-furan-2-yl-ethanol
To a stirred suspension of lithium aluminium hydride (1.62 g, 21.4 mmol) in ether at 0° C. was added furan-2-yl-acetic acid ethyl ester (3.3 g, 21.4 mmol) dropwise and the resulting mixture was stirred at r.t. for 1 hr. The reaction was quenched with sat. ammonium chloride solution and extracted with ether. The combined organics were washed with brine, dried over anhydrous sodium sulfate, filtered and concentrated in vacuo to afford 2-furan-2-yl-ethanol (1.68 g, 70%) as an oil.

c) Preparation of toluene-4-sulfonic acid 2-furan-2-yl-ethyl ester
To a stirred solution of 2-furan-2-yl-ethanol (1.6 g, 14.0 mmol) in a mixture of pyridine (5 mL) and chloroform (15 mL) was added para-toluenesulfonyl chloride (5.5 g, 28.0 mmol) and heated at 60° C. for 3 hrs. The reaction was cooled and concentrated in vacuo. The residue was dissolved in ethyl acetate and washed with water, sat. sodium bicarbonate solution and dried over anhydrous sodium sulfate. The filtrate was concentrated, and the crude compound purified by column chromatography over silica gel (60-120 mesh) using 10% ethyl acetate/petroleum ether as eluent to afford toluene-4-sulfonic acid 2-furan-2-yl-ethyl ester (2.0 g, 32%) as an oil.

Reference Example 77

1-Furan-2-ylmethyl-4-(4-nitrophenyl)-piperazine

To a solution of 1-(4-nitrophenyl)-piperazine (0.6 g, 2.89 mmol) in THF (10 mL) was added fufaraldehyde (0.41 g, 4.31 mmol), acetic acid (3 mL) and water (1.5 mL) and the mixture stirred at r.t. for half an hour. Sodium cyanoborohydride (0.27 g, 4.31 mmol) was added and the reaction heated at reflux for four hours. The reaction was cooled and the solvent evaporated. The resulting residue was diluted with water and extracted with dichloromethane. The combined organic layers were washed with saturated sodium bicarbonate and brine solution, dried over sodium sulfate, filtered and concentrated. Purification by column chromatography over silica gel (60-120 mesh) using 5% methanol/chloroform as eluent afforded 1-furan-2-ylmethyl-4-(4-nitrophenyl)-piperazine (0.45 g, 54%) as a yellow solid.

Reference Examples 78 to 81

The compounds set out below were prepared in a manner analogous to Reference Example 77 using the appropriate starting materials:

| Example | Compound |
|---|---|
| 78 | 1-(4-Nitrophenyl)-4-thiophen-2-ylmethyl piperazine |
| 79 | 1-Furan-2-ylmethyl-4-(5-nitro-pyridin-2-yl)-piperazine |
| 80 | 1-(5-Nitro-pyridin-2-yl)-4-thiophene-2-ylmethyl piperazine |
| 81 | 1-(4-Nitrophenyl)-4-(tetrahydro-pyran-4-yl-methyl)-piperazine |

Reference Example 82

2,6-Dimethyl-4-[1-(4-nitrophenyl)-piperidin-4-yl) morpholine

To an ice-cooled solution of 1-(4-nitro-phenyl)-piperidin-4-one (400 mg, 1.8 mmol) in acetic acid was added cis-2,6-dimethyl-morpholine (0.32 mL, 2.68 mmol) and sodium cyanoborohydride (220 mg, 3.50 mmol). The mixture was heated at reflux overnight then allowed to cool and concentrated to dryness under reduced pressure. The residue was partitioned between 5% sodium hydroxide solution and ethyl acetate. The organic phase was washed with water, brine, dried and concentrated to afford 2,6-dimethyl-4-[1-(4-nitrophenyl)-piperidin-4-yl]-morpholine (500 mg, 86%) as a yellow solid.

Reference Example 83

The compound set out below was prepared in a manner analogous to Reference Example 82 using the appropriate starting materials:

| Example | Compound |
|---|---|
| 83 | 4-[1-(4-Nitrophenyl)-piperidine-4-yl]-morpholine |

Reference Example 84

N-(4,6-dimethyl-pyridin-2-yl)-N'-(4-nitro-phenyl)-oxalamide a) Preparation of N-(4-nitro-phenyl)-oxalamic acid ethyl ester Ethyl oxalyl chloride (5.4 g, 36.2 mmol) was added slowly to a cold (0° C.) solution of 4-nitroaniline (5 g, 36.2 mmol) and triethylamine (7.3 g, 72 mmol) in THF (15 mL) then the mixture was stirred at ambient temperature overnight. The mixture was concentrated to dryness, diluted with ethyl acetate and washed with 2N hydrochloric acid; the aqueous layer was re-extracted with ethyl acetate. The combined organic layers were washed with sodium bicarbonate solution and brine, then dried over anhydrous sodium sulfate and concentrated in vacuo to afford N-(4-nitro-phenyl)-oxalamic acid ethyl ester (4.9 g, 57%).

b) Preparation of N-(4,6-dimethyl-pyridin-2-yl)-N'-(4-nitro-phenyl)-oxalamide

A solution of N-(4-nitro-phenyl)-oxalamic acid ethyl ester (4.9 g, 20.5 mmol), triethylamine (4.2 g, 41 mmol) and 2-amino-4,6-dimethylpyridine (2.5 g, 20.5 mmol) in dry toluene (30 mL) was heated at reflux overnight. The mixture was cooled to 0° C., and a precipitate was filtered and washed with water. Drying under vacuum afforded N-(4,6-dimethyl-pyridin-2-yl)-N'-(4-nitro-phenyl)-oxalamide (4.8 g, 74%).

Reference Example 85

2,2-Dimethyl-1-[4-(6-nitro-pyridin-3-yl)-piperazin-1-yl]-propan-1-one

To a stirred solution of 1-(6-nitro-pyridin-3-yl)-piperazine (3.00 g, 14.4 mmol) in dichloromethane (30 mL) was added triethylamine (2.91 g, 28.8 mmol) followed by the dropwise addition of pivaloyl chloride (1.90 g, 15.9 mmol) at r.t. and the resulting solution was stirred for 15 min. The reaction was quenched with sat. sodium bicarbonate solution and extracted with dichloromethane (×3). The combined organics were dried over anhydrous sodium sulfate, filtered and concentrated. The crude material was washed with petroleum ether to afford 2,2-dimethyl-1-[4-(6-nitro-pyridin-3-yl)-piperazin-1-yl]-propan-1-one (2.50 g, 59%) as pale yellow solid.

Reference Example 86

1-(2,2-Dimethyl-propyl)-4-(6-nitro-pyridin-3-yl)-piperazine

To a solution of 2,2-dimethyl-1-[4-(6-nitro-pyridin-3-yl)-piperazin-1-yl]-propan-1-one (1.0 g, 3.42 mmol) in THF (10 mL) was added BH$_3$.DMS (0.6 mL, 6.84 mmol) at r.t. and the reaction was then heated to reflux for 6 h. The reaction was cooled, quenched with ammonium chloride solution and extracted with ethyl acetate. The combined organic layers were washed with brine solution, dried over anhydrous sodium sulfate, filtered and concentrated under vacuum. The crude material was purified by column chromatography over silica gel (60-120 mesh) using 20% ethyl acetate/petroleum ether as eluent to afford 1-(2,2-dimethyl-propyl)-4-(6-nitro-pyridin-3-yl)-piperazine (0.5 g, 52.5%).

Reference Examples 87 to 92

The compounds set out below were prepared in a manner analogous to Reference Example 86:

| Example | Compound |
|---------|----------|
| 87 | (4,6-Dimethyl-pyridin-2-yl)-[2-(4-nitro-phenoxy)-ethyl]-amine |
| 88 | N-(4,6-Dimethyl-pyridin-2-yl)-N'-(4-nitrophenyl)-ethane-1,2-diamine (alternative preparation, by reduction of N-(4,6-dimethyl-pyridin-2-yl)-N'-(4-nitro-phenyl)-oxalamide) |
| 89 | (4,6-Dimethyl-pyridin-2-yl)-[3-(4-nitrophenyl)-propyl]-amine |
| 90 | N'-(4,6-dimethyl-pyridin-2-yl)-N-methyl-N-(4-nitro-phenyl)-ethane-1,2-diamine |
| 91 | N-(4,6-Dimethyl-pyridin-2-yl)-N-methyl-N'-(4-nitro-phenyl)-ethane-1,2-diamine |
| 92 | N-(4,6-Dimethyl-pyridin-2-yl)-N,N'-dimethyl-N'-(4-nitro-phenyl)-propane-1,3-diamine |

Reference Example 93

N-(4-Nitro-benzoyl)-methanesulfonamide

A solution of p-nitrobenzoylchloride (0.925 g, 5.0 mmol) and methanesulfonamide (0.465 g, 4.9 mmol) in dry DCM (10 mL) was cooled to 0° C. To this was added triethylamine (1.48 g, 14.7 mmol) then the mixture was allowed to warm to r.t. and stirred for 12 h. Concentration in vacuo gave the crude title compound, which was used without further purification.

Reference Example 94

(4-Nitrophenyl)-(3,4,4-trimethyl-oxazolidin-2-ylidene)-amine a) Preparation of 1-(2-hydroxy-1,1-dimethyl-ethyl)-3-(4-nitro-phenyl)-thiourea A solution of 4-nitro-phenyl-isothiocyanate (4 g, 22.2 mmol) and 2-amino-2-methyl-propan-1-ol (1.9 g, 21.3 mmol) in THF was stirred overnight at r.t. The solvent was evaporated to give a residue which was triturated with ether to give 1-(2-hydroxy-1,1-dimethyl-ethyl)-3-(4-nitro-phenyl)-thiourea (3.8 g, 66%).

b) Preparation of (4,4-dimethyl-oxazolidin-2-ylidene)-(4-nitro-phenyl)-amine

To a solution of 1-(2-hydroxy-1,1-dimethyl-ethyl)-3-(4-nitro-phenyl)-thiourea (3.25 g, 12 mmol) in THF was added 0.5 M aqueous sodium hydroxide (60.4 mL, 30.2 mmol), followed by dropwise addition of a solution of p-toluenesulfonyl chloride (2.52 g, 13.2 mmol) in THF (20 mL). The mixture was stirred at r.t. for 3 h then diluted with water and extracted with ethyl acetate. The organic extracts were washed with brine, dried over anhydrous sodium sulfate and concentrated in vacuo to give (4,4-dimethyl-oxazolidin-2-ylidene)-(4-nitro-phenyl)-amine (2.7 g, 95%).

c) Preparation of (4-nitrophenyl)-(3,4,4-trimethyl-oxazolidin-2-ylidene)-amine

To a stirred suspension of sodium hydride (0.2 g of 50% in mineral oil, 4.2 mmol) in THF was added (4,4-dimethyl-oxazolidin-2-ylidene)-(4-nitro-phenyl)-amine (1 g, 4.25 mmol), stirred for 30 min at r.t., followed by addition of iodomethane (0.71 g, 5.0 mmol). After a further 6 hours at r.t. the reaction was quenched with water and extracted with ethyl acetate. The extracts were washed with brine, dried over anhydrous sodium sulfate and concentrated in vacuo to give a residue which was purified by column chromatography over silica gel (60-120 mesh) using 15% ethyl acetate/petroleum ether as eluent to give (4-nitro phenyl)-(3,4,4-trimethyl-oxazolidin-2-ylidene)-amine (0.7 g, 66%).

Reference Example 95

(4,4-Dimethyl-4,5-dihydro-oxazol-2-yl)-(2-ethoxy-ethyl)-(4-nitro-phenyl)-amine

To a stirred suspension of sodium hydride (50% in mineral oil, 0.9 g, 37.6 mmol) in DMF (5 mL) was added 2-(4-nitrophenyl)-4,4-dimethyl-(4,5-dihydro-oxazol-2-yl)-amine (4.42 g, 18.8 mmol) and stirred for 30 min at r.t. 1-Bromo-2-ethoxy-ethane (3.45 g, 22.5 mmol) was added and the reaction mixture heated at 90° C. for 6 hrs. The reaction was cooled to r.t., quenched with water and extracted with ethyl acetate; the combined organic extracts were washed with water, brine, dried over anhydrous sodium sulfate, filtered and concentrated in vacuo. Purification by column chromatography over silica gel (60-120 mesh) using 15% ethyl acetate/petroleum ether as eluent afforded (4,4-dimethyl-4,5-dihydro-oxazol-2-yl)-(2-ethoxy-ethyl)-(4-nitrophenyl)-amine (0.8 g, 13%) as a solid.

Reference Example 96

1-(1-Ethyl-propyl)-4-(5-nitro-pyridin-2-yl)-piperazine

To a solution of 1-(5-nitro-pyridin-2-yl)-piperazine (2.2 g, 10.5 mmol) in DMF (10 mL) were added potassium carbonate (2.9 g, 21 mmol) and 3-bromopentane (4.8 g, 31.7 mmol). The mixture was heated at 120° C. for six hours. DMF was removed in vacuo to give a residue which was partitioned between water and DCM. The organic phase was washed with brine, dried over sodium sulfate and concentrated to give 1-(1-ethyl-propyl)-4-(5-nitro-pyridin-2-yl)-piperazine (550 mg, 19%) as a yellow solid.

Reference Examples 97 to 99

The following compounds were prepared in a manner analogous to Reference Example 96:

| Example | Compound |
| --- | --- |
| 97 | 1-(4-Nitrophenyl)-4-(2-pyridin-2-yl-ethyl)-piperazine |
| 98 | 1-(2-Furan-2-yl-ethyl)-4-(5-nitro-pyridin-2-yl)-piperazine |
| 99 | 1-(2-Furan-2-yl-ethyl)-4-(4-nitrophenyl)-piperazine |

Reference Example 100

2-Hydroxy-4-nitro-benzoic acid tetrahydro-pyran-4-yl ester a) Preparation of 2-hydroxy-4-nitro-benzoyl chloride Thionyl chloride (1.6 mL, 22 mmol) was added slowly to a solution of 4-nitrosalicylic acid (1.0 g, 5.46 mmol) in chloroform (20 mL) at 0° C. The mixture was brought to reflux and maintained for 5 h. Excess thionyl chloride was evaporated to give 2-hydroxy-4-nitro-benzoyl chloride (0.82 g, 75%).

b) Preparation of 2-hydroxy-4-nitro-benzoic acid tetrahydro-pyran-4-yl ester

2-Hydroxy-4-nitro-benzoyl chloride (0.82 g, 4.07 mmol) in THF (15 mL) was added portionwise to a solution of 4-hydroxytetrahydropyran (0.8 mL, 8.1 mmol) in pyridine (4 μL) at 0° C., followed by a catalytic amount of 4-(dimethylamino)-pyridine (DMAP). The mixture was maintained overnight at 40-50° C. then diluted with water and extracted with ethyl acetate. The organic extract was washed successively with saturated sodium bicarbonate solution, water and brine solution, dried and concentrated to give a residue which was triturated with a mixture of DCM and petroleum ether. The residue was purified by flash column chromatography on silica, eluting with ethyl acetate/petroleum ether (2-15%) to give 2-hydroxy-4-nitro-benzoic acid tetrahydro-pyran-4-yl ester (0.32 g, 29%).

Reference Example 101

1-(3-Chloro-propoxy)-2-methyl-4-nitro-benzene

To a stirred solution of 2-methyl-4-nitrophenol (1.0 g, 6.5 mmol) and potassium carbonate (1.8 g, 13.0 mmol) in acetonitrile was added 1-chloro-3-iodopropane (1.2 g, 5.9 mmol). The mixture was heated at reflux overnight then cooled to r.t. and filtered, the solids being further washed with acetonitrile. The combined filtrates were evaporated to dryness. The crude residue was dissolved in ethyl acetate and washed successively with saturated sodium bicarbonate solution, water and brine solution. The organic phase was dried over sodium sulfate, filtered and concentrated to afford 1-(3-chloro-propoxy)-2-methyl-4-nitro-benzene (700 mg, 52%) as an oil.

Reference Examples 102 and 103

The following compounds were prepared in a manner analogous to Reference Example 101:

| Example | Compound |
| --- | --- |
| 102 | 1-(3-Chloro-propoxy)-2-isopropyl-4-nitro-benzene |
| 103 | 1-(2-Bromo-ethoxy)-4-nitro-benzene |

Reference Example 104

2,4-Dimethyl-6-[2-(4-nitro-phenoxy)-ethoxy]pyridine

A mixture of 2-hydroxy-4,6-dimethylpyridine (1.7 g, 13.8 mmol), potassium carbonate (3.82 g, 27.6 mmol) and 1-(2-bromo-ethoxy)-4-nitro-benzene (4.0 g, 16.6 mmol) in DMF (30 mL) was heated to 120° C. and maintained for 15 h. The mixture was cooled to ambient temperature, filtered and concentrated to give a residue which was purified by column chromatography using 4% ethyl acetate/petroleum ether as eluent to afford 2,4-dimethyl-6-[2-(4-nitro-phenoxy)-ethoxy]-pyridine as yellow solid (530 mg, 11%)

Reference Example 105

The following compound was prepared in a manner analogous to Reference Example 104:

| Example | Compound |
| --- | --- |
| 105 | 2,6-Dimethyl-4-[2-(4-nitro-phenoxy)-ethoxy]-pyridine |

Reference Example 106

2-Isopropyl-1-[3-(2-methyl-4-nitro-phenoxy)-propyl]-1H-imidazole

To a stirred solution of 50% sodium hydride (200 mg, 4 mmol) in DMF (5 mL) at 0° C. was added a solution of 1-(3-chloro-propoxy)-2-methyl-4-nitro-benzene (700 mg, 3 mmol) in dry DMF (3 mL). To this was added a solution of 2-isopropyl imidazole (300 mg, 3 mmol) in DMF (4 mL). The mixture was allowed to warm to r.t. and stirred for 5 hours. The mixture was poured into ice-water and extracted with ethyl acetate. The organic phase was washed with water and brine then dried over sodium sulfate. Concentration in vacuo gave a residue which was purified by column chromatography on silica gel, eluting with 20% methanol in chloroform to afford 2-isopropyl-1-[3-(2-methyl-4-nitro-phenoxy)-propyl]-1H imidazole (380 mg, 41%) as an oil.

Reference Example 107

The compound set out below was prepared a manner analogous to Reference Example 106:

| Reference Example | Compound |
| --- | --- |
| 107 | 1-[3-(2-Isopropyl-4-nitro-phenoxy)-propyl]-2-methyl-1H-imidazole |

Reference Example 108

2-Isopropyl-4-nitro-benzoic acid 2-(2-isopropyl-imidazol-1-yl)-ethyl ester

2-Isopropyl-4-nitro-benzoic acid 2-bromo-ethyl ester (0.19 g, 0.6 mmol) was dissolved in DMF (5 mL), then triethylamine (0.5 mL, 3.6 mmol) and 2-isopropylimidazole (0.2 g, 1.8 mmol) were added. The mixture was heated at reflux for 15 h then allowed to cool, diluted with water and extracted with ethyl acetate. The organic phase was washed with water and brine, dried over sodium sulfate and concentrated. The crude product was purified by column chromatography on silica gel (60-120 mesh), eluting with ethyl acetate, to afford 2-isopropyl-4-nitro-benzoic acid 2-(2-isopropyl-imidazol-1-yl)-ethyl ester (90 mg, 43%) as an oil.

Reference Example 109

The compound set out below was prepared a manner analogous to Reference Example 108:

| Reference Example | Compound |
| --- | --- |
| 109 | 2-Methyl-2-(4-nitrophenyl)-propionic acid 2-(2-isopropyl-imidazol-1-yl)-ethyl ester |

Reference Example 110

2-Methyl-2-(3-nitro-phenyl)-propionic acid 2-(2-isopropyl-imidazol-1-yl)-ethyl ester To a solution of 2-methyl-2-(3-nitro-phenyl)-propionic acid 2-bromo-ethyl ester (1.5 g, 4.74 mmol) in DMF (8 mL) was added sodium iodide (0.73 g, 4.87 mmol) and heated at 100° C. for 1 h. 2-Isopropyl-imidazole (2.15 g, 19.5 mmol) and triethylamine (2 mL, 14.6 mmol) were added and then refluxed for 4 h. The reaction was diluted with water and extracted with DCM. The organic layer was washed thoroughly with water, dried over sodium sulfate and evaporated to obtain crude compound. Purification by column chromatography on silica gel (60-120 mesh), eluting with 30% ethyl acetate/hexane gave 2-methyl-2-(3-nitro-phenyl)-propionic acid 2-(2-isopropyl-imidazol-1-yl)-ethyl ester (320 mg, 20%) as a solid.

Reference Example 111

4-Isopropyl-2-methyl-1-[1-methyl-(3-nitrophenyl)ethyl]-1H-imidazole a) Preparation of 2-methyl-2-(3-nitrophenyl)propionamide 2-methyl-2-(3-nitrophenyl) propionic acid (1.8 g, 8.6 mmol) was heated at reflux in thionyl chloride (8 mL, 110 mmol) overnight. Excess thionyl chloride was distilled and the residue poured slowly into ammonium hydroxide solution (20 mL) at <10° C. A solid precipitated. The mixture was stirred at this temperature for a further 30 min. then extracted with ethyl acetate. The organic phase was separated, washed with water and brine, dried over sodium sulfate and concentrated to dryness to afford 2-methyl-2-(3-nitrophenyl)-propionamide (1.6 g, 88.5%) as an off-white solid.

b) Preparation of 1-methyl-1-(3-nitro-phenyl)-ethylamine hydrochloride

Bromine (0.3 mL, 5.70 mmol) was added to a solution of sodium hydroxide (730 mg, 18.2 mmol) in water (15 mL) maintained between at −5 to 0° C. After 10 min., finely-powdered 2-methyl-2-(3-nitrophenyl)-propionamide (1 g, 4.8 mmol) was added in one portion and the mixture stirred at 0° C. for 30 min. The mixture was extracted with DCM (×2). The combined organic phases were washed with water and brine, dried over sodium sulfate and filtered. A solution of 2M HCl in dioxane was added until the pH was approximately 2. Concentration under reduced pressure gave a residue which was triturated with pentane to afford 1-methyl-1-(3-nitrophenyl)-ethylamine hydrochloride (600 mg, 58%) as a white solid.

c) Preparation of 3-methyl-1-[1-methyl-1-(3-nitro-phenyl)-ethylamino]-butan-2-one To a solution of 1-methyl-1-(3-nitro-phenyl)-ethylamine hydrochloride (600 mg, 2.8 mmol) in DMF (8 mL) was added anhydrous potassium carbonate (1.5 g, 11 mmol) and 1-bromo-3-methyl-2-butanone (prepared according to *Organic Syntheses*, Collective Volume 6, page 193) (0.45 mL, 3.62 mmol). The mixture was stirred for 3 h then diluted with water and extracted twice with ethyl acetate. The combined organic phases were washed with water and brine, dried and concentrated to dryness under reduced pressure to afford 3-methyl-1-[1-methyl-1-(3-nitro-phenyl)-ethylamino]-butan-2-one (650 mg, 89%) as an oil which was used immediately in the following step.

d) Preparation of N-[1-methyl-1-(3-nitro-phenyl)-ethyl]-N-(3-methyl-2-oxo-butyl)-acetamide Acetyl chloride (0.24 mL, 3.4 mmol) was added to an ice-cooled solution of 3-methyl-1-[1-methyl-1-(3-nitro-phenyl)-ethylamino]-butan-2-one (600 mg, 2.27 mmol) and triethylamine (0.79 mL, 5.6 mmol) in DCM (10 mL). The mixture was maintained between 0 and 5° C. for 30 min. then concentrated in vacuo. The residue was redissolved in ethyl acetate, washed with water then brine and dried over sodium sulfate. Concentration afforded N-[1-methyl-1-(3-nitro-phenyl)-ethyl]-N-(3-methyl-2-oxo-butyl)-acetamide (620 mg, 89%) as an oil.

e) Preparation of 4-isopropyl-2-methyl-1-[1-methyl-(3-nitrophenyl)-ethyl]-1H-imidazole To a solution of N-[1-methyl-1-(3-nitro-phenyl)-ethyl]-N-(3-methyl-2-oxo-butyl)-acetamide (600 mg, 1.96 mmol) in DMF (1 mL) was added ammonium acetate (0.6 g, 7.8 mmol) and acetic acid (8 mL) and the whole mass heated at 90-95° C. for 24 h. The mixture was concentrated to dryness under reduced pressure, the residue diluted with water and basified with 5% sodium hydroxide solution to approximately pH 10. This was extracted twice with ethyl acetate, then the combined organic phases were washed with water then brine and dried over sodium sulfate. Concentration under reduced pressure gave a crude product which was purified by column chromatography on silica gel (60-120 mesh), eluting with 60% ethyl acetate/petroleum ether to afford of 4-isopropyl-2-methyl-1-[1-methyl-(3-nitrophenyl)-ethyl]-1H-imidazole (200 mg, 35.5%) as a solid.

Reference Example 112

3-methyl-3-(3-nitro-phenyl)-butan-2-one

Thionyl chloride (2 mL, 27.4 mmol) was added to 2-methyl-2-(3-nitro-phenyl)-propionic acid (5.6 g, 26.7 mmol) and heated at 95° C. for 6 h. The mixture was then concentrated to afford the crude acid chloride. Separately, a mixture of diethyl malonate (4.8 mL, 32 mmol), triethylamine (7.5 mL, 52.6 mmol) and magnesium chloride (2.5 g, 26.3 mmol) in toluene (30 mL) was stirred under nitrogen for 1 h. The crude acid chloride was added to this and the whole mass stirred for a further 1 h. Dilute hydrochloric acid was added and the organic layer was separated and concentrated. The residue was partitioned between water and ethyl acetate then the organic layer was dried over sodium sulfate and concentrated to afford the intermediate keto-diester. This was dissolved in 2:1 DMSO/water and heated at 160° C. overnight. The mixture was cooled to r.t. and partitioned between water and ethyl acetate, the organic phase then being further washed thoroughly with water before being dried and concentrated to afford 3-methyl-3-(3-nitro-phenyl)-butan-2-one (2.8 g, 44%).

Reference Example 113

3-Methyl-3-(4-nitro-phenyl)-butan-2-one

This compound was prepared in a manner analogous to Reference Example 102.

Reference Example 114

1-Bromo-3-methyl-3-(3-nitro-phenyl)-butan-2-one

To a solution of 3-methyl-3-(3-nitro-phenyl)-butan-2-one (2.1 g, 10.5 mmol) in acetic acid (25 mL) was added pyridinium perbromide (3.6 g, 12.2 mmol). The mixture was heated for 12 hours at 60° C. then quenched with ice-water and extracted with ethyl acetate. The combined organic layers were washed with sodium bicarbonate solution, dried over sodium sulfate and evaporated to afford 1-bromo-3-methyl-3-(3-nitro-phenyl)-butan-2-one (2.28 g, 78%).

Reference Example 115

1-Bromo-3-methyl-3-(4-nitro-phenyl)-butan-2-one

This compound was prepared in a manner analogous to Reference Example 114.

Reference Example 116

2-Isopropyl-4-[1-methyl-1-(3-nitro-phenyl)-ethyl]-1H-imidazole

A solution of 1-bromo-3-methyl-3-(3-nitro-phenyl)-butan-2-one (2.28 g, 8.0 mmol), isobutyramidine hydrochloride (3.58 g, 23.7 mmol) and 1,1,3,3-tetramethylguanidine (2.4 mL, 19.1 mmol) in DMF (10 mL) was heated at reflux for 24 h. The mixture was diluted with water and extracted with ethyl acetate. The organic phase was dried over sodium sulfate and concentrated to afford 2-isopropyl-4-[1-methyl-1-(3-nitro-phenyl)-ethyl]-1H-imidazole (0.65 g, 30%) as a cream-coloured solid.

Reference Example 117

2-Isopropyl-4-[1-methyl-1-(4-nitro-phenyl)-ethyl]-1H-imidazole

This compound was prepared in a manner analogous to Reference Example 116.

Reference Example 118

2-Isopropyl-1-methyl-4-[1-methyl-1-(3-nitro-phenyl)-ethyl]-1H-imidazole

To a solution of 2-isopropyl-4-[1-methyl-1-(3-nitro-phenyl)-ethyl]-1H-imidazole (0.35 g, 1.28 mmol) in THF (2 mL) was added potassium carbonate (0.21 g, 1.5 mmol) and iodomethane (0.12 mL, 1.92 mmol). The mixture was heated at 50° C. for 5 h then concentrated in vacuo. The residue was partitioned between water and DCM then the organic phase was dried over sodium sulfate and evaporated to afford 2-isopropyl-1-methyl-4-[1-methyl-1-(3-nitro-phenyl)-ethyl]-1H-imidazole (0.2 g, 56%) as colourless semisolid.

Reference Example 119

2-Isopropyl-1-methyl-4-[1-methyl-1-(4-nitro-phenyl)-ethyl]-1H-imidazole

This compound was prepared in a manner analogous to Reference Example 118.

Reference Example 120

2-Isopropyl-1-methyl-5-[1-methyl-1-(3-nitro-phenyl)ethyl]-1H-imidazole

To a cold (0° C.) slurry of 50% sodium hydride (84 mg, 1.75 mmol) in THF (3 mL) was added 2-isopropyl-4-[1-methyl-1-(3-nitro-phenyl)-ethyl]-1H-imidazole (0.4 g, 1.46 mmol). The mixture was warmed to r.t. and stirred for 30 min. Iodomethane (0.13 mL, 2.1 mmol) was added and the reaction maintained for 2 h. The solvent was evaporated under reduced pressure and the residue partitioned between DCM and water. The organic phase was dried over sodium sulfate, filtered and concentrated. The residue was purified by column chromatography on silica gel (60-120 mesh), eluting with 25% ethyl acetate/hexane to obtain 2-isopropyl-1-methyl-5-[1-methyl-1-(3-nitro-phenyl)-ethyl]-1H-imidazole (0.148 g, 35%) as a colourless semisolid.

Reference Examples 121 to 125

The compounds set out below were prepared in a manner analogous to Reference Example 120:

| Example | Compound |
|---|---|
| 121 | 2-Isopropyl-1-methyl-5-(1-methyl-1-(4-nitrophenyl)-ethyl)-1H-imidazole |
| 122 | N-(4,6-Dimethyl-pyridin-2-yl)-N,N'-dimethyl-N'-(4-nitrophenyl)-ethane-1,2-diamine (dimethylation of N-(4,6-dimethyl-pyridin-2-yl)-N'-(4-nitrophenyl)-ethane-1,2-diamine) |
| 123 | (4,6-Dimethyl-pyridin-2-yl)-methyl-[2-(4-nitro-phenoxy)-ethyl]-amine |
| 124 | (4,6-Dimethyl-pyridin-2-yl)-methyl-[3-(4-nitrophenyl)-propyl]-amine |
| 125 | 2-(5-Bromo-pyridin-2-ylamino)-ethanol (N, O dimethylation) |

Reference Example 126

4-(6-chloro-pyridin-3-yl-methyl)-morpholine a) Preparation of 5-bromomethyl-2-chloro-pyridine N-bromosuccinimide (6.1 g, 3.44 mmol) and benzoyl peroxide (218 mg, 0.09 mmol) were added successively to a solution of 2-chloro-5-methyl-pyridine (4.0 g, 3.13 mmol) in carbon tetrachloride (20 mL) and refluxed for 90 min. The reaction mixture was cooled to room temperature, water added and the organic layer separated. The organic layer was washed successively with water, brine, dried over anhydrous sodium sulfate and filtered. The resultant solution of 5-bromomethyl-2-chloro-pyridine was used as such for the next step.

b) Preparation of 4-(6-chloro-pyridin-3-yl-methyl)-morpholine

Morpholine (7.0 g, 8.8 mmol) was added to the solution of 5-bromomethyl-2-chloro-pyridine in carbon tetrachloride (20 mL) and stirred at room temperature for 6 h. Water was added to the reaction mixture and the separated organic layer was washed with water, brine, dried over anhydrous sodium sulfate, filtered and concentrated to afford the crude product. Purification by column chromatography using silica gel (60-120 mesh) and ethyl acetate as eluent afforded 4-(6-chloro-pyridin-3-yl-methyl)-morpholine (1.2 g, 21%) as a brown oily liquid.

Reference Example 127

4,6-Dimethyl-1H-pyrimidin-2-one hydrochloride

To a mixture of acetyl acetone (4.0 g, 40.0 mmol) and urea (2.0 g, 33.3 mmol) in ethanol (40 mL) was added concentrated HCl (10 mL) and stirred at reflux for 3 h. The reaction mixture was cooled to 0° C. and filtered; the colourless solid was washed thoroughly with ice cold ethanol then ether and dried under vacuum to afford 4,6-dimethyl-1H-pyrimidin-2-one hydrochloride (3.5 g, 55%) as a solid.

Reference Example 128

2,6-Dimethyl-2,5-dihydro-3H-pyrimidin-4-one

To a solution of ethyl acetoacetate (0.8 g, 6.14 mmol) in ethanol (8 mL) was added acetamidine hydrochloride (0.6 g, 6.3 mmol) and stirred at r.t. for 10 min. A solution of sodium ethoxide [prepared from sodium (0.28 g, 12.3 mmol) and ethanol (3 mL)] was added dropwise and the whole mixture refluxed for 6 h. The reaction mass was cooled, acidified with acetic acid and concentrated under reduced pressure to give a residue which was washed twice with ethyl acetate to afford 2,6-dimethyl-2,5-dihydro-3H-pyrimidin-4-one (460 mg, 60%) as a solid.

Reference Example 129

2-Chloro-4,6-dimethyl-pyrimidine

A suspension of 4,6-dimethyl-1H-pyrimidin-2-one hydrochloride (3.0 g, 18.75 mmol) in dry $POCl_3$ (25 mL, 272 mmol) was refluxed for 18 hours. The reaction mixture was evaporated to dryness and the residue dissolved in dichloromethane. The solution was washed with sodium bicarbonate solution until the pH of the aqueous washings were neutral, then with brine, dried over anhydrous sodium sulfate, filtered and concentrated under vacuum to afford 2-chloro-4,6-dimethyl-pyrimidine (1.5 g, 56%) as a solid.

Reference Example 130

The compound set out below was prepared in a manner analogous to Reference Example 129 using 2,6-dimethyl-2,5-dihydro-3H-pyrimidin-4-one:

| Example | Compound |
|---|---|
| 130 | 4-Chloro-2,6-dimethyl-pyrimidine |

Reference Example 131

4,6-Dimethyl-2-[4-(4-nitrophenyl)-piperazin-1-yl]-pyrimidine 1-(4-Nitrophenyl)-piperazine (2.18 g, 10.6 mmol) was added to 2-chloro-4,6-dimethyl-pyrimidine (1.5 g, 10.6 mmol) in pyridine (10 mL) and the mixture was heated at reflux for 7 h. The solvent was removed in vacuo and the residue partitioned between ethyl acetate and water. The organic phase was separated, washed with water and brine, dried over anhydrous sodium sulfate and concentrated to afford 4,6-dimethyl-2-[4-(4-nitro-phenyl)-piperazin-1-yl]-pyrimidine (0.8 g, 24%) as a solid.

Reference Example 132

The compound set out below was prepared in a manner analogous to Ref example 131:

| Example | Compound |
|---|---|
| 132 | 2,4-Dimethyl-6-[4-(4-nitrophenyl)-piperazin-1-yl]-pyrimidine |

Reference Example 133

1-(4,6-Dimethyl-pyridin-2-yl)-4-(4-nitro-phenyl)-piperazine a) Preparation of 2-chloro-4,6-dimethyl-pyridine 2-Amino-4,6-dimethyl-pyridine (4 g, 32.7 mmol) was dissolved in conc. hydrochloric acid (50 mL) and cooled to 0° C. A solution of sodium nitrite (3.39 g, 49.1 mmol) in water (20 mL) was added dropwise, followed by a solution of sodium chloride (3.8 g, 65 nmol) in water (20 mL). The mixture was stirred for 30 min. then basified with 20% sodium hydroxide solution and extracted with ethyl acetate. The combined extracts were washed with brine, dried over sodium sulfate and concentrated in vacuo to give a residue which was purified by column chromatography on silica gel (60-120 mesh) using 5% ethyl acetate/petroleum ether as eluent to afford 2-chloro-4,6-dimethyl-pyridine (1 g, 22%) as a solid.

The following compounds were prepared in an analogous manner:

| Example | Compound |
|---|---|
| 134 | 2-Chloro-6-ethyl-pyridine |
| 135 | 2-Chloro-4-ethyl-pyridine | b) Preparation of 1-(4,6-dimethyl-pyridin-2-yl)-piperazine

A solution of 2-chloro-4,6-dimethyl-pyridine (1 g, 7.09 mmol) and piperazine (2 g, 23.2 mmol) in DMSO was heated at 140° C. for 24 h. The mixture was allowed to cool, diluted with water and extracted with ethyl acetate. The combined extracts were washed with water and brine, dried over anhydrous sodium sulfate and concentrated in vacuo to give a residue which was purified by column chromatography on silica gel (60-120 mesh), eluting with 5% methanol/chloroform to afford 1-(4,6-dimethyl-pyridin-2-yl)-piperazine (0.7 g, 52%).

| Reference Example | Reagents | Compound |
|---|---|---|
| 136 | 1-(4-Nitro-phenyl)-piperazine and 2-chloropyridine | 1-(4-Nitrophenyl)-4-pyridin-2-yl-piperzine | c) Preparation of 1-(4,6-dimethyl-pyridin-2-yl)-4-(4-nitro-phenyl)-piperazine

To a solution of 1-(4,6-dimethyl-pyridin-2-yl)-piperazine (0.7 g, 3.66 mmol) and 1-chloro-4-nitro-benzene (0.69 g, 4.39 mmol) in toluene was added caesium carbonate (2.38 g, 7.32 mmol), then the mixture was stirred for 30 min. under an argon atmosphere. A solution of palladium(II) acetate (50 mg, 0.22 mmol) and (2'-dicyclohexylphosphanyl-biphenyl-2-yl)-dimethyl-amine (50 mg, 0.13 mmol) in THF was purged with argon for 30 min then added to the substrate mixture, and the resulting mixture was heated at 80° C. for 4 h. It was then allowed to cool and concentrated to dryness, and the resulting residue was diluted with water and extracted with ethyl acetate. The combined extracts were washed with brine, dried over sodium sulfate and concentrated in vacuo to a residue which was purified by column chromatography on silica gel (60-120 mesh) using 10% ethyl acetate/petroleum ether as eluent. This afforded 1-(4,6-dimethyl-pyridin-2-yl)-4-(4-nitro-phenyl)-piperazine (0.4 g, 35%).

Reference Examples 137 to 152

The compounds set out below were prepared in a manner analogous to Reference Example 136 using the appropriate starting materials:

| Example | Reagents | Compound |
|---|---|---|
| 137 | 1-(4-Nitro-phenyl)-piperazine and 2-chloro-6-methyl-pyridine | 1-(6-Methyl-pyridin-2yl)-4-(4-nitrophenyl)-piperazine |
| 138 | 1-(4-Nitro-phenyl)-piperazine and 2-chloro-6-methyl-pyridine | 1-(4,6-Dimethyl-pyridin-2-yl)-4-(3-nitrophenyl)-piperazine |
| 139 | 1-(3-Nitro-phenyl)-[1,4]diazepane and 2-chloro-6-methyl-pyridine | 1-(4,6-Dimethyl-pyridin-2-yl)-4-(4-nitrophenyl)-[1,4]diazepane |

-continued

| Example | Reagents | Compound |
|---|---|---|
| 140 | 1-(4-Nitro-phenyl)-piperazine and 3-bromo-pyridine | 1-(4-Nitrophenyl)-4-pyridin-3-yl-piperazine |
| 141 | Bis-[2-(tert-butyl-dimethyl-silanyloxy)-ethyl]-(6-chloro-pyridin-2-yl)-amine | Bis-[2-(tert-butyl-dimethyl-silanyloxy)-ethyl]-{6-[4-(4-nitrophenyl)-piperazin-1-yl]-pyridin-2-yl}-amine |
| 142 | From 1-(4-Nitro-phenyl)-piperazine and 4-iodobenzaldehyde | 4-[4-(4-Nitro-phenyl)-piperazin-1-yl]-benzaldehyde |
| 143 | From 1-(4-Nitro-phenyl)-piperazine and [2-(tert-Butyl-dimethyl-silanyloxy)-ethyl]-(6-chloro-pyridin-2-yl)-amine | [2-(tert-butyl-dimethyl-silanyloxy)-ethyl]-{6-[4-(4-nitro-phenyl)-piperazin-1-yl]-pyridin-2-yl}-amine |
| 144 | 1-(4-Nitro-phenyl)-piperazine and (5-bromo-pyridin-2-yl)-(2-methoxy-ethyl)-methyl-amine | (2-Methoxy-ethyl)-methyl-{5-[4-(4-nitro-phenyl)-piperazin-1-yl]-pyridin-2-yl}-amine |
| 145 | 1-(4-Nitro-phenyl)-piperazine and 2-chloro-6-ethyl-pyridine | 1-(6-Ethyl-pyridin-2-yl)-4-(4-nitro-phenyl)-piperazine |
| 146 | 1-(4-Nitro-phenyl)-piperazine and 2-chloro-5-methyl-pyridine | (Buchwald on chloropyridine) 1-(5-methyl-pyridin-2-yl)-4-(4-nitro-phenyl)-piperazine |
| 147 | 1-(4-Nitro-phenyl)-piperazine and 2-chloro-4-ethyl-pyridine | 1-(4-Ethyl-pyridin-2-yl)-4-(4-nitro-phenyl)-piperazine |
| 148 | 1-(4-Nitro-phenyl)-piperazine and 2-[2-tert-butyldimethylsilanyloxy)ethyl]-6-chloro-pyridine | 1-{6-[2-(tert-butyl-dimethyl-silanyloxy)-ethyl]-pyridin-2-yl}-4-(4-nitro-phenyl)-piperazine |
| 149 | 1-(4-Nitro-phenyl)-piperazine and 4-(6-chloro-pyridin-3-ylmethyl)-morpholine | 4-{6-[4-(4-nitro-phenyl)-piperazin-1-yl]-pyridin-3-yl-methyl}-morpholine |
| 150 | 1-(4-Nitro-phenyl)-piperazine and 4-piperidone | 4',6'-dimethyl-2,3,5,6-tetrahydro-[1,2']-bipyridinyl-4-one |
| 151 | 1-Chloro-2-methyl-4-nitro-benzene and 1-(4,6-dimethyl-pyridin-2-yl)-piperazine | 1-(4,6-Dimethyl-pyridin-2-yl)-4-(2-methyl-4-nitro-phenyl)-piperazine |
| 152 | 4-Chloro-2-methoxymethyl-1-nitro-benzene and 1-(4,6-dimethyl-pyridin-2-yl)-piperazine | 1-(4,6-dimethyl-pyridin-2-yl)-4-(3-methoxymethyl-4-nitro-phenyl)-piperazine |

Reference Example 153

1-(4,6-Dimethyl-pyridin-2-yl)-4-(3-methyl-4-nitro-phenyl)-piperazine

A solution of 5-chloro-2-nitro-toluene (895 mg, 5.23 mmol) in diglyme (2.5 mL) was added to a stirred suspension of 1-(4,6-dimethyl-pyridin-2-yl)-piperazine (500 mg, 2.62 mmol) and potassium carbonate (900 mg, 6.54 mmol) in diglyme (5 mL) and heated at reflux overnight. The mixture was cooled, the inorganic salts filtered off and washed with ethyl acetate. The filtrate was concentrated to dryness under high vacuum to obtain a residue which was dissolved in 6N hydrochloric acid (10 mL) and washed with toluene. The aqueous layer was basified to pH 8 with ammonium hydroxide solution and extracted with ethyl acetate. The organic layer was washed with water, bicarbonate solution, and brine dried over sodium sulfate, filtered and concentrated to dryness to give the crude compound. Purification by column chromatography over silica gel (60-120 mesh) using 15% ethyl acetate in hexane as a eluent afforded 1-(4,6-dimethyl-pyridin-2-yl)-4-(3-methyl-4-nitro-phenyl)-piperazine (380 mg, 45%).

Reference Examples 154 to 159

The compounds set out below were prepared in a manner analogous to Reference Example 153 using the appropriate starting materials:

| Example | Reagents | Compound |
|---|---|---|
| 154 | 1-(4-Nitro-phenyl)-piperazine and 2-chloro-4-(2-methoxy-ethoxy)-6-methyl-pyridine 1-oxide | 1-[4-(2-Methoxy-ethoxy)-6-methyl-1-oxy-pyridin-2-yl]-4-(4-nitrophenyl)-piperazine |
| 155 | 1-(4-Nitro-phenyl)-piperazine and 2-chloro-4-[2-(2-methoxy-ethoxy)-ethoxy]-6-methyl-pyridine 1-oxide | 1-{4-[2-(2-methoxy-ethoxy)-ethoxy]-6-methyl-1-oxy-pyridin-2-yl}-4-(4-nitro-phenyl)-piperazine |
| 156 | 1-(4-Nitro-phenyl)-piperazine and 2-chloro-4-methyl-pyridine | 1-(4-Methyl-pyridin-2yl)-4-(4-nitrophenyl)-piperazine |
| 157 | 1-(4-Nitro-phenyl)-piperazine and 4-(2-Benzyloxy-ethoxy)-2-chloro-pyridine | 1-[4-(2-Benzyloxy-ethoxy)-pyridin-2-yl]-4-(4-nitrophenyl)-piperazine |

| Example | Reagents | Compound |
|---|---|---|
| 158 | 1-Chloro-2-methoxymethyl-4-nitro-benzene and 1-(4,6-dimethyl-pyridin-2-yl)-piperazine | 1-(4,6-dimethyl-pyridin-2-yl)-4-(2-methoxymethyl-4-nitro-phenyl)-piperazine |
| 159 | 2-Chloro-5-nitro-benzoic acid and 1-(4,6-dimethyl-pyridin-2-yl)-piperazine | 2-[4-(4,6-Dimethyl-pyridin-2-yl)-piperazin-1-yl]-5-nitro-benzoic acid |

Reference Example 160

2-{2-[4-(4-Nitrophenyl)-piperazin-1-yl]-pyridin-4-yloxy}-ethanol

Conc. HCl (6 mL, 65.7 mmol) was added to a solution of 1-[4-(2-benzyloxy-ethoxy)-pyridin-2-yl]-4-(4-nitrophenyl)-piperazine-(0.8 g, 1.84 mmol) in TFA (10 mL) at r.t. followed by heating to 70-75° C. for 7 h. The excess TFA and HCl were evaporated, the residue diluted with water and basified with saturated aq. sodium bicarbonate solution to pH 8-9 and extracted with dichloromethane. The organic layer was washed with water followed by brine solution and dried over sodium sulfate, filtered and concentrated under reduced pressure. The resulting residue was triturated with petroleum ether to afford 2-{2-[4-(4-nitrophenyl)-piperazin-1-yl]-pyridin-4-yloxy}-ethanol (0.5 g, 84%) as a solid.

Reference Example 161

Acetic acid-(2-[2-{4-(4-nitrophenyl)-piperazin-1-yl]-pyridin-4-yloxy}-ethyl ester Pyridine (0.1 mL) was added to a solution of 2-{2-[4-(4-nitrophenyl)-piperazin-1-yl]-pyridin-4-yloxy}-ethanol (0.50 g, 1.45 mmol) in acetic anhydride (4 mL) at 0° C., then stirred at r.t. for 3 h under nitrogen. The reaction mixture was cooled to 0° C., quenched onto excess ice-water, neutralised with saturated aq. sodium bicarbonate solution and extracted with dichloromethane. The organic layer was washed with water followed by brine solution, dried over sodium sulfate, filtered and concentrated. The residue was triturated with petroleum ether and dried under high vacuum to afford acetic acid-(2-{2-[4-(4-nitrophenyl)-piperazin-1-yl]-pyridin-4-yloxy}-ethyl ester (0.53 g, 94%) as a solid.

Reference Example 162

4-{4-[4-(4-nitro-phenyl)-piperazin-1-yl]-benzyl}-morpholine

A mixture of water (1 mL), acetic acid (1 mL), 4-[4-(4-nitro-phenyl)-piperazin-1-yl]-benzaldehyde (700 mg, 2.25 mmol) and morpholine (215 mg, 2.47 mmol) in tetrahydrofuran (10 mL) was stirred at room temperature for 1 h. Sodium cyanoborohydride (212 mg, 3.37 mmol) was added at room temperature then the mixture was heated at reflux for 10 h. The tetrahydrofuran was removed in vacuo and the residue was partitioned between water and ethyl acetate. The organic layer was washed with saturated sodium bicarbonate solution, dried over anhydrous sodium sulfate and evaporated in vacuo to afford a residue which was purified by column chromatography on silica gel (60-120 mesh) using 1% methanol in chloroform as eluent to afford 4-{4-[4-(4-nitro-phenyl)-piperazin-1-yl]-benzyl}-morpholine (450 mg, 52%) as a brownish yellow solid.

Reference Example 163

4-(4-amino-phenyl)-4',6'-dimethyl-3,4,5,6-tetrahydro-2H-[1,2']-bipyridinyl-4-ol n-Butyl lithium (1 mL, 1.6 M in hexane, 1.6 mmol) was added dropwise to a solution of 2-(4-bromo-phenyl)-1,1,1,3,3,3-hexamethyl-disilazane (0.7 g, 2.20 mmol) in dry diethyl ether (10 mL) and stirred at room temperature for 15 min then cooled in an ice bath. A solution of 4',6'-dimethyl-2,3,5,6-tetrahydro-[1,2']bipyridinyl-4-one (0.3 g, 1.47 mmol) in dry tetrahydrofuran (15 mL) was added and the resulting mixture heated at 50° C. for 2.5 h. The reaction mixture was brought to room temperature and stirred overnight, then cooled to 0° C. and quenched into ammonium chloride solution. The organics were extracted with ethyl acetate, washed with water, brine, dried over anhydrous sodium sulfate, filtered and evaporated in vacuo to yield the crude compound, to which was added 2N HCl and the resulting mixture was stirred overnight at room temperature. The pH of the solution was adjusted to pH 10 with dilute sodium hydroxide and the organics extracted with chloroform. The extract was dried over anhydrous sodium sulfate, filtered and evaporated to dryness to give a red viscous oil which was purified by washing with pentane (5×10 mL) to afford 4-(4-amino-phenyl)-4',6'-dimethyl-3,4,5,6-tetrahydro-2H-[1,2']-bipyridinyl-4-ol (0.25 g, 57.3%).

Reference Example 164

1-Ethyl-2-(4-nitrobenzyl)-1H-imidazole a) Preparation of ethyl-2-(4-nitrophenyl)-acetimidate HCl Hydrogen chloride gas was passed through a solution of 4-nitrophenyl acetonitrile (5.0 g, 30.8 mmol) in ethanol (400 mL) until saturation, keeping the temperature between 0-5° C. The solvent was removed under reduced pressure at 15° C. to give a residue which on trituration with diethyl ether gave a solid. The solid was filtered under a nitrogen atmosphere and washed thoroughly with diethyl ether. Drying under vacuum afforded ethyl 2-(4-nitrophenyl)-acetimidate hydrochloride (3.5 g, 47%) which was hygroscopic in nature.

b) Preparation of 2-(4-nitrobenzyl)-1H-imidazole

To a solution of ethyl 2-(4-nitrophenyl)-acetimidate hydrochloride (3.5 g, 14.3 mmol) in ethanol (15 mL) was added amino acetaldehyde dimethyl acetal (1.87 mL, 17.2 mmol) and the reaction heated at reflux for 18 h. The reaction mixture was concentrated which was mixed with 2N hydrochloric acid (30 mL) and heated to 60° C. for 18 h. The solvent was evaporated, diluted with water and extracted with ethyl acetate. The organic layer was separated, the aqueous layer basified with sodium carbonate and extracted with chloroform (×2). The combined chloroform extracts was dried over sodium sulfate, filtered and evaporated under reduced pressure to obtain 2-(4-nitro-benzyl)-1H-imidazole (1.5 g, 51%) as a brown solid.

c) Preparation of 1-ethyl-2-(4-nitrobenzyl)-1H-imidazole

To a solution of 2-(4-nitro-benzyl)-1H-imidazole (1.58 g, 7.37 mmol) in DMF (10 mL) was added N,N-diisopropyl-ethyl amine (1.93 mL, 11.05 mmol) and heated to 5° C. for 30 min. Ethyl iodide (1.18 mL, 7.37 mmol) was added dropwise and the reaction mixture heated to reflux for 6 h. The solvent was evaporated under reduced pressure, the residue dissolved in dichloromethane and washed with water. The organic layer was dried over sodium sulfate, filtered, evaporated and the residue purified by column chromatography over silica gel (60-120 mesh) using 3% methanol/chloroform as eluent to afford 1-ethyl-2-(4-nitrobenzyl)-1H-imidazole (0.35 g, 21%).

Reference Example 165

1-(4-Nitrophenyl)-4-(pyridine-3-sulfonyl)-piperazine

To a solution of 1-(4-nitrophenyl)-piperazine (2.50 g, 12.1 mmol) in pyridine (15 mL) was added a solution of pyridine-3-sulfonyl chloride (2.78 g, 15.7 mmol) in THF (30 mL) under an argon atmosphere at 0° C. The reaction was warmed to r.t. and stirred for 2 h, before the mixture was evaporated to dryness. The residue was partitioned between water and dichloromethane, the organic layer separated and washed successively with sat. sodium bicarbonate solution, water and brine. The organics were dried over sodium sulfate, filtered and concentrated under reduced pressure. The crude residue was subjected to column chromatography over neutral alumina using 5% to 70% ethyl acetate in petroleum ether as eluent to afford 1-(4-nitrophenyl)-4-(pyridine-3-sulfonyl)-piperazine (1.63 g, 39%) as a yellow solid.

Reference Example 166

2,2,2-Trifluoro-1-[5-(4-methyl-piperazin-1-yl)-2-(4-nitrophenyl)-oxazol-4-yl]-ethanone a) Preparation of (4-nitro-benzoylamino)-acetic acid ethyl ester To a stirred solution of glycine ethyl ester hydrochloride (5.0 g, 35.7 mmol) and diisopropyl ethylamine (9.2 g, 71.4 mmol) in acetonitrile (30 mL) was added 4-nitro-benzoyl chloride (7.2 g, 39.2 mmol) in acetonitrile (20 mL) and heated at reflux overnight. The mixture was cooled to r.t., evaporated to dryness and the crude residue was dissolved in ethyl acetate and washed successively with saturated sodium bicarbonate solution, water and brine. The organics were dried over sodium sulfate, filtered and concentrated to afford (4-nitro-benzozylamino)-acetic acid ethyl ester (7.0 g, 78%) as a solid.

b) Preparation of (4-nitro-benzozylamino)-acetic acid

To a stirred solution of sodium hydroxide (1.1 g, 29.7 mmol) in methanol (30 mL) at 0° C. was added a solution of (4-nitro-benzozylamino)-acetic acid ethyl ester (5.0 g, 19.4 mmol) in methanol (3 mL), and the resulting mixture stirred at r.t. overnight. The pH of the mixture was made acidic with acetic acid then concentrated to dryness. The residue was taken into water and extracted with ethyl acetate, washed with water, brine solution and dried over sodium sulfate. The filtered layer was concentrated to afford (4-nitro-benzozy-lamino)-acetic acid (2.8 g, 64%) as an oil.

c) N-[2-(4-methyl-piperazin-1yl)-oxo-ethyl]-4-nitro-benzamide

To a stirred solution of (4-nitro-benzozylamino)-acetic acid (2 g, 8.9 mmol) in dry DMF (20 mL) was added 1-ethyl-3-(3-dimethyl-aminopropyl)-carbodiimide hydrochloride (EDC) (2.56 g, 13.4 mmol), 1-hydroxybenzotriazole (HOBt) (1.82 g, 13.4 mmol), triethylamine (1.4 g, 17.9 mmol) and finally a solution of N-methyl-piperazine (1.8 g, 17.9 mmol) in DMF (5 mL) and the mixture was stirred at r.t. overnight. The reaction was diluted with water and extracted with ethyl acetate (×2). The combined organic layers were washed with saturated bicarbonate solution, water and brine solution. The organics were dried over sodium sulfate, filtered and concentrated to afford N-[2-(4-methyl-piperazin-1yl)-oxo-ethyl]-4-nitro-benzamide (1.77 g, 65%) as a solid.

d) Preparation of 2,2,2-trifluoro-1-[5-(4-methyl-piper-azin-1-yl)-2-(4-nitrophenyl)-oxazol-4-yl]-ethanone N-[2-(4-Methyl-piperazin-1yl)-oxo-ethyl]-4-nitro-benza-mide (1.0 g, 3.2 mmol) was stirred at r.t. for 24 hours in trifluoroacetic anhydride (20 mL). The resulting solid was filtered, washed with excess of water, and dried to afford 2,2,2-trifluoro-1-[5-(4-methyl-piperazin-1-yl)-2-(4-nitrophenyl)-oxazol-4-yl]-ethanone (700 mg, 56%) as a pale yellow solid.

Reference Example 167

4-[4-(2,6-Dimethyl-pyridin-4-yl)-1-(4-nitrophenyl) piperazine

To a solution of trifluoro-methanesulfonic acid 2,6-dimethyl-pyridin-4-yl ester (0.50 g, 1.96 mmol) in diglyme (50 mL) was added 4-nitrophenyl piperazine (0.37 g, 0.76 mmol) and heated in the microwave at 165° C. for 40 minutes. The mixture was diluted with chloroform (100 mL) and washed with water (5×50 mL). The organic layer was separated, washed with brine solution (5×40 mL), dried over sodium sulfate and filtered. The solvent was evaporated, and the crude material was purified by column chromatography over silica gel (60-120 mesh) using 12% methanol in chloroform as eluent to afford 4-[4-(2,6-dimethyl-pyridin-4-yl)-1-(4-nitrophenyl)-piperazine (0.30 g, 49%) as a yellow solid.

Reference Example 168

1-[4-(2-Methoxy-ethoxy)-6-methyl-pyridin-2-yl]-4-(4-nitrophenyl)-piperazine

Phosphorus trichloride (1.75 mL, 20.1 mmol) was added dropwise to a solution of 1-[4-(2-methoxy-ethoxy)-6-methyl-1-oxy-pyridin-2-yl]-4-(4-nitrophenyl)-piperazine (2.60 g, 6.70 mmol) in chloroform (30 mL) and refluxed for 2 h. The reaction mixture was cooled and neutralised with saturated bicarbonate solution. The organic layer was separated, washed thoroughly with water (3×10 mL) and brine (15 mL), dried (sodium sulfate), filtered and concentrated in vacuo. The crude material was purified by column chromatography over silica gel (60-120 mesh) using 20% ethyl acetate in chloroform as eluent to afford 1-[4-(2-methoxy-ethoxy)-6-methyl-pyridin-2-yl]-4-(4-nitrophenyl)-piperazine (1.78 g, 71.5%) as a solid.

Reference Example 169

The compounds set out below were prepared a manner analogous to Reference Example 168:

| Example | Compound |
| --- | --- |
| 169 | 1-{4-[2-(2-methoxy-ethoxy)-ethoxy]-6-methyl-pyridin-2-yl}-4-(4-nitro-phenyl)-piperazine |

Reference Example 170

4-(1,1-Dioxo-1$\lambda^6$-thiomorpholin-4-yl)-phenylamine

Zinc powder (0.47 g, 7.2 mmol) was added to a solution of 4-(4-nitro-phenyl)-thiomorpholine 1,1-dioxide (155 mg, 0.60 mmol) in acetic acid (3 mL) and the mixture was stirred at 60° C. for 2 h. The reaction mixture was concentrated to dryness, diluted with ethyl acetate and washed with sodium bicarbonate solution and water then dried over sodium sulfate. The organic layer was concentrated to dryness to afford 4-(1,1-dioxo-1$\lambda^6$-thiomorpholin-4-yl)-phenylamine (70 mg, 51%).

Reference Example 171 to 172

The compounds set out below were prepared a manner analogous to Reference Example 170:

| Example | Compound |
| --- | --- |
| 171 | N-(4-Amino-benzoyl)-methanesulfonamide |
| 172 | N-(4-Amino-phenyl)-N-(4,6-dimethyl-pyridin-2-ylmethyl)-2,2,2-trifluoro-acetamide |

Reference Example 173

(N-(4-Aminophenyl)-2,2,2-trifluoro-N-[2-pyridin-2-yloxy)-ethyl]-acetamide

Nitro Reduction with NH$_4$Cl/Zinc dust

To a solution of 2,2,2-trifluoro-N-(4-nitrophenyl)-N-[2-(pyridine-2-yloxy)-ethyl]-acetamide (550 mg, 1.50 mmol) in ethanol (15 mL) was added zinc dust (2.60 g, 8.70 mmol) and ammonium chloride (414 mg, 7.70 mmol) and the mixture heated to 40° C. for 2 hrs. The reaction mixture was filtered through celite washed with excess ethanol. The filtrate was concentrated to give N-(4-aminophenyl)-2,2,2-trifluoro-N-[2-pyridin-2-yloxy)-ethyl]-acetamide (500 mg, 99%) as a brown liquid.

Reference Example 174 to 175

The compounds set out below were prepared a manner analogous to Reference Example 173:

| Reference Example | Compound |
| --- | --- |
| 174 | N-(4-Amino-phenyl)-N-[2-(4,6-dimethyl-pyridin-2-ylamino)-ethyl]-2,2,2-trifluoro-acetamide |
| 175 | 5-Amino-2-[4-(4,6-dimethyl-pyridin-2-yl)-piperazin-1-yl]-benzoic acid |

Reference Example 176

1-(4-Aminophenyl)-4-piperidone

A solution of 1-(4-nitrophenyl)-4-piperidone (400 mg, 1.8 mmol) in methanol (5 μL) was hydrogenated over Raney nickel (0.08 g) at atmospheric pressure for 3 hours at r.t. The mixture was filtered through Celite and the filtrate evaporated to dryness to obtain 1-(4-aminophenyl)-4-piperidone (310 mg, 89%) as a semisolid.

Reference Examples 177 to 222

The compounds set out below were prepared a manner analogous to Reference Example 176:

| Reference Example | Compound |
| --- | --- |
| 177 | 4-(4-aminophenyl)-oxazole |
| 178 | 6-[4-(1-ethyl-propyl)-piperazin-1-yl]-pyridin-3-ylamine |
| 179 | 4-amino-2-isopropyl-benzoic acid 2-(2-isopropyl-imidazol-1-yl)-ethyl ester |
| 180 | 2-(4-aminophenyl)-2-methyl-propionic acid 2-(2-isopropyl-imidazol-1-yl)-ethyl ester |
| 181 | 2-(3-amino-phenyl)-2-methyl-propionic acid 2-(2-isopropyl-imidazol-1-yl)-ethyl ester |
| 182 | 3-[1-(2-Isopropyl-1-methyl-1H-imidazole-4-yl)-1-methyl-ethyl]-phenyl amine |
| 183 | 4-[1-(2-Isopropyl-1-methyl-1H-imidazole-4-yl)-1-methyl-ethyl]-phenyl amine |
| 184 | 3-[1-(2-Isopropyl-3-methyl-3H-imidazol-4-yl)-1-methyl-ethyl]-phenylamine |
| 185 | 4-[1-(2-Isopropyl-3-methyl-3H-imidazol-4-yl)-1-methyl-ethyl]-phenylamine |
| 186 | 3-[1-(4-Isopropyl-2-methyl-imidazol-1-yl)-1-methyl-ethyl]-phenylamine |
| 187 | 3-Isopropyl-4-[3-(2-methyl-imidazol-1-yl)-propoxy]-phenyl amine |
| 188 | 4-[4-(4,6-dimethyl-pyridin-2-yl)-piperazin-1-yl]-phenyl amine |
| 189 | 8-(4-aminophenyl)-1,4-dioxa-8-aza-spiro[4,5]decane |
| 190 | 2,6-dimethyl-4-[1-(4-aminophenyl)-piperidin-4-yl)morpholine |
| 191 | 4-(4-Morpholin-4-yl-piperidin-1-yl)-phenylamine |
| 192 | 4-(4-Pyridin-2-yl-piperazin-1-yl)-phenylamine |
| 193 | 5-Amino-2-methyl pyridine |
| 194 | 4-[4-(6-Methyl-pyridin-2-yl)-piperazin-1-yl]-phenyl amine |
| 195 | 4-[4-(4-Methyl-pyridin-2-yl)-piperazin-1-yl]-phenyl amine |
| 196 | 1-(4-Aminophenyl)-4-(tetrahydro-pyran-4-ylmethyl)-piperazine |
| 197 | N-{2-[(4,6-Dimethyl-pyridin-2-yl)-methyl-amino]-ethyl}-N-methyl-benzene-1,4-diamine |
| 198 | {6-[4-(4-Amino-phenyl)-piperazin-1-yl]-pyridin-2-yl}-bis-[2-(tert-butyl-dimethyl-silanyloxy)-ethyl]-amine |
| 199 | Acetic acid-(2-{2-[4-(4-amino-phenyl)-piperazin-1-yl]-pyridin-4-yloxy}-ethyl ester |

-continued

| Reference Example | Compound |
|---|---|
| 200 | {5-[4-(4-Amino-phenyl)-piperazin-1-yl]-pyridin-2-yl}-(2-methoxy-ethyl)-methyl-amine |
| 201 | 4-[4-(4,6-Dimethyl-pyrimidin-2-yl)-piperazin-1-yl]-phenylamine |
| 202 | 4-[4-(2,6-Dimethyl-pyrimidin-4-yl)-piperazin-1-yl]-phenyl amine |
| 203 | 4-[4-Pyridine-3-sulfonyl)-piperazin-1-yl]-phenyl amine |
| 204 | 4-[4-(2,6-Dimethyl-pyridin-4-yl)-piperazin-1-yl]-phenyl amine |
| 205 | [2-(4-Amino-phenoxy)-ethyl]-(4,6-dimethyl-pyridin-2-yl)-methyl-amine |
| 206 | 4-[2-(2,6-Dimethyl-pyridin-4-yloxy)-ethoxy]-phenyl-amine |
| 207 | 4-(1-Ethyl-1H-imidazol-2yl methyl)-phenyl amine |
| 208 | [3-(4-Amino-phenyl)-propyl]-(4,6-dimethyl-pyridin-2-yl)-methyl-amine |
| 209 | 4-[4-(4-morpholin-4-ylmethyl-phenyl)-piperazin-1-yl]-phenylamine |
| 210 | {6-[4-(4-amino-phenyl)-piperazin-1-yl]-pyridin-2-yl}-[2-(tert-butyl-dimethyl-silanyloxy)-ethyl]-amine |
| 211 | N-[2-(4,6-dimethyl-pyridin-2-ylamino)-ethyl]-N-methyl-benzene-1,4-diamine |
| 212 | N-{2-[(4,6-Dimethyl-pyridin-2-yl)-methyl-amino]-ethyl}-benzene-1,4-diamine |
| 213 | N-{3-[(4,6-Dimethyl-pyridin-2-yl)-methyl-amino]-propyl}-N-methyl-benzene-1,4-diamine |
| 214 | 4-[4-(6-Ethyl-pyridin-2-yl)-piperazin-1-yl]-phenylamine |
| 215 | 4-[4-(5-methyl-pyridin-2-yl)-piperazin-1-yl]-phenyl amine |
| 216 | 4-[4-(4-ethyl-pyridin-2-yl)-piperazin-1-yl]-phenyl amine |
| 217 | 4-(4-{6-[2-(tert-butyl-dimethyl-silanyloxy)-ethyl]-pyridin-2-yl}-piperazin-1-yl)-phenylamine |
| 218 | 4-[4-(5-morpholin-4-yl-methyl-pyridin-2-yl)-piperazin-1-yl]-phenyl amine |
| 219 | 4-[4-(4,6-Dimethyl-pyridin-2-yl)-piperazin-1-yl]-2-methyl-phenylamine |
| 220 | 4-[4-(4,6-Dimethyl-pyridin-2-yl)-piperazin-1-yl]-3-methoxymethyl-phenylamine |
| 221 | 4-[4-(4,6-Dimethyl-pyridin-2-yl)-piperazin-1-yl]-3-methyl-phenylamine |
| 222 | 4-[4-(4,6-Dimethyl-pyridin-2-yl)-piperazin-1-yl]-2-methoxymethyl-phenylamine |

Reference Example 223

4-Amino-2-hydroxy-benzoic acid tetrahydro-pyran-4-yl ester

2-Hydroxy-4-nitro-benzoic acid tetrahydro-pyran-4-yl ester (0.32 g, 1.20 mmol) was hydrogenated in ethanol (25 mL) with 10% palladium on charcoal catalyst (70 mg) until hydrogen uptake ceased. The mixture was filtered through Celite and concentrated to give a residue which was purified by flash column chromatography on silica, eluting with ethyl acetate/petroleum ether (5-35% gradient) to give 4-amino-2-hydroxy-benzoic acid tetrahydro-pyran-4-yl ester (100 mg, 35%).

Reference Examples 224 to 225

The compounds shown below were prepared a manner analogous to Reference Example 223:

| Example | Compound |
|---|---|
| 224 | 4-{4-[4-(2-Methoxy-ethoxy)-6-methyl-pyridin-2-yl]-piperazin-1-yl}-phenylamine |
| 225 | 4-(4-{4-[2-(2-methoxy-ethoxy)-ethoxy]-6-methyl-pyridin-2-yl}-piperazin-1-yl)-phenylamine |

Reference Example 226

4-[4-(4,6-dimethyl-pyridin-2-yl)-butyl]-phenylamine

Palladium on carbon (10%, 50 mg) was added to a solution of 2,4-dimethyl-6-[4-(4-nitro-phenyl)-buta-1,3-dienyl]-pyridine (0.5 g, 1.78 mmol) in methanol (20 mL) under a nitrogen atmosphere. The reaction mixture was hydrogenated under balloon pressure for 4 h at room temperature, then filtered through celite and washed with methanol. The filtrate was evaporated under reduced pressure and the residue was washed with pentane (20 mL) to afford 4-[4-(4,6-dimethyl-pyridin-2-yl)-butyl]-phenylamine (320 mg, 71%) as a brownish pink semi-solid.

Reference Example 227

4-Methylene-1-(4-aminophenyl)piperidine

To a solution of 4-methylene-1-(4-nitrophenyl)-piperidine (230 mg, 1.05 mmol) in ethyl acetate (5 mL) was added stannous chloride dihydrate (1.19 g, 5.2 mmol). The mixture was heated to 60° C. and maintained for 4 hrs. The mixture was evaporated to dryness then sodium hydroxide solution was added to give a final pH of 8. The mixture was extracted with ethyl acetate and the combined organic layers were washed with water, then brine, and then dried. Concentration under reduced pressure afforded 4-methylene-1-(4-aminophenyl)-piperidine (150 mg, 75%) as a semisolid.

Reference Examples 228 to 246

The compounds set out below were prepared a manner analogous to Reference Example 217:

| Reference Example | Compound |
|---|---|
| 228 | N-(3,4,4-Trimethyl-oxazolidin-2-ylidene)-benzene-1,4-diamine |

-continued

| Reference Example | Compound |
|---|---|
| 229 | 4-[3-(2-Isopropyl-imidazol-yl)-propoxy]-3-methyl-phenylamine |
| 230 | 4-(4-Methyl-piperazin-1-yl)-3-oxazol-2-yl-phenylamine |
| 231 | 5-Amino-1,3-dihydro-indol-2-one |
| 232 | Diethyl-carbamic acid-5-(4-amino-phenyl)-isoxazol-3-yl ester |
| 233 | N-(4,4-Dimethyl-4,5,-dihydro-oxazol-2-yl)-N-(2-ethoxy-ethyl)-benzene-1,4-diamine |
| 234 | 1-[2-(4-Amino-phenyl)-5-(4-methyl-piperazin-1-yl]-2,2,2,-trifluoro-ethanone |
| 235 | 6-[4-(1-Ethyl-propyl)-piperazin-1yl]-pyridin-3-ylamine |
| 236 | 1-(4-Aminophenyl)-4-thiophen-2-yl methyl piperazine |
| 237 | 6-(4-Furan-2-ylmethyl-piperazin-1yl)-pyridin-3-ylamine |
| 238 | 1-(4-Aminophenyl)-4-(2-pyridin-2-yl-ethyl)-piperazine |
| 239 | 6-(4-Thiophen-2-y-lmethyl-piperazin-1-yl)-pyridine-3-yl amine |
| 240 | 6-[4-(2-Furan-2-yl-ethyl)-piperazin-1-yl]-pyridin-3-yl amine |
| 241 | 4-[4-(2-Furan-2-yl-ethyl)-piperazin-1-yl]-phenyl amine |
| 242 | 3-[4-(4,6-Dimethyl-pyridin-2-yl)-piperazin-1-yl]-phenyl amine |
| 243 | 5-[4-(2,2-Dimethyl-propyl)-piperazin-1-yl]-pyridin-2-ylamine |
| 244 | 4-[4-(4,6-Dimethyl-pyridin-2-yl)-[1,4]diazepan-1-yl]-phenylamine |
| 245 | 4-(4-Pyridin-3-yl-piperazin-1-yl)-phenylamine |
| 246 | 4-[2-(4,6-Dimethyl-pyridin-2-yloxy)-ethoxy]-phenylamine |

Reference Example 247

1-(4-Nitro phenyl)-piperidine-4-one O-methyl-oxime

A solution of 1-(4-aminophenyl)-4-piperidone (300 mg, 1.58 mmol) and methoxylamine hydrochloride (250 mg, 3.0 mmol) in methanol (5 mL) was heated at reflux for 30 min. The solvent was evaporated, water added and extracted with ethyl acetate. The combined organic layers were washed with water and brine then dried over sodium sulfate. Concentration to dryness afforded 1-(4-amino-phenyl)-piperidin-4-one O-methyl-oxime (220 mg, 64%) as a semisolid.

Reference Example 248

5-Fluoro-2-methylpyridine

5-Amino-2-methylpyridine (2.8 g, 25.9 mmol) was added to a mixture of water (15 mL) and conc. HCl (7 mL) and cooled to 0° C. NaNO$_2$ (3.5 g, 51.8 mmol) was added portionwise with stirring over 10 min whilst keeping the reaction temperature between −5° C. and 0° C. After stirring for 10 min 60% w/w HPF$_6$ (14 mL) was added dropwise with cooling, at which point a precipitate formed. This was filtered, washed with cold water and diethyl ether and dried. The solid was then heated slowly to 100° C.; the reaction being very exothermic. After 5 min a dark red oily material formed which was then cooled to r.t. The oil was basified with dilute sodium hydroxide to pH ~10 and extracted with dichloromethane. The combined organics were dried over sodium sulfate, filtered and evaporated in vacuo. The residue was purified by column chromatography over neutral alumina using 20% dichloromethane-petroleum ether to yield 5-fluoro-2-methylpyridine (1.57 g, 55%) as an oil.

Reference Example 249

1-Methyl-piperidine-4-carboxylic acid

A solution of 4-piperidine carboxylic acid (1.0 g, 7.75 mmol) in a mixture of 90% formic acid (3 mL) and 37% formaldehyde solution (2 mL) was heated at reflux for 20 h. The volatiles were removed in vacuo and conc. HCl added to the residue. The reaction mixture was extracted with dichloromethane and washed with brine solution. The organic layer was dried over sodium sulfate, filtered and dried to afford 1-methyl-piperidine-4-carboxylic acid (0.20 g, 18%).

Reference Example 250

2-Methyl-nicotinic acid

A solution of methyl 2-methylnicotinate (13.0 g, 86.1 mmol) in conc. HCl (65 mL) was heated to reflux overnight. The mixture was concentration under reduced pressure to give a solid which was washed twice with chloroform and dried to afford 2-methyl-nicotinic acid hydrochloride. The salt was dissolved in a minimum amount of methanol and the pH was adjusted with triethylamine to pH 3-4. The precipitated solid was filtered, washed with acetone and dried under high vacuum to afford 2-methyl-nicotinic acid (10.2 g, 87%) as an off-white-solid.

Reference Example 251

2-(2-Methyl-pyridine-3-carbonyl)-malonic acid diethyl ester

To a slurry of 2-methyl-nicotinic acid (10.2 g, 74.45 mmol) in THF (30 mL) chilled to −10° C. was added sodium hydride (60% in mineral oil; 3.89 g, 89.3 mmol) portionwise and the reaction mixture stirred till no further gas evolution was noticed. Ethyl chloroformate (6.0 mL, 74.45 mmol) was added slowly at the same temperature and stirring continued for another 1 h, whereby a thick white slurry developed. Simultaneously, in a separate vessel, diethyl malonate (11.9 mL, 74.45 mmol) was added dropwise to a slurry of sodium hydride (60% in mineral oil; 3.24 g, 74.45 mmol)) in THF (20 mL) at −10° C., stirred for 30 min and slowly added to the slurry of the mixed anhydride. The reaction mixture was allowed to warm to r.t. and stirred overnight. The pH was adjusted to ~pH 6 with acetic acid and evaporated to dryness. The residue was partitioned between water and ethyl acetate, the organics separated, then washed with water, brine, dried over sodium sulfate, filtered and concentrated to yield 2-(2-methyl-pyridine-3-carbonyl)-malonic acid diethyl ester (18.16 g, 87%) as an oil.

Reference Example 252

2-Cyclopentanecarbonyl malonic acid diethyl ester

Cyclopentanecarboxylic acid (10.0 g, 87.7 mmol) was heated under reflux with thionyl chloride (13 mL, 176 mmol). After 2 hrs the thionyl chloride was distilled under reduced pressure to give the crude acid chloride (9.8 g, 74.2 mmol) as a liquid. In another vessel, 50% sodium hydride (4.28 g, 89.09 mmol) was taken up in THF (100 mL) and diethyl malonate (11.88 g, 74.24 mmol) was added dropwise at 0° C. Into this mixture the previously-prepared acid chloride (9.8 g, 74.2 mmol) was added dropwise at 0° C. and the reaction mixture was stirred at r.t. for an hour. The reaction was quenched with cold water and extracted with ethyl acetate. The combined organic layer was washed with water, sodium bicarbonate solution, brine solution, dried over sodium sulfate, filtered and concentrated to afford 2-cyclopentanecarbonyl malonic acid diethyl ester (19.2 g, 85.5%) as a liquid.

Reference Example 253

1-Cyclopentyl-ethanone

2-Cyclopentanecarbonyl malonic acid diethyl ester (19.0 g, 74.2 mmol) was heated with conc. hydrochloric acid at 90° C. overnight. The reaction mixture was cooled and diluted with water. The product was extracted with diethyl ether and the combined organics washed with water, Sodium bicarbonate solution and brine. It was dried over sodium sulfate, filtered and concentrated in vacuo to yield 1-cyclopentyl-ethanone (3.1 g, 37%) as a liquid.

Reference Example 254

The compound set out below was prepared a manner analogous to Reference Example 253:

| Example | Compound |
| --- | --- |
| 254 | 1-(2-Methyl-pyridin-3-yl)-ethanone |

Reference Example 255

2-bromo-1-(4-bromophenyl)ethanone

Bromine (1.29 mL, 25.1 mmol) was added dropwise at 15-20° C. to a solution of 4-bromoacetophenone (5 g, 25.1 mmol) in DCM (40 mL) and the mixture was stirred at this temperature until the bromine colour was discharged. The mixture was diluted with water and the organic phase was separated. This was dried over sodium sulfate and concentrated to afford 2-bromo-1-(4-bromo-phenyl)-ethanone (6 g, 86%).

Reference Example 256

2-Bromo-1-cyclopropyl-ethanone

Bromine (6.2 mL, 119 mmol) was added slowly to a solution of 1-cyclopropyl-ethanone (10.0 g, 119 mmol) in methanol (50 mL) at 0° C. The reaction mixture was warmed to 10° C. and stirred for 45 min, during which time the colour was discharged. The mixture was diluted with water (50 mL) and stirred overnight. The mixture was further diluted with water (200 mL) and whole extracted with ether. The organic phase was washed successively with 10% sodium carbonate solution, water and brine, dried over anhydrous calcium chloride and concentrated to afford 2-bromo-1-cyclopropyl-ethanone (17.0 g, 88%).

Reference Examples 257 to 261

The compounds set out below were prepared a manner analogous to Reference Example 256:

| Example | Compound |
| --- | --- |
| 257 | 2-Bromo-1-(1-bromo-cyclopentyl)-ethanone (from 1-cyclopentylethanone) |
| 258 | 2-Bromo-1-cyclohexyl-ethanone |
| 259 | 1-Bromo-3-methyl-butan-2-one |
| 260 | 1-Bromo-3,3-dimethyl-butan-2-one |
| 261 | 2-Bromo-1-(2-methyl-pyridin-3-yl)-ethanone HBr salt |

Reference Example 262

2-Bromo-1-(1-methyl-piperidin-4-yl)-ethanone. hydrobromide

A mixture of 1-methyl-piperidine-4-carboxylic acid (0.40 g, 2.79 mmol) and thionyl chloride (0.32 mL, 4.44 mmol) in dichloromethane (10 mL) was heated to reflux for 6 h. The reaction mixture was distilled under reduced pressure and the residue dissolved in dry acetonitrile (4 mL). Trimethylsilyl diazomethane (4 mL, 8.08 mmol) was added and the mixture stirred for 2 h at ambient temperature. The reaction was cooled to 0° C. and 30% HBr in acetic acid (2 mL) added dropwise. The reaction mixture was warmed to room temperature and stirred for 1 h. The precipitate was filtered and washed with ether to afford 2-bromo-1-(1-methyl-piperidin-4-yl)-ethanone hydrobromide (200 mg, 33%).

Reference Example 263

The compound set out below was prepared a manner analogous to Reference Example 262:

| Example | Compound |
| --- | --- |
| 263 | 2-bromo-1-(tetrahydro-pyran-4-yl)-ethanone |

Reference Example 264

2-Methyl-1-(2-oxo-2-phenyl-ethyl)-pyridinium-bromide

2-Picoline (10.0 g, 0.1 mol) was added to a solution of alpha-bromoacetophenone (21.4 g, 0.1 mol) in methanol (150 mL). The solution was heated to reflux for 1 hr. The solvent was evaporated under vacuum to yield a solid which was recrystallised from ethyl acetate/methanol. The resulting white solid was dried under vacuum to give 2-methyl-1-(2-oxo-2-phenyl-ethyl)-pyridinium bromide (18.0 g, 86%).

Reference Examples 265 to 277

The compounds set out below were prepared a manner analogous to Reference Example 264:

| Reference Example | Compound |
| --- | --- |
| 265 | 2-Methyl-1-(2-oxo-2-phenyl-ethyl)-quinolinium bromide |
| 266 | 2-Benzyl-1-(2-oxo-propyl)-pyridinium bromide |
| 267 | 1-[2-(4-Bromo-phenyl)-2-oxo-ethyl]-2-methyl-pyridinium bromide |
| 268 | 1-[2-(2-Chloro-phenyl)-2-oxo-ethyl]-2-methyl-pyridinium bromide |
| 269 | 5-Fluoro-2-methyl-1-(2-oxo-2-phenyl ethyl)-pyridinium bromide |

-continued

| Reference Example | Compound |
|---|---|
| 270 | 1-(2-Cyclopent-1-enyl-2-oxo-ethyl)-2-methyl-pyridinium bromide (from 2-bromo-1-(1-bromo-cyclopentyl)-ethanone, with concomitant elimination of HBr) |
| 271 | 1-(2-Cyclopropyl-2-oxo-ethyl)-2-methyl-pyridinium bromide |
| 272 | 1-(2-Cyclohexyl-2-oxo-ethyl)-2-methyl-pyridinium bromide |
| 273 | 2-Methyl-1-(3-methyl-2-oxo-butyl)-pyridinium bromide |
| 274 | 1-(3,3-Dimethyl-2-oxo-butyl)-2-methyl-pyridinium bromide |
| 275 | 2-Methyl-1-[2-(1-methyl-piperidin-4-yl)-2-oxo-ethyl]-pyridinium bromide |
| 276 | 2-Methyl-1-[2-(2-methyl-pyridin-3-yl)-2-oxo-ethyl]-pyridinium bromide |
| 277 | 2-Methyl-1-[2-oxo-2-(tetrahydro-pyran-4-yl)-ethyl]-pyridinium bromide |

Reference Example 278

1-(2-Cyclopentyl-2-oxo-ethyl)-2-methyl-pyridinium bromide 1-(2-Cyclopent-1-enyl-2-oxo-ethyl)-2-methyl-pyridinium bromide salt (3.65 g, 12.94 mmol) was dissolved in methanol (25 mL) and hydrogenated over 10% palladium on carbon (180 mg). After completion of the reaction the Pd/C was removed by filtration through celite, washing twice with methanol. Concentration of the filtrate afforded 1-(2-cyclopentyl-2-oxo-ethyl)-2-methyl-pyridinium bromide salt (3.4 g, 93%).

Reference Example 279

2-Phenyl-indolizine

A solution of sodium hydrogen carbonate (10.5 g, 120 mmol) in water (125 mL) was added to 2-methyl-1-(2-oxo-2-phenyl-ethyl)-pyridinium bromide (35.0 g, 120 mmol) and the reaction heated to reflux for 30 min. The resultant solid was filtered, washed with water and then dried under vacuum to yield 2-phenyl-indolizine (16.0 g, 70%).

Reference Examples 280 to 292

The compounds set out below were prepared a manner analogous to Reference Example 279:

| Reference Example | Compound |
|---|---|
| 280 | 2-Phenyl-pyrrolo[1,2-a]quinoline |
| 281 | 2-Methyl-1-phenyl-indolizine |
| 282 | 2-(4-bromophenyl)-indolizine |
| 283 | 2-(2-chlorophenyl)-indolizine |
| 284 | 6-Fluoro-2-Phenyl indolizine |
| 285 | 2-Cyclopentyl-indolizine |
| 286 | 2-Cyclopropyl-indolizine |
| 287 | 2-Cyclohexyl-indolizine |
| 288 | 2-Isopropyl-indolizine |
| 289 | 2-tert-Butyl-indolizine |
| 290 | 2-(1-Methyl-piperidin-4-yl)-indolizine |
| 291 | 2-(2-Methyl-pyridin-3-yl)-indolizine |
| 292 | 2-(Tetrahydro-pyran-4-yl)-indolizine |

Reference Example 293

2-(4-Morpholin-4-yl-phenyl)-indolizine

To 2-(4-bromo-phenyl)-indolizine (1.2 g, 4.42 mmol) in toluene (8 mL) was added cesium carbonate (4.3 g, 13.24 mmol) and morpholine (1.15 mL, 13.24 mmol). To this was added a mixture of bis-(triphenylphosphine)-palladium (II) chloride (120 mg) and 2-dicyclohexylphosphino-2'-(N,N'-dimethylamino)biphenyl (150 mg) in toluene (10 mL). The reaction mixture was degassed for 15 min and then refluxed for 16 h under an atmosphere of argon. The cooled reaction mixture was concentrated in vacuo and the residue dissolved in dichloromethane. The organic layer was washed with water and brine solution (×2), dried over sodium sulfate, filtered and concentrated. The crude compound was purified by column chromatography over silica gel (60-120 mesh) with 80% chloroform/petroleum ether to afford 2-(4-morpholin-4-yl-phenyl)-indolizine (300 mg, 24%) as a solid.

Reference Example 294

Oxo-(2-phenyl-indolizin-3-yl)-acetyl chloride

Oxalyl chloride (2.23 mL, 25.9 mmol) was added to an ice-cold solution of 2-phenylindolizine (4.0 g, 20.7 mmol) in a mixture of toluene (40 mL) and THF (8 mL). The reaction mixture was stirred at r.t. for 5 h then concentrated in vacuo. The residue obtained was recrystallised from DCM-hexane to yield oxo-(2-phenyl-indolizin-3-yl)-acetyl chloride (4.6 g, 80%) as a solid.

Reference Examples 295 to 308

The compounds set out below were prepared a manner analogous to Reference Example 294:

| Reference Example | Compound |
|---|---|
| 295 | Oxo-(2-phenyl-pyrrolo[1,2-a]quinolin-1-yl)-acetyl chloride |
| 296 | (2-Methyl-1-phenyl-indolizin-3-yl)-oxo-acetyl chloride |
| 297 | [2-(4-bromo-phenyl)-indolizin-3-yl]-oxo-acetyl chloride |
| 298 | [2-(2-Chloro-phenyl)-indolizin-3-yl]-oxo-acetyl chloride |
| 299 | 2-(4-Morpholin-4-yl-phenyl)-indolizin-3-yl]-oxo-acetyl chloride |
| 300 | 6-Fluoro-2-phenyl-indolizin-3-yl)-oxo-acetyl chloride |
| 301 | (2-Cyclopentyl-indolizin-3-yl)-oxo-acetyl chloride |
| 302 | (2-Cyclopropyl-indolizin-3-yl)-oxo-acetyl chloride |
| 303 | (2-Cyclohexyl-indolizin-3-yl)-oxo-acetyl chloride |
| 304 | (2-Isopropyl-indolizin-3-yl)-oxo-acetyl chloride |
| 305 | (2-tert-Butyl-indolizin-3-yl)-oxo-acetyl chloride |
| 306 | [2-(1-Methyl-piperidin-4-yl)-indolizine-3-yl]-oxo-acetyl chloride |
| 307 | [2-(2-Methyl-pyridin-3-yl)-indolizine-3-yl]-oxo-acetyl chloride |
| 308 | Oxo-[2-(tetrahydro-pyran-4-yl)-indolizin-3-yl]-acetyl chloride |

Example 1

N-[4-(1,1-Dioxo-1λ⁶-thiomorpholin-4-yl)-phenyl]-2-oxo-2-(2-phenyl-indolizin-3-yl)-acetamide A solution of oxo-(2-phenyl-indolizin-3-yl)-acetyl chloride (0.12 g, 0.42 mmol) in THF was added to a solution of 4-(1,1-dioxo-1λ⁶-thiomorpholin-4-yl)-phenylamine (70 mg, 0.31 mmol) and triethylamine (85 mg, 0.85 mmol) in THF (10 mL) at 0° C., then the mixture was stirred for 8 h at r.t. The mixture was concentrated to dryness and washed with water to give a crude product which was triturated with methanol to afford the title compound (70 mg, 48%) as a solid.

Examples 2 to 84

The compounds set out below were prepared in a manner analogous to Example 1, using combinations of solvent and base appropriate to the substrate. These included triethylamine or THF as the solvent in conjunction with triethylamine or pyridine as the base, or pyridine as both solvent and base. No additional base was necessary where the compound included a basic centre.

| Example | Compound |
| --- | --- |
| 2 | 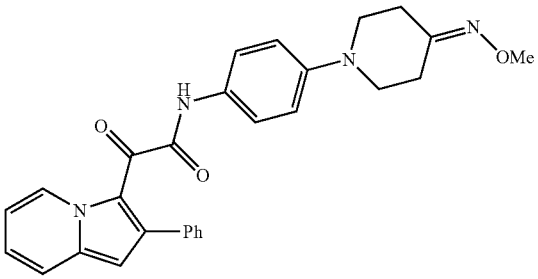 [SMILES: CON=C1CCN(c2ccc(NC(=O)C(=O)c3c(-c4ccccc4)cc4ccccn34)cc2)CC1]<br>N-[4-(4-methoxyimino-piperidin-1-yl)-phenyl]-2-oxo-2-(2-phenyl-indolizin-3-yl)-acetamide |
| 3 | 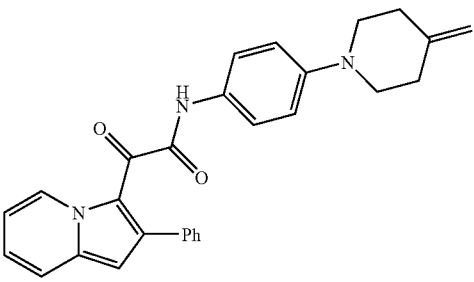 [SMILES: C=C1CCN(c2ccc(NC(=O)C(=O)c3c(-c4ccccc4)cc4ccccn34)cc2)CC1]<br>N-[4-(4-methylene-piperidin-1-yl)-phenyl]-2-oxo-2-(2-phenyl-indolizin-3yl) acetamide |
| 4 | 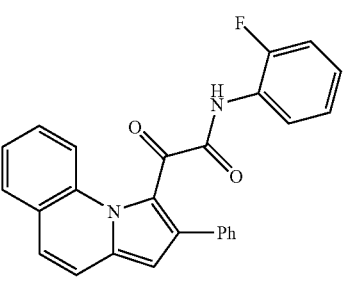 [SMILES: O=C(Nc1ccccc1F)C(=O)c1c(-c2ccccc2)cc2ccc3ccccc3n12]<br>N-(2-fluoro-phenyl)-2-oxo-2-(2-phenyl-pyrrolo[1,2-a]quinolin-1-yl)-acetamide |
| 5 | 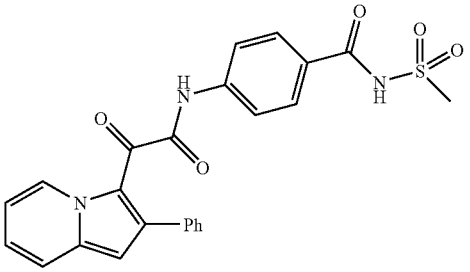 [SMILES: CS(=O)(=O)NC(=O)c1ccc(NC(=O)C(=O)c2c(-c3ccccc3)cc3ccccn23)cc1]<br>N-(4-methanesulfonylaminocarbonyl-phenyl)-2-oxo-2-(2-phenyl-indolizin-3-yl)-acetamide |

| Example | Compound |
|---|---|
| 6 | 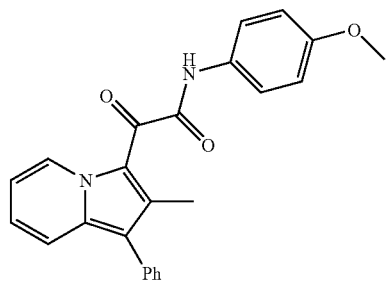 [SMILES: COc1ccc(NC(=O)C(=O)c2c(C)c(-c3ccccc3)c3ccccn23)cc1]<br>N-(4-methoxy-phenyl)-2-(2-methyl-1-phenyl-indolizin-3-yl)-2-oxo-acetamide |
| 7 | 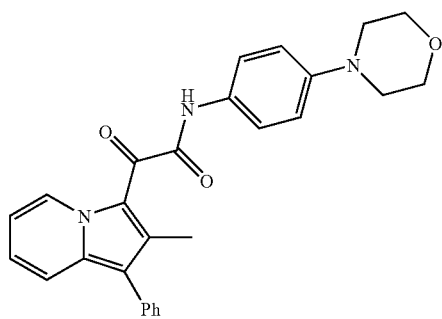 [SMILES: Cc1c(-c2ccccc2)c2ccccn2c1C(=O)C(=O)Nc1ccc(N2CCOCC2)cc1]<br>2-(2-methyl-1-phenyl-indolizin-3-yl)-N-(4-morpholin-4-yl-phenyl)-2-oxo-acetamide |
| 8 | 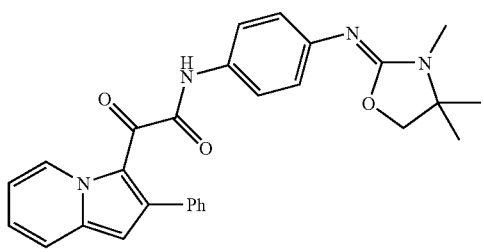 [SMILES: CN1/C(=N/c2ccc(NC(=O)C(=O)c3c(-c4ccccc4)cc4ccccn34)cc2)OCC1(C)C]<br>2-oxo-2-(2-phenyl-indolizin-3-yl)-N-{4-[3,4,4-trimethyl-oxazolidin-(2Z)-ylideneamino]-phenyl}-acetamide |
| 9 | 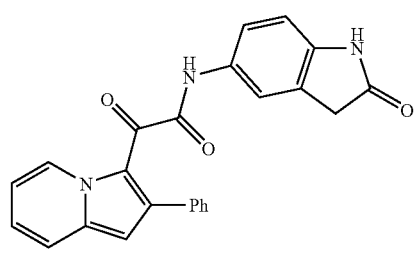 [SMILES: O=C1Cc2cc(NC(=O)C(=O)c3c(-c4ccccc4)cc4ccccn34)ccc2N1]<br>2-Oxo-N-(2-oxo-2,3-dihydro-1H-indol-5-yl)-2-(2-phenyl-indolizin-3-yl)-acetamide |

| Example | Compound |
|---|---|
| 10 | 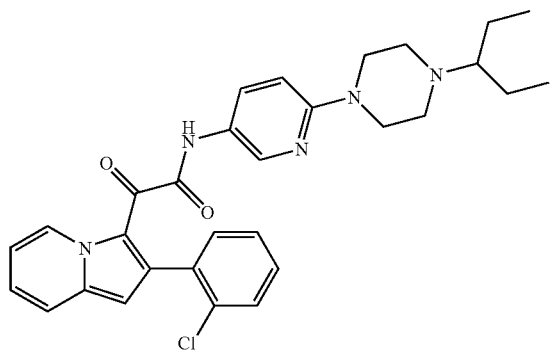 [SMILES: CCC(CC)N1CCN(c2ccc(NC(=O)C(=O)c3c(-c4ccccc4Cl)cc4ccccn34)cn2)CC1]
2-[2-(2-chloro-phenyl)-indolizin-3-yl]-N-{6-[4-(1-ethyl-propyl)-piperazin-1-yl]-pyridin-3-yl}-2-oxo-acetamide |
| 11 | 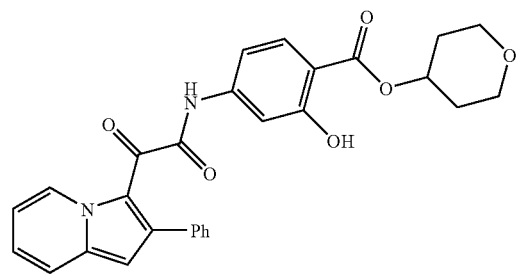 [SMILES: O=C(Nc1ccc(C(=O)OC2CCOCC2)c(O)c1)C(=O)c1c(-c2ccccc2)cc2ccccn12]
2-hydroxy-4-[2-oxo-2-(2-phenyl-indolizin-3-yl)-acetylamino]-benzoic acid tetrahydro-pyran-4-yl ester |
| 12 | 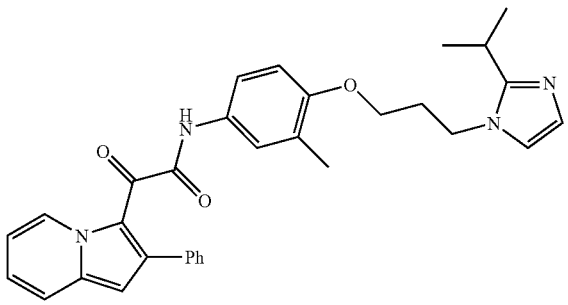 [SMILES: Cc1cc(NC(=O)C(=O)c2c(-c3ccccc3)cc3ccccn23)ccc1OCCCn1ccnc1C(C)C]
N-{4-[3-(2-Isopropyl-imidazol-1-yl)-propoxy]-3-methyl-phenyl}-2-oxo-2-(2-phenyl-indolizin-3-yl)-acetamide |
| 13 | 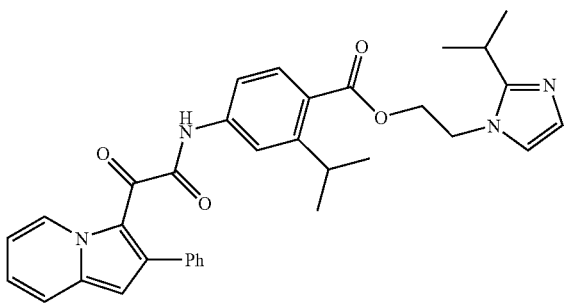 [SMILES: CC(C)c1cc(NC(=O)C(=O)c2c(-c3ccccc3)cc3ccccn23)ccc1C(=O)OCCn1ccnc1C(C)C]
2-Isopropyl-4-[2-oxo-2-(2-phenyl-indolizin-3-yl)-acetylamino]-benzoic acid 2-(2-isopropyl-imidazol-1-yl)-ethyl ester |

| Example | Compound |
|---|---|
| 14 | 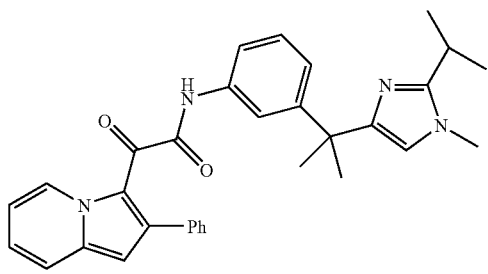 [SMILES: CC(C)c1nc(C(C)(C)c2cccc(NC(=O)C(=O)c3c(-c4ccccc4)cc4ccccn34)c2)cn1C]<br>N-{3-[1-(2-Isopropyl-1-methyl-1H-imidazol-4-yl)-1-methyl-ethyl]-phenyl}-2-oxo-2-(2-phenyl-indolizin-3-yl)-acetamide |
| 15 | 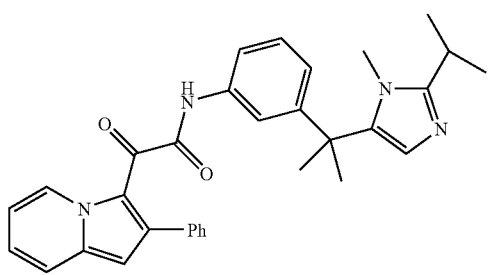 [SMILES: CC(C)c1ncc(C(C)(C)c2cccc(NC(=O)C(=O)c3c(-c4ccccc4)cc4ccccn34)c2)n1C]<br>N-{3-[1-(2-Isopropyl-3-methyl-3H-imidazol-4-yl)-1-methyl-ethyl]-phenyl}-2-oxo-2-(2-phenyl-indolizin-3-yl)-acetamide |
| 16 | 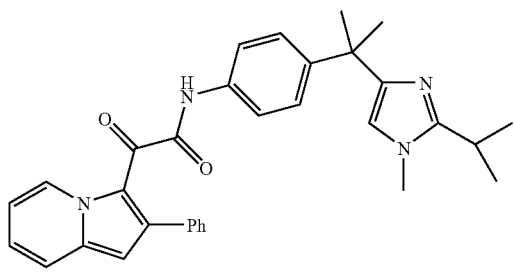 [SMILES: CC(C)c1nc(C(C)(C)c2ccc(NC(=O)C(=O)c3c(-c4ccccc4)cc4ccccn34)cc2)cn1C]<br>N-{4-[1-(2-isopropyl-1-methyl-1H-imidazol-4-yl)-1-methyl-ethyl]-phenyl}-2-oxo-2-(2-phenyl-indolizin-3-yl)-acetamide |
| 17 | 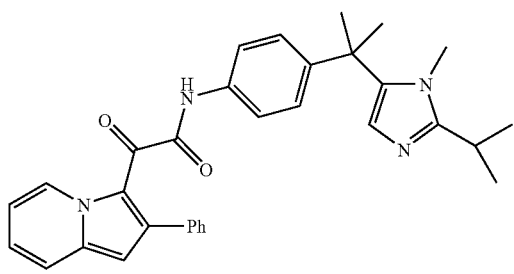 [SMILES: CC(C)c1ncc(C(C)(C)c2ccc(NC(=O)C(=O)c3c(-c4ccccc4)cc4ccccn34)cc2)n1C]<br>N-{4-[1-(2-Isopropyl--3-methyl-3H-imidazol-4-yl)-1-methyl-ethyl]-phenyl}-2-oxo-2-(2-phenyl-indolizin-3-yl)-acetamide |

| Example | Compound |
|---|---|
| 18 | 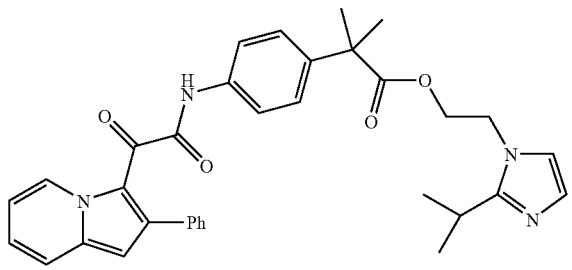 [SMILES: CC(C)c1nccn1CCOC(=O)C(C)(C)c1ccc(NC(=O)C(=O)c2c(-c3ccccc3)cc3ccccn23)cc1]<br>2-methyl-2-{4-[2-oxo-2-(2-phenyl-indolizin-3-yl)-acetylamino]-phenyl}-propionic acid 2-(2-isopropyl-imidazol-1-yl)-ethyl ester |
| 19 | 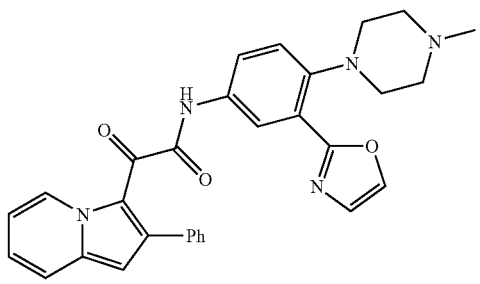 [SMILES: CN1CCN(c2ccc(NC(=O)C(=O)c3c(-c4ccccc4)cc4ccccn34)cc2-c2ncco2)CC1]<br>N-[4-(4-methyl-piperazin-1-yl)-3-oxazol-2-yl-phenyl]-2-oxo-2-(2-phenyl-indolizin-3-yl)-acetamide |
| 20 | 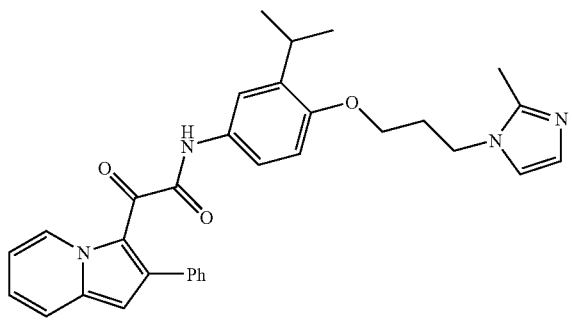 [SMILES: Cc1nccn1CCCOc1ccc(NC(=O)C(=O)c2c(-c3ccccc3)cc3ccccn23)cc1C(C)C]<br>N-{3-Isopropyl-4-[3-(2-methyl-imidazol-1-yl)-propoxy]-phenyl}-2-oxo-2-(2-phenyl-indolizin-3-yl)-acetamide |
| 21 | 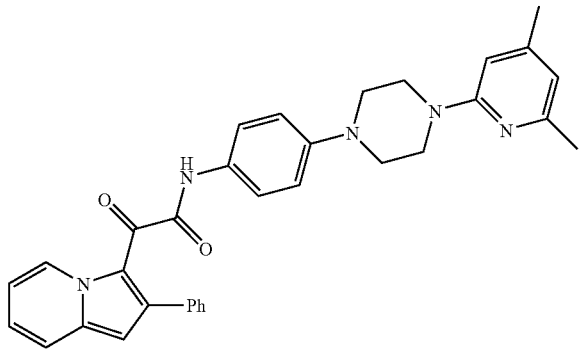 [SMILES: Cc1cc(C)nc(N2CCN(c3ccc(NC(=O)C(=O)c4c(-c5ccccc5)cc5ccccn45)cc3)CC2)c1]<br>N-{4-[4-(4,6-Dimethyl-pyridin-2-yl)-piperazin-1-yl]-phenyl}-2-oxo-2-(2-phenyl-indolizin-3-yl)-acetamide |

-continued

| Example | Compound |
|---|---|
| 22 | 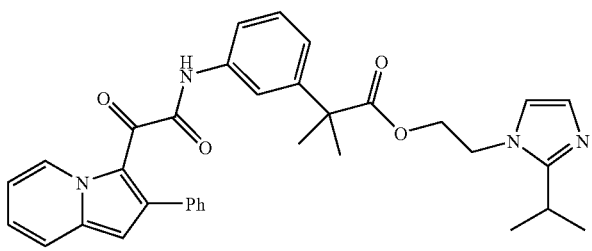 [SMILES: CC(C)c1nccn1CCOC(=O)C(C)(C)c1cccc(NC(=O)C(=O)c2c(-c3ccccc3)cc3ccccn23)c1]

2-Methyl-2-{3-[2-oxo-2-(2-phenyl-indolizin-3-yl)-acetylamino]-phenyl}-propionic acid 2-(2-isopropyl-imidazol-1-yl)-ethyl ester |
| 23 | 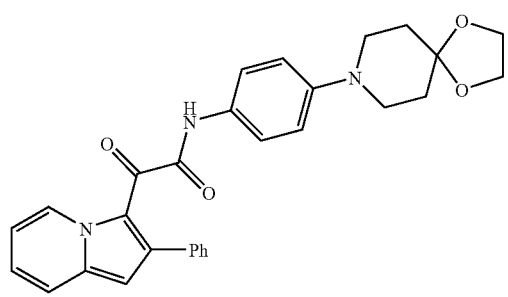 [SMILES: O=C(Nc1ccc(N2CCC3(CC2)OCCO3)cc1)C(=O)c1c(-c2ccccc2)cc2ccccn12]

N-[4-(1,4-dioxa-8-aza-spiro[4.5]dec-8-yl)-phenyl]-2-oxo-2-(2-phenyl-indolizine-3-yl)-acetamide |
| 24 | 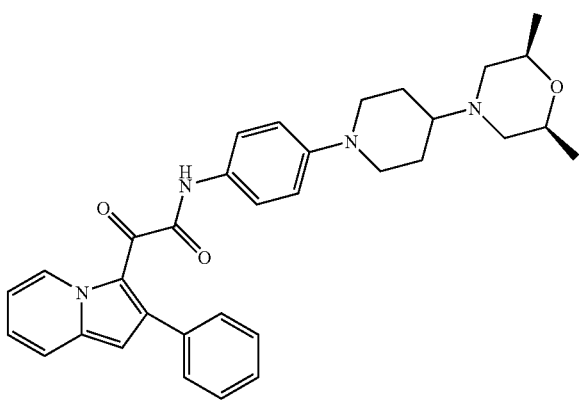 [SMILES: C[C@@H]1CN(C2CCN(c3ccc(NC(=O)C(=O)c4c(-c5ccccc5)cc5ccccn45)cc3)CC2)C[C@H](C)O1]

N-{4-[4-(2,6-Dimethyl-morpholin-4-yl)-piperidin-1-yl]-phenyl}-2-oxo-2-(2-phenyl-indolizin-3-yl)-acetamide |
| 25 | 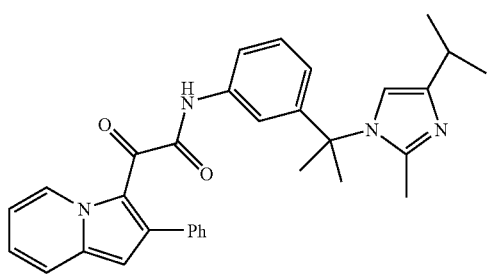 [SMILES: Cc1nc(C(C)C)cn1C(C)(C)c1cccc(NC(=O)C(=O)c2c(-c3ccccc3)cc3ccccn23)c1]

N-{3-[1-(4-isopropyl-2-methyl-imdazol-1-yl)-1-methyl-ethyl]-phenyl-2-oxo-2-(2-phenyl-indolizin-3-yl)-acetamide |

| Example | Compound |
|---|---|
| 26 | 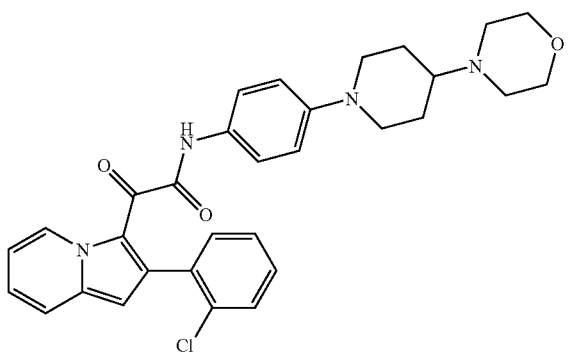 [SMILES: O=C(Nc1ccc(N2CCC(N3CCOCC3)CC2)cc1)C(=O)c1c(-c2ccccc2Cl)cc2ccccn12]
2-[2-(2-Chloro-phenyl)-indolizin-3-yl]-N-[4-(4-morpholin-4-yl-piperidin-1-yl)-phenyl]-2-oxo-acetamide |
| 27 | 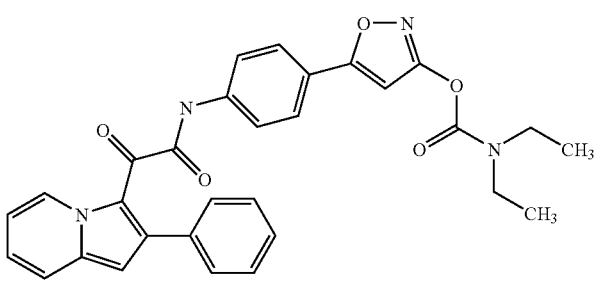 [SMILES: CCN(CC)C(=O)Oc1cc(-c2ccc(NC(=O)C(=O)c3c(-c4ccccc4)cc4ccccn34)cc2)on1]
Diethyl-carbamic acid-5-{4-[2-oxo-2-(2-phenyl-indolizin-3-yl)-aeetyl amino]-phenyl}-isoxazol-3-yl ester |
| 28 | 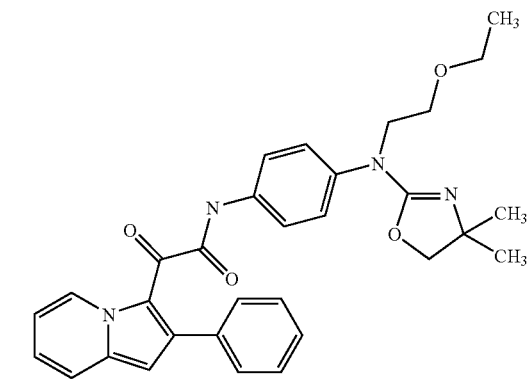 [SMILES: CCOCCN(C1=NC(C)(C)CO1)c1ccc(NC(=O)C(=O)c2c(-c3ccccc3)cc3ccccn23)cc1]
N-{4-[(4,4-Dimethyl-4,5-dihydro-oxazol-2-yl)-(2-ethoxy-ethyl)-amino]-phenyl}-2-oxo-2-phenyl-indolizin-3-yl)-acetamide |
| 29 | 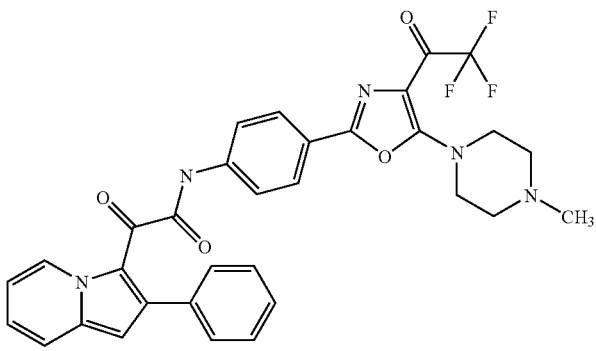 [SMILES: CN1CCN(c2oc(-c3ccc(NC(=O)C(=O)c4c(-c5ccccc5)cc5ccccn45)cc3)nc2C(=O)C(F)(F)F)CC1]
N-{4-[5-(4-Methyl-piperazin-1-yl)-4-(2,2,2-trifluoro-acetyl)-oxazol-2-yl]-phenyl}-2-oxo-2-(2-phenyl-indolizin-3-yl)-acetamide |

| Example | Compound |
|---|---|
| 30 | 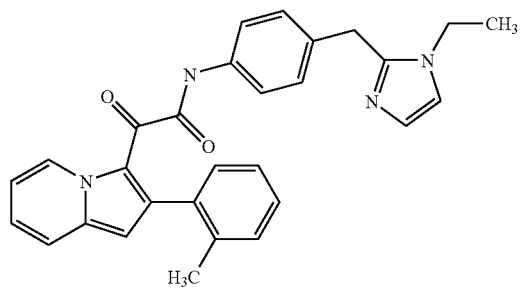 [SMILES: CCn1ccnc1Cc1ccc(NC(=O)C(=O)c2c(-c3ccccc3C)cc3ccccn23)cc1]
N-[4-(3-Ethyl-1H-imidazol-2yl methyl)-phenyl]-2-oxo-2-(2-o-tolyl-indolizin-3yl)-acetamide |
| 31 | 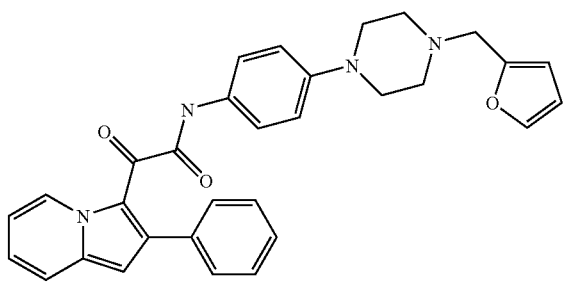 [SMILES: O=C(Nc1ccc(N2CCN(Cc3ccco3)CC2)cc1)C(=O)c1c(-c2ccccc2)cc2ccccn12]
4-[4-(2-Furan-2-yl-methyl-piperazin-yl)-phenyl]-2-oxo-2-(2-phenyl-indolizin-3-yl)-acetamide |
| 32 | 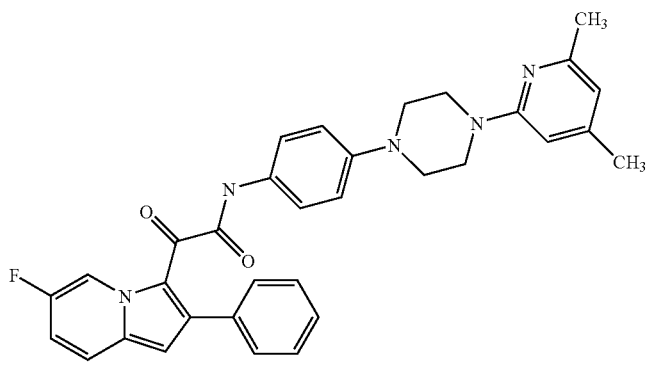 [SMILES: Cc1cc(C)nc(N2CCN(c3ccc(NC(=O)C(=O)c4c(-c5ccccc5)cc5ccc(F)cn45)cc3)CC2)c1]
N-{4-[4-(4,6-Dimethyl-pyridin-2-yl)-piperazin-1-yl]-phenyl}-2-(6-fluoro-2-phenyl-indolizin-3-yl)-2-oxo-acetamide |
| 33 | 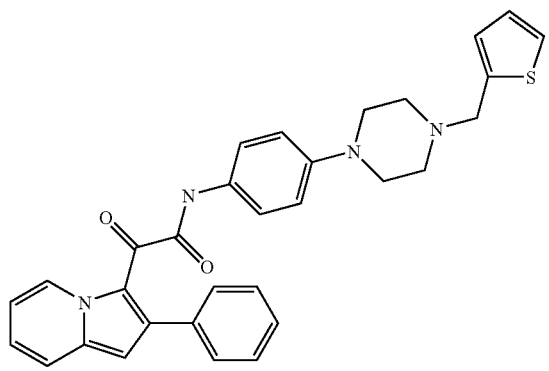 [SMILES: O=C(Nc1ccc(N2CCN(Cc3cccs3)CC2)cc1)C(=O)c1c(-c2ccccc2)cc2ccccn12]
2-Oxo-2-(2-phenyl indolizin-3-yl)-N-[4-(4-thiophen-2-yl methyl piperazin-1-yl) phenyl] acetamide |

-continued
| Example | Compound |
|---|---|
| 34 | 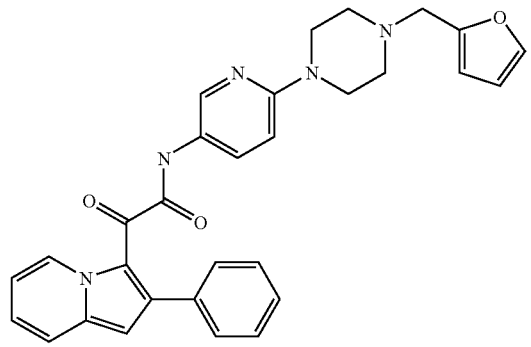 [SMILES: O=C(Nc1ccc(N2CCN(Cc3ccco3)CC2)nc1)C(=O)c1c(-c2ccccc2)cc2ccccn12]
N-[5-(2-Furan-2-yl-methyl-piperazin-yl)-peridin-2-yl]-2-oxo-2-(2-phenylindolizin-3-yl)-acetamide |
| 35 | 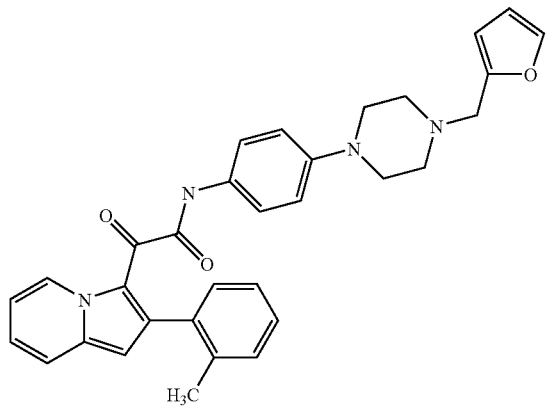 [SMILES: Cc1ccccc1-c1cc2ccccn2c1C(=O)C(=O)Nc1ccc(N2CCN(Cc3ccco3)CC2)cc1]
N-[5-(2-Furan-2-yl-methyl-piperazin-yl)-peridin-2-yl]-2-oxo-2-(2-o-tolyl-indolizin-3-yl)-acetamide |
| 36 | 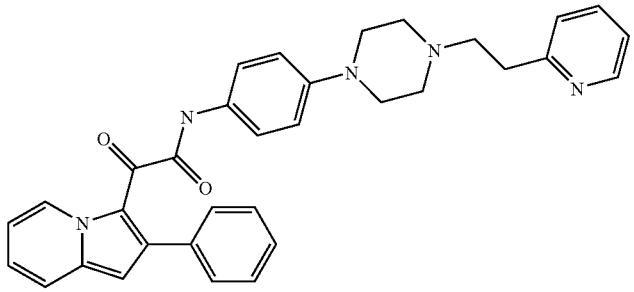 [SMILES: O=C(Nc1ccc(N2CCN(CCc3ccccn3)CC2)cc1)C(=O)c1c(-c2ccccc2)cc2ccccn12]
2-Oxo-2-(2-phenyl-indolizin-3-yl)-N-{4-[4-(2-pyridin-yl-ethyl)-perazin-1-yl]-phenyl}-acetamide |
| 37 | 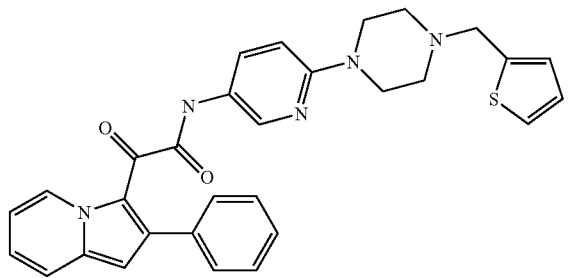
2-Oxo-2-(2-phenyl-indolizin-3-yl)-N-[4-{4-thiophen-2-ylmethyl-piperazin-1-yl}-pyridine-3-yl]-acetamide |

-continued
| Example | Compound |
|---|---|
| 38 | 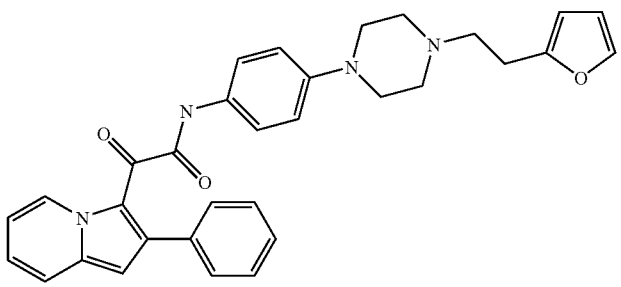 [SMILES: O=C(Nc1ccc(N2CCN(CCc3ccco3)CC2)cc1)C(=O)c1c(-c2ccccc2)cc2ccccn12]
N-{4-[4-(2-Furan-2-yl-ethyl)-piperazin-1-yl]-pyridin-3-yl}-2-oxo-2-(2-phenyl-indolizin-3-yl)-acetamide |
| 39 | 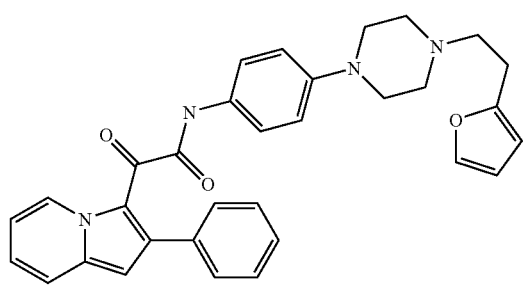 [SMILES: O=C(Nc1ccc(N2CCN(CCc3ccco3)CC2)cc1)C(=O)c1c(-c2ccccc2)cc2ccccn12]
N-{4-[4-(2-Furan-2-yl-ethyl)-piperazin-1-yl]-phenyl}-2-oxo-2-(2-phenyl-indolizin-3-yl)-acetamide |
| 40 | 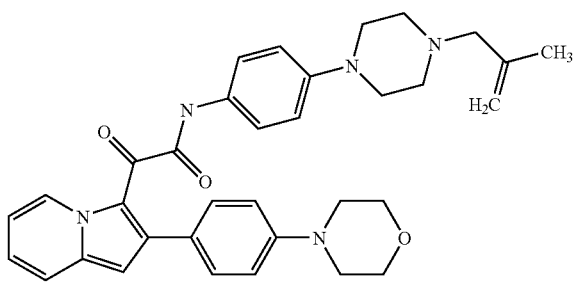 [SMILES: C=C(C)CN1CCN(c2ccc(NC(=O)C(=O)c3c(-c4ccc(N5CCOCC5)cc4)cc4ccccn34)cc2)CC1]
N-{4-[4-(2-Methyl-allyl)-piperazin-1-yl]-phenyl}-2-[2-(4-morpholin-4-yl-phenyl)-indolizin-3-yl]-2-oxo-acetamide |
| 41 | 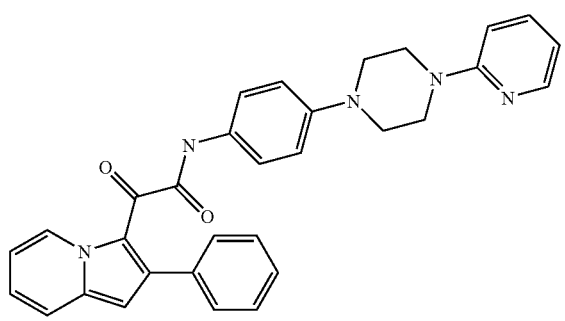 [SMILES: O=C(Nc1ccc(N2CCN(c3ccccn3)CC2)cc1)C(=O)c1c(-c2ccccc2)cc2ccccn12]
2-Oxo-2-(2-phenyl-indolizin-3yl)-N-[4-(4-pyridin-2-yl-piperizin-1-yl)-phenyl]-acetamide |

-continued
| Example | Compound |
|---|---|
| 42 | 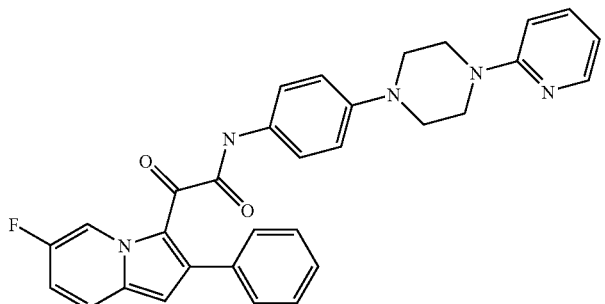
2-(6-Fluoro-2-phenyl-indolizin-3-yl)-2-oxo-N-[4-(4-pyridin-2-yl-piperazin-1-yl) phenyl] acetamide |
| 43 | 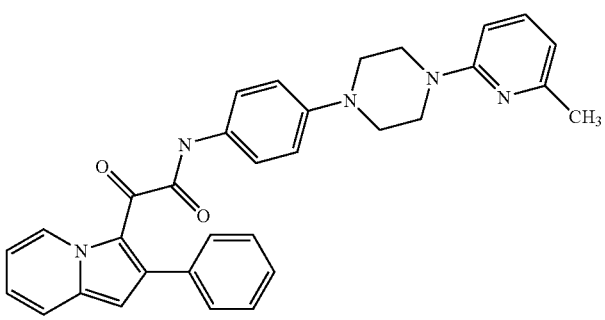 [SMILES: Cc1cccc(N2CCN(c3ccc(NC(=O)C(=O)c4c(-c5ccccc5)cc5ccccn45)cc3)CC2)n1]
N-{4-[4-(6-Methyl-pyridin-2-yl)-piperazin-1-yl]-phenyl}-2-oxo-2-(2-phenyl-indolizin-3-yl)-acetainide |
| 44 | 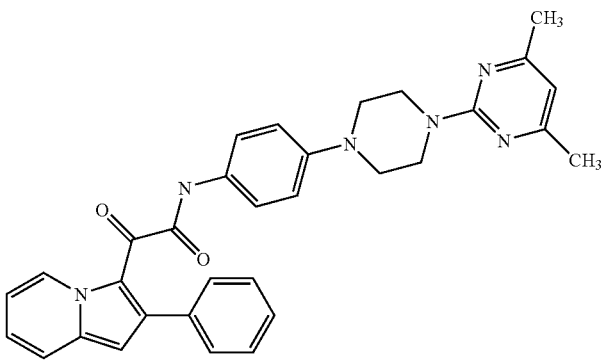 [SMILES: Cc1cc(C)nc(N2CCN(c3ccc(NC(=O)C(=O)c4c(-c5ccccc5)cc5ccccn45)cc3)CC2)n1]
N-{4-[4-(4,6-Dimethyl-pyrimidin-2-yl)-piperazin-1-yl]-phenyl}-2-oxo-2-(2-phenyl-indolizin-3-yl)-acetamide |
| 45 | 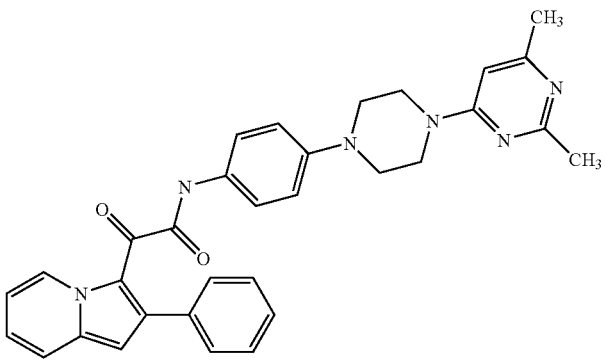 [SMILES: Cc1cc(N2CCN(c3ccc(NC(=O)C(=O)c4c(-c5ccccc5)cc5ccccn45)cc3)CC2)nc(C)n1]
N-{4-[4-(2,6-Dimethyl-pyrimidin-4-yl)-piperazin-1-yl]-phenyl}-2-(2-phenyl-indolizin-3-yl)-acetamide |

| Example | Compound |
| --- | --- |
| 46 | 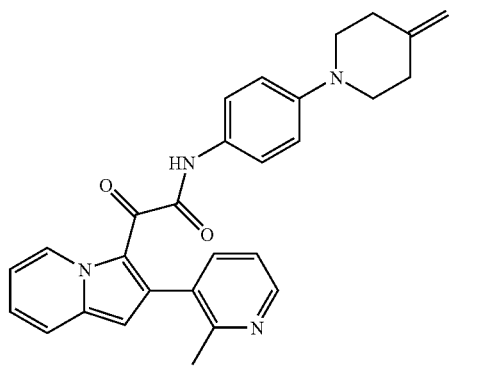 [SMILES: C=C1CCN(c2ccc(NC(=O)C(=O)c3c(-c4cccnc4C)cc4ccccn34)cc2)CC1]<br>N-[4-(4-Methylene-piperidin-1-yl)-phenyl]-2-[2-(2-methyl-pyridin-3-yl)-indolizin-3-yl]-2-oxo-acetamide |
| 47 | 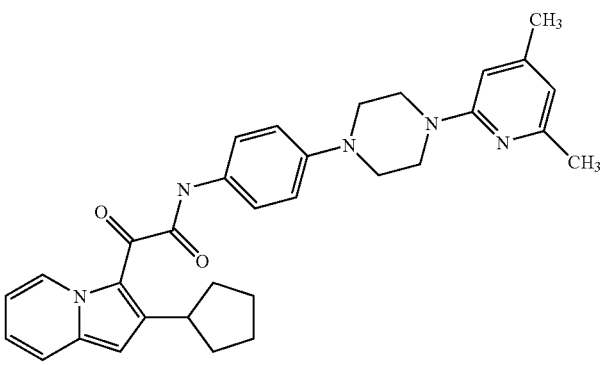 [SMILES: Cc1cc(C)nc(N2CCN(c3ccc(NC(=O)C(=O)c4c(C5CCCC5)cc5ccccn45)cc3)CC2)c1]<br>2-(2-Cyclopentyl-indolizin-3-yl)-N-{4-[4-(4,6-dimethyl-pyridin-2-yl)-piperazin-1-yl]-phenyl}-2-oxo-acetamide |
| 48 | 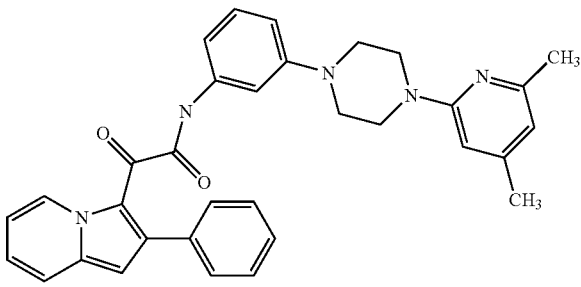 [SMILES: Cc1cc(C)nc(N2CCN(c3cccc(NC(=O)C(=O)c4c(-c5ccccc5)cc5ccccn45)c3)CC2)c1]<br>N-{3-[4-(4, 6-Dimethyl-pyridin-2-yl)-piperazin-1-yl]-phenyl}-2-oxo-2-(2-phenyl-indolizin-3-yl)-acetamide |
| 49 | 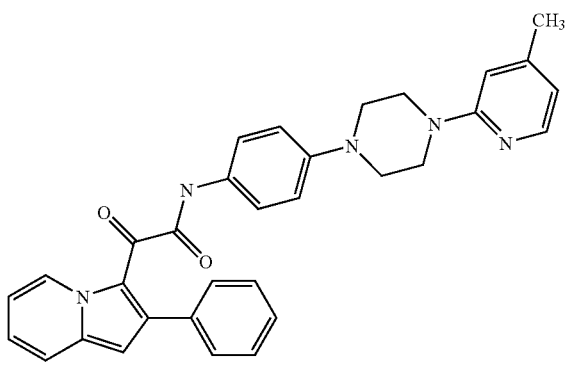 [SMILES: Cc1ccnc(N2CCN(c3ccc(NC(=O)C(=O)c4c(-c5ccccc5)cc5ccccn45)cc3)CC2)c1]<br>N-{4-[4-(4-Methyl-pyridin-2-yl)-piperazin-1-yl]-phenyl}-2-oxo-2-(2-phenyl-indolizin-3-yl)-acetamide |

| Example | Compound |
|---|---|
| 50 | 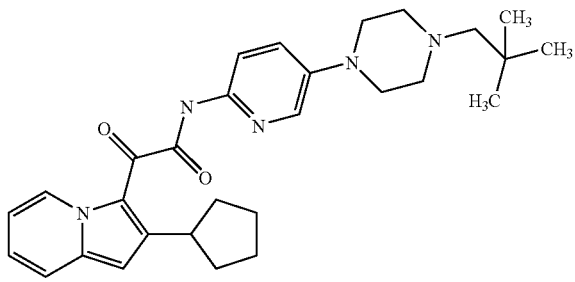 [SMILES: CC(C)(C)CN1CCN(c2ccc(NC(=O)C(=O)c3c(C4CCCC4)cc4ccccn34)nc2)CC1]<br>N-{5-[4-(2,2-Dimethyl-propyl)-piperazin-1-yl]-pyridin-2-yl}-2-oxo-2-(2-phenyl-indolizin-3-yl)-acetamide |
| 51 | 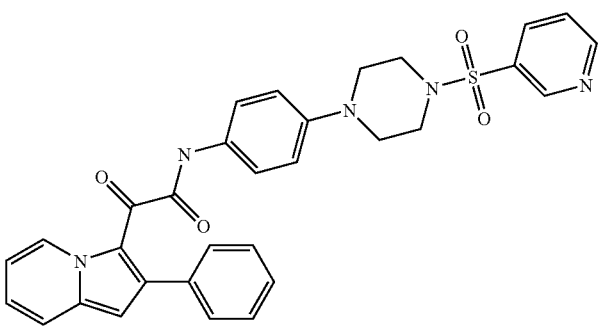 [SMILES: O=C(Nc1ccc(N2CCN(S(=O)(=O)c3cccnc3)CC2)cc1)C(=O)c1c(-c2ccccc2)cc2ccccn12]<br>2-Oxo-2-(2-phenyl-indolizin-3-yl)-N-{4-[4-(pyridine-3-sulfonyl)-piperazin-1-yl]-phenyl}-acetamide |
| 52 | 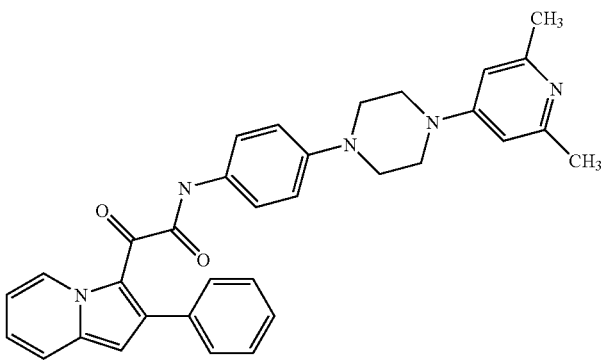 [SMILES: Cc1cc(N2CCN(c3ccc(NC(=O)C(=O)c4c(-c5ccccc5)cc5ccccn45)cc3)CC2)cc(C)n1]<br>N-{4-[4-(2, 6-Dimethyl-pyridin-4-yl)-piperazin-1-yl]-phenyl}-2-oxo-2-(2-phenyl-indolizin-3-yl)-acetamide |
| 53 | 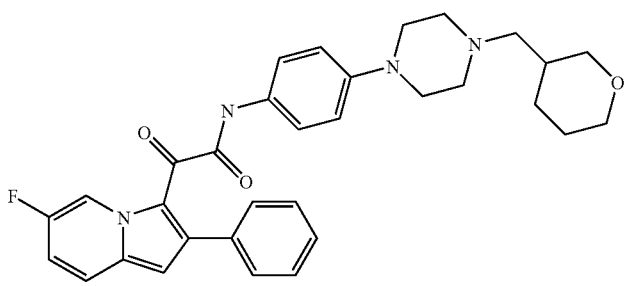 [SMILES: O=C(Nc1ccc(N2CCN(CC3CCCOC3)CC2)cc1)C(=O)c1c(-c2ccccc2)cc2ccc(F)cn12]<br>2-(6-Fluoro-2-phenyl-indolizin-3-yl)-2-oxo-N-{4-[4-(tetrahydro-pyran-4-ylmethyl)-piperazin-1-yl]-phenyl}-acetamide |

-continued
| Example | Compound |
|---------|----------|
| 54 | 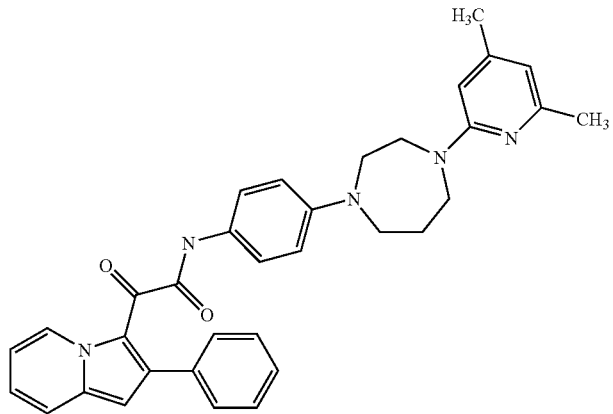 [SMILES: Cc1cc(C)nc(N2CCCN(c3ccc(NC(=O)C(=O)c4c(-c5ccccc5)cc5ccccn45)cc3)CC2)c1]  N-{4-[4-(4,6-Dimethyl-pyridin-2-yl)-[1,4]diazepan-1-yl]-phenyl}-2-oxo-2-(2-phenyl-indolizin-3-yl)-acetamide |
| 55 | 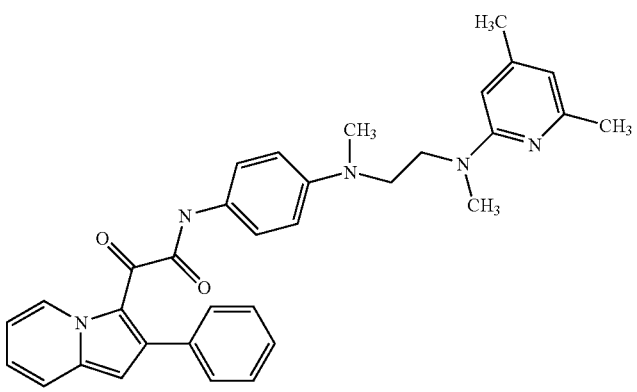 [SMILES: Cc1cc(C)nc(N(C)CCN(C)c2ccc(NC(=O)C(=O)c3c(-c4ccccc4)cc4ccccn34)cc2)c1]  N-[4-({2-[(4,6-Dimethyl-pyridin-2-yl)-methyl-amino]-ethyl}-methyl-amino)-phenyl]-2-oxo-2-(2-phenyl-indolizin-3-yl)-acetamide |
| 56 | 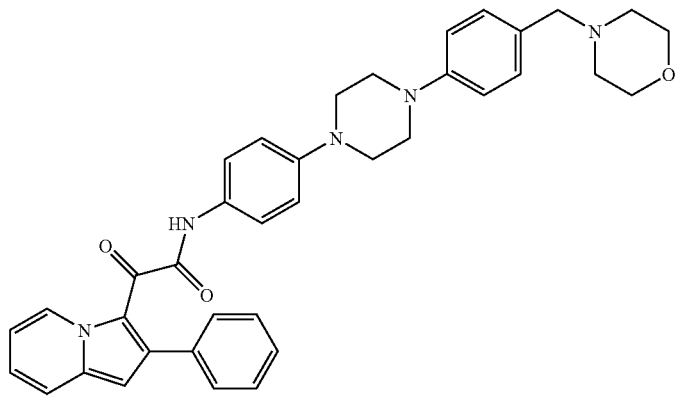 [SMILES: O=C(Nc1ccc(N2CCN(c3ccc(CN4CCOCC4)cc3)CC2)cc1)C(=O)c1c(-c2ccccc2)cc2ccccn12]  N-{4-[4-(4-Morpholin-4-ylmethyl-phenyl)-piperazin-1-yl]-phenyl}-2-oxo-2-(2-phenyl-indolizin-3-yl)-acetamide |

| Example | Compound |
|---|---|
| 57 | 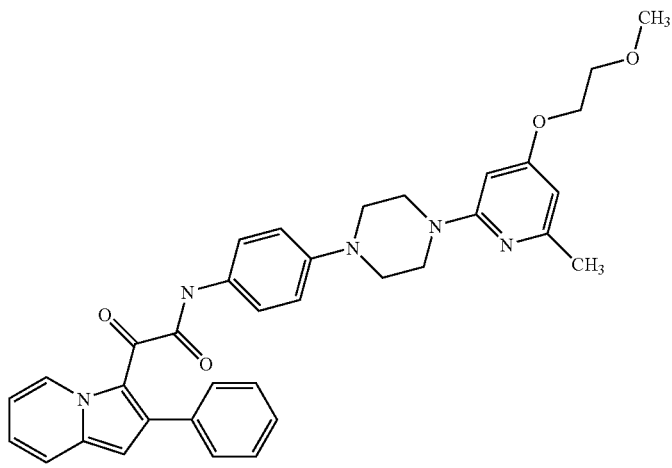 [SMILES: COCCOc1cc(C)nc(N2CCN(c3ccc(NC(=O)C(=O)c4c(-c5ccccc5)cc5ccccn45)cc3)CC2)c1]
N-(4-{4-[4-(2-Methoxy-ethoxy)-6-methyl-pyridin-2-yl]-piperazin-1-yl}-phenyl)-2-oxo-2-(2-phenyl-indolizin-3-yl)-acetamide |
| 58 | 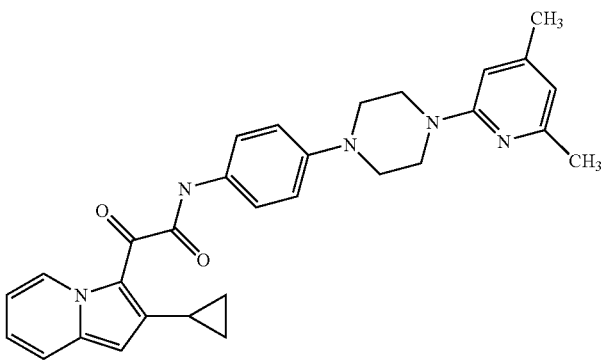 [SMILES: Cc1cc(C)nc(N2CCN(c3ccc(NC(=O)C(=O)c4c(C5CC5)cc5ccccn45)cc3)CC2)c1]
2-(2-Cyclopropyl-indolizin-3-yl)-N-{4-[4-(4,6-dimethyl-pyridin-2-yl)-piperazin-1-yl]-phenyl}-2-oxo-acetamide |
| 59 | 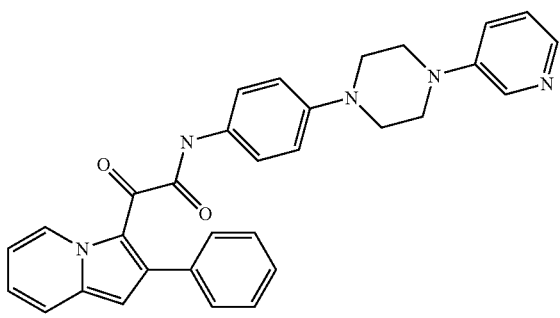 [SMILES: O=C(Nc1ccc(N2CCN(c3cccnc3)CC2)cc1)C(=O)c1c(-c2ccccc2)cc2ccccn12]
2-Oxo-2-(2-phenyl-indolizin-3-yl)-N-[4-(4-pyridin-3-yl-piperazin-1-yl)-phenyl]-acetamide |

| Example | Compound |
|---|---|
| 60 | 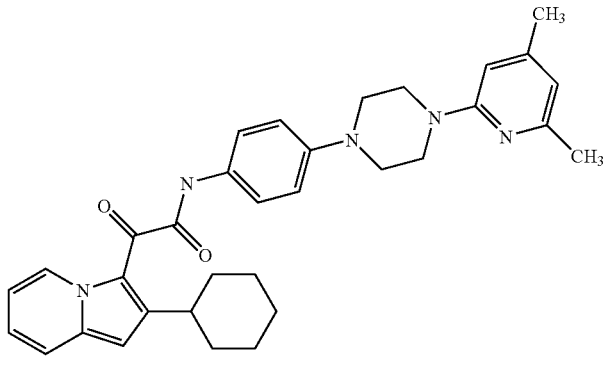 [SMILES: Cc1cc(C)nc(N2CCN(c3ccc(NC(=O)C(=O)c4c(C5CCCCC5)cc5ccccn45)cc3)CC2)c1]
2-(2-Cyclohexyl-indolizin-3-yl)-N-{4-[4-(4,6-dimethyl-pyridin-2-yl)-piperazin-1-yl]-phenyl}-2-oxo-acetamide |
| 61 | 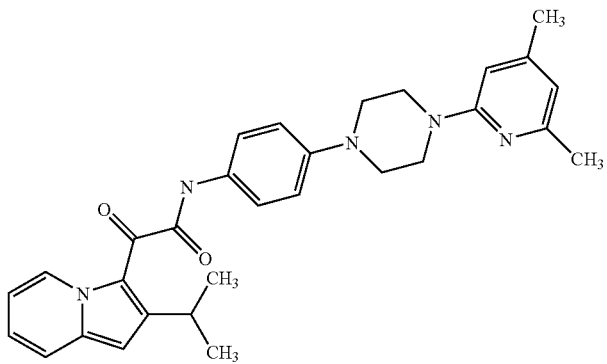 [SMILES: Cc1cc(C)nc(N2CCN(c3ccc(NC(=O)C(=O)c4c(C(C)C)cc5ccccn45)cc3)CC2)c1]
N-{4-[4-(4,6-Dimethyl-pyridin-2-yl)-piperazin-1-yl]-phenyl}-2-(2-isopropyl-indolizin-3-yl)-2-oxo-acetamide |
| 62 | 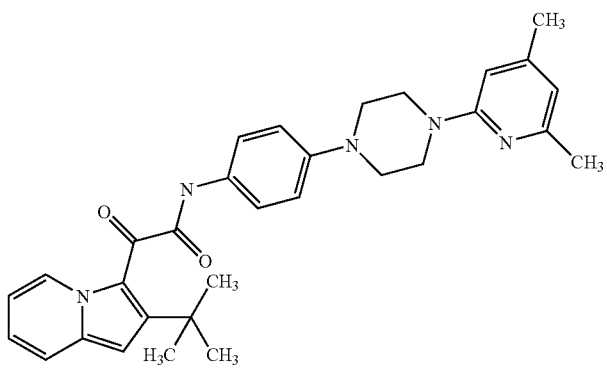 [SMILES: Cc1cc(C)nc(N2CCN(c3ccc(NC(=O)C(=O)c4c(C(C)(C)C)cc5ccccn45)cc3)CC2)c1]
2-(2-tert-Butyl-indolizin-3-yl)-N-{4-[4-(4,6-dimethyl-pyridin-2-yl)-piperazin-1-yl]-phenyl}-2-oxo-acetamide |

| Example | Compound |
|---|---|
| 63 | 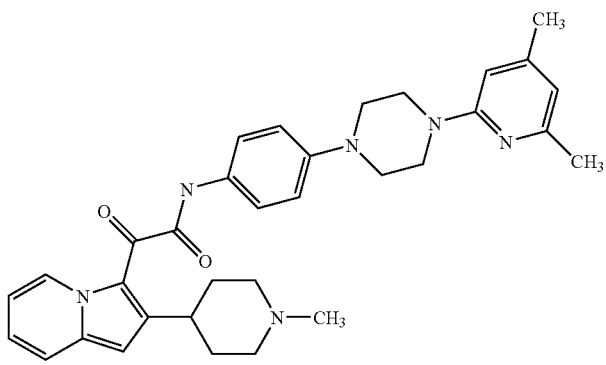 [SMILES: Cc1cc(C)nc(N2CCN(c3ccc(NC(=O)C(=O)c4c(C5CCN(C)CC5)cc5ccccn45)cc3)CC2)c1]<br>N-{4-[4-(4,6-Dimethyl-pyridin-2-yl)-piperazin-1-yl]-phenyl}-2-[2-(1-methyl-piperidin-4-yl)-indolizin-3-yl]-2-oxo-acetamide |
| 64 | 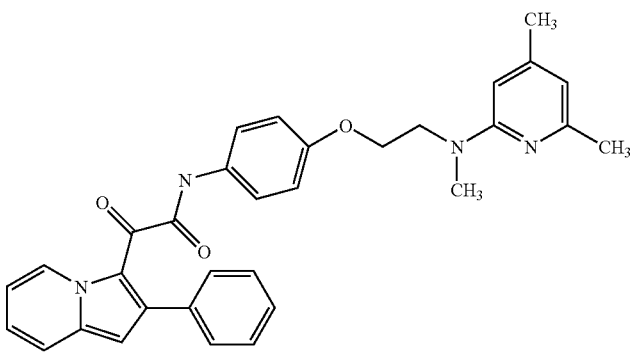 [SMILES: Cc1cc(C)nc(N(C)CCOc2ccc(NC(=O)C(=O)c3c(-c4ccccc4)cc4ccccn34)cc2)c1]<br>N-(4-{2-[(4,6-Dimethyl-pyridin-2-yl)-methyl-amino]-ethoxy}-phenyl)-2-oxo-2-(2-phenyl-indolizin-3-yl)-acetamide |
| 65 | 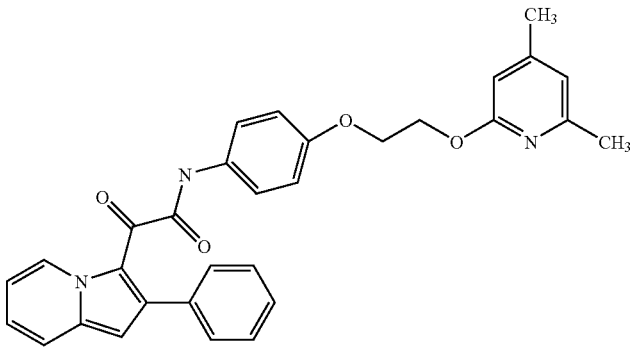 [SMILES: Cc1cc(C)nc(OCCOc2ccc(NC(=O)C(=O)c3c(-c4ccccc4)cc4ccccn34)cc2)c1]<br>N-{4-[2-(4,6-Dimethyl-pyridin-2-yloxy)-ethoxy]-phenyl}-2-oxo-2-(2-phenyl-indolizin-3-yl)-acetamide |
| 66 | 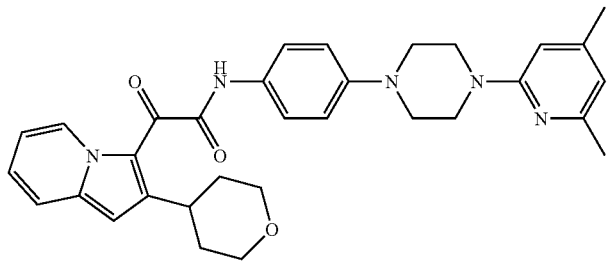 [SMILES: Cc1cc(C)nc(N2CCN(c3ccc(NC(=O)C(=O)c4c(C5CCOCC5)cc5ccccn45)cc3)CC2)c1]<br>N-{4-[4-(4,6-Dimethyl-pyridin-2-yl)-piperazin-1-yl]-phenyl}-2-oxo-2-[2-(tetrahydro-pyran-4-yl)-indolizin-3-yl]-acetamide |

| Example | Compound |
|---|---|
| 67 | 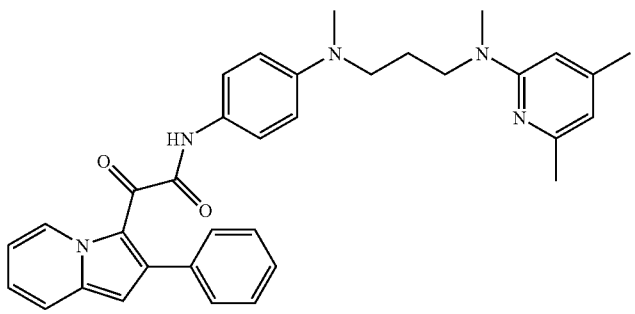 [SMILES: Cc1cc(C)nc(N(C)CCCN(C)c2ccc(NC(=O)C(=O)c3c(-c4ccccc4)cc4ccccn34)cc2)c1]
N-[4-({3-[(4,6-dimethyl-pyridin-2-yl)-methyl-amino]-propyl}-methyl-amino)-phenyl]-2-oxo-2-(2-phenyl-indolizin-3-yl)-acetamide |
| 68 | 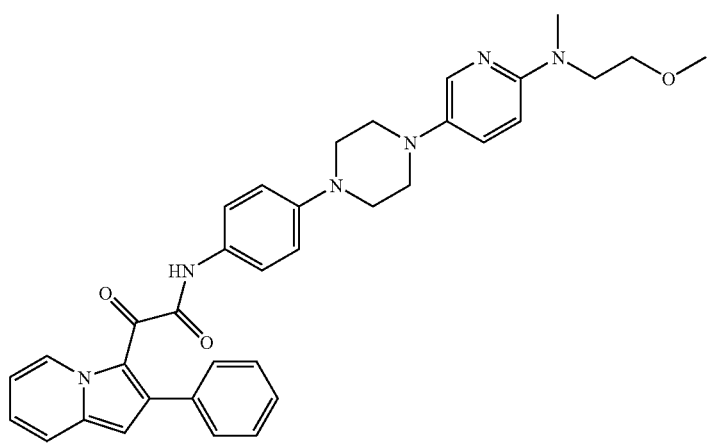 [SMILES: COCCN(C)c1ccc(N2CCN(c3ccc(NC(=O)C(=O)c4c(-c5ccccc5)cc5ccccn45)cc3)CC2)cn1]
N-[4-(4-{6-[(2-Methoxy-ethyl)-methyl-amino]-pyridin-3-yl}-piperazin-1-yl)-phenyl]-2-oxo-2-(2-phenyl-indolizin-3-yl)-acetamide |
| 69 | 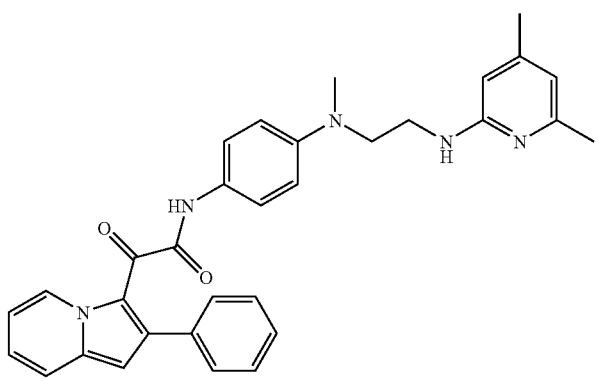 [SMILES: Cc1cc(C)nc(NCCN(C)c2ccc(NC(=O)C(=O)c3c(-c4ccccc4)cc4ccccn34)cc2)c1]
N-(4-{[2-(4,6-dimethyl-pyridin-2-ylamino)-ethyl]-methyl-amino}-phenyl)-2-oxo-2-(2-phenyl-indolizin-3-yl)-acetamide |

-continued
| Example | Compound |
|---|---|
| 70 | 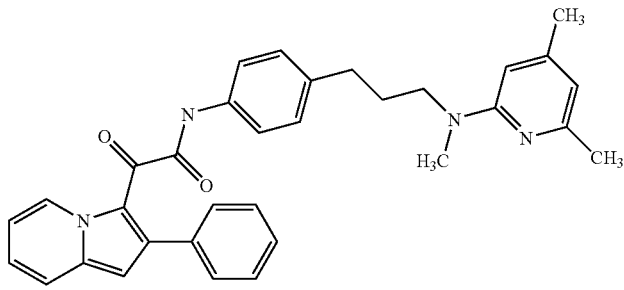 [SMILES: Cc1cc(C)nc(N(C)CCCc2ccc(NC(=O)C(=O)c3c(-c4ccccc4)cc4ccccn34)cc2)c1]
N-(4-{3-[(4,6-Dimethyl-pyridin-2-yl)-methyl-amino]-propyl}-phenyl)-2-oxo-2-(2-phenyl-indolizin-3-yl)-acetamide |
| 71 | 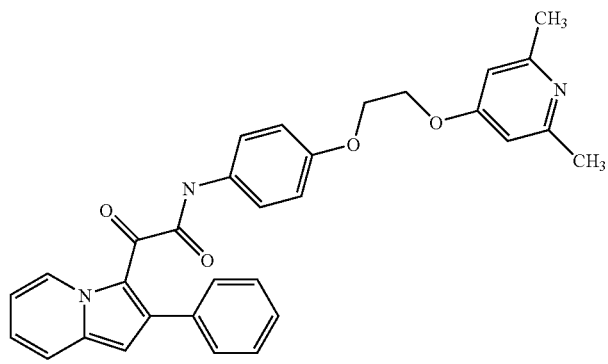 [SMILES: Cc1cc(OCCOc2ccc(NC(=O)C(=O)c3c(-c4ccccc4)cc4ccccn34)cc2)cc(C)n1]
N-{4-[2-(2,6-Dimethyl-pyridin-4-yloxy)-ethoxy]-phenyl}-2-oxo-2-(2-phenyl-indolizin-3-yl)-acetamide |
| 72 | 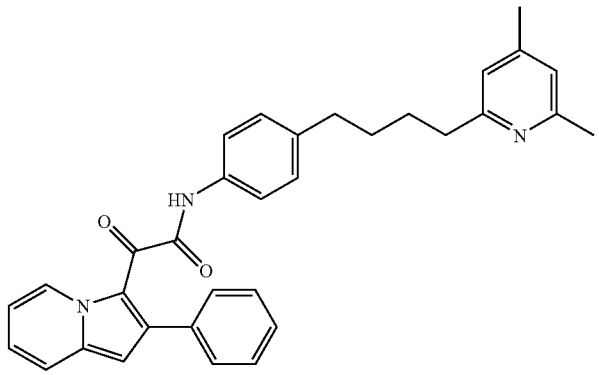 [SMILES: Cc1cc(C)nc(CCCCc2ccc(NC(=O)C(=O)c3c(-c4ccccc4)cc4ccccn34)cc2)c1]
N-{4-[4-(4,6-Dimethyl-pyridin-2-yl)-butyl]-phenyl}-2-oxo-2-(2-phenyl-indolizin-3-yl)-acetamide |
| 73 | 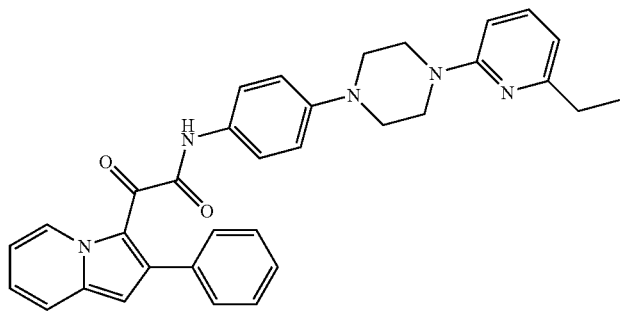 [SMILES: CCc1cccc(N2CCN(c3ccc(NC(=O)C(=O)c4c(-c5ccccc5)cc5ccccn45)cc3)CC2)n1]
N-{4-[4-(6-ethyl-pyridin-2-yl)-piperazin-1-yl]-phenyl}-2-oxo-2-(2-phenyl-indolizin-3-yl)-acetamide |

| Example | Compound |
|---------|----------|
| 74 | 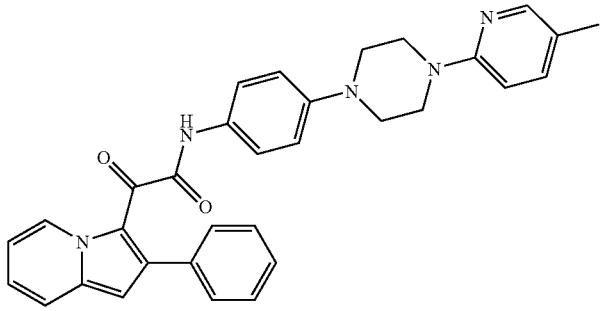 [SMILES: Cc1ccc(N2CCN(c3ccc(NC(=O)C(=O)c4c(-c5ccccc5)cc5ccccn45)cc3)CC2)nc1]<br>N-{4-[4-(5-Methyl-pyridin-2-yl)-piperazin-1-yl]-phenyl}-2-oxo-2-(2-phenyl-indolizin-3-yl)-acetamide |
| 75 | 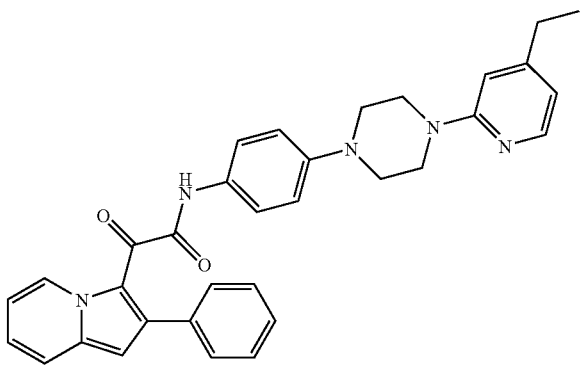 [SMILES: CCc1ccnc(N2CCN(c3ccc(NC(=O)C(=O)c4c(-c5ccccc5)cc5ccccn45)cc3)CC2)c1]<br>N-{4-[4-(4-ethyl-pyridin-2-yl)-piperazin-1-yl]-phenyl}-2-oxo-2-(2-phenyl-indolizin-3-yl)-acetamide |
| 76 | 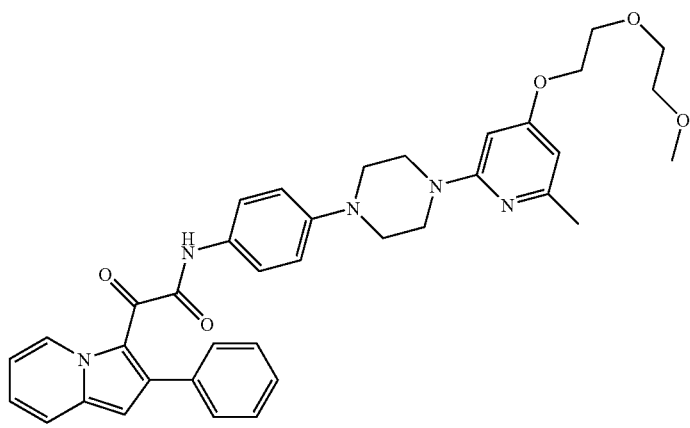 [SMILES: COCCOCCOc1cc(C)nc(N2CCN(c3ccc(NC(=O)C(=O)c4c(-c5ccccc5)cc5ccccn45)cc3)CC2)c1]<br>N-[4-(4-{4-[2-(2-methoxy-ethoxy)-ethoxyl]-6-methyl-pyridin-2-yl}-piperazin-1-yl)-phenyl]-2-oxo-2-(2-phenyl-indolizin-3-yl)-acetamide |

| Example | Compound |
|---|---|
| 77 | 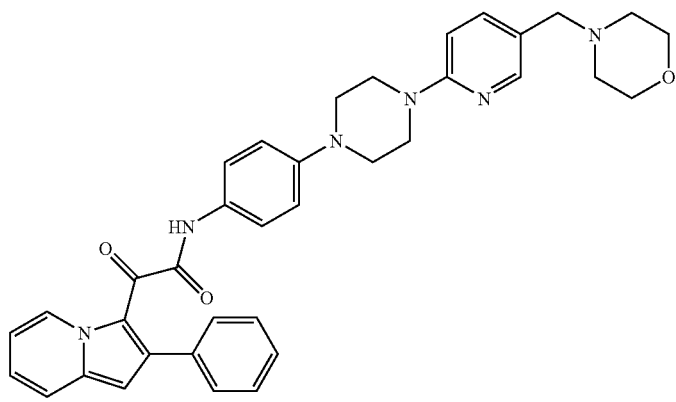 [SMILES: O=C(Nc1ccc(N2CCN(c3ccc(CN4CCOCC4)cn3)CC2)cc1)C(=O)c1c(-c2ccccc2)cc2ccccn12]<br>N-{4-[4-(5-morpholin-4-yl-methyl-pyridin-2-yl)-piperazin-1-yl]-phenyl}-2-oxo-2-(2-phenyl-indolizin-3-yl)-acetamide |
| 78 | 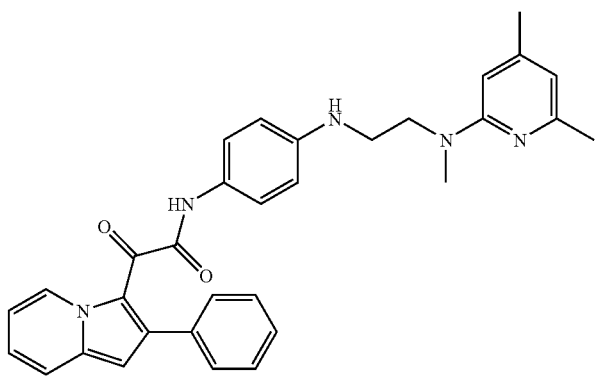 [SMILES: Cc1cc(C)nc(N(C)CCNc2ccc(NC(=O)C(=O)c3c(-c4ccccc4)cc4ccccn34)cc2)c1]<br>N-(4-{2-[(4,6-Dimethyl-pyridin-2-yl)-methyl-amino]-ethylamino}-phenyl)-2-oxo-2-(2-phenyl-indolizin-3-yl)-acetamide |
| 79 | 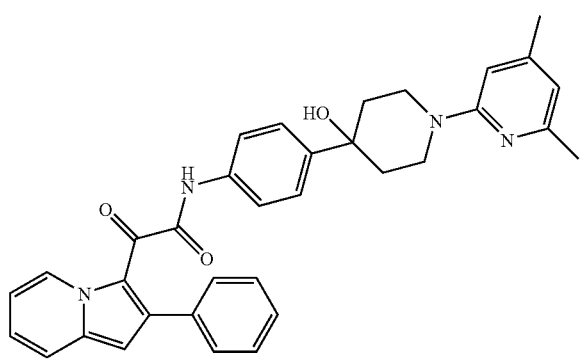 [SMILES: Cc1cc(C)nc(N2CCC(O)(c3ccc(NC(=O)C(=O)c4c(-c5ccccc5)cc5ccccn45)cc3)CC2)c1]<br>N-[4-(4-hydroxy-4',6'-dimethyl-3,4,5,6-tetrahydro-2H-[1,2']-bipyridinyl-4-yl)-phenyl]-2-oxo-2-(2-phenyl-indolizin-3-yl)-acetamide |

-continued
| Example | Compound |
|---|---|
| 80 | 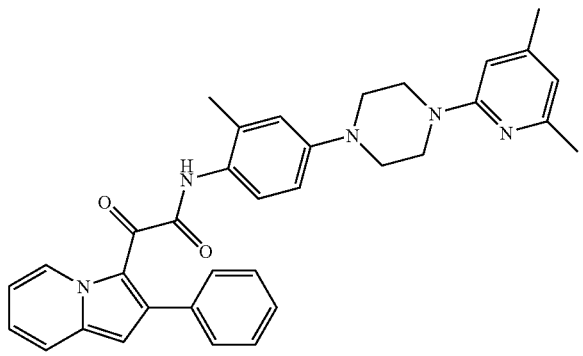 [SMILES: Cc1cc(C)nc(N2CCN(c3ccc(NC(=O)C(=O)c4c(-c5ccccc5)cc5ccccn45)c(C)c3)CC2)c1]<br>N-{4-[4-(4,6-Dimethyl-pyridin-2-yl)-piperazin-1-yl]-2-methyl-phenyl}-2-oxo-2-(2-phenyl-indolizin-3-yl)-acetamide |
| 81 | 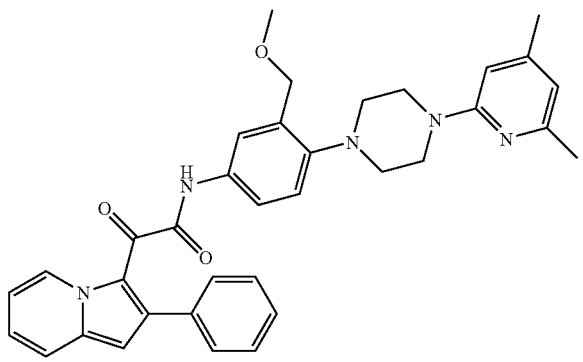 [SMILES: COCc1cc(NC(=O)C(=O)c2c(-c3ccccc3)cc3ccccn23)ccc1N1CCN(c2cc(C)cc(C)n2)CC1]<br>N-{4-[4-(4,6-Dimethyl-pyridin-2-yl)-piperazin-1-yl]-3-methoxymethyl-phenyl}-2-oxo-2-(2-phenyl-indolizin-3-yl)-acetamide |
| 82 | 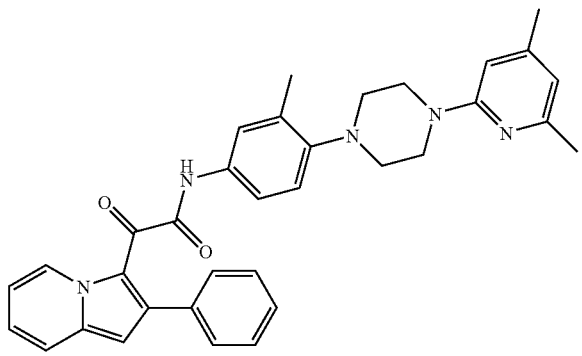 [SMILES: Cc1cc(C)nc(N2CCN(c3ccc(NC(=O)C(=O)c4c(-c5ccccc5)cc5ccccn45)cc3C)CC2)c1]<br>N-{4-[4-(4,6-Dimethyl-pyridin-2-yl)-piperazin-1-yl]-3-methyl-phenyl}-2-oxo-2-(2-phenyl-indolizin-3-yl)-acetamide |

| Example | Compound |
|---|---|
| 83 | 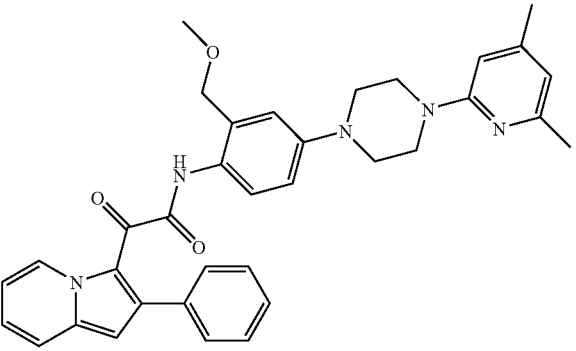 [SMILES: COCc1cc(N2CCN(c3cc(C)cc(C)n3)CC2)ccc1NC(=O)C(=O)c1c(-c2ccccc2)cc2ccccn12]<br>N-{4-[4-(4,6-Dimethyl-pyridin-2-yl)-piperazin-1-yl]-2-methoxymethyl-phenyl}-2-oxo-2-(2-phenyl-indolizin-3-yl)-acetamide |
| 84 | 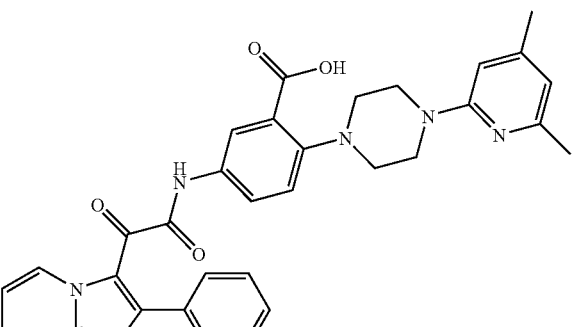<br>2-[4-(4,6-Dimethyl-pyridin-2-yl)-piperazin-1-yl]-5-[2-oxo-2-(2-phenyl-indolizin-3-yl)-acetylamino]-benzoic acid |

These compounds were prepared in a manner analogous to Example 1.

Reference Examples 309 to 316

309 2-[2-(4-bromo-phenyl)-indolizin-3-yl]-N-(4-oxazol-4-yl-phenyl)-2-oxo-acetamide
310 (2,2,2-Trifluoro-N-[4-[2-oxo-2-(2-phenyl-indolizin-3-yl)-acetylamino]-phenyl}-N-[2-pyridin-2-yloxy)-ethyl]-acetamide
311 N-{4-[4-(6-{Bis-[2-(tert-butyl-dimethyl-silanyloxy)-ethyl]-amino}-pyridin-2-yl)-piperazin-1-yl]-phenyl}-2-oxo-2-(2-phenyl-indolizin-3-yl)-acetamide
312 Acetic acid 2-[2-(4-{4-[2-oxo-2-(2-phenyl-indolizin-3-yl)-acetylamino]-phenyl}-piperazin-1-yl)-pyridin-4-yloxy]-ethyl ester
313 N-[4-(4-{6-[2-(tert-butyl-dimethyl-silanyloxy)-ethylamino]-pyridin-2-yl}-piperazin-1-yl)-phenyl]-2-oxo-2-(2-phenyl-indolizin-3-yl)-acetamide
314 N-(4,6-Dimethyl-pyridin-2-ylmethyl)-2,2,2-trifluoro-N-{4-[2-oxo-2-(2-phenyl-indolizin-3-yl)-acetyl amino]-phenyl}-acetamide
315 N-{2-(4,6-Dimethyl-pyridin-2yl-amino)-2,2,2,-trifluoro-N-{4-[2-oxo-2-(2-phenyl indolizin-3-yl) acetylamino] phenyl acetamide
316 N-[4-(4-{6-[2-(tert-butyl-dimethyl-silanyloxy)-ethyl]-pyridin-2-yl}-piperazin-1-yl)-phenyl]-2-oxo-2-(2-phenyl-indolizin-3-yl)-acetamide Example 85

2-(2-Biphenyl-4-yl-indolizin-3-yl)-N-(4-oxazol-4-yl-phenyl)-2-oxo-acetamide

A solution of 2-[2-(4-bromo-phenyl)-indolizin-3-yl]-N-(4-oxazol-4-yl-phenyl)-2-oxo-acetamide (500 mg, 1.03 mmol) and phenylboronic acid (248 mg, 2.05 mmol) in dry DMF (10 mL) was degassed thoroughly. Potassium carbonate (422 mg, 3.06 mmol) was added and purging continued for another 10 min.

Bis(triphenylphosphine)palladium(II) dichloride (35 mg, 0.05 mmol) was added, the mixture heated to 80-90° C. and maintained for 5 h. The mixture was cooled to r.t., diluted with water and extracted twice with ethyl acetate. The combined organic phases were washed with water (×4) then brine, dried over sodium sulfate and concentrated. The residue was purified by column chromatography on silica gel (60-120 mesh), eluting with 50% ethyl acetate/petroleum ether to afford 2-(2-biphenyl-4-yl-indolizin-3-yl)-N-(4-oxazol-4-yl-phenyl)-2-oxo-acetamide (200 mg, 40%) as a yellow solid.

Example 86

N-[4-(4-{6-[Bis-(2-hydroxy-ethyl)-amino]-pyridin-2-yl}-piperazin-1-yl)-phenyl]-2-oxo-2-(2-phenyl-indolizin-3-yl)-acetamide

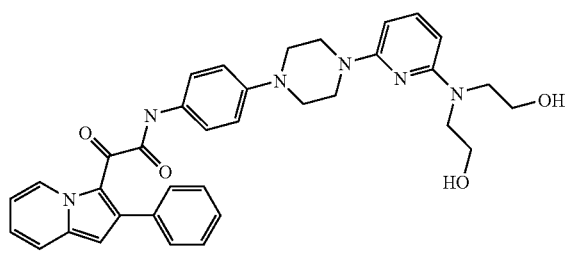 [SMILES: O=C(Nc1ccc(N2CCN(c3cccc(N(CCO)CCO)n3)CC2)cc1)C(=O)c1c(-c2ccccc2)cc2ccccn12]

To a solution of N-{4-[4-(6-{bis-[2-(tert-butyl-dimethyl-silanyloxy)-ethyl]-amino}-pyridin-2-yl)-piperazin-1-yl]-phenyl}-2-oxo-2-(2-phenyl-indolizin-3-yl)-acetamide (0.7 g, 0.81 mmol) in THF (10 mL) was added tetra-n-butylammonium fluoride (1.28 g, 4.06 mmol) at 0° C. The reaction mixture was stirred at r.t. for 1 h. The solvent was evaporated in vacuo, the residue diluted with dichloromethane and washed with water, brine, dried over sodium sulfate filtered and concentrated. The crude compound was purified by column chromatography over silica gel (60-120 mesh) using 3% methanol/chloroform to yield N-[4-(4-{6-[bis-(2-hydroxy-ethyl)-amino]-pyridin-2-yl}-piperazin-1-yl)-phenyl]-2-oxo-2-(2-phenyl-indolizin-3-yl)-acetamide (180 mg, 36%) as a light yellow solid.

Examples 87 to 88

The compounds set out below were prepared a manner analogous to Example 86:

| Example | Compound |
|---|---|
| 87 | 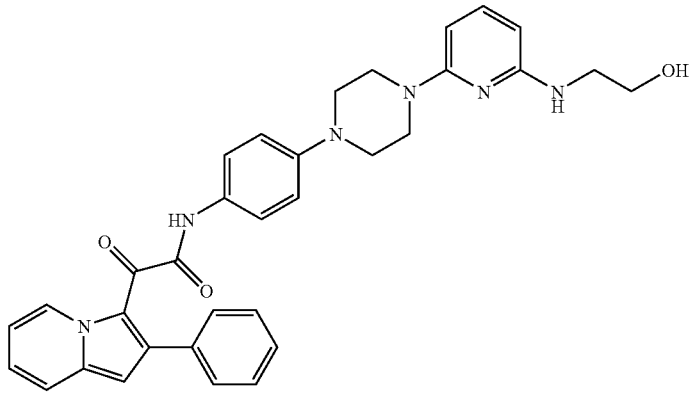 [SMILES: O=C(Nc1ccc(N2CCN(c3cccc(NCCO)n3)CC2)cc1)C(=O)c1c(-c2ccccc2)cc2ccccn12]<br>N-(4-{4-[6-(2-hydroxy-ethylamino)-pyridin-2-yl]-piperazin-1-yl}-phenyl)-2-oxo-2-(2-phenyl-indolizin-3-yl)-acetamide |
| 88 | 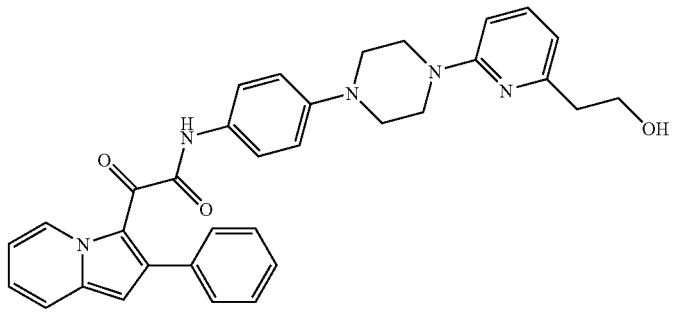 [SMILES: O=C(Nc1ccc(N2CCN(c3cccc(CCO)n3)CC2)cc1)C(=O)c1c(-c2ccccc2)cc2ccccn12]<br>N-(4-{4-[6-(2-hydroxy-ethyl)-pyridin-2-yl]-piperazin-1-yl}-phenyl)-2-oxo-2-(2-phenyl-indolizin-3-yl)-acetamide |

Example 89

N-(4-{4-[4-(2-Hydroxy-ethoxy)-pyridin-2-yl]-piperazin-1-yl}-phenyl)-2-oxo-2-(2-phenyl-indolizin-3-yl)-acetamide

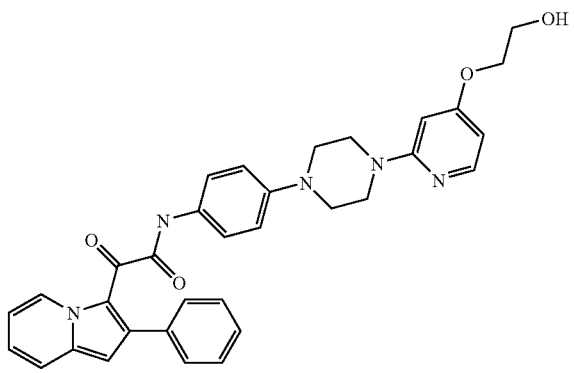 [SMILES: O=C(Nc1ccc(N2CCN(c3cc(OCCO)ccn3)CC2)cc1)C(=O)c1c(-c2ccccc2)cc2ccccn12]

Lithium hydroxide monohydrate (0.048 g, 1.16 mmol) was added to a stirred solution of acetic acid 2-[2-(4-{4-[2-oxo-2-(2-phenyl-indolizin-3-yl)-acetylamino]-phenyl}-piperazin-1-yl)-pyridin-4-yloxy]-ethyl ester (0.35 g, 0.58 mmol) in methanol (15 mL) at r.t. under nitrogen and stirred for 3 h. The reaction mixture was evaporated to dryness, diluted with water and extracted with dichloromethane. The organic layer was washed with water and brine solution, dried over sodium sulfate and filtered. The filtrate was concentrated and purified by column chromatography over neutral alumina using 0-1% methanol in dichloromethane to afford N-(4-{4-[4-(2-hydroxy-ethoxy)-pyridin-2-yl]-piperazin-1-yl}-phenyl)-2-oxo-2-(2-phenyl-indolizin-3-yl)-acetamide (0.142 g, 44%) as a yellow solid.

Examples 90 to 92

The compounds set out below were prepared a manner analogous to Example 89:

| Example | Compound |
|---|---|
| 90 | 2-Oxo-2-(2-phenyl-indolizin-3-yl)-N-{4-[2-(pyridin-2-yloxy)-ethylamino]-phenyl}-acetamide |
| 91 | N-{4-[(4,6-Dimethyl-pyridin-2-ylmethyl)-amino]-phenyl}-2-oxo-2-(2-phenyl-indolizin-3-yl)-acetamide |

| Example | Compound |
|---|---|
| 92 | 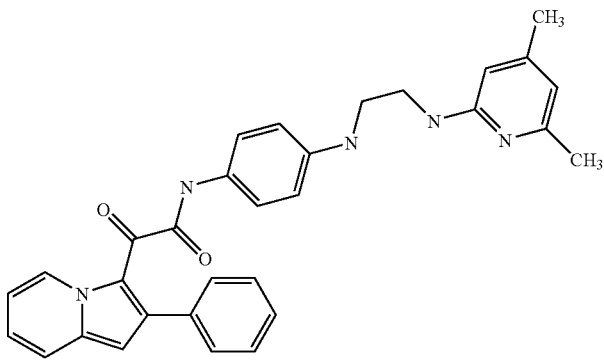<br>N-{4-[2-(4,6-dimethyl-pyridin-2-yl-amino)-ethyl amino]-phenyl}-2-oxo-2-(2-phenyl-indolizin-3-yl)-acetamide |
| Example number | NMR Data | Molecular ion |
|---|---|---|
| 1 | $^1$H (400 MHz, DMSO-d$_6$) 10.29 (s, 1H), 9.83 (d, 1H); 7.82 (d, 1H), 7.46 (t, 1H), 7.42-7.36 (m, 2H), 7.24-7.14 (m, 4H), 7.05 (d, 2H), 6.86 (d, 2H), 6.74 (s, 1H), 3.69 (s, 4H), 3.11 (s, 4H) | 474 (M + H) |
| 2 | $^1$H (400 MHz, CDCl$_3$) 9.7 (d, 1H), 8.1 (s, 1H), 7.6 (d, 1H), 7.5 (d, 2H), 7.2-7.4 (m, 4H), 7.1 (d, 2H), 7.0 (t, 1H), 6.8 (d, 2H), 6.6 (s, 1H), 3.9 (s, 3H), 3.35 (t, 2H), 3.3 (t, 2H), 2.7 (t, 2H), 2.5 (t, 2H). | 467 (M + H) |
| 3 | $^1$H (400 MHz, CDCl$_3$): δ 9.7 (d, 1H), 8.1 (s, 1H), 7.58 (d, 1H), 7.45 (m, 2H), 7.3 (m, 4H), 7.1 (d, 2H), 7.0 (t, 1H), 6.8 (m, 2H), 6.7 (s, 1H), 4.8 (s, 2H), 3.2 (t, 4H), 2.4 (t, 4H). | 436 (M + H) |

-continued
| Example number | NMR Data | Molecular ion |
|---|---|---|
| 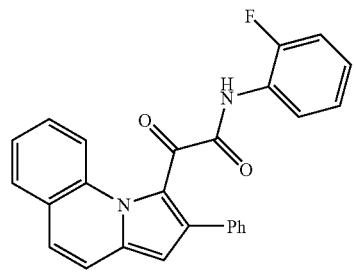<br>4 | ¹H (300 MHz, CDCl₃): δ 9.1 (s, 1H), 7.82-7.73 (m, 3H), 7.56-7.31 (9H, m), 7.11-7.00 (3H, m), 6.73 (s, 1H) | 409 (M + H) |
| 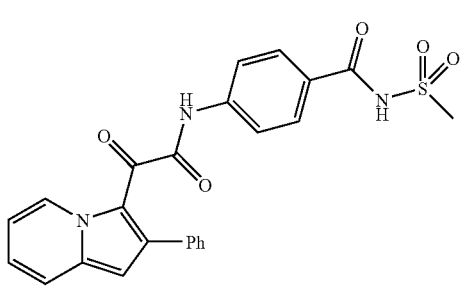<br>5 | ¹H (400MHz, DMSO-d₆) 12.0 (br.s, 1H), 10.86 (s, 1H), 9.85 (d, 1H), 7.84 (d, 1H), 7.77 (d, 2H), 7.47 (t, 1H), 7.37-7.34 (m, 2H), 7.30 (d, 2H), 7.24 (t, 1H), 7.25-7.06 (m, 3H), 6.76 (s, 1H), ~3.3 (s, 3H, obscured by solvent) | 462 (M + H) |
| 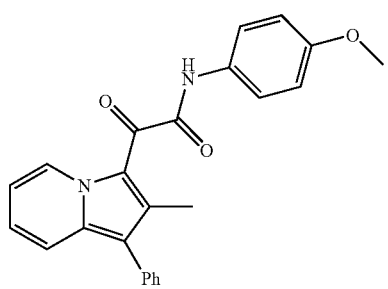<br>6 | ¹H (400 MHz, CDCl₃): δ 9.78 (d, 1H), 8.38 (s, 1H), 7.62 (d, 2H), 7.33-7.46 (m, 3H), 7.42-7.37 (m, 3H), 7.25-7.22 (m, 1H), 6.96-6.91 (m, 3H), 3.83 (s, 3H), 2.50 (s, 3H) | 385 (M + H) |
| 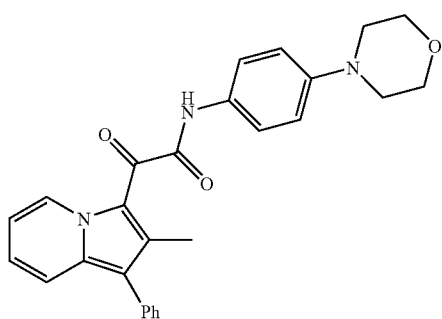<br>7 | ¹H (400 MHz, CDCl₃): δ 9.76 (d, 1H), 8.52 (s, 1H), 7.61 (d, 2H), 7.50-7.45 (m, 3H), 7.40-7.36 (m, 3H), 7.23-7.18 (m, 1H), 6.94-6.87 (m, 3H), 3.88-3.85 (m, 4H), 3.15-3.13 (m, 4H), 2.49 (s, 3H). | 440 (M + H) |

-continued
| Example number | | NMR Data | Molecular ion |
|---|---|---|---|
| 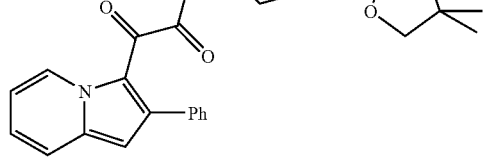<br>8 | | $^1$H (400 MHz, CDCl$_3$): δ 9.72 (d, 1H), 8.32 (s, 1H), 7.59 (d, 1H), 7.46-7.42 (m, 2H), 7.35-7.28 (m, 4H), 7.18-7.11 (m, 4H), 6.99 (td, 1H), 6.65 (s, 1H), 3.97 (s, 2H), 3.31 (s, 3H), 1.31 (s, 6H) | 467 (M + H) |
| 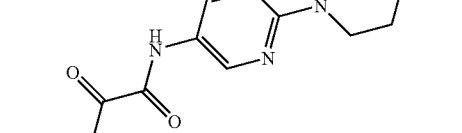<br>9 | | $^1$H (400 MHz, CDCl$_3$): δ 9.93 (d, 1H), 7.75 (d, 1H), 7.46-7.41 (m, 3H), 7.24-7.12 (m, 4H), 7.02-6.92 (m, 2H), 6.76-6.64 (t, 2H), 3.46 (s, 2H), 1.38-1.25 (broad s, 2H) | 396 (M + H) |
| 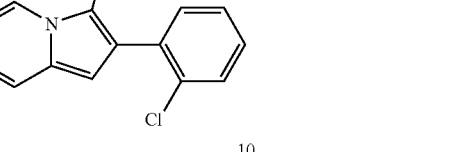<br>10 | | $^1$H (400 MHz, CDCl$_3$): δ 9.74 (d, 1H), 8.05 (br.s, 1H), 7.9 (d, 1H), 7.6 (d, 1H), 7.4-7.5 (m, 2H), 7.28-7.38 (m, 2H), 7.20-7.23 (m, 2H), 7.0 (t, 1H), 6.6 (s, 1H), 6.5 (d, 1H), 3.48 (t, 4H), 2.6 (t, 4H), 2.3 (m, 1H), 1.5 (q, 4H), 0.9 (t, 6H). | 530 (M + H) |
| 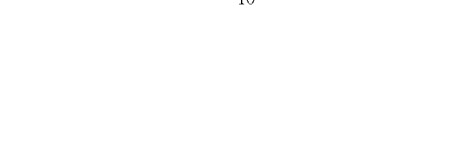<br>11 | | $^1$H (400 MHz, CDCl$_3$): δ 10.84 (s, 1H), 9.74 (d, 1H), 8.36 (br.s, 1H), 7.73 (d, 1H), 7.60 (d, 1H), 7.43-7.40 (m, 2H), 7.35-7.28 (m, 4H), 7.02 (t, 1H), 6.87 (s, 1H), 6.79 (d, 1H), 6.66 (s, 1H), 5.26-5.18 (m, 1H), 4.02-3.96 (m, 2H), 3.68-3.60 (m, 2H), 2.09-2.02 (m, 2H), 1.90-1.80 (m, 2H) | 485 (M + H) |

| Example number | NMR Data | Molecular ion |
|---|---|---|
| 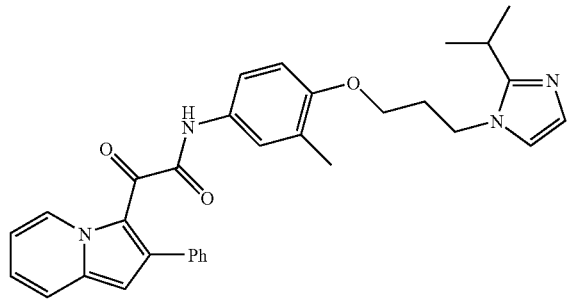<br>12 | ¹H (400 MHz, CDCl₃): δ 9.8 (d, 1H), 8.1 (br.s, 1H), 7.6-7.7 (m, 1H), 7.4-7.45 (m, 2H), 7.28-7.38 (m, 3H), 6.97 (m, 4H), 6.79 (s, 2H), 6.64 (m, 2H), 4.1 (d, 2H), 3.9 (d, 2H), 3.0 (m, 1H), 2.2 (m, 2H), 2.1 (s, 3H), 1.25 (d, 6H). | 521 (M + H) |
| 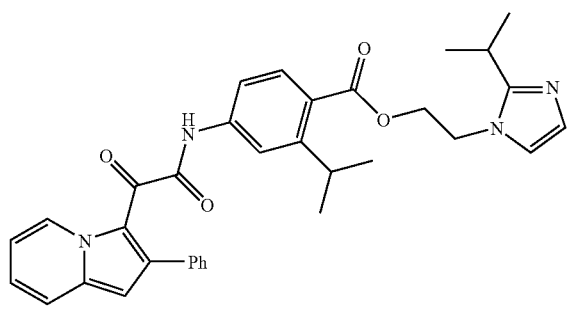<br>13 | ¹H (400 MHz, CDCl₃): δ 9.8 (d, 1H), 8.4 (s, 1H), 7.6 (m, 2H), 7.4 (m, 2H), 7.2-7.3 (m, 5H), 7.1 (dd, 1H), 7.0 (m, 2H), 6.9 (s, 1H), 6.6 (s, 1H), 4.5 (t, 2H), 4.2 (t, 2H), 3.8 (m, 1H), 3.0 (m, 1H), 1.3 (d, 6H), 1.2 (d, 6H). | 563 (M + H) |
| 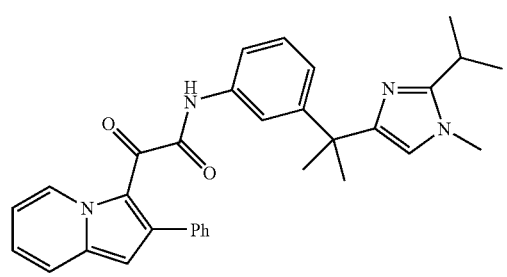<br>14 | ¹H (400 MHz, CDCl₃): δ 9.7 (d, 1H), 8.2 (s, 1H), 7.6 (d, 1H), 7.45 (m, 2H), 7.3 (m, 4H), 7.11 (m, 4H), 7.0- (t, 1H), 6.7 (s, 1H), 6.35 (s, 1H), 3.6 (s, 3H), 3.0 (m, 1H), 1.6 (s, 6H), 1.3 (d, 6H). | 505 (M + H) |
| 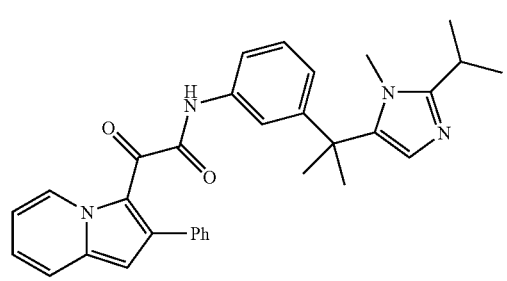<br>15 | ¹H (400 MHz, CDCl₃): δ 9.7 (s, 1H), 8.2 (s, 1H), 7.60 (d, 1H), 7.45 (m, 2H), 7.22-7.30 (m, 4H), 7.1-7.18 (m, 2H), 7.0 (m, 2H), 6.93 (m, 1H), 6.9 (d, 1H), 6.65 (s, 1H), 3.05 (s, 3H), 2.9 (m, 1H), 1.6 (s, 6H), 1.25 (d, 6H). | 505 (M + H) |

| Example number | NMR Data | Molecular ion |
|---|---|---|
| 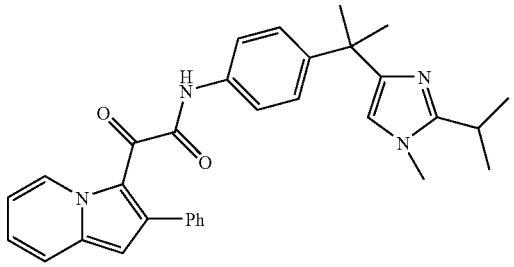 16 | ¹H (400 MHz, CDCl₃): δ 9.7 (d, 1H), 8.2 (s, 1H), 7.6 (d, 1H), 7.43-7.44 (d, 3H), 7.28-7.31 (m, 4H), 7.22 (s, 1H), 7.0 (d, 2H), 6.9 (t, 1H), 6.64 (s, 1H), 6.29 (s, 1H), 3.5 (s, 3H), 3.0 (m, 1H), 1.6 (s, 6H), 1.3 (d, 6H). | 505 (M + H) |
| 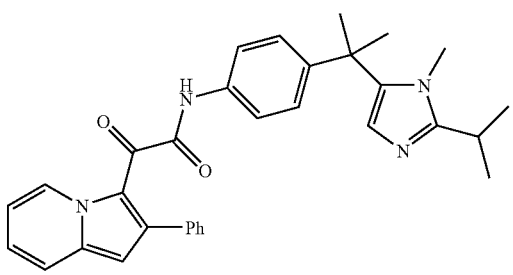 17 | ¹H (400 MHz, CDCl₃): δ 9.75 (d,1H), 8.25 (br.s, 1H), 7.60 (d, 1H), 7.40-7.48 (d, 2H), 7.28-7.36 (m, 4H), 7.06-7.12 (m, 4H), 7.10 (t, 1H), 6.96 (s, 1H), 6.66 (s, 1H), 2.98 (s, 3H), 2.88-2.92 (m, 1H), 1.75 (s, 6H), 1.35 (d, 6H) | 503 (M − H) |
| 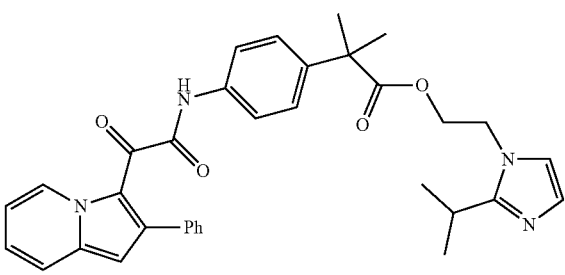 18 | ¹H (400 MHz, CDCl₃): δ 9.78 (d, 1H), 8.43 (br.s, 1H), 7.6-7.7 (d, 1H), 7.4-7.5 (m, 2H), 7.28-7.38 (m, 4H), 7.1-7.2 (m, 4H), 7.0 (t, 1H), 6.9 (s, 1H), 6.64 (s, 1H), 6.58 (s, 1H), 4.2 (t, 2H), 4.0 (t, 2H), 2.9 (q, 1H), 1.5 (s, 6H), 1.2 (d, 6H). | 563 (M + H) |
| 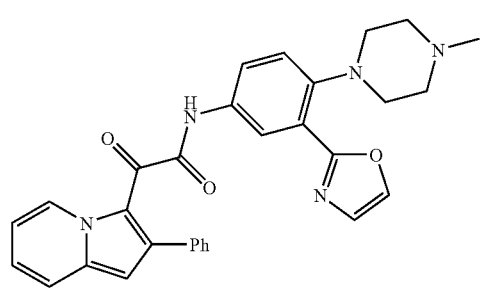 19 | ¹H (400 MHz, CDCl₃): δ 9.75 (d, 1H), 8.25 (s, 1H), 7.74 (s, 1H), 7.6 (m, 2H), 7.42 (d, 2H), 7.26-7.35 (m, 6H), 6.95 (m, 2H), 6.6 (s, 1H), 3.0 (s, 4H), 2.7 (s, 4H), 2.42 (s, 3H). | 506 (M + H) |

-continued
| Example number | NMR Data | Molecular ion |
|---|---|---|
| 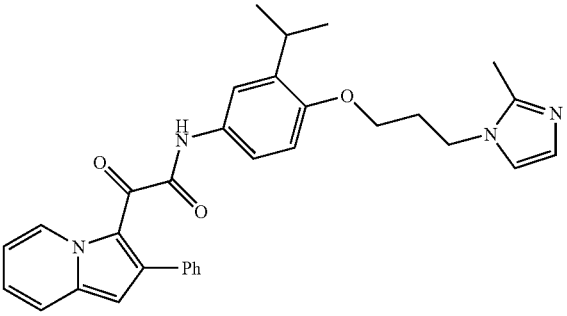<br>20 | ¹H (400 MHz, CDCl₃): δ 9.74 (d, 1H), 8.19 (s, 1H), 7.59 (d, 2H), 7.48 (d, 2H), 7.3 (m, 4H), 6.98 (d, 2H), 6.91 (br.s, 1H), 6.81 (s, 1H), 6.62 (s, 2H), 4.08-4.1 (t, 2H), 3.88-3.89 (t, 2H), 3.28 (m, 1H), 2.37 (s, 3H), 2.19 (t, 2H), 1.2 (d, 6H). | 521 (M + H) |
| 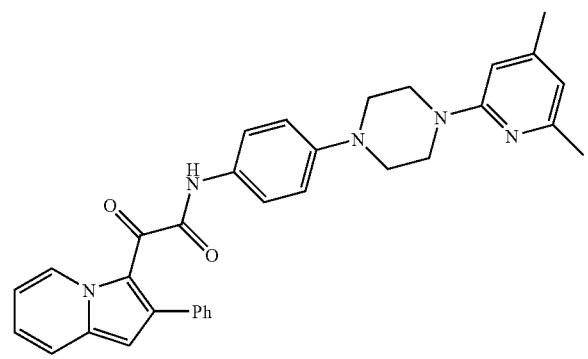<br>21 | ¹H (400 MHz, CDCl₃): δ 9.7 (d, 1H), 8.15 (s, 1H), 7.59 (d, 1H), 7.43 (m, 2H), 7.32-7.24 (m, 4H), 7.1 (d, 2H), 6.94 (t, 1H), 6.83 (d, 2H), 6.62 (s, 1H), 6.4 (s, 1H), 6.31-6.33 (br.s, 1H), 3.68 (s, 4H), 3.24 (s, 4H), 2.39 (s, 3H), 2.24 (s, 3H). | 530 (M + H) |
| 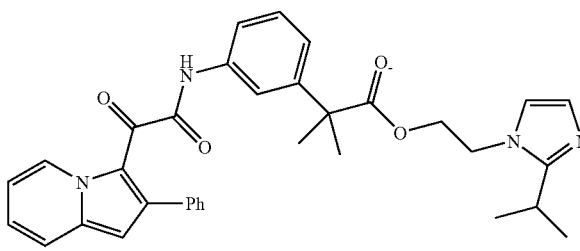<br>22 | ¹H (CDCl₃, 400 MHz) δ 9.79 (1H, s), 8.43 (1H, s), 7.60 (1H, m), 7.46 (2H, m), 7.32-7.24 (5H, m), 7.19 (2H, m), 7.06 (1H, m), 7.02-6.90 (3H, m), 6.20 (1H, m), 4.30 (2H, m), 4.05 (2H, m), 2.95 (1H, m), 1.50 (6H, s), 1.20 (6H, d). | 563 (M + H) |
| 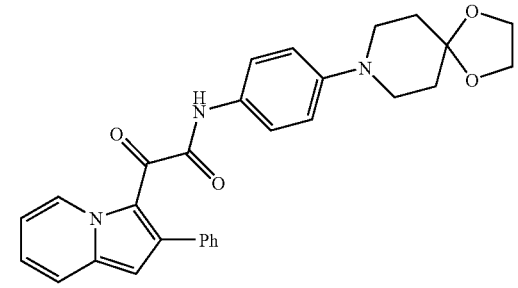<br>23 | ¹H (CDCl₃, 400 MHz) 9.7 (1H, d), 8.1 (1H, s), 7.6 (1H, d), 7.5 (2H, m), 7.4 (4H, m), 7.1 (2H, m), 7.0 (1H, t), 6.8 (2H, m), 6.6 (1H, s), 4.0 (4H, s), 3.3 (4H, m), 1.8 (4H, m). | 480 (M − H) |

-continued
| Example number | NMR Data | Molecular ion |
|---|---|---|
| 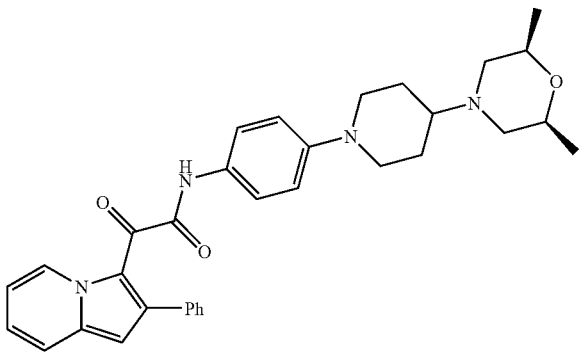<br>24 | ¹H (400 MHz, CDCl₃) 9.7 (d, 1H), 8.2 (s, 1H), 7.58 (d, 1H), 7.45 (m, 2H), 7.3 (m, 4H), 7.08 (d, 2H), 6.98 (t, 1H), 6.8 (d, 2H), 6.6 (s, 1H), 3.7 (m, 4H), 2.8 (d, 2H), 2.6 (t, 2H), 2.3 (m, 1H), 1.9 (m, 4H), 1.6 (m, 2H), 1.2 (d, 6H). | 537 (M + H) |
| 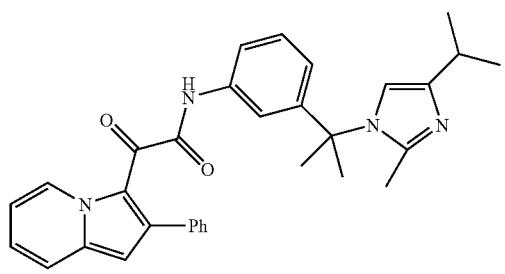<br>25 | ¹H (400 MHz, CDCl₃): δ 9.72 (d, 1H), 8.2 (s, 1H), 7.58 (d, 1H), 7.50-7.42 (m, 2H), 7.35-7.25 (m, 4H), 7.20-7.15 (t, 1H), 7.10 (d, 1H), 7.05 (s, 1H), 7.00 (t, 1H), 6.85 (s, 1H), 6.70 (d, 1H), 6.65 (s, 1H), 3.85 (m, 1H), 1.85 (s, 3H), 1.75 (s, 6H), 1.30 (d, 6H) | 505 (M + H) |
| 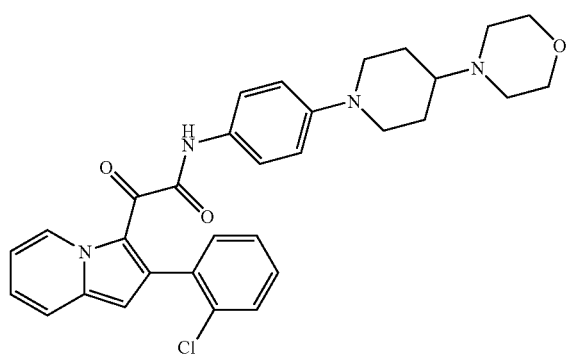<br>26 | ¹H (400 MHz, CDCl₃): δ 9.78 (d, 1H), 8.0 (s, 1H), 7.6 (d, 1H), 7.4 (d, 1H), 7.3 (d, 2H), 7.2 (m, 2H), 7.05 (d, 2H), 7.15 (t, 1H), 6.8 (d, 2H), 6.6 (s, 1H), 4.3 (d, 2H), 4.2 (m, 4H), 3.7 (t, 1H), 3.4 (m, 4H), 3.3 (t, 2H), 1.9 (d, 2H), 1.6 (m, 2H) | 543 (M + H) |
| 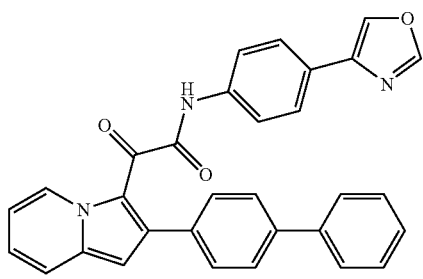<br>85 | ¹H (400 MHz, CDCl₃): δ 9.77 (d, 1H), 8.28 (s, 1H), 7.93-7.92 (m, 1H), 7.82 (s, 1H), 7.63-7.56 (m, 3H), 7.54-7.42 (m, 6H), 7.39-7.27 (m, 6H), 7.03 (d, 1H), 6.70 (s, 1H) | 484 (M + H) |

-continued
| Example number | | NMR Data | Molecular ion |
|---|---|---|---|
| 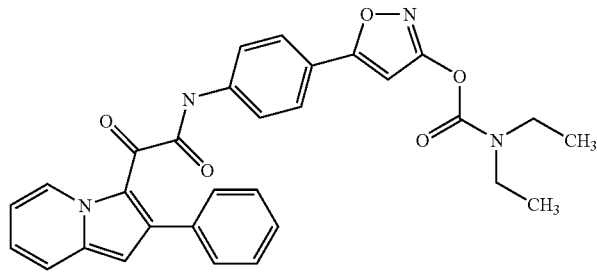<br>27 | | $^1$H (400 MHz, CDCl$_3$): δ 9.78 (d, 1H), 8.39 (broad s, 1H), 7.6-7.7 (m, 3H), 7.40-7.45 (m, 2H), 7.28-7.38 (m, 6H), 7.0 (t, 1H), 6.7 (s, 2H), 3.4 (q, 4H), 1.2 (m, 6H) | 523 (M + H) |
| 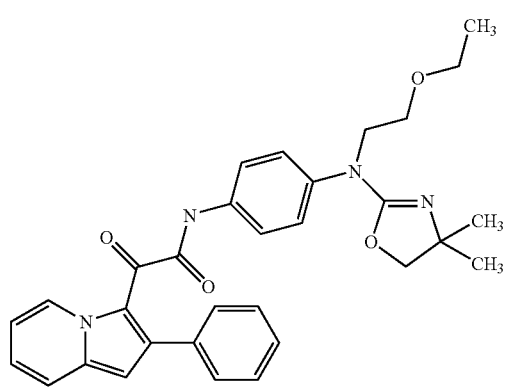<br>28 | | $^1$H (400 MlHz, CDCl$_3$): δ 9.70 (d, 1H), 8.20 (s, 1H), 7.58-7.54 (d, 1H), 7.46-7.43 (m, 2H), 7.32-7.24 (m, 4H), 7.12-7.08 (m, 2H), 7.02-6.94 (m, 3H), 6.63 (s, 1H), 4.00 (s, 2H), 3.67 (t, 2H), 3.54 (q, 2H), 3.40 (t, 2H), 1.30 (s, 6H), 1.20 (t, 3H) | 525 (M + H) |
| 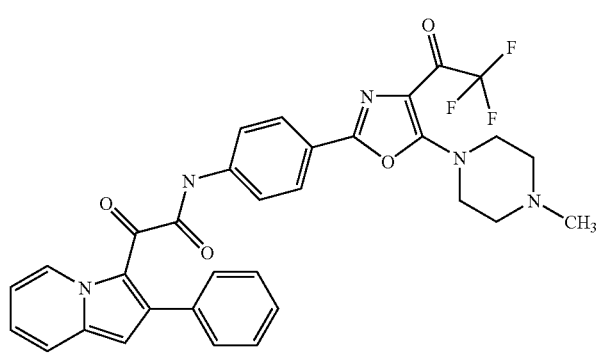<br>29 | | $^1$H (400 MHz, CDCl$_3$): δ 9.70 (d, 1H), 8.40 (broad s, 1H), 7.80 (m, 2H), 7.60 (m, 1H), 7.40-7.45 (m, 2H), 7.28-7.38 (m, 6H), 6.97 (m, 1H), 6.69 (s, 1H), 4.00 (b, 4H), 2.70 (b, 4H), 2.40 (s, 3H) | 602 (M + H) |
| 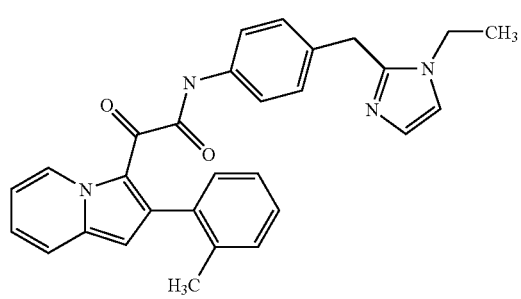<br>25 | | $^1$H (400 MHz, CDCl$_3$): δ 9.80 (d, 1H), 7.97 (s, 1H) 7.55 (d, 1H), 7.32 (t, 1H), 7.15 (m, 3H), 7.08 (t, 7H), 6.90 (s, 1H), 6.35 (s, 1H), 4.15 (s, 2H), 3.70 (q, 2H), 2.35 (s, 3H), 1.2 (t, 3H) | 462 (M + H) |

-continued
| Example number | NMR Data | Molecular ion |
|---|---|---|
| 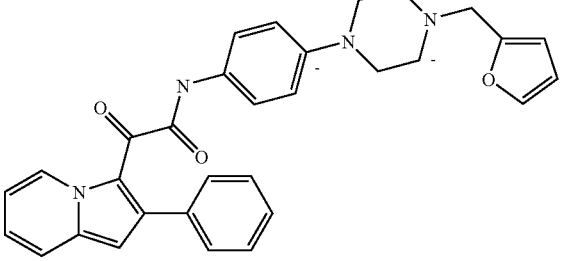 31 | $^1$H (400 MHz, CDCl$_3$): δ 9.74 (d, 1H), 8.05 (s, 1H), 7.60 (d, 1H), 7.40-7.50 (m, 3H), 7.20-7.23 (m, 4H) 7.10 (d, 2H), 7.00 (t, 1H), 6.80 (d, 2H), 6.60 (s, 1H), 6.40 (d, 2H), 3.70 (s, 2H), 3.20 (s, 4H), 2.70 (s, 4H) | 505 (M + H) |
| 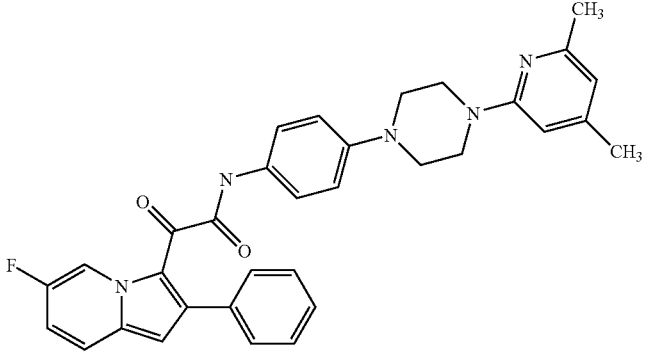 32 | $^1$H (400 MHz, CDCl$_3$): δ 10.30 (s, 1H), 9.83 (s, 1H), 7.95 (d, 1H), 7.60 (t, 1H), 7.40 (dd, 2H), 7.20 (d, 3H), 7.05 (d, 2H), 6.85 (d, 3H), 6.55 (s, 2H), 3.60 (t, 4H), 3.15 (t, 4H), 2.30 (s, 3H), 2.20 (s, 3H) | 548 (M + H) |
| 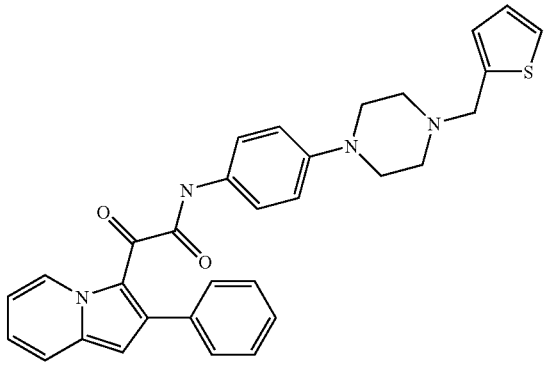 33 | $^1$H (400 MHz, CDCl$_3$): δ 9.75 (d, 1H), 8.15 (s, 1H), 7.58 (d, 1H), 7.50-7.40 (m, 2H), 7.36-7.28 (m, 5H), 7.14-7.08 (d, 2H), 7.04-6.98 (m, 3H), 6.82-6.78 (d, 2H), 6.65 (s, 1H), 3.90-3.82 (m, 2H), 3.40-3.20 (m, 4H), 3.00-2.60 (broad, 4H) | 521 (M + H) |
| 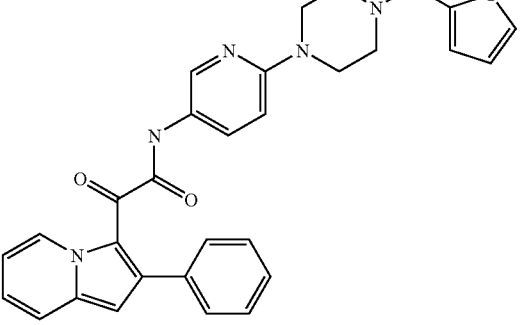 34 | $^1$H (400 MHz, CDCl$_3$): δ 9.74 (d, 1H), 8.05 (d, 2H), 7.60 (d, 1H), 7.40-7.50 (m, 4H), 7.28-7.38 (m, 4H), 7.00 (t, 1H), 6.65 (s, 1H), 6.50 (m, 1H), 6.35 (d, 2H), 3.65 (s, 2H), 3.55 (s, 4H), 2.6 (s, 4H). | 506 (M + H) |

-continued
| Example number | | NMR Data | Molecular ion |
|---|---|---|---|
| 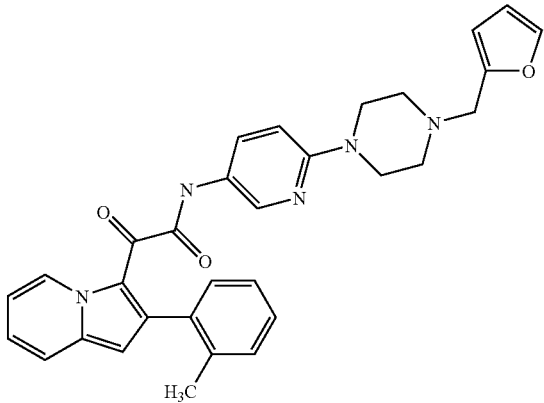<br>35 | | $^1$H (400 MHz, CDCl$_3$): δ 9.80 (d, 1H), 7.90 (d, 1H), 7.70 (d, 1H), 7.60 (d, 1H), 7.40-7.50 (m, 1H), 7.28-7.34 (m, 1H), 7.18-7.22 (m, 3H), 7.10 (m, 1H), 7.00-7.10 (m, 2H), 6.60 (s, 1H), 6.50 (d, 1H), 6.30 (s, 2H), 3.80 (s, 2H), 3.40 (s, 4H), 2.60 (s, 4H), 2.30 (s, 3H) | 520 (M + H) |
| 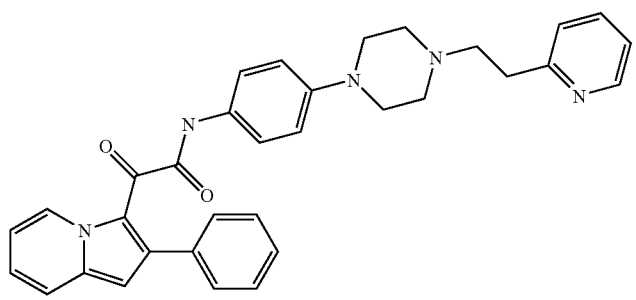<br>36 | | $^1$H (400 MHz, CDCl$_3$): δ 9.74 (d, 1H), 8.60 (s, 1H), 8.17 (broad s, 1H), 7.60 (d, 2H), 7.40-7.45 (m, 2H), 7.28-7.38 (m, 4H), 7.10-7.20 (m, 4H), 7.00 (t, 1H), 6.80 (d, 2H), 6.60 (s, 1H), 2.70-3.40 (m, 12H) | 531 (M + H) |
| 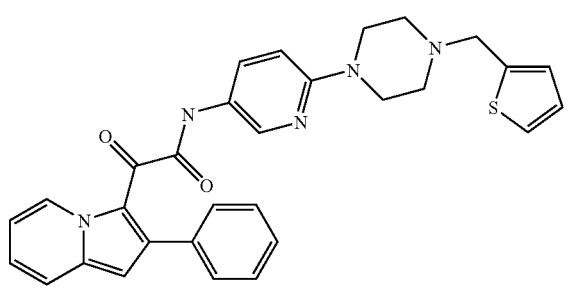<br>37 | | $^1$H (400 MHz, CDCl$_3$): δ 9.72 (d, 1H), 8.07 (s, 1H), 7.95 (s, 1H), 7.58 (d, 1H), 7.47-7.39 (m, 4H), 7.31-7.26 (s, 4H), 7.00- 6.98 (m, 3H), 6.63 (s, 1H), 6.49 (d, 1H), 3.80 (s, 2H), 3.53 (s, 4H), 2.62 (s, 4H) | 522 (M + H) |
| 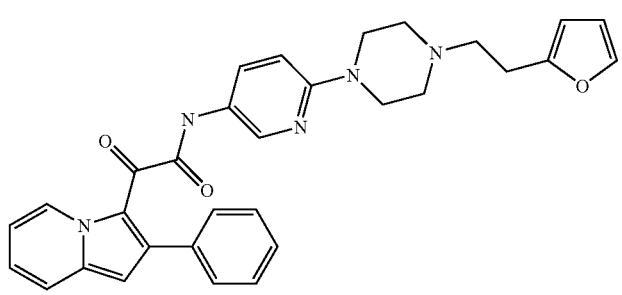<br>38 | | $^1$H (400 MHz, CDCl$_3$): δ 9.75 (d, 1H), 8.13 (s, 1H), 7.99 (s, 1H), 7.61 (d, 1H), 7.48-7.43 (m, 3H), 7.36-7.31 (m, 4H), 7.18 (d, 1H), 7.05 (t, 1H), 6.55 (s, 1H), 6.58-6.54 (d, 1H), 6.31 (s, 1H), 6.17 (s, 1H), 4.2 (broad s, 2H), 3.5 (broad s, 4H), 3.34 (t, 2H), 3.19 (t, 2H), 2.9 (broad s) | 518 (M − H) |

| Example number | NMR Data | Molecular ion |
|---|---|---|
| 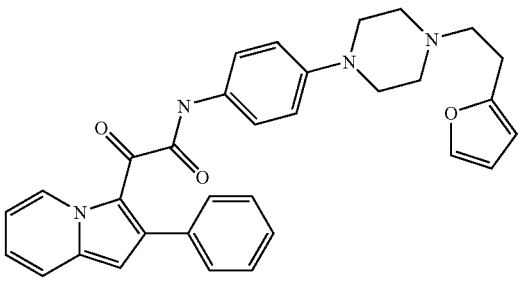<br>39 | ¹H (400 MHz, CDCl₃): δ 9.75 (d, 1H), 8.15 (s, 1H), 7.58-7.56 (d, 1H), 7.48-7.42 (m, 2H) 7.38-7.30 (m, 5H), 7.10 (d, 2H), 6.88 (t, 1H), 6.80 (d, 2H), 6.64 (s, 1H), 6.30 (s, 1H), 6.18 (s, 1H), 3.29 (broad s 4H), 2.98-2.60 (m, 8H) | 519 (M + H) |
| 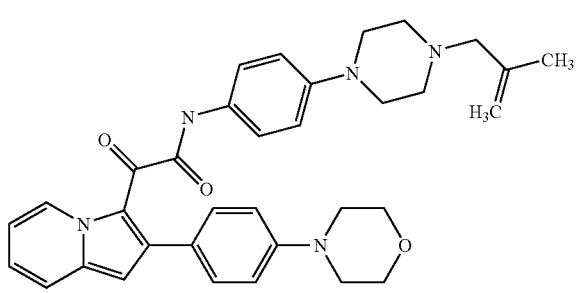<br>40 | ¹H (400 MHz, CDCl₃): δ 9.73 (d, 1H), 8.04 (s, 1H), 7.56-7.54 (d, 1H), 7.34 (d, 2H), 7.22 (m, 1H), 7.14 (d, 2H), 6.96-6.93 (t, 1H), 6.82-6.78 (m, 4H), 6.59 (s, 1H), 4.96 (s, 2H), 3.83 (m, 4H), 3.20 (m, 4H), 3.09-3.07 (m, 4H), 2.90 (s, 2H), 2.58 (m, 4H), 1.83 (s, 3H) | 564 (M + H) |
| 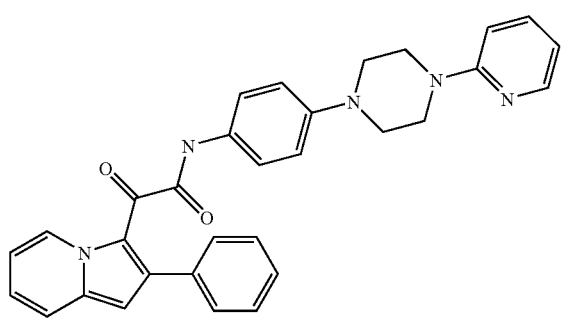<br>41 | ¹H (400 MHz, CDCl₃): δ 9.72 (d, 1H), 8.30 (d, 1H), 8.18 (s, 1H), 7.61 (d, 2H), 7.47 (d, 2H), 7.30 (m, 4H), 7.12 (d, 2H), 7.00 (t, 1H), 6.90 (d, 2H), 6.70-6.80 (m, 2H), 6.60 (s, 1H), 3.80 (s, 4H) 3.30 (s, 4H) | 502 (M + H) |
| 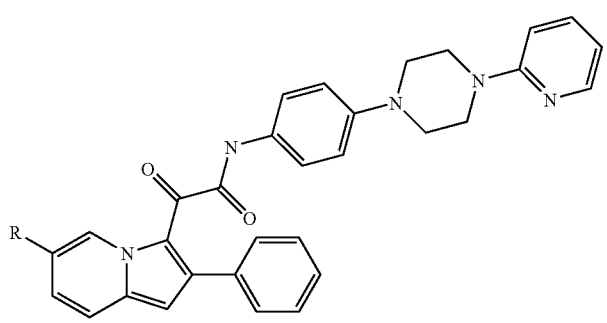<br>42 | ¹H (400 MHz, CDCl₃): δ 9.72 (d, 1H), 8.22 (d, 1H), 8.17 (s, 1H), 7.55 (d, 2H), 7.43 (d, 2H), 7.31 (d, 3H), 7.22 (t, 1H), 7.11 (d, 2H), 6.85 (d, 2H), 6.71 (d, 2H), 6.68 (s, 1H), 3.71 (s, 4H), 3.24-3.25 (s, 4H) | 520 (M + H) |

| Example number | NMR Data | Molecular ion |
|---|---|---|
| 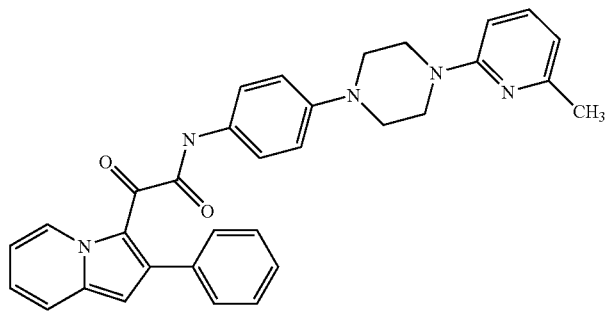<br>43 | $^1$H (400 MHz, CDCl$_3$): δ 9.75 (d, 1H), 8.18 (s, 1H), 7.58 (d, 1H), 7.48-7.36 (m, 3H), 7.34-7.28 (m, 3H), 7.13 (d, 2H), 6.98 (t, 1H), 6.86 (d, 2H), 6.68 (s, 1H), 6.54 (broad s, 3H), 3.68 (broad s, 4H), 3.25 (broad s, 4H), 2.45 (broad s, 3H) | 516 (M + H) |
| 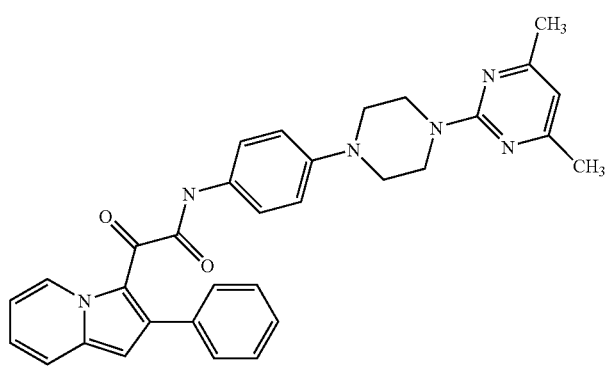<br>44 | $^1$H (400 MHz, CDCl$_3$): δ 9.72 (d, 1H), 8.14 (s, 1H), 7.58 (d, 1H), 7.46-7.43 (m, 2H), 7.30-7.23 (m, 4H), 7.12 (m, 2H), 6.98 (t, 1H), 6.85 (s, 2H), 6.64 (s, 1H), 6.31 (s, 1H), 3.99 (broad s, 4H), 3.19 (s, 4H), 2.31 (s, 3H), 1.53 (s, 3H) | 531 (M + H) |
| 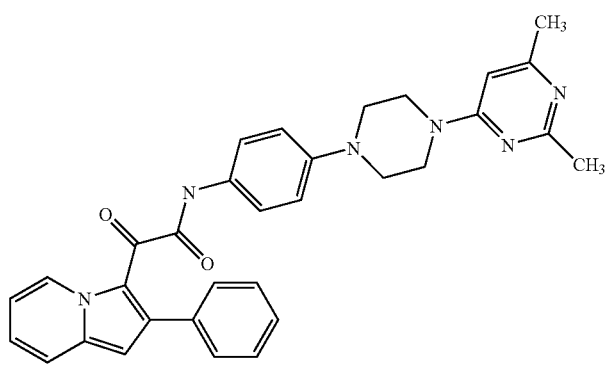<br>45 | $^1$H (400 MHz, CDCl$_3$): δ 9.74 (d, 1H), 8.17 (s, 1H), 7.58 (d, 1H), 7.46 (m, 2H), 7.36-7.28 (s, 4H), 7.13 (d, 2H), 6.99 (t, 1H), 6.84 (d, 2H), 6.64 (s, 1H), 6.24 (s, 1H), 3.82 (s, 4H), 3.20 (s, 4H), 2.45 (s, 3H), 2.35 (s, 3H) | 531 (M + H) |
| 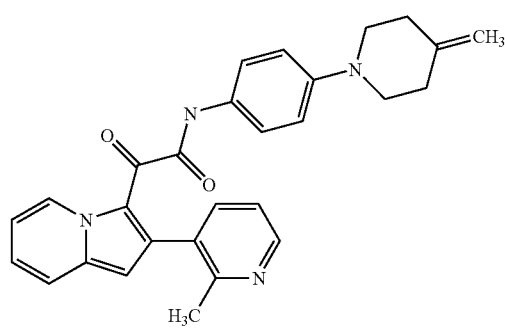<br>46 | $^1$H (400 MHz, CDCl$_3$): δ 9.78 (d, 1H), 8.42 (d, 1H), 8.00 (s, 1H), 7.60 (d, 1H), 7.46 (d, 1H), 7.32 (t, 1H), 7.06-6.98 (m, 4H), 6.92 (d, 2H), 6.58 (s, 1H), 4.78 (s, 2H), 3.22 (m, 4H), 2.48 (s, 3H), 2.35 (m, 4H) | 451 (M + H) |

-continued
| Example number | NMR Data | Molecular ion |
|---|---|---|
| 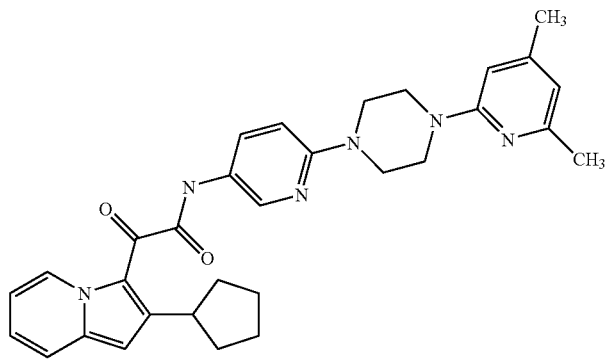 47 | $^1$H (400 MHz, CDCl$_3$): δ 9.64 (d, 1H), 8.34 (broad s, 1H), 7.58 (d, 2H), 7.44 (d, 1H), 7.20 (t, 1H), 7.00 (d, 2H), 6.85 (t, 1H), 6.48 (s, 1H), 6.40 (s, 1H), 6.32 (s, 1H), 3.70 (m, 4H), 3.30 (m, 4H), 2.40 (s, 3H), 2.25 (s, 3H), 2.10 (m, 1H), 1.80-1.55 (m, 8H) | 522 (M + H) |
| 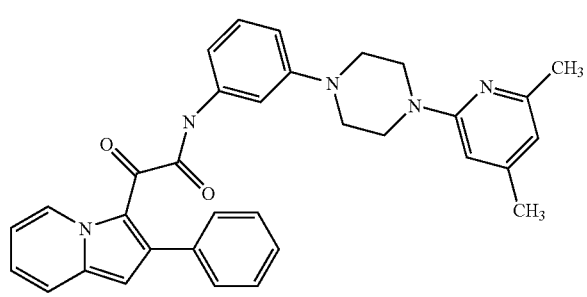 48 | $^1$H (400 MHz, CDCl$_3$): δ 9.78 (d, 1H), 8.22 (broad s, 1H), 7.58 (d, 1H), 7.46 (d, 2H), 7.38-7.28 (m, 4H), 7.14 (t, 1H), 6.98 (t, 1H), 6.89 (s, 1H), 6.72-6.60 (m, 3H), 6.54-6.2 (m, 2H), 3.64 (broad s, 4H), 3.24 (s, 4H), 2.42 (s, 3H), 2.26 (s, 3H) | 530 (M + H) |
| 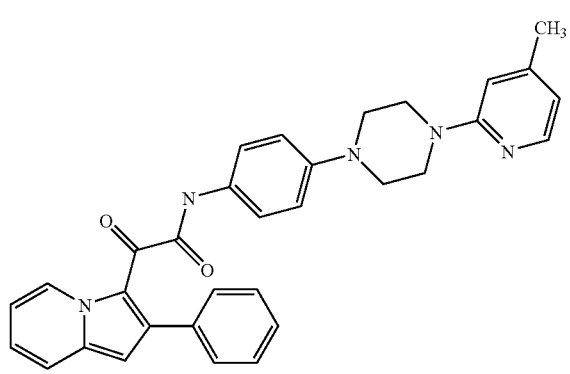 49 | $^1$H (400 MHz, CDCl$_3$): δ 9.70 (d, 1H), 8.18 (s, 1H), 8.14 (d, 1H), 7.58 (d, 1H), 7.46 (d, 2H), 7.28 (d, 4H), 7.11 (d, 2H), 6.98 (t, 1H), 6.85 (d, 2H), 6.64 (broad, 1H), 6.52 (d, 2H), 3.70 (s, 4H), 3.25 (s, 4H), 2.35 (s, 3H) | 516 (M + H) |
| 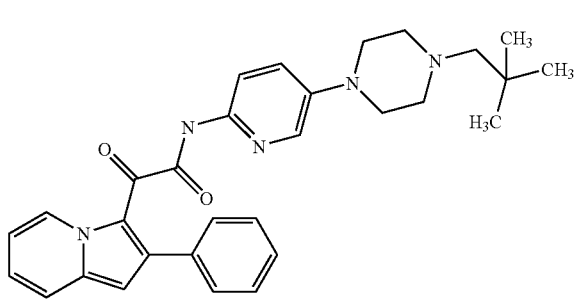 50 | $^1$H (400 MHz, CDCl$_3$): δ 9.78 (d, 1H), 8.83 (s, 1H), 7.91 (s, 1H), 7.57 (d, 1H), 7.43-7.38 (m, 3H), 7.30-7.18 (m, 4H), 7.09 (dd, 1H), 6.98 (t, 1H), 6.62 (s, 1H), 3.10 (t, 4H), 2.66 (t, 4H), 2.15 (s, 2H), 0.89 (s, 9H) | 496 (M + H) |

-continued
| Example number | NMR Data | Molecular ion |
|---|---|---|
| 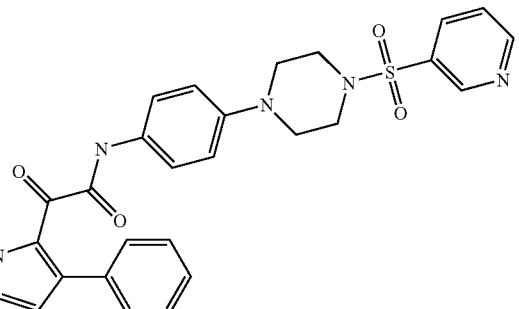 51 | ¹H (400 MHz, CDCl₃): δ 9.72 (d, 1H), 9.02 (s, 1H), 8.84 (d, 1H), 8.17 (s, 1H), 8.07 (d, 1H), 7.57 (d, 1H), 7.51 (t, 1H), 7.49-7.40 (m, 2H), 7.32-7.28 (m, 4H), 7.07 (d, 2H), 6.97 (t, 1H), 6.74 (d, 2H), 6.63 (s, 1H), 3.20 (m, 8H) | 566 (M + H) |
| 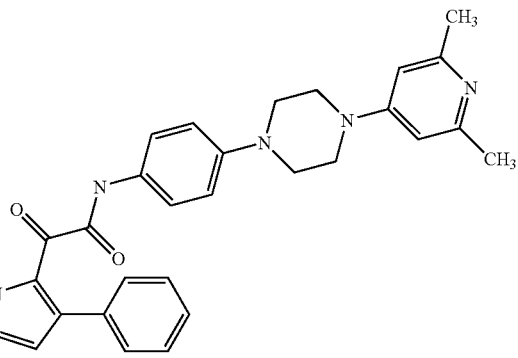 52 | ¹H (400 MHz, CDCl₃): δ 13.25 (brs, 1H), 10.25 (s, 1H), 9.82 (d, 1H), 7.84 (d, 1H), 7.46 (t, 1H), 7.44-7.36 (m, 2H), 7.24-7.14 (m, 4H), 7.10-7.02 (m, 3H), 6.84 (d, 2H), 6.75 (s, 1H), 3.82 (brs, 4H), 3.42 (brs, 4H), 2.43 (s, 6H) | 530 (M + H) |
| 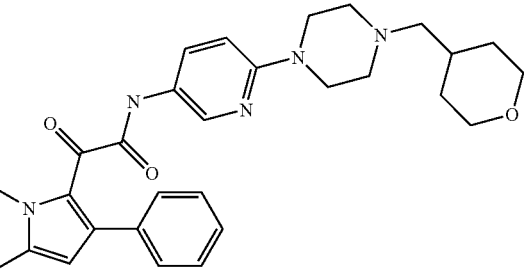 53 | ¹H (400 MHz, CDCl₃): δ 9.70 (d, 1H), 8.15 (s, 1H), 7.56 (dd, 1H), 7.47-7.41 (m, 2H), 7.30 (d, 3H), 7.20 (t, 1H), 7.09 (d, 2H), 6.80 (d, 2H), 6.68 (s, 1H), 3.95 (d, 2H), 3.40 (t, 2H), 3.15 (m, 4H), 2.50 (m, 4H), 2.25 (m, 2H), 1.70 (m, 3H), 1.30 (m, 2H) | 541 (M + H) |
| 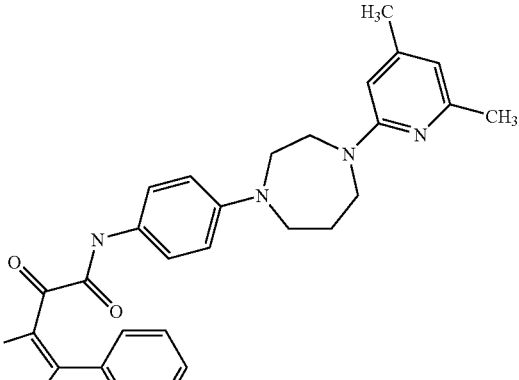 54 | ¹H (400 MHz, CDCl₃): δ 9.78 (d, 1H), 8.10 (s, 1H), 7.58 (d, 1H), 7.45 (m, 2H), 7.36-7.24 (m, 4H), 7.02 (d, 2H), 6.98 (t, 1H), 6.64-6.58 (m, 3H), 6.26 (s, 1H), 6.12 (s, 1H), 3.85 (t, 2H), 3.62 (t, 2H), 3.44 (m, 4H), 2.32 (s, 3H), 2.19 (s, 3H), 2.08 (m, 2H) | 544 (M + H) |

-continued
| Example number | NMR Data | Molecular ion |
|---|---|---|
| 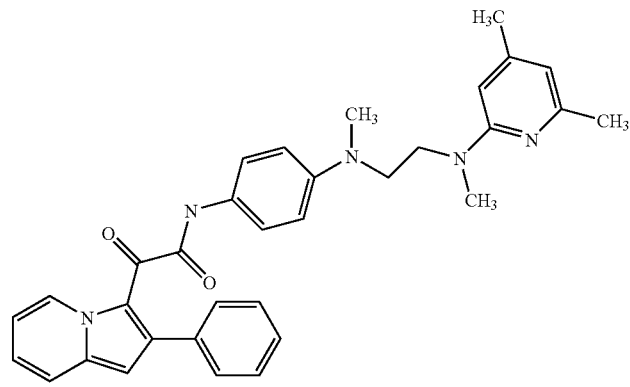<br>55 | ¹H (400 MHz, CDCl₃): δ 9.78 (d, 1H), 8.09 (s, 1H), 7.56 (d, 1H), 7.45 (d, 2H), 7.40-7.28 (m, 4H), 7.04 (d, 2H), 6.98 (t, 1H), 6.73 (d, 2H), 6.64 (d, 1H), 6.29 (s, 1H), 6.05 (s, 1H), 3.71 (t, 2H), 3.45 (t, 2H) 2.99 (s, 3H), 2.93 (s, 3H), 2.40 (s, 3H), 2.20 (s, 3H) | 532 (M + H) |
| 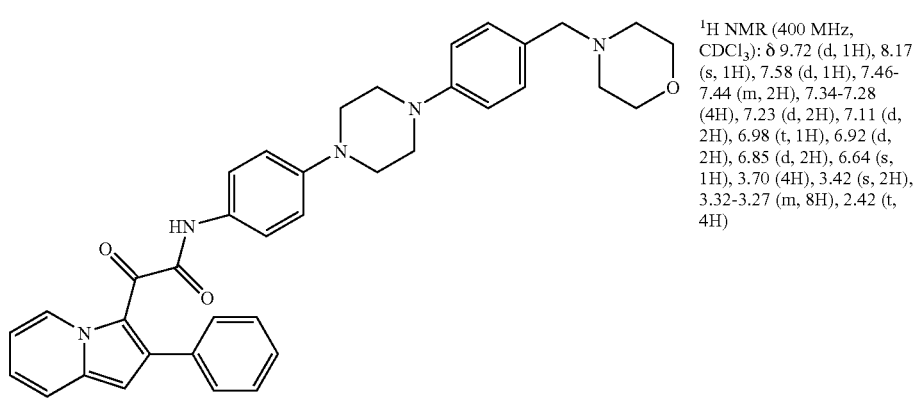<br>56 | ¹H NMR (400 MHz, CDCl₃): δ 9.72 (d, 1H), 8.17 (s, 1H), 7.58 (d, 1H), 7.46-7.44 (m, 2H), 7.34-7.28 (4H), 7.23 (d, 2H), 7.11 (d, 2H), 6.98 (t, 1H), 6.92 (d, 2H), 6.85 (d, 2H), 6.64 (s, 1H), 3.70 (4H), 3.42 (s, 2H), 3.32-3.27 (m, 8H), 2.42 (t, 4H) | 600 (M + H) |
| 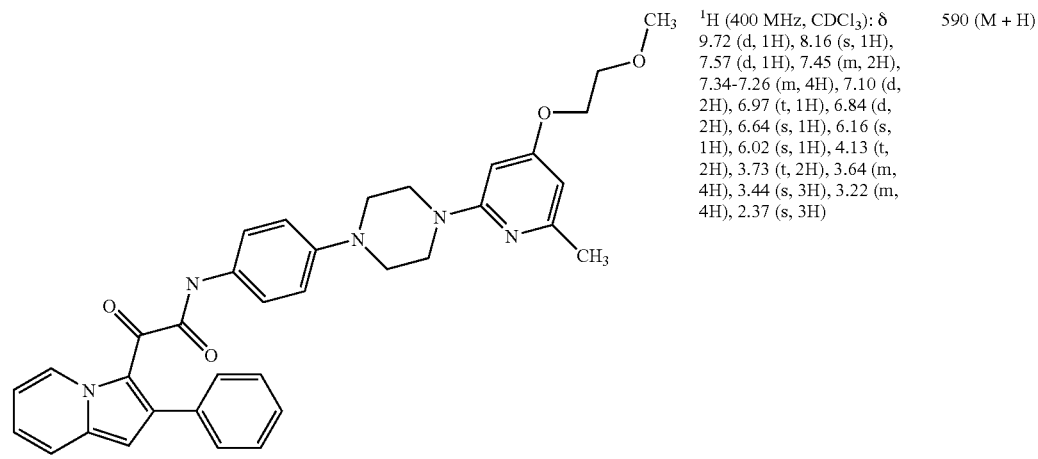<br>57 | ¹H (400 MHz, CDCl₃): δ 9.72 (d, 1H), 8.16 (s, 1H), 7.57 (d, 1H), 7.45 (m, 2H), 7.34-7.26 (m, 4H), 7.10 (d, 2H), 6.97 (t, 1H), 6.84 (d, 2H), 6.64 (s, 1H), 6.16 (s, 1H), 6.02 (s, 1H), 4.13 (t, 2H), 3.73 (t, 2H), 3.64 (m, 4H), 3.44 (s, 3H), 3.22 (m, 4H), 2.37 (s, 3H) | 590 (M + H) |

-continued
| Example number | | NMR Data | Molecular ion |
|---|---|---|---|
| 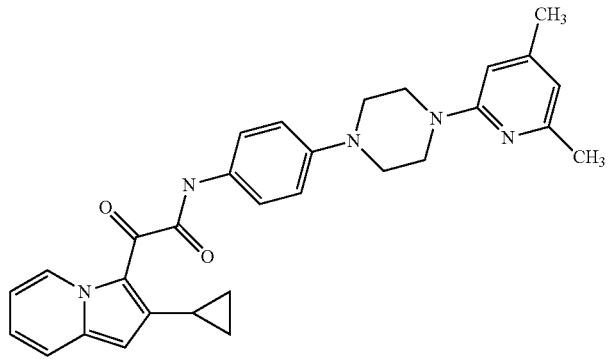
58 | | ¹H (400 MHz, CDCl₃): δ 9.70 (d, 1H), 8.21 (s, 1H), 7.58 (d, 2H), 7.41 (d, 1H), 7.18 (t, 1H), 6.98 (d, 2H), 6.86 (t, 1H), 6.39- (s, 1H), 6.32 (s, 1H), 6.19 (s, 1H), 3.68 (t, 4H), 3.28 (t, 4H), 2.39 (m, 1H), 2.38 (s, 3H), 2.23 (s, 3H), 0.94 (m, 2H), 0.70 (m, 2H) | 494 (M + H) |
| 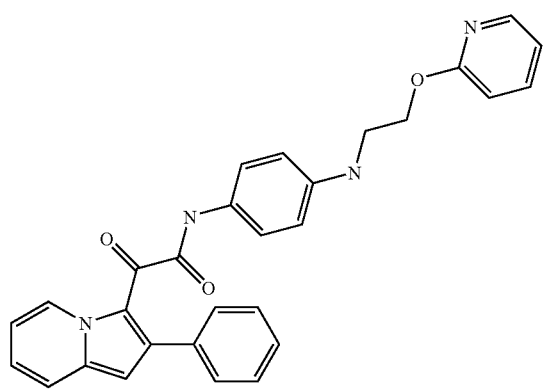
90 | | ¹H (400 MHz, CDCl₃): δ 9.71-9.73 (d, 1H), 8.15-8.16 (dd, 1H), 8.07 (s, 1H), 7.60-7.61 (d, 2H), 7.46-7.59 (m, 2H), 7.44-7.46 (m, 2H), 7.26-7.34 (m, 3H), 6.97-7.01 (b, 2H), 6.95-6.98 (t, 1H), 6.89-6.90 (t, 1H), 6.75-6.77 (d, 1H), 6.64 (s, 1H), 6.54-6.56 (d, 2H), 4.51-4.53 (t, 2H), 3.48-3.51 (t, 2H) | 477 (M + H) |
| 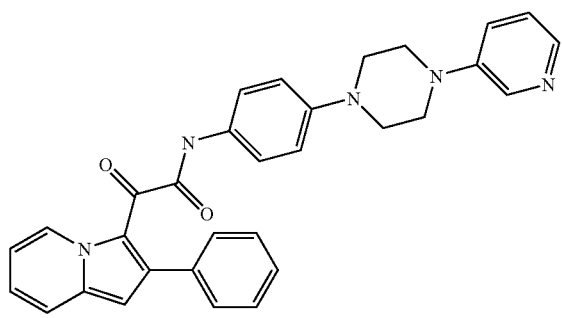
59 | | ¹H (400 MHz, CDCl₃): δ 9.72 (d, 1H), 8.37 (s, 1H), 8.20 (s, 1H), 8.17 (d, 1H), 7.58 (d, 1H), 7.46 (m, 2H), 7.25 (m, 4H), 7.22 (m, 2H), 7.12 (d, 2H), 6.98 (t, 1H), 6.85 (d, 2H), 6.64 (s, 1H), 3.36 (t, 4H), 3.28 (t, 4H). | 502 (M + H) |
| 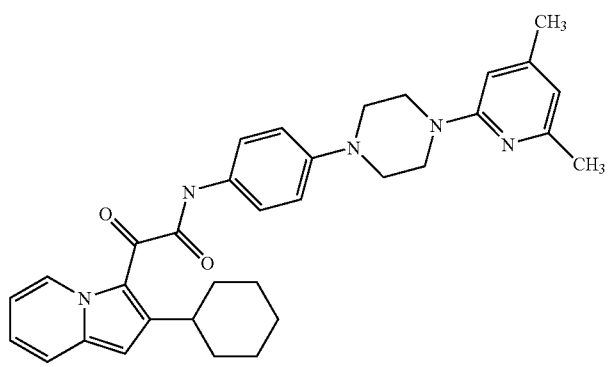
60 | | ¹H (400 MHz, CDCl₃): δ 9.67 (d, 1H), 8.28 (s, 1H), 7.59 (d, 2H), 7.45 (d, 1H), 7.18 (t, 1H), 7.00 (d, 2H), 6.84 (t, 1H), 6.47 (s, 1H), 6.39 (s, 1H), 6.33 (s, 1H), 3.69 (t, 4H), 3.29 (t, 4H), 3.20 (t, 1H), 2.38 (s, 3H), 2.24 (s, 3H), 2.02 (s, 2H), 1.78-1.68 (m, 3H), 1.42-1.21 (m, 5H) | 536 (M + H) |

-continued
| Example number | | NMR Data | Molecular ion |
|---|---|---|---|
| 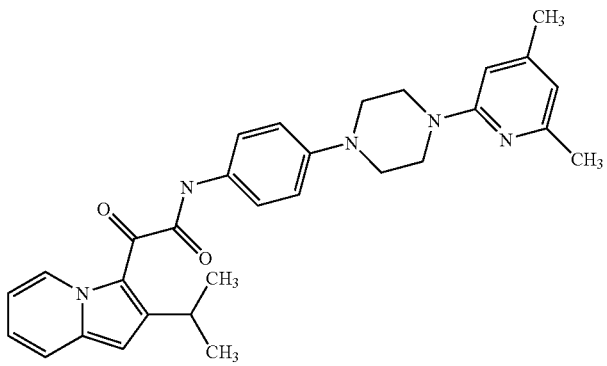<br>61 | | $^1$H (400 MHz, CDCl$_3$): δ 9.69 (d, 1H), 8.34 (s, 1H), 7.58 (d, 2H), 7.45 (d, 1H), 7.20 (t, 1H), 6.99 (d, 2H), 6.87 (t, 1H), 6.51 (s, 1H), 6.39 (s, 1H), 6.33 (s, 1H), 3.69 (s, 4H), 3.67-3.60 (m, 1H), 3.29 (s, 4H), 2.38 (s, 3H), 2.24 (s, 3H), 1.30 (d, 6H) | 496 (M + H) |
| 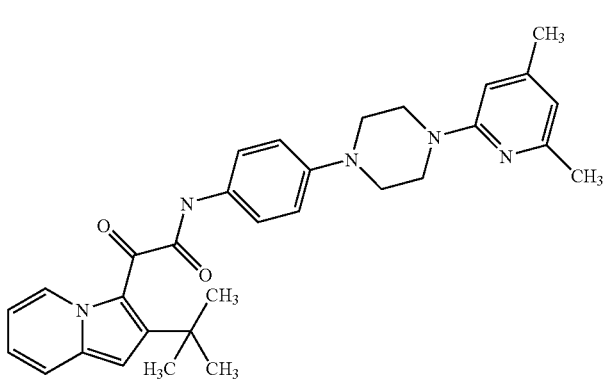<br>62 | | $^1$H (400 MHz, CDCl$_3$): δ 8.82 (s, 1H), 8.49 (d, 1H), 7.63 (d, 2H), 7.37 (d, 1H), 7.03-6.98 (m, 3H), 6.63 (t, 1H), 6.53 (s, 1H), 6.39 (s, 1H), 6.32 (s, 1H), 3.68 (t, 4H), 3.29 (t, 4H), 2.38 (s, 3H), 2.23 (s, 3H), 1.46 (s, 9H) | 510 (M + H) |
| 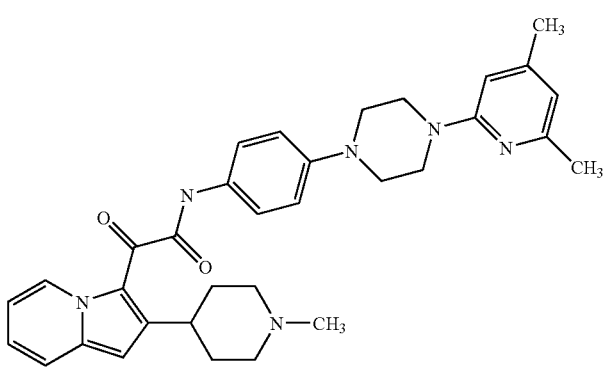<br>63 | | $^1$H (400 MHz, CDCl$_3$): δ 9.67 (d, 1H), 8.36 (s, 1H), 7.60 (d, 2H), 7.47 (d, 1H), 7.21 (m, 1H), 7.01 (d, 2H), 6.88 (m, 1H), 6.51 (s, 1H), 6.40 (s, 1H), 6.33 (s, 1H), 3.70 (s, 4H), 3.30 (s, 4H), 3.32 (m, 1H), 2.95 (m, 2H), 2.38 (s, 3H), 2.30-2.24 (2 s, 6H), 2.02 (m, 4H), 1.85 (m, 2H) | 551.5 (M + H) |

| Example number | NMR Data | Molecular ion |
|---|---|---|
| 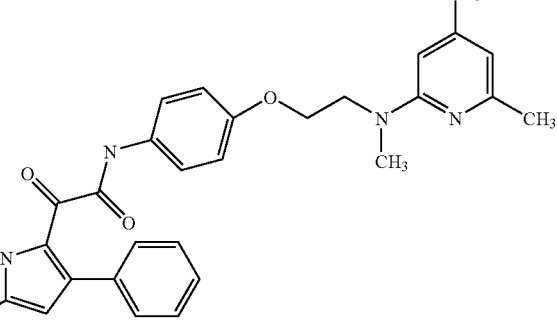 64 | ¹H (400 MHz, CDCl₃): δ 9.74 (d, 1H), 8.14 (s, 1H), 7.59 (d, 1H), 7.45 (m, 2H), 7.32 (m, 4H), 7.09 (d, 2H), 6.99 (t, 1H), 6.84 (d, 2H), 6.65 (s, 1H), 6.31 (s, 1H), 6.15 (s, 1H), 4.15 (t, 2H), 3.95 (t, 2H), 3.12 (s, 3H), 2.37 (s, 3H), 2.23 (s, 3H) | 519 (M + H) |
| 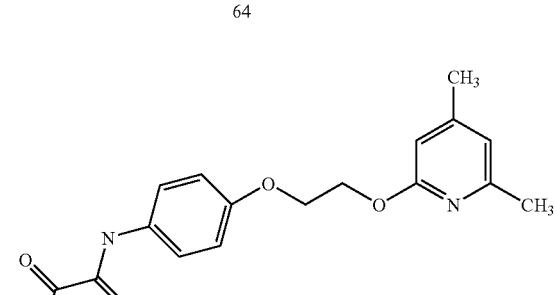 65 | ¹H (400 MHz, CDCl₃): δ 9.72 (d, 1H), 8.15 (s, 1H), 7.57 (d, 1H), 7.44 (m, 2H), 7.30-7.28 (m, 4H), 7.10 (d, 2H), 6.97 (t, 1H), 6.84 (d, 2H), 6.64 (s, 1H), 6.57 (s, 1H), 6.40 (s, 1H), 4.62 (t, 2H), 4.26 (t, 2H), 2.39 (s, 3H), 2.24 (s, 3H) | 506 (M + H) |
| 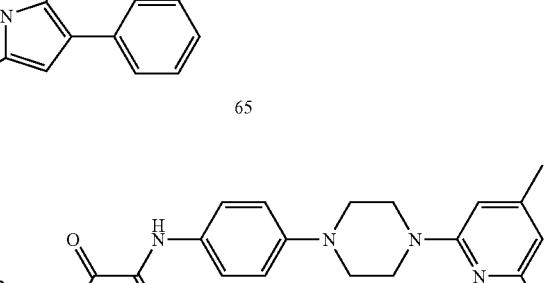 66 | ¹H NMR (400 MHz, CDCl₃): δ 10.71 (s, 1H), 9.83 (d, 1H), 7.74 (d, 1H), 7.58 (d, 2H), 7.39 (t, 1H), 7.12 (t, 1H), 7.01 (d, 2H), 6.71 (s, 1H), 6.53 (s, 1H), 6.40 (s, 1H), 3.81 (d, 2H), 3.61 (m, 4H), 3.21 (m, 4H), 3.12 (m, 1H), 3.02 (m, 2H), 2.28 (s, 3H), 2.19 (s, 3H), 1.72 (m, 4H). | 538 (M + H) |
| 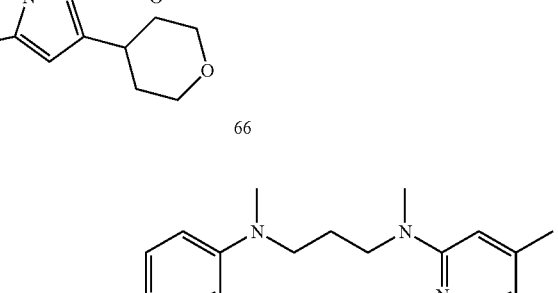 67 | ¹H NMR (400 MHz, CDCl₃): δ 9.71 (d, 1H), 8.08 (s, 1H), 7.57 (d, 1H), 7.45 (d, 2H), 7.33-7.26 (m, 4H), 7.02 (d, 2H), 6.96 (t, 1H), 6.63 (s, 1H), 6.56 (d, 2H), 6.26 (s, 1H), 6.07 (s, 1H), 3.57 (t, 2H), 3.30 (t, 2H), 2.99 (s, 3H), 2.89 (s, 3H), 2.34 (s, 3H), 2.19 (s, 3H), 1.84 (m, 2H) | 546 (M + H) |

| Example number | NMR Data | Molecular ion |
|---|---|---|
| 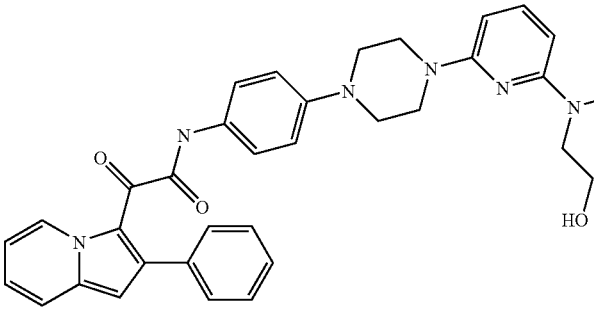 86 | ¹H (400 MHz, CDCl₃): δ 9.72 (d, 1H), 8.15 (s, 1H), 7.58 (d, 1H), 7.46 (t, 2H), 7.35-7.29 (m, 5H), 7.10 (d, 2H), 6.99 (m, 1H), 6.84 (d, 2H), 6.65 (s, 1H), 6.03-5.95 (dd, 2H), 3.98 (t, 4H), 3.20 (t, 4H), 3.62 (t, 4H), 3.22 (t, 4H) | 605 (M + H) |
| 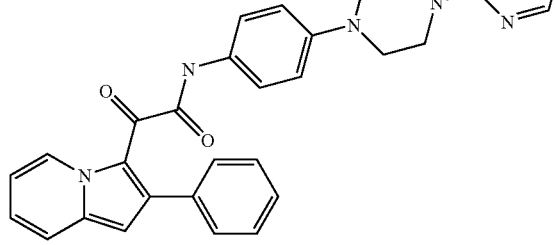 89 | ¹H (400 MHz, CDCl₃): δ 9.78 (d, 1H), 8.16 (s, 1H), 8.08 (d, 1H), 7.58 (d, 1H), 7.44 (m, 2H), 7.36-7.28 (m, 4H), 7.10 (d, 2H), 6.98 (t, 1H), 6.84 (d, 2H), 6.64 (s, 1H), 6.28 (m, 1H), 6.18 (s, 1H), 4.12 (t, 2H), 3.98 (t, 2H), 3.67 (t, 4H), 3.23 (t, 4H) | 562 (M + H) |
| 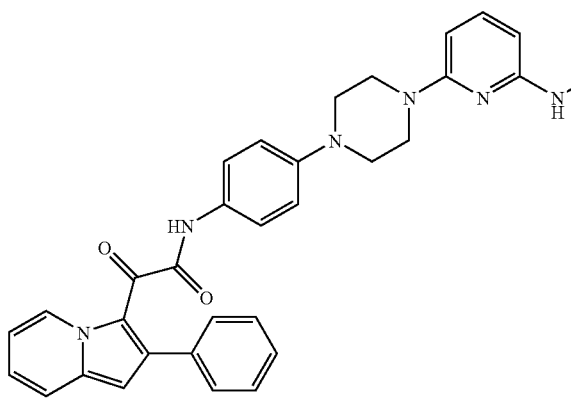 87 | ¹H NMR (400 MHz, CDCl₃): δ 9.72 (d, 1H), 8.13 (s, 1H), 7.58 (d, 1H), 7.46-7.44 (m, 2H), 7.32-7.28 (m, ~6H, solvent overlap), 7.10 (d, 2H), 6.98 (t, 1H), 6.83 (d, 2H), 6.64 (s, 1H), 5.99 (d, 1H), 5.85 (d, 1H), 3.81 (t, 2H), 3.63-3.59 (m, 6H), 3.22 (t, 4H) | 561 (M + H) |

-continued
| Example number | NMR Data | Molecular ion |
|---|---|---|
| 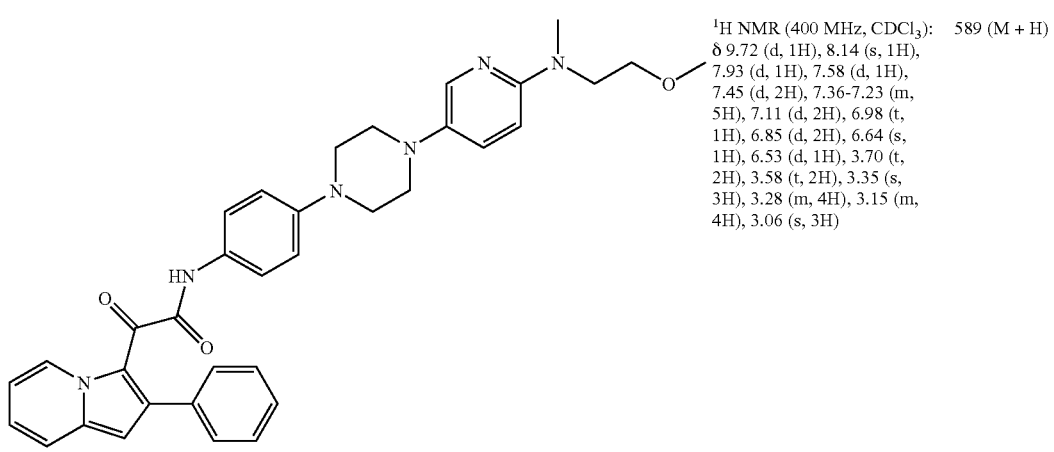<br>68 | $^1$H NMR (400 MHz, CDCl$_3$): δ 9.72 (d, 1H), 8.14 (s, 1H), 7.93 (d, 1H), 7.58 (d, 1H), 7.45 (d, 2H), 7.36-7.23 (m, 5H), 7.11 (d, 2H), 6.98 (t, 1H), 6.85 (d, 2H), 6.64 (s, 1H), 6.53 (d, 1H), 3.70 (t, 2H), 3.58 (t, 2H), 3.35 (s, 3H), 3.28 (m, 4H), 3.15 (m, 4H), 3.06 (s, 3H) | 589 (M + H) |
| 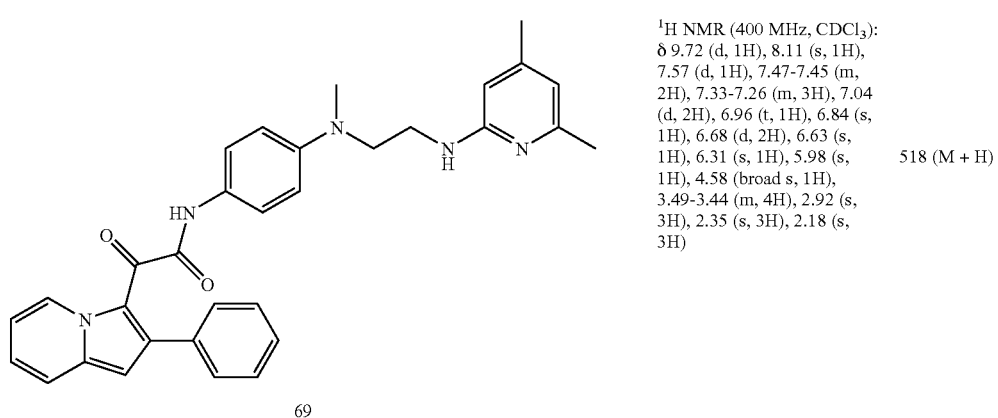<br>69 | $^1$H NMR (400 MHz, CDCl$_3$): δ 9.72 (d, 1H), 8.11 (s, 1H), 7.57 (d, 1H), 7.47-7.45 (m, 2H), 7.33-7.26 (m, 3H), 7.04 (d, 2H), 6.96 (t, 1H), 6.84 (s, 1H), 6.68 (d, 2H), 6.63 (s, 1H), 6.31 (s, 1H), 5.98 (s, 1H), 4.58 (broad s, 1H), 3.49-3.44 (m, 4H), 2.92 (s, 3H), 2.35 (s, 3H), 2.18 (s, 3H) | 518 (M + H) |
| 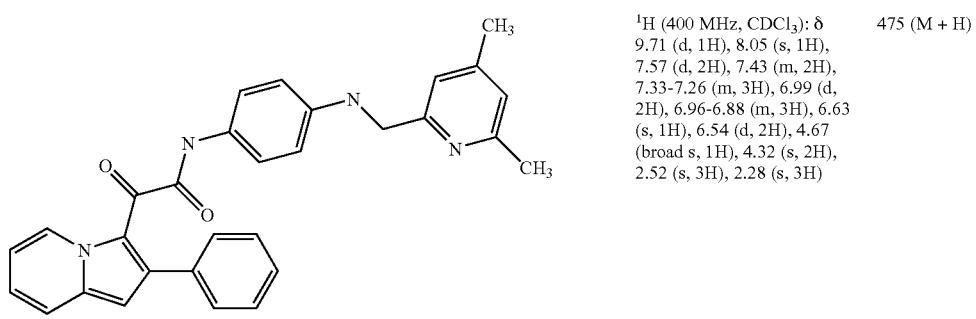<br>91 | $^1$H (400 MHz, CDCl$_3$): δ 9.71 (d, 1H), 8.05 (s, 1H), 7.57 (d, 2H), 7.43 (m, 2H), 7.33-7.26 (m, 3H), 6.99 (d, 2H), 6.96-6.88 (m, 3H), 6.63 (s, 1H), 6.54 (d, 2H), 4.67 (broad s, 1H), 4.32 (s, 2H), 2.52 (s, 3H), 2.28 (s, 3H) | 475 (M + H) |

-continued
| Example number | NMR Data | Molecular ion |
|---|---|---|
| 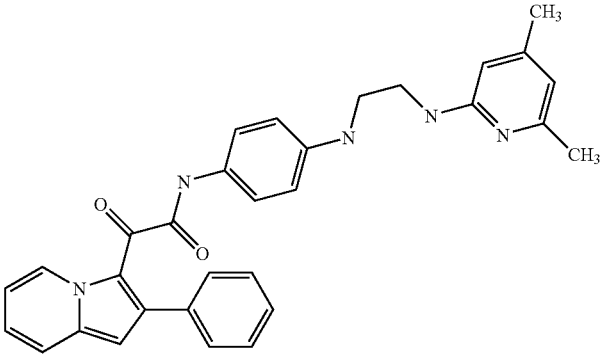 92 | ¹H (400 MHz, CDCl₃): δ 9.71 (d, 1H), 8.10 (s, 1H), 7.56 (d, 1H), 7.45-7.43 (m, 2H), 7.31-7.26 (m, 4H), 6.98-6.94 (m, 3H), 6.62 (s, 1H), 6.50 (d, 2H), 6.22 (s, 1H), 6.09 (s, 1H), 3.43-3.37 (m, 4H), 2.38 (s, 3H), 2.20 (s, 3H) | 504 (M + H) |
| 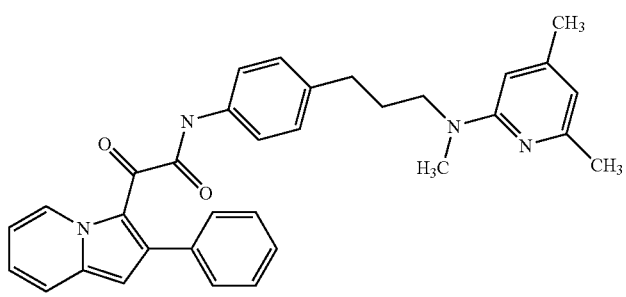 70 | ¹H (400 MHz, CDCl₃): δ 9.72 (d, 1H), 8.22 (s, 1H), 7.58 (d, 1H), 7.45 (m, 2H), 7.30-7.26 (m, 4H), 7.09 (m, 4H), 6.98 (t, 1H), 6.64 (s, 1H), 6.24 (s, 1H), 6.03 (s, 1H), 3.52 (t, 2H), 3.00 (s, 3H), 2.59 (t, 2H), 2.24 (s, 3H), 2.18 (t, 3H), 1.87 (m, 2H) | 515 (M + H) |
| 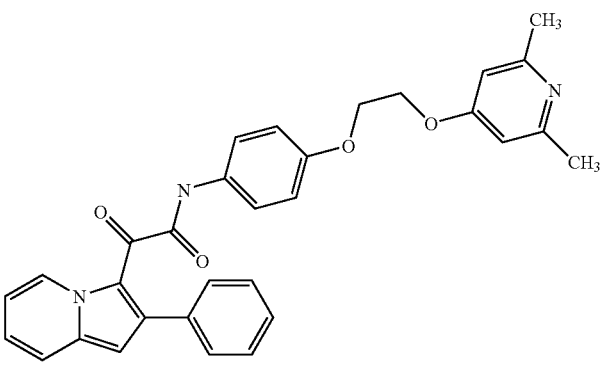 71 | ¹H (400 MHz, CDCl₃): δ 9.73 (d, 1H), 8.17 (s, 1H), 7.58 (d, 1H), 7.46-7.44 (dd, 2H), 7.32-7.25 (m, 5H), 7.12 (d, 2H), 6.98 (t, 1H), 6.80 (d, 2H), 6.64 (s, 1H), 6.57 (s, 1H), 4.33-4.27 (m, 4H), 2.52 (s, 6H) | 506 (M + H) |
| 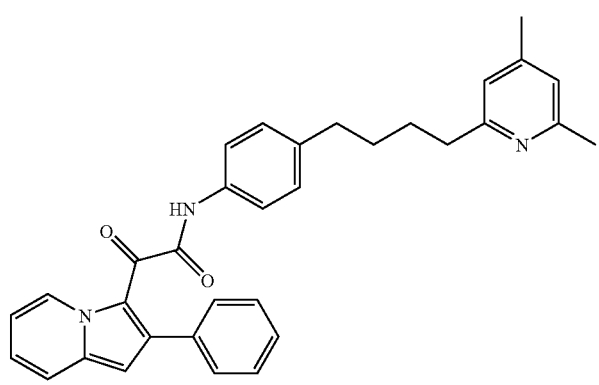 72 | ¹H (400 MHz, CDCl₃): δ 9.72 (d, 1H), 8.25 (s, 1H), 7.57 (d, 1H), 7.43 (d, 2H), 7.32-7.28 (m, 4H), 7.08 (d, 2H), 7.03 (d, 2H), 6.97 (t, 1H), 6.79 (s, 1H), 6.75 (s, 1H), 6.34 (s, 1H), 2.73 (t, 2H), 2.58 (t, 2H), 2.48 (s, 3H), 2.26 (s, 3H), 1.73-1.62 (m, 4H) | 502.2 (M + H) |

-continued
| Example number | | NMR Data | Molecular ion |
|---|---|---|---|
| 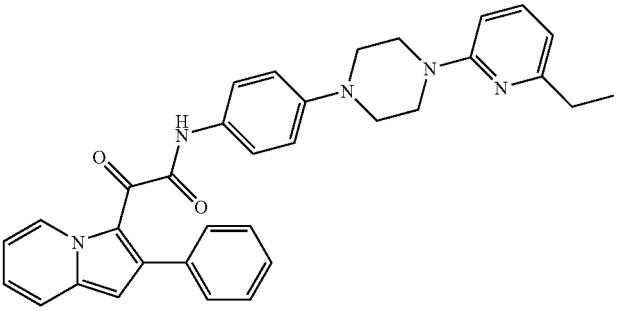 73 | | ¹H (400 MHz, CDCl₃): δ 9.72 (d, 1H), 8.17 (s, 1H), 7.58 (d, 1H), 7.52 (t, 1H), 7.46-7.44 (m, 2H), 7.34-7.25 (m, 4H), 7.11 (d, 2H), 6.98 (t, 1H), 6.84 (d, 2H), 6.64 (s, 1H), 6.58 (d, 2H), 3.76 (t, 4H), 3.27 (t, 4H), 2.79 (q, 2H), 1.29 (t, 3H) | 530.2 (M + H) |
| 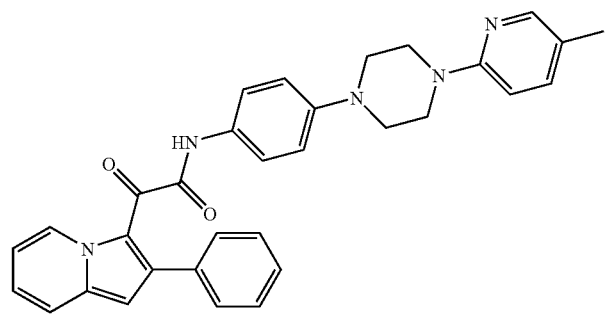 74 | | ¹H (400 MHz, CDCl₃): δ 9.72 (d, 1H), 8.15 (s, 1H), 8.04 (s, 1H), 7.57 (d, 1H), 7.46-7.43 (m, 2H), 7.35-7.28 (m, 5H), 7.11 (d, 2H), 6.98 (t, 1H), 6.85 (d, 2H), 6.65-6.63 (m, 2H), 3.63 (t, 4H), 3.24 (t, 4H), 2.21 (s, 3H) | 516.3 (M + H) |
| 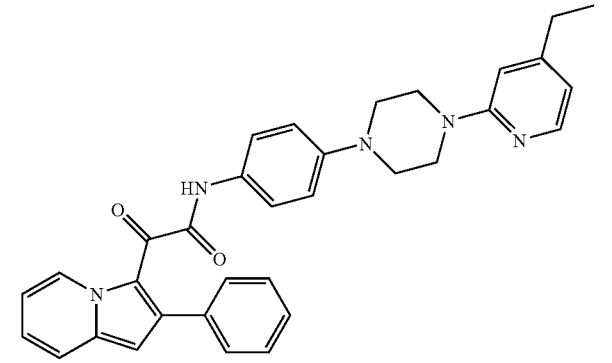 75 | | ¹H (400 MHz, CDCl₃): δ 9.72 (d, 1H), 8.15 (s, 1H), 8.10 (d, 1H), 7.58 (d, 1H), 7.44 (m, 2H), 7.35-7.29 (m, 5H), 7.11 (d, 2H), 6.98 (t, 1H), 6.85 (d, 2H), 6.64 (s, 1H), 6.54 (s, 1H), 3.69 (s, 4H), 3.24 (s, 4H), 2.58 (q, 2H), 1.23 (t, 3H) | 530.3 (M + H) |
| 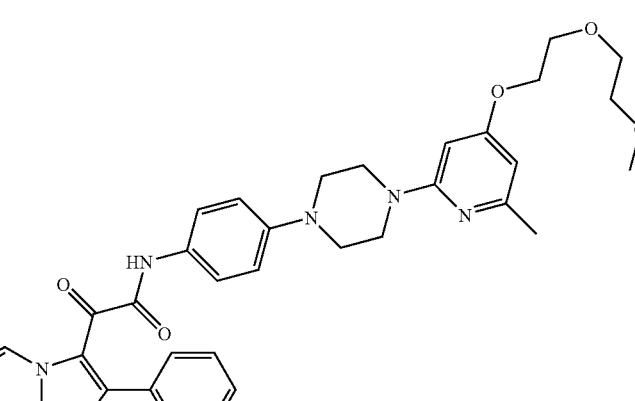 76 | | ¹H (400 MHz, CDCl₃): δ 9.72 (d, 1H), 8.16 (s, 1H), 7.58 (d, 1H), 7.46-7.44 (m, 2H), 7.32-7.28 (m, 3H), 7.10 (d, 2H), 6.68 (t, 1H), 6.84 (d, 2H), 6.64 (s, 1H), 6.15 (s, 1H), 6.01 (s, 1H), 4.22 (t, 1H), 4.15 (t, 2H), 3.84 (t, 2H), 3.71 (t, 2H), 3.64 (m, 4H), 3.58 (t, 2H), 3.38 (s, 3H), 3.22 (t, 4H), 2.37 (s, 3H) | 634.3 (M + H) |

-continued
| Example number | NMR Data | Molecular ion |
|---|---|---|
| 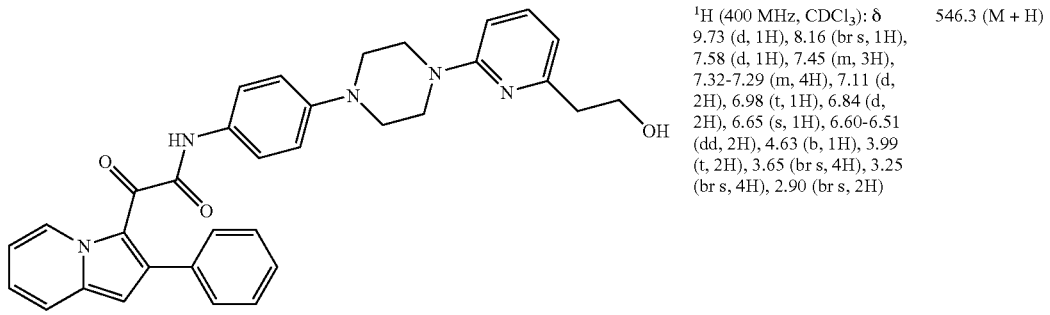<br>88 | ¹H (400 MHz, CDCl₃): δ 9.73 (d, 1H), 8.16 (br s, 1H), 7.58 (d, 1H), 7.45 (m, 3H), 7.32-7.29 (m, 4H), 7.11 (d, 2H), 6.98 (t, 1H), 6.84 (d, 2H), 6.65 (s, 1H), 6.60-6.51 (dd, 2H), 4.63 (b, 1H), 3.99 (t, 2H), 3.65 (br s, 4H), 3.25 (br s, 4H), 2.90 (br s, 2H) | 546.3 (M + H) |
| 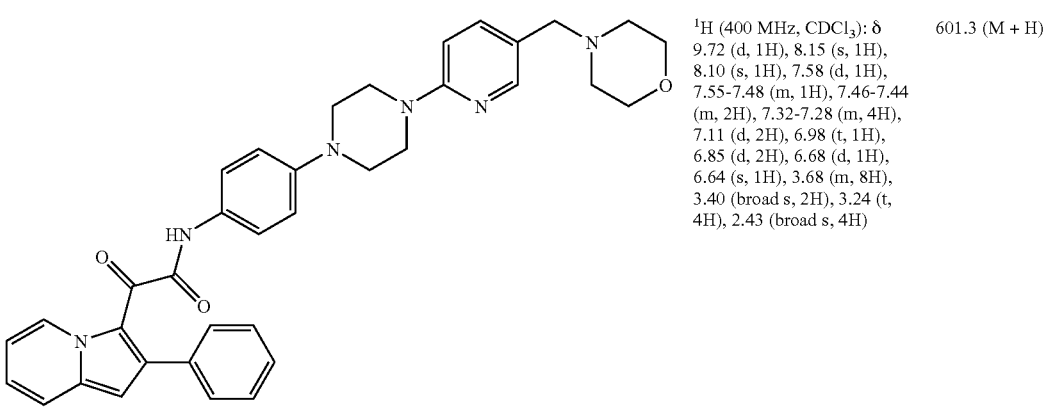<br>77 | ¹H (400 MHz, CDCl₃): δ 9.72 (d, 1H), 8.15 (s, 1H), 8.10 (s, 1H), 7.58 (d, 1H), 7.55-7.48 (m, 1H), 7.46-7.44 (m, 2H), 7.32-7.28 (m, 4H), 7.11 (d, 2H), 6.98 (t, 1H), 6.85 (d, 2H), 6.68 (d, 1H), 6.64 (s, 1H), 3.68 (m, 8H), 3.40 (broad s, 2H), 3.24 (t, 4H), 2.43 (broad s, 4H) | 601.3 (M + H) |
| 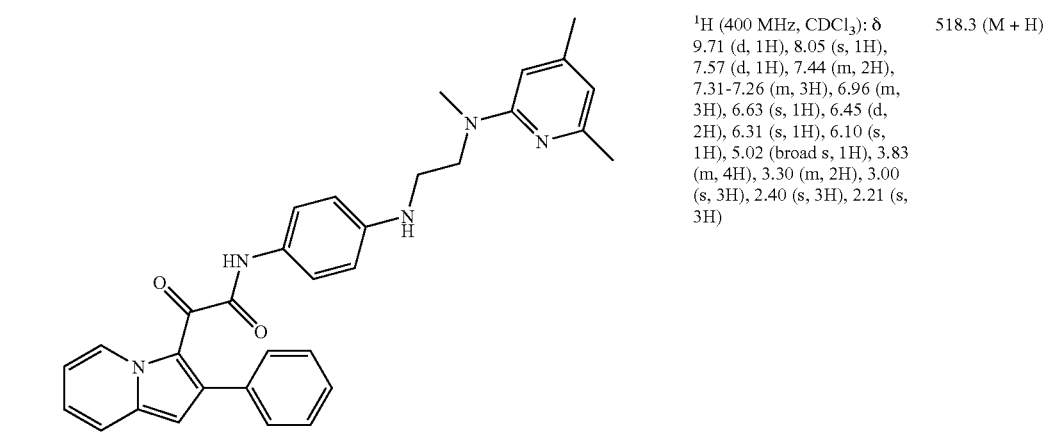<br>78 | ¹H (400 MHz, CDCl₃): δ 9.71 (d, 1H), 8.05 (s, 1H), 7.57 (d, 1H), 7.44 (m, 2H), 7.31-7.26 (m, 3H), 6.96 (m, 3H), 6.63 (s, 1H), 6.45 (d, 2H), 6.31 (s, 1H), 6.10 (s, 1H), 5.02 (broad s, 1H), 3.83 (m, 4H), 3.30 (m, 2H), 3.00 (s, 3H), 2.40 (s, 3H), 2.21 (s, 3H) | 518.3 (M + H) |

| Example number | NMR Data | Molecular ion |
|---|---|---|
| 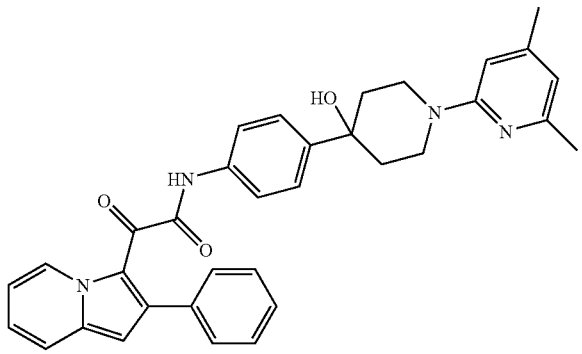<br>79 | ¹H (400 MHz, CDCl₃): δ 9.73 (d, 1H), 8.30 (s, 1H), 7.58 (d, 1H), 7.44-7.29 (m, 8H), 7.17 (d, 2H), 6.98 (t, 1H), 6.64 (s, 1H), 6.34 (s, 2H), 4.22 (d, 2H), 3.31 (m, 2H), 2.38 (s, 3H), 2.23 (s, 3H), 2.11 (m, 2H), 1.81 (d, 3H) | 545.3 (M + H) |
| 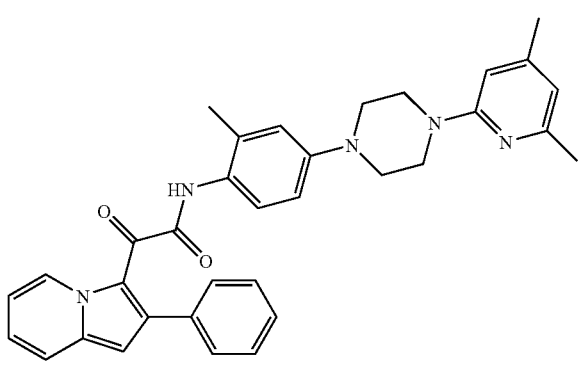<br>80 | ¹H (400 MHz, CDCl₃): δ 9.72 (d, 1H), 8.08 (s, 1H), 7.57 (d, 1H), 7.47-7.46 (m, 2H), 7.35-7.28 (m, 4H), 7.11 (d, 1H), 6.97 (t, 1H), 6.75 (s, 2H), 6.68 (d, 1H), 6.38 (s, 1H), 6.31 (s, 1H), 3.65 (t, 4H), 3.22 (t, 4H), 2.38 (s, 3H), 2.28 (s, 3H), 2.23 (s, 3H) | 543.9 (M + H) |
| 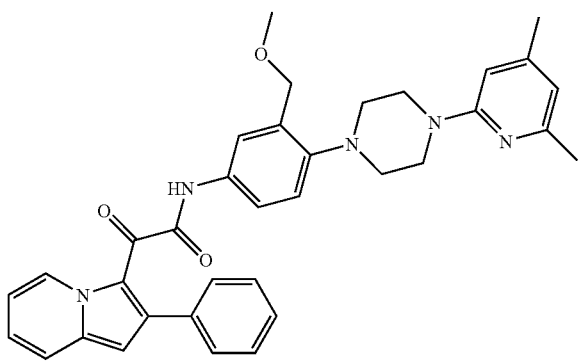<br>81 | ¹H (400 MHz, CDCl₃): δ 9.73 (d, 1H), 8.23 (s, 1H), 1.58 (d, 1H), 7.45 (m, 2H), 7.32-7.26 (m, 4H), 7.18 (m, 2H), 6.97 (m, 2H), 6.64 (s, 1H), 6.38 (s, 1H), 6.32 (s, 1H), 4.51 (s, 2H), 3.64 (s, 4H), 3.43 (s, 3H), 2.99 (s, 4H), 2.38 (s, 3H), 2.23 (s, 3H) | 574 (M + H) |
| 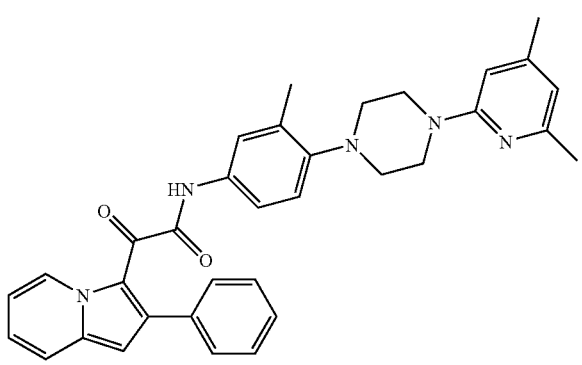<br>82 | ¹H (400 MHz, CDCl₃): δ 9.72 (d, 1H), 8.13 (s, 1H), 7.58 (d, 1H), 7.46-7.44 (m, 2H), 7.33-7.29 (m, 5H), 6.99-6.97 and 6.90 (m and d, 4H), 6.64 (s, 1H), 6.38 (s, 1H), 6.31 (s, 1H), 3.64 (m, 4H), 2.96 (m, 4H), 2.37 (s, 3H), 2.28 (s, 3H), 2.23 (s, 3H) | 544.3 (M + H) |

-continued

| Example number | NMR Data | Molecular ion |
|---|---|---|
| 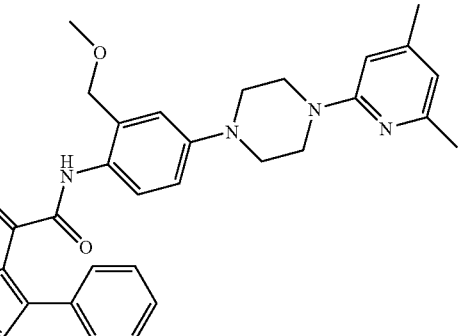 83 | ¹H (400 MHz, CDCl₃): δ 9.76 (d, 1H), 9.33 (s, 1H), 7.57 (d, 1H), 7.49-7.47 (m, 2H), 7.34-7.32 (m, 3H), 7.25-7.23 (m, 2H), 6.95 (t, 1H), 6.78 (m, 2H), 6.63 (s, 1H), 6.39 (s, 1H), 6.31 (s, 1H), 4.52 (s, 2H), 3.65 (m, 4H), 3.48 (s, 3H), 3.22 (m, 4H), 2.37 (s, 3H), 2.23 (s, 3H) | 574.3 (M + H) |
| 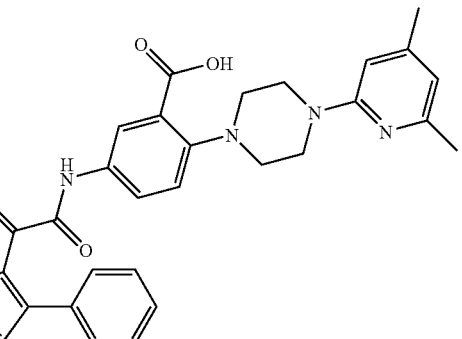 84 | ¹H (400 MHz, CDCl₃): δ 9.76 (d, 1H), 8.39 (s, 1H), 7.87 (s, 1H), 7.17 (d, 1H), 7.60 (d, 1H), 7.36 (d, 2H), 7.34-7.26 (m, 5H), 7.03-6.99 (m, 1H), 6.65 (s, 1H), 6.45 (s, 1H), 6.33 (s, 1H), 4.25 (broad s, 2H), 3.5 (broad s, 2H), 3.13-3.08 (m, 4H), 2.38 (s, 3H), 2.26 (s, 3H) | 574.3 (M + H) |

Example 93

Measurement of Minimum Inhibitory Concentrations (MICs)

Between 1 and 5 mgs of compound were accurately weighed out into a sterile Eppendorf tube. The compound was dissolved in DMSO to give a solution containing mg/mL. Tubes were stored at −20° C. until required.

On the day of testing thawed solutions were vortex mixed to ensure homogeneity. 30 μL of solution was removed and added to 570 μL of sterile water in a separate sterile Eppendorf. The thoroughly mixed solution was used to prepare a series of doubling dilutions in water, in a deep well plate. Thirteen replicate plates were prepared using a Minitrak by aspirating 20 μL from each well into eleven clear polystyrene 96 well plates.

Spores of *Aspergillus* spp. (*Aspergillus fumigatus* [two strains], *Aspergillus terreus* [two strains], *Aspergillus niger* and *Aspergillus flavus*) were harvested from cultures grown on Sabarauds agar for 5 days, and resuspended in PBS/Tween 80 to approx $1 \times 10^7$ cfu/mL. Other filamentous fungi (*Absidia corymbifera, Fusarium solani, Rhizomucor, Scedosporium* spp., *Trichophyton* spp.), were grown on Sabarauds agar for 2-10 days and spores/hyphae resuspended in PBS/Tween to give approx $1 \times 10^7$ cfu/mL. *Candida* species (*Candida albicans, Candida glabrata, Candida krusei, Candida parapsilosis* and *Candida tropicalis*) were grown on Sabarauds agar, cells were harvested from the agar using a sterile loop and resuspended in PBS/Tween 80 to approx $1 \times 10^6$ cfu/mL. Each organism suspension was diluted in RPMI medium, containing 2% glucose and 0.135 M MOPS buffer (pH 7.0) to 0.5-$2 \times 10^4$ cfu/mL for *Aspergillus* spp. and other filamentous fungi and 0.5-$2 \times 10^3$ cfu/mL for yeast. 80 μL of an organism suspension was added to each well of the plate containing drug dilutions.

This produced MIC plates with a drug range 50-0.05 mg/L and organism inocula of 1-$2 \times 10^4$ cfu/mL for *Aspergillus* spp. and other filamentous fungi and 1-$2 \times 10^3$ cfu/mL for yeasts. All plates were incubated for 24-48 hrs at 35° C. Growth was assessed by monitoring the optical density at 485 nm for each well. The MIC of a compound is the lowest drug concentration that inhibits growth of an organism by >80% compared with a drug free control. MICs are recorded as mg/L. Other growth media can be used for susceptibility testing, and the activity of the described compounds can also be assessed in a medium comprising 1% glucose, 1% ammonium chloride and 0.5% yeast extract (YAG medium). To perform MIC tests in this medium, dilutions of compounds are prepared in microtitre plates as described above. Fungal strains to be tested are grown and harvested in an identical manner to that described above, each organism suspension is then diluted in YAG medium to 0.5-$2 \times 10^4$ cfu/mL for *Aspergillus* spp. and other filamentous fungi and 0.5-$2 \times 10^3$ cfu/mL for yeast. 80 μL of an organism suspension was added to each well of the plate containing drug dilutions. This produced MIC plates with a drug range 50-0.05 mg/L and organism inocula of 1-$2 \times 10^4$ cfu/mL for *Aspergillus* spp. and other filamentous fungi and 1-2×10³ cfu/mL for yeasts. All plates were incubated for 24 hrs at 35° C. Growth was assessed by monitoring the optical density at 485 nm for each well. The MIC of a compound is the lowest drug concentration that inhibits growth of an organism by >70% compared with a drug free control. MICs are recorded as mg/L. In cases where the MIC of an organism is >=0.05 mg/L the MIC is repeated using a concentration range of 0.5-0.0005 mg/L. MIC tests in YAG medium have more clear-cut endpoints and have slightly lower MICs than those performed in RPMI medium.

The following organisms were tested: *Absidia corymbifera, Aspergillus flavus, Aspergillus fumigatus* AF293 and AF210, *Aspergillus niger, Aspergillus terreus* AT4 and AT49, *Candida albicans, Candida glabrata, Candida krusei, Candida parapsilosis, Candida tropicalis, Fusarium solani, Rhizomucor* sp., *Scedosporium apiospermum, Scedosporium prolificans, Trichophyton mentagrophytes*, and *Trichophyton rubrum*.

Other fungi including *Acremonium* spp; *Alternaria alternata; Aspergillus nidulans; Aspergillus parasiticus; Bipolaris* spp; *Blastomyces dermatitidis; Blumeria graminis; Cladosporium cladosporoides; Cladosporium herbarium; Coccidioides immitis; Coccidioides posadasii; Colletotrichium trifolii; Curvularia lunata; Colletotrichium trifolii; Cryptococcus neoformans; Encephalitozoon cuniculi; Epicoccum nigrum; Epidermophyton floccosum; Exophiala* spp; *Exserohilum rostratum; Fusarium graminearium; Fusarium sporotrichoides; Histoplasma capsulatum; Leptosphaeria nodorum; Magnaporthe grisea; Microsporum canis; Mycosphaerella graminicola; Neurospora crassa; Paecilomyces lilanicus; Paecilomyces varioti; Penicillium chrysogenum; Phytophthora capsici; Phytophthora infestans; Plasmopara viticola; Pneumocystis jiroveci; Puccinia coronata; Puccinia graminis; Pyricularia oryzae; Pythium ultimum; Rhizoctonia solani; Rhizomucor* spp.; *Rhizopus* spp.; *Scopulariopsis brevicaulis; Trichophyton interdigitale; Trichosporon asahii; Trichosporon beigelii*; and *Ustilago maydis* may also be used in the above assay. Fungi are cultured by standard methods known to those skilled in the art, and MICs determined as above.

MIC Results in mg/L (YAG Medium):

The following MIC results have been banded into grades. Thus, a grade of 1 represents an MIC of greater than 10 mg/L. A grade of 2 represents an MIC of from 1 to 10. A grade of 3 represents an MIC of less than 1 mg/L.

| Example no. | A. flavus | A. fumigatus | A. fumigatus 210 | A. niger | A. terreus | A. terreus 49 |
|---|---|---|---|---|---|---|
| 1 | 2 | 1 | 1 | 1 | 2 | 1 |
| 2 | 3 | 3 | 3 | 3 | 3 | 3 |
| 3 | 3 | 3 | 3 | 3 | 3 | 3 |
| 4 | 1 | 1 | 1 | 1 | 1 | 1 |
| 5 | 1 | 1 | 1 | 1 | 1 | 1 |
| 6 | 1 | 1 | 1 | 1 | 1 | 1 |
| 7 | 1 | 1 | 1 | 1 | 1 | 1 |
| 8 | 1 | 1 | 1 | 1 | 1 | 2 |
| 9 | 1 | 1 | 1 | 1 | 1 | 1 |
| 10 | 3 | 3 | 3 | 3 | 3 | 3 |
| 11 | 3 | 3 | 3 | 3 | 3 | 3 |
| 12 | 3 | 2 | 2 | 1 | 2 | 2 |
| 13 | 3 | 3 | 2 | 1 | 2 | 3 |
| 14 | 2 | 1 | 1 | 1 | 2 | 2 |
| 15 | 1 | 1 | 1 | 1 | 1 | 1 |
| 16 | 3 | 2 | 2 | 2 | 3 | 3 |
| 17 | 1 | 1 | 1 | 2 | 2 | 2 |
| 18 | 1 | 1 | 1 | 1 | 1 | 2 |
| 19 | 1 | 1 | 1 | 1 | 2 | 2 |
| 20 | 3 | 2 | 2 | 1 | 2 | 3 |
| 21 | 3 | 3 | 3 | 3 | 3 | 3 |
| 22 | 2 | 1 | 1 | 1 | 2 | 2 |
| 23 | 3 | 3 | 3 | 3 | 3 | 3 |
| 24 | 3 | 3 | 3 | 3 | 3 | 3 |
| 25 | 2 | 1 | 1 | 1 | 2 | 2 |
| 26 | 3 | 2 | 3 | 2 | 2 | 3 |
| 85 | 3 | 1 | 1 | 1 | 3 | 3 |
| 27 | 3 | 3 | 3 | 3 | 3 | 3 |
| 28 | 2 | 2 | 2 | 3 | 2 | 2 |
| 29 | 3 | 3 | 2 | 3 | 3 | 3 |
| 30 | 1 | 1 | 1 | 1 | 1 | 1 |
| 31 | 3 | 3 | 3 | 3 | 3 | 3 |
| 32 | 3 | 3 | 3 | 3 | 3 | 3 |
| 33 | 3 | 3 | 3 | 3 | 3 | 3 |
| 34 | 3 | 3 | 3 | 3 | 3 | 3 |
| 35 | 3 | 3 | 3 | 3 | 3 | 3 |
| 36 | 3 | 3 | 3 | 3 | 3 | 3 |
| 37 | 3 | 3 | 3 | 3 | 3 | 3 |
| 38 | 3 | 3 | 3 | 3 | 3 | 3 |
| 39 | 3 | 3 | 3 | 3 | 3 | 3 |
| 40 | 2 | 1 | 1 | 1 | 1 | 1 |
| 41 | 3 | 3 | 3 | 3 | 3 | 3 |
| 42 | 3 | 3 | 3 | 3 | 3 | 3 |
| 43 | 3 | 3 | 3 | 3 | 3 | 3 |
| 44 | 3 | 3 | 3 | 3 | 3 | 3 |
| 45 | 3 | 3 | 3 | 2 | 3 | 3 |
| 46 | 3 | 3 | 3 | 3 | 3 | 3 |
| 47 | 3 | 3 | 3 | 3 | 3 | 3 |
| 48 | 3 | 3 | 3 | 3 | 3 | 3 |
| 49 | 3 | 3 | 3 | 3 | 3 | 3 |
| 50 | 3 | 3 | 3 | 3 | 3 | 3 |
| 51 | 3 | 3 | 3 | 3 | 3 | 3 |
| 52 | 1 | 1 | 1 | 1 | 1 | 1 |
| 53 | 2 | 2 | 2 | 1 | 2 | 2 |
| 54 | 3 | 3 | 3 | 3 | 3 | 3 |
| 55 | 3 | 3 | 3 | 3 | 3 | 3 |
| 56 | 3 | 3 | 3 | 3 | 3 | 3 |
| 57 | 3 | 3 | 3 | 3 | 3 | 3 |
| 58 | 3 | 3 | 3 | 3 | 3 | 3 |
| 90 | 3 | 3 | 3 | 3 | 3 | 3 |
| 59 | 3 | 3 | 3 | 3 | 3 | 3 |
| 60 | 3 | 3 | 3 | 3 | 3 | 3 |
| 61 | 3 | 3 | 3 | 3 | 3 | 3 |
| 62 | 1 | 1 | 1 | 1 | 2 | 1 |
| 63 | 1 | 1 | 1 | 1 | 1 | 1 |
| 64 | 3 | 3 | 3 | 3 | 3 | 3 |
| 65 | 3 | 3 | 3 | 3 | 3 | 3 |
| 66 | 3 | 3 | 3 | 3 | 3 | 3 |
| 67 | 3 | 3 | 3 | 3 | 3 | 3 |
| 86 | 3 | 3 | 2 | 2 | 2 | 2 |
| 89 | 3 | 2 | 2 | 2 | 2 | 3 |
| 87 | 3 | 3 | 2 | 1 | 2 | 3 |
| 68 | 3 | 3 | 3 | 3 | 3 | 3 |
| 69 | 3 | 3 | 3 | 3 | 3 | 3 |
| 91 | 3 | 3 | 3 | 3 | 3 | 3 |
| 92 | 3 | 3 | 3 | 2 | 3 | 3 |
| 70 | 3 | 3 | 3 | 3 | 3 | 3 |
| 71 | 2 | 3 | 3 | 2 | 3 | 3 |
| 72 | 3 | 3 | 3 | 3 | 3 | 3 |
| 73 | 3 | 3 | 3 | 3 | 3 | 3 |
| 74 | 3 | 3 | 3 | 3 | 3 | 3 |
| 75 | 3 | 3 | 3 | 3 | 3 | 3 |
| 76 | 3 | 3 | 3 | 3 | 3 | 3 |
| 88 | 3 | 3 | 3 | 3 | 3 | 3 |
| 77 | 3 | 3 | 3 | 3 | 3 | 3 |
| 78 | 3 | 3 | 3 | 3 | 3 | 3 |
| 79 | 1 | 1 | 1 | 1 | 1 | 1 |
| 80 | 3 | 3 | 3 | 3 | 3 | 3 |
| 81 | 3 | 3 | 3 | 3 | 3 | 3 |
| 82 | 3 | 3 | 3 | 3 | 3 | 3 |
| 83 | 3 | 3 | 3 | 3 | 3 | 3 |
| 84 | 3 | 3 | 2 | 2 | 2 | 2 |

24 hr *Fusarium solani* MIC Results (RPMI medium, FS2):
Again, the following MIC results have been banded into grades as described above.

| Example number | MIC |
| --- | --- |
| 2 | 3 |
| 3 | 3 |
| 13 | 2 |
| 21 | 3 |
| 23 | 3 |
| 24 | 2 |

The invention claimed is:

1. A compound which is an indolizinyl derivative of formula (I), or a pharmaceutically acceptable salt thereof:

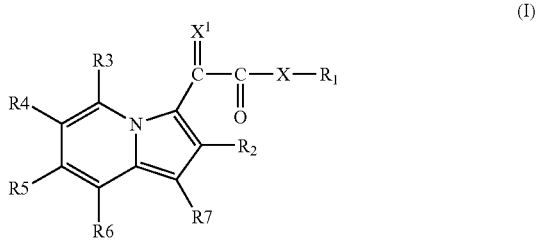

(I)

wherein:

X is —NR8-, —O—, —S—, —SO—, or —SO$_2$—;

X$^1$ is O or NOR9, wherein R9 is hydrogen or an unsubstituted or substituted C1-C4 alkyl group;

R1 represents -A3-L3-A4, -A3-L1-(A4)$_p$-(A11)$_q$-L3-A5, -A6-L1-A7, -A3-L4-A8, -A3-W, -A9, -A3-L1-A9 or A10, wherein p and q are the same or different and represent zero or 1, R8 represents hydrogen, or an unsubstituted or substituted group selected from C6-C10 aryl, a 5- to 12-membered heterocyclyl group, C1-C8 alkyl, C2-C8 alkenyl, C2-C8 alkynyl, C3-C6 cycloalkyl, -A1-L1-A2, -L2-A2, —COR' and —Y—Z;

L1 is a bond, —NR'—, —OCO—, —OCONR'R" or —CONR'R"—;

L2 is a substituted or unsubstituted C1-C4 alkylene or C2-C4 alkenylene group;

L3 is a bond, a group of formula -(Het)$_r$-Alk$^1$-(Het)$_s$-, or, wherein Alk$^1$, and Alk$^4$ are the same or different and represent unsubstituted C1-C4 alkylene groups, r and s are the same or different and represent zero or 1, and Het represents —O— or —NR9- where R9 is hydrogen or unsubstituted C1-C4 alkyl;

L4 is an imino group —N═ wherein the double bond is bonded to group A8;

A1 is an unsubstituted or substituted C6-C10 arylene group;

A2, A3, A4, A5, A7 and A11 are the same or different and are unsubstituted or substituted C6-C10 aryl or 5- to 12-membered heterocyclyl groups;

A6 is a C6-C10 aryl or 5- to 12-membered heterocyclyl group which is substituted with at least a C6-C10 aryl or a 5- to 12-membered heterocyclyl group which is itself unsubstituted or substituted;

A8 is an unsubstituted or substituted 5- to 12-membered heterocyclyl group;

A9 is an unsubstituted or substituted 5- to 12-membered heterocyclyl group wherein 1 or 2 ring carbon atoms are replaced with a group selected from >C(═O), >S(═O)$_2$, >C(═NOR11) where R11 is hydrogen or a C1-C4 alkyl group, >C═CH$_2$ or >C(—OCH$_2$CH$_2$O—);

A10 is an unsubstituted or substituted tricyclic 13- to 15-membered heterocyclyl group;

W is a group of formula —C(═O)—NR10-S(═O)$_2$—R'" where R10 and R'" are the same or different and represent hydrogen or C1-C4 alkyl;

R2 is an unsubstituted or substituted group selected from C6-C10 aryl, a 5- to 12-membered heterocyclyl group, C1-C8 alkyl and C3-C6 cycloalkyl, halogen or a group of formula -B1-B2 or -B3;

B1 is an unsubstituted or substituted C6-C10 aryl group;

B2 is an unsubstituted or substituted C6-C10 aryl or 5- to 12-membered heterocyclyl group;

B3 is an unsubstituted or substituted 5- to 12-membered heterocyclyl group where 1 or 2 ring carbon atoms are replaced with a group selected from >C(═O), >S(═O)$_2$, >C(═NOR11) where R11 is hydrogen or a C1-C4 alkyl group, >C═CH$_2$ or >C(—OCH$_2$CH$_2$O—);

either (i) R3 represents C6-C10 aryl, a 5- to 12-membered heterocyclyl group, —(C1-C4 alkylene)-(C6-C10 aryl), —(C1-C4 alkylene)-(5-to 12-membered heterocyclyl), hydrogen, halogen, C1-C8 alkyl, C2-C8 alkenyl, C2-C8 alkynyl, —OR', —CO$_2$R', —CONR'R", —COR, —CN, —NO$_2$, —NR'R", CF$_3$, or —Y—Z, and R4 represents C6-C10 aryl, a 5- to 12-membered heterocyclyl group, —(C1-C4 alkylene)-(C6-C10 aryl), —(C1-C4 alkylene)-(5-to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, —Y—Z or a group of formula -Het-Alk$^5$-A11 where Het is —NR12 or —O— with R12 being hydrogen or C1-C4 alkyl, Alk$^5$ is C1-C6 alkylene and A11 is C6-C10 aryl or a 5- to 12-membered heterocyclyl group, or (ii) R3 and R4, together with the ring carbon atoms to which they are bonded, form an unsubstituted or substituted C6-C10 aryl or a 5- to 12-membered heterocyclyl group, R5 and R6 independently represent C6-C10 aryl, a 5- to 12-membered heterocyclyl group, —(C1-C4 alkylene)-(C6-C10 aryl), —(C1-C4 alkylene)-(5-to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z;

R7 represents hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, —Y—Z, C6-C10 aryl or a group of formula -Alk$^6$-L5-A12, where Alk$^6$ is a C1-C4 alkylene group, L5 is a group of formula —O—C(═O)—, —C(═O)— or —NR13-C(═O)— and R13 is hydrogen or C1-C4 alkyl, and A12 is an unsubstituted or substituted C6-C10 aryl or a 5- to 12-membered heterocyclyl group;

Y is C1-C8 alkylene, C2-C8 alkenylene or C2-C8 alkynylene;

Z is halogen, C3-C6 cycloalkyl, —OR', —SR', —SOR', —SO$_2$R', —SO$_2$NR'R",
—SO$_3$H, —NR'R", —NR'COR', —NO$_2$, —CO$_2$R', —CONR'R", —COR', —OCOR', —CN,
—CF$_3$—NSO$_2$R', —OCONR'R" or —CR'═NOR"; and R' and R" independently represent hydrogen, C1-C8 alkyl, C2-C8 alkenyl or C2-C8 alkynyl, wherein unless otherwise specified an alkyl, alkenyl, alkynyl, alkylene, cycloalkyl, aryl or heterocyclyl group or moiety can be substituted or unsubstituted;

and wherein:

a substituted alkyl, alkenyl, alkynyl or alkylene group or moiety is said alkyl, alkenyl, alkynyl or alkylene group or moiety which is substituted with up to three substituents selected from halogen, hydroxyl, amino, (C1-C4 alkyl)amino, di(C1-C4 alkyl)amino, C1-C4 alkoxy, —CO2H and —CO2(C1-C4 alkyl), wherein the substituents on a substituted alkyl, alkenyl, alkynyl or alkylene group or moiety are themselves unsubstituted;

a substituted cycloalkyl group is a said cycloalkyl group which is substituted with up to three substituents selected from C1-C8 alkyl, C2-C8 alkenyl, C2-C8 alkynyl, Z and —Y—Z;

a substituted aryl or heterocyclyl group or moiety is said aryl or heterocyclyl group or moiety which is substituted with up to three substituents selected from C1-C8 alkyl, C2-C8 alkenyl, C2-C8 alkynyl, unsubstituted phenyl, Z and —Y—Z, provided the compound is not one of the following compounds or their pharmaceutically acceptable salts:

N-(2,4-Dimethoxy-phenyl-phenyl)-2-oxo-2-(2-phenyl-indolizin-3-yl)-acetamide,

2-Oxo-2-(2-phenyl-indolizin-3-yl)-N-(4-thiomorpholin-4-yl-phenyl)-acetamide,

2-Oxo-2-(2-phenyl-indolizin-3-yl)-N-(4-pyrrolidin-1-yl-phenyl)-acetamide,

N-[4-(4-Methyl-piperazin-1-yl)-phenyl]-2-oxo-2-(2-phenyl-indolizin-3-yl)-acetamide, N-Benzyl-N-methyl-3-[2-oxo-2-(2-phenyl-indolizin-3-yl)-acetylamino]-benzamide, N-[4-(2-Methyl-[1,3]dioxolan-2-yl)-phenyl]-2-oxo-2-(2-phenyl-indolizin-3-yl)-acetamide, 1-Methyl-4-{4-[2-oxo-2-(2-phenyl-indolizin-3-yl)-acetylamino]-phenyl}-thiomorpholin-1-ium, N-(4-Oxazol-2-yl-phenyl)-2-oxo-2-(2-phenyl-indolizin-3-yl)-acetamide, 2-Oxo-2-(2-phenyl-indolizin-3-yl)-N-[4-(pyridin-2-ylamino)-phenyl]-acetamide, 2-Oxo-2-(2-phenyl-indolizin-3-yl)-N-[4-(1H-tetrazol-5-yl)-phenyl]-acetamide, 2-Oxo-N-[4-(4-oxo-piperidin-1-yl)-phenyl]-2-(2-phenyl-indolizin-3-yl)-acetamide, 1-{4-[2-Oxo-2-(2-phenyl-indolizin-3-yl)-acetylamino]-phenyl}-pyrrolidine-2-carboxylic acid methyl ester, 2-Oxo-2-(2-phenyl-indolizin-3-yl)-N-[4-(pyrimidin-2-ylamino)-phenyl]-acetamide, 2-Oxo-2-(2-phenyl-indolizin-3-yl)-N-[4-(thiazol-2-ylamino)-phenyl]-acetamide, N-[4-(3,5-Dimethyl-isoxazol-4-yl)-phenyl]-2-oxo-2-(2-phenyl-indolizin-3-yl)-acetamide, N-(3-Oxazol-2-yl-phenyl)-2-oxo-2-(2-phenyl-indolizin-3-yl)-acetamide, N-(4-Oxazol-5-yl-phenyl)-2-oxo-2-(2-phenyl-indolizin-3-yl)-acetamide, N-(4-Dimethylamino-3-oxazol-2-yl-phenyl)-2-oxo-2-(2-phenyl-indolizin-3-yl)-acetamide, 2-Oxo-2-(2-phenyl-indolizin-3-yl)-N-(4-thiazol-2-yl-phenyl)-acetamide, N-(1,5-Dimethyl-3-oxo-2-phenyl-2,3-dihydro-1H-pyrazol-4-yl)-2-oxo-2-(2-phenyl-indolizin-3-yl)-acetamide, alpha-Oxo-2-phenyl-N-[4-(1-piperidinyl)phenyl]-3-indolizineacetamide, N-(2,3-Dihydro-1,5-dimethyl-3-oxo-2-phenyl-1H-pyrazol-4-yl)-alpha-oxo-2-phenyl-3-indolizineacetamide, 2-Oxo-2-(2-phenyl-indolizin-3-yl)-N-(4-piperidin-1-yl-phenyl)-acetamide.

2. A compound as claimed in claim 1 wherein X is —NR8- or —O—.

3. A compound as claimed in claim 2 wherein X is —NR8-.

4. A compound as claimed in claim 1 wherein A3 is an unsubstituted or substituted C6-C10 aryl group or an unsubstituted or substituted 5- or 6-membered unsaturated heterocyclic group, A4 is an unsubstituted or substituted 5- to 7-membered heterocyclyl group, A5 is an unsubstituted or substituted 5- to 6-membered heterocyclyl group, A6 is a phenyl group which is substituted with a phenyl or a 5- to 6-membered heterocyclyl group which is itself unsubstituted or substituted, A7 is an unsubstituted or substituted 5- to 6-membered heterocyclyl group, A8 is an unsubstituted or substituted 5- to 6-membered heterocyclyl group, A9 is an unsubstituted or substituted 8- to 12-membered heterocyclyl group wherein 1 ring carbon atom has been replaced with a C(=O) group, A10 is an unsubstituted or substituted tricyclic 13- to 15-membered heterocyclyl group, A11 is an unsubstituted or substituted C6-C10 aryl group or an unsubstituted or substituted 5- or 6-membered unsaturated heterocyclic group, L1 is a bond or a group
—NR'— or —CONR'R" where R' and R" are the same or different and represent hydrogen or unsubstituted C1-C4 alkyl, L3 is a bond or a group of formula -(Het)$_r$-Alk$^1$-(Het)$_s$-, -(Alk$^2$)$_m$-C(=O)-Het-(Alk$^3$)$_n$-, -Alk$^4$- or —SO$_2$—, wherein Alk$^1$ is an unsubstituted C1-C3 alkylene group, Alk$^2$ is an unsubstituted C2-C3 alkylene group, Alk$^3$ is an unsubstituted C1-C2 alkylene group, Alk$^4$ is an unsubstituted C1-C4 alkylene group, and Het is —O— or —NR9- where R9 is hydrogen or unsubstituted C1-C2 alkyl, L4 is an imino group —N=wherein the double bond is bonded to group A8, W is a group of formula —C(=O)—NR10-S(=O)$_2$—R''' where R10 and R''' are the same or different and represent hydrogen or C1-C2 alkyl.

5. A compound as claimed in claim 1 wherein X is —NR8- and R8 is hydrogen or unsubstituted C1-C4 alkyl.

6. A compound as claimed in claim 1 wherein X$^1$ is O.

7. A compound as claimed in claim 1 wherein R2 is an unsubstituted or substituted group selected from C6-C10 aryl, a 5- to 12-membered heterocyclyl group, C1-C8 alkyl, C3-C6 cycloalkyl, and halogen.

8. A compound as claimed in claim 1 wherein R2 is a group of formula -B1-B2 or -B3.

9. A compound as claimed in claim 8 wherein B1 is an unsubstituted or substituted phenyl group, B2 is an unsubstituted or substituted phenyl or 5- to 6-membered heterocyclyl group, and B3 is a 5- to 6-membered heterocyclyl group where 1 ring carbon atom is replaced with >C(=O)—, >S(=O)$_2$—, >C(=NOR11), >C(NR11), >C(=CH$_2$) or >C(—OCH$_2$CH$_2$O—), where R11 is hydrogen or C1-C2 alkyl.

10. A compound as claimed in claim 1 wherein R3 and R4 are the same or different and represent C6-C10 aryl, a 5- to 12-membered heterocyclyl group, —(C1-C4 alkylene)-(C6-C10 aryl), —(C1-C4 alkylene)-(5-to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO2, —NR'R", CF3, or —Y—Z.

11. A compound as claimed in claim 1 wherein either (i) R3 represents C6-C10 aryl, a 5- to 12-membered heterocyclyl group, —(C1-C4 alkylene)-(C6-C10 aryl), —(C1-C4 alkylene)-(5-to 12-membered heterocyclyl), hydrogen, halogen, C1-C8 alkyl, C2-C8 alkenyl, C2-C8 alkynyl, —OR', —CO$_2$R', —CONR'R", —COR', —CN, —NO$_2$, —NR'R", CF$_3$, or —Y—Z, and R4 represents a group of formula -Het-Alk$^5$-A11 where Het is —NR12 or —O— with R12 being hydrogen or C1-C4 alkyl, Alk⁵ is C1-C6 alkylene and A11 is C6-C10 aryl or a 5- to 12-membered heterocyclyl group, or (ii) R3 and R4, together with the ring carbon atoms to which they are bonded, form an unsubstituted or substituted C6-C10 aryl or 5- to 12-membered heterocyclyl group.

12. A compound as claimed in claim 11 wherein R4 is a group of formula -Het-Alk⁵-A11 and R3 is hydrogen, unsubstituted C1-C4 alkyl or unsubstituted C1-C4 alkoxy.

13. A compound as claimed in claim 12 wherein Het represents —NR12- or —O— where R12 is hydrogen or C1-C2 alkyl, Alk⁵ is an unsubstituted C1-C4 alkylene group, and A11 is an unsubstituted or substituted 5- to 6-membered heterocyclyl group.

14. A compound as claimed in claim 11 wherein R3 and R4, together with the ring carbon atoms to which they are bonded, form an unsubstituted or substituted phenyl ring.

15. A compound as claimed in claim 1 wherein R7 is hydrogen, halogen, C1-C8 alkyl, C2-C8 alkenyl, C2-C8 alkynyl, —OR', —CO₂R', —CONR'R", —COR', —CN, —NO₂, —NR'R", CF₃ or —Y—Z.

16. A compound as claimed in claim 1 wherein R7 is an unsubstituted or substituted C6-C10 aryl or a group of formula -Alk⁶-L5-A12, where Alk⁶ is a C1-C4 alkylene group, L5 is a group of formula —O—C(=O)—, —C(=O)— or —NR13-C(=O)— and R13 is hydrogen or C1-C4 alkyl, and A12 is an unsubstituted or substituted C6-C10 aryl or 5- to 12-membered heterocyclyl group.

17. A compound as claimed in claim 1 selected from:
2-(2-Methyl-1-phenyl-indolizin-3-yl)-N-(4-morpholin-4-yl -phenyl)-2-oxo-acetamide,
2-(2-Biphenyl-4-yl-indolizin-3-yl)-N-(4-oxazol-4-yl-phenyl) -2-oxo-acetamide,
N-{4-[3-(2-Isopropyl-imidazol-1-yl)-propoxy]-3-methyl -phenyl}-2-oxo-2-(2-phenyl-indolizin-3-yl)-acetamide,
N-{3-Isopropyl-4-[3-(2-methyl-imidazol-1-yl)-propoxy]-phenyl}-2-oxo-2-(2-phenyl-indolizin-3-yl)-acetamide,
N-[4-(2-Morpholin-4-yl-ethoxy)-phenyl]-2-oxo-2-(2-phenyl-indolizin-3-yl)-acetamide,
2-Hydroxy-4-[2-oxo-2-(2-phenyl-indolizin-3-yl) -acetylamino]-benzoic acid tetrahydro-pyran-4-yl ester,
2-Isopropyl-4-[2-oxo-2-(2-phenyl-indolizin-3-yl) -acetylamino]-benzoic acid 2-(2-isopropyl-imidazol-1-yl)-ethyl ester,
2-Methyl-2-{3-[2-oxo-2-(2-phenyl-indolizin-3-yl) -acetylamino]-phenyl}-propionic acid 2-(2-isopropyl-imidazol -1-yl)-ethyl ester,
N-[4-(2-Morpholin-4-yl-ethyl)-phenyl]-2-oxo-2-(2-phenyl -indolizin-3-yl)-acetamide,
N-{3-[1-(2-Isopropyl-1-methyl-1H-imidazol-4-yl)-1-methyl -ethyl]-phenyl}-2-oxo-2-(2-phenyl-indolizin-3-yl)-acetamide,
N-{4-[1-(2-Isopropyl-1-methyl-1H-imidazol-4-yl)-1-methyl -ethyl]-phenyl}-2-oxo-2-(2-phenyl-indolizin-3-yl)-acetamide,
N-{3-[1-(2-Isopropyl-3-methyl-3H-imidazol-4-yl)-1-methyl -ethyl]-phenyl}-2-oxo-2-(2-phenyl-indolizin-3-yl)-acetamide,
N-{4-[1-(2-Isopropyl-3-methyl-3H-imidazol-4-yl)-1-methyl -ethyl]-phenyl}-2-oxo-2-(2-phenyl-indolizin-3-yl)-acetamide,
N-{3-[1-(4-Isopropyl-2-methyl-imidazol-1-yl)-1-methyl -ethyl]-phenyl}-2-oxo-2-(2-phenyl-indolizin-3-yl)-acetamide,
N-{4-[4-(2,6-Dimethyl-morpholin-4-yl)-piperidin-1-yl]-phenyl}-2-oxo-2-(2-phenyl-indolizin-3-yl)-acetamide,
2-[2-(2-Chloro-phenyl)-indolizin-3-yl]-N-[4-(4-morpholin-4-yl-piperidin-1-yl)-phenyl]-2-oxo-acetamide,
N-{4-[4-(4,6-Dimethyl-pyridin-2-yl)-piperazin-1-yl]-phenyl}-2-oxo-2-(2-phenyl-indolizin-3-yl)-acetamide,
N-[4-(4-Methyl-piperazin-1-yl)-3-oxazol-2-yl-phenyl]-2-oxo -2-(2-phenyl-indolizin-3-yl)-acetamide,
2-Oxo-2-(2-phenyl-indolizin-3-yl)-N-{4-[3,4,4-trimethyl -oxazolidin-(2Z)-ylideneamino]-phenyl}-acetamide,
N-(4-Methanesulfonylaminocarbonyl-phenyl)-2-oxo-2-(2-phenyl-indolizin-3-yl)-acetamide,
2-Oxo-N-(2-oxo-2,3-dihydro-1H-indol-5-yl)-2-(2-phenyl -indolizin-3-yl)-acetamide
N-[4-(1,1-Dioxo-1λ⁶-thiomorpholin-4-yl)-phenyl]-2-oxo-2-(2-phenyl-indolizin-3-yl)-acetamide,
N-[4-(4-Methoxyimino-piperidin-1-yl)-phenyl]-2-oxo-2-(2-phenyl-indolizin-3-yl)-acetamide,
N-(4-{3-[(Z)-Methoxyimino]-pyrrolidin-1-yl}-phenyl)-2-oxo -2-(2-phenyl-indolizin-3-yl)-acetamide,
N-[4-(4-Methylene-piperidin-1-yl)-phenyl]-2-oxo-2-(2-phenyl-indolizin-3-yl)-acetamide,
N-[4-(1,4-Dioxa-8-aza-spiro[4.5]dec-8-yl)-phenyl]-2-oxo-2-(2-phenyl-indolizin-3-yl)-acetamide,
2-[2-(2-Chloro-phenyl)-indolizin-3-yl]-N-(2-ethyl-2,3,4,5-tetrahydro-1H-pyrido[4,3-b]indol-7-yl)-2-oxo-acetamide,
2-methyl-2-{4-[2-oxo-2-(2-phenyl-indolizin-3-yl) -acetylamino]-phenyl}-propionic acid 2-(2-isopropyl-imidazol -1-yl)-ethyl ester,
Diethyl-carbamic acid-5-{4-[2-oxo-2-(2-phenyl-indolizin-3-yl)-acetyl amino]-phenyl}-isoxazol-3-yl ester,
N-{4-[(4,4-Dimethyl-4,5-dihydro-oxazol-2-yl)-(2-ethoxy -ethyl)-amino]-phenyl}-2-oxo-2-phenyl-indolizin-3-yl) -acetamide,
N-{4-[5-(4-Methyl-piperazin-1-yl)-4-(2,2,2-trifluoro-acetyl) -oxazol-2-yl]-phenyl}-2-oxo-2-(2-phenyl-indolizin-3-yl) -acetamide,
N-[4-(3-Ethyl-1H-imidazol-2yl methyl)-phenyl]-2-oxo-2-(2-o -tolyl-indolizin-3yl)-acetamide,
4-[4-(2-Furan-2-yl-methyl-piperazin-yl)-phenyl]-2-oxo-2-(2-phenyl-indolizin-3-yl)-acetamide,
N-{4-[4-(4,6-Dimethyl-pyridin-2-yl)-piperazin-1-yl]-phenyl}-2-(6-fluoro-2-phenyl-indolizin-3-yl)-2-oxo-acetamide,
2-Oxo-2-(2-phenyl indolizin-3-yl)-N-[4-(4-thiophen-2-yl methyl piperazin-1-yl) phenyl]acetamide,
N-[5-(2-Furan-2-yl-methyl-piperazin-yl)-piperidin-2-yl]-2-oxo-2-(2-phenylindolizin-3-yl)-acetamide,
N-[5-(2-Furan-2-yl-methyl-piperazin-yl)-piperidin-2-yl]-2-oxo-2-(2-o-tolyl-indolizin-3-yl)-acetamide,
2-Oxo-2-(2-phenyl-indolizin-3-yl)-N-{4-[4-(2-pyridin-yl -ethyl)-perazin-1-yl]-phenyl}acetamide,
2-Oxo-2-(2-phenyl-indolizin-3-yl)-N-[4-{4-thiophen-2-ylmethyl-piperazin-1-yl}-pyridine-3-yl]-acetamide,
N-{4-[4-(2-Furan-2-yl-ethyl)-piperazin-1-yl]-pyridin-3-yl}-2-oxo-2-(2-phenyl-indolizin-3-yl)-acetamide,
N-{4-[4-(2-Furan-2-yl-ethyl)-piperazin-1-yl]-phenyl}-2-oxo-2-(2-phenyl-indolizin-3-yl)-acetamide,
N-{4-[4-(2-Methyl-allyl)-piperazin-1-yl]-phenyl}-2-[2-(4-morpholin-4-yl-phenyl)-indolizin-3-yl]-2-oxo-acetamide,
2-Oxo-2-(2-phenyl-indolizin-3yl)-N-[4-(4-pyridin-2-yl-piperizin-1-yl)-phenyl]-acetamide,
2-(6-Fluoro-2-phenyl-indolizin-3-yl)-2-oxo-N-[4-(4-pyridin-2-yl-piperazin-1-yl) phenyl]acetamide,
N-{4-[4-(6-Methyl-pyridin-2-yl)-piperazin-1-yl]-phenyl}-2-oxo-2-(2-phenyl-indolizin-3-yl)-acetamide, N-{4-[4-(4,6-Dimethyl-pyrimidin-2-yl)-piperazin-1-yl]-phenyl}-2-oxo-2-(2-phenyl-indolizin-3-yl)-acetamide,
N-{4-[4-(2,6-Dimethyl-pyrimidin-4-yl)-piperazin-1-yl]-phenyl}-2-(2-phenyl-indolizin-3-yl)-acetamide,
N-[4-(4-Methylene-piperidin-1-yl)-phenyl]-2-[2-(2-methyl-pyridin-3-yl)-indolizin-3-yl]-2-oxo-acetamide,
2-(2-Cyclopentyl-indolizin-3-yl)-N-{4-[4-(4,6-dimethyl-pyridin-2-yl)-piperazin-1-yl]-phenyl}-2-oxo-acetamide,
N-{3-[4-(4,6-Dimethyl-pyridin-2-yl)-piperazin-1-yl]-phenyl}-2-oxo-2-(2-phenyl-indolizin-3-yl)-acetamide,
N-{4-[4-(4-Methyl-pyridin-2-yl)-piperazin-1-yl]-phenyl}-2-oxo-2-(2-phenyl-indolizin-3-yl)-acetamide,
N-{5-[4-(2,2-Dimethyl-propyl)-piperazin-1-yl]-pyridin-2-yl}-2-oxo-2-(2-phenyl-indolizin-3-yl)-acetamide,
N-{4-[4-(2,6-Dimethyl-pyridin-4-yl)-piperazin-1-yl]-phenyl}-2-oxo-2-(2-phenyl-indolizin-3-yl)-acetamide,
2-(6-Fluoro-2-phenyl-indolizin-3-yl)-2-oxo-N-{4-[4-(tetrahydro-pyran-4-ylmethyl)-piperazin-1-yl]-phenyl}-acetamide,
N-{4-[4-(4,6-Dimethyl-pyridin-2-yl)-[1,4]diazepan-1-yl]-phenyl}-2-oxo-2-(2-phenyl-indolizin-3-yl)-acetamide,
N-[4-({2-[(4,6-Dimethyl-pyridin-2-yl)-methyl-amino]-ethyl}-methyl-amino)-phenyl]-2-oxo-2-(2-phenyl-indolizin-3-yl)-acetamide,
N-{4-[4-(4-Morpholin-4-ylmethyl-phenyl)-piperazin-1-yl]-phenyl}-2-oxo-2-(2-phenyl-indolizin-3-yl)-acetamide,
N-(4-{4-[4-(2-Methoxy-ethoxy)-6-methyl-pyridin-2-yl]-piperazin-1-yl}-phenyl)-2-oxo-2-(2-phenyl-indolizin-3-yl)-acetamide,
2-(2-Cyclopropyl-indolizin-3-yl)-N-{4-[4-(4,6-dimethyl-pyridin-2-yl)-piperazin-1-yl]-phenyl}-2-oxo-acetamide,
2-Oxo-2-(2-phenyl-indolizin-3-yl)-N-[4-(4-pyridin-3-yl-piperazin-1-yl)-phenyl]-acetamide,
2-(2-Cyclohexyl-indolizin-3-yl)-N-{4-[4-(4,6-dimethyl-pyridin-2-yl)-piperazin-1-yl]-phenyl}-2-oxo-acetamide,
N-{4-[4-(4,6-Dimethyl-pyridin-2-yl)-piperazin-1-yl]-phenyl}-2-(2-isopropyl-indolizin-3-yl)-2-oxo-acetamide,
2-(2-tert-Butyl-indolizin-3-yl)-N-{4-[4-(4,6-dimethyl-pyridin-2-yl)-piperazin-1-yl]-phenyl}-2-oxo-acetamide,
N-{4-[4-(4,6-Dimethyl-pyridin-2-yl)-piperazin-1-yl]-phenyl}-2-[2-(1-methyl-piperidin-4-yl)-indolizin-3-yl]-2-oxo-acetamide,
N-(4-{2-[(4,6-Dimethyl-pyridin-2-yl)-methyl-amino]-ethoxy}-phenyl)-2-oxo-2-(2-phenyl-indolizin-3-yl)-acetamide,
N-{4-[2-(4,6-Dimethyl-pyridin-2-yloxy)-ethoxy]-phenyl}-2-oxo-2-(2-phenyl-indolizin-3-yl)-acetamide,
N-{4-[4-(4,6-Dimethyl-pyridin-2-yl)-piperazin-1-yl]-phenyl}-2-oxo-2-[2-(tetrahydro-pyran-4-yl)-indolizin-3-yl]-acetamide,
N-[4-({3-[(4,6-dimethyl-pyridin-2-yl)-methyl-amino]-propyl}-methyl-amino)-phenyl]-2-oxo-2-(2-phenyl-indolizin-3-yl)-acetamide,
N-[4-(4-{6-[(2-Methoxy-ethyl)-methyl-amino]-pyridin-3-yl}-piperazin-1-yl)-phenyl]-2-oxo-2-(2-phenyl-indolizin-3-yl)-acetamide,
N-(4-{[2-(4,6-dimethyl-pyridin-2-ylamino)-ethyl]-methyl-amino}-phenyl)-2-oxo-2-(2-phenyl-indolizin-3-yl)-acetamide,
N-(4-{3-[(4,6-Dimethyl-pyridin-2-yl)-methyl-amino]-propyl}-phenyl)-2-oxo-2-(2-phenyl-indolizin-3-yl)-acetamide,
N-{4-[2-(2,6-Dimethyl-pyridin-4-yloxy)-ethoxy]-phenyl}-2-oxo-2-(2-phenyl-indolizin-3-yl)-acetamide,
N-{4-[4-(4,6-Dimethyl-pyridin-2-yl)-butyl]-phenyl}-2-oxo-2-(2-phenyl-indolizin-3-yl)-acetamide,
N-{4-[4-(6-ethyl-pyridin-2-yl)-piperazin-1-yl]-phenyl}-2-oxo-2-(2-phenyl-indolizin-3-yl)-acetamide,
N-{4-[4-(5-Methyl-pyridin-2-yl)-piperazin-1-yl]-phenyl}-2-oxo-2-(2-phenyl-indolizin-3-yl)-acetamide,
N-{4-[4-(4-ethyl-pyridin-2-yl)-piperazin-1-yl]-phenyl}-2-oxo-2-(2-phenyl-indolizin-3-yl)-acetamide,
N-[4-(4-{4-[2-(2-methoxy-ethoxy)-ethoxy]-6-methyl-pyridin-2-yl}-piperazin-1-yl)-phenyl]-2-oxo-2-(2-phenyl-indolizin-3-yl)-acetamide,
N-{4-[4-(5-morpholin-4-yl-methyl-pyridin-2-yl)-piperazin-1-yl]-phenyl}-2-oxo-2-(2-phenyl-indolizin-3-yl)-acetamide,
N-(4-{2-[(4,6-Dimethyl-pyridin-2-yl)-methyl-amino]-ethylamino}-phenyl)-2-oxo-2-(2-phenyl-indolizin-3-yl)-acetamide,
N-[4-(4-hydroxy-4',6'-dimethyl-3,4,5,6-tetrahydro-2H-[1,2']-bipyridinyl-4-yl)-phenyl]-2-oxo-2-(2-phenyl-indolizin-3-yl)-acetamide,
N-{4-[4-(4,6-Dimethyl-pyridin-2-yl)-piperazin-1-yl]-2-methyl-phenyl}-2-oxo-2-(2-phenyl-indolizin-3-yl)-acetamide,
N-{4-[4-(4,6-Dimethyl-pyridin-2-yl)-piperazin-1-yl]-3-methoxymethyl-phenyl}-2-oxo-2-(2-phenyl-indolizin-3-yl)-acetamide,
N-{4-[4-(4,6-Dimethyl-pyridin-2-yl)-piperazin-1-yl]-3-methyl-phenyl}-2-oxo-2-(2-phenyl-indolizin-3-yl)-acetamide,
N-{4-[4-(4,6-Dimethyl-pyridin-2-yl)-piperazin-1-yl]-2-methoxymethyl-phenyl}-2-oxo-2-(2-phenyl-indolizin-3-yl)-acetamide,
2-[4-(4,6-Dimethyl-pyridin-2-yl)-piperazin-1-yl]-5-[2-oxo-2-(2-phenyl-indolizin-3-yl)-acetylamino]-benzoic acid,
N-[4-(4-{6-[Bis-(2-hydroxy-ethyl)-amino]-pyridin-2-yl}-piperazin-1-yl)-phenyl]-2-oxo-2-(2-phenyl-indolizin-3-yl)-acetamide,
N-(4-{4-[6-(2-hydroxy-ethylamino)-pyridin-2-yl]-piperazin-1-yl}-phenyl)-2-oxo-2-(2-phenyl-indolizin-3-yl)-acetamide,
N-(4-{4-[6-(2-hydroxy-ethyl)-pyridin-2-yl]-piperazin-1-yl}-phenyl)-2-oxo-2-(2-phenyl-indolizin-3-yl)-acetamide,
N-(4-{4-[4-(2-Hydroxy-ethoxy)-pyridin-2-yl]-piperazin-1-yl}-phenyl)-2-oxo-2-(2-phenyl-indolizin-3-yl)-acetamide,
2-Oxo-2-(2-phenyl-indolizin-3-yl)-N-{4-[2-(pyridin-2-yloxy)-ethylamino]-phenyl}-acetamide,
N-{4-[(4,6-Dimethyl-pyridin-2-ylmethyl)-amino]-phenyl}-2-oxo-2-(2-phenyl-indolizin-3-yl)-acetamide and
N-{4-[2-(4,6-dimethyl-pyridin-2-yl-amino)-ethyl amino]-phenyl}-2-oxo-2-(2-phenyl-indolizin-3-yl)-acetamide
and pharmaceutically and agriculturally acceptable salts thereof.

18. A composition comprising a compound as defined claim 1 and a pharmaceutically acceptable carrier or diluent or an agriculturally acceptable carrier or diluent.

19. A method of treating a subject suffering from or susceptible to a fungal disease, which method comprises administering to said subject an effective amount of a compound as defined in claim 1.

20. A method of controlling a fungal disease in a plant, which method comprises applying to the locus of the plant a compound as defined in claim 1.

21. A method according to claim 19 wherein the disease is caused by an *Aspergillus* or *Candida* species.

22. A method according to claim 19, wherein the disease is caused by a fungal dermatophyte.

23. A method according to claim 19 wherein the disease is Allergic Bronchopulmonary *Aspergillosis* (ABPA) or asthma.

* * * * *

UNITED STATES PATENT AND TRADEMARK OFFICE
CERTIFICATE OF CORRECTION

PATENT NO. : 8,604,029 B2
APPLICATION NO. : 12/515354
DATED : December 10, 2013
INVENTOR(S) : Downham et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 663 days.

Signed and Sealed this

Twenty-third Day of May, 2017

Michelle K. Lee
*Director of the United States Patent and Trademark Office*